(12) United States Patent
Shanley

(10) Patent No.: US 8,939,937 B2
(45) Date of Patent: Jan. 27, 2015

(54) METHOD FOR PROVIDING SURGICAL ACCESS

(75) Inventor: John F. Shanley, Emerald Hills, CA (US)

(73) Assignee: Entourage Medical Technologies, Inc., Menlo Park, CA (US)

( * ) Notice: Subject to any disclaimer, the term of this patent is extended or adjusted under 35 U.S.C. 154(b) by 0 days.

(21) Appl. No.: 13/214,115

(22) Filed: Aug. 19, 2011

(65) Prior Publication Data

US 2012/0089092 A1 Apr. 12, 2012

Related U.S. Application Data

(60) Provisional application No. 61/384,659, filed on Sep. 20, 2010, provisional application No. 61/484,175, filed on May 9, 2011.

(51) Int. Cl.

| | | |
|---|---|---|
| *A61M 5/178* | (2006.01) | |
| *A61B 17/04* | (2006.01) | |
| *A61B 17/00* | (2006.01) | |
| *A61B 17/06* | (2006.01) | |
| *A61B 19/00* | (2006.01) | |

(52) U.S. Cl.
CPC ......... *A61B 17/0469* (2013.01); *A61B 17/0057* (2013.01); *A61B 17/06* (2013.01); *A61B 17/0482* (2013.01); *A61B 17/0487* (2013.01); *A61B 2017/00243* (2013.01); *A61B 2017/00575* (2013.01); *A61B 2017/00663* (2013.01); *A61B 2017/0414* (2013.01); *A61B 2017/0417* (2013.01); *A61B 2017/0443* (2013.01); *A61B 2017/0472* (2013.01); *A61B 2017/0475* (2013.01); *A61B 2017/0496* (2013.01); *A61B 2017/06023* (2013.01); *A61B 2017/06042* (2013.01); *A61B 2017/06076* (2013.01); *A61B 2017/06171* (2013.01); *A61B 2019/462* (2013.01); *A61B 2019/465* (2013.01); *A61B 2019/4836* (2013.01)
USPC .................................................. 604/164.01

(58) Field of Classification Search
USPC ...................................................... 604/164.01
See application file for complete search history.

(56) References Cited

U.S. PATENT DOCUMENTS

| | | | | |
|---|---|---|---|---|
| 6,626,917 | B1 * | 9/2003 | Craig | ............................. 606/144 |
| 7,104,949 | B2 | 9/2006 | Anderson et al. | |
| 7,776,059 | B2 * | 8/2010 | Craig | ............................. 606/148 |
| 2007/0118151 | A1 | 5/2007 | Davidson | |

FOREIGN PATENT DOCUMENTS

| | | |
|---|---|---|
| WO | 00/60995 | 10/2000 |
| WO | 02/078571 | 10/2002 |

OTHER PUBLICATIONS

Invitation to Pay Additional Fees for PCT Applicaiton No. PSC/US2011/052404, Applicant Entourage Medical Technologies, LLC, Form PCT/ISA/206, dated Dec. 7, 2011 (8 pages).
PCT International Search Report and Written Opinion, forms PCT/ISA 210, 220 and 237, dated Mar. 5, 2012, for PCT/US2011/052404, filed Sep. 20, 2011, Applicant Entourage Medical Technologies, (26 pages).

\* cited by examiner

*Primary Examiner* — Jason Flick

(74) *Attorney, Agent, or Firm* — David C. Lundmark

(57) ABSTRACT

One embodiment is directed to a method for advancing a needle into a tissue structure, comprising: advancing a distal end of a needle insertion assembly, the assembly comprising an insertion member coupled to a tissue interface indentor member and movably coupled to an elongate needle member, against a targeted tissue structure such that a distally protruding shape feature of the tissue interface indentor member engages one or more portions of the targeted tissue structure adjacent a distal tip of the elongate needle member at a position at which the elongate needle member distal tip is configured to be advanced through the insertion member and into the tissue structure, and locally changes an available angle of penetration between such portions and the distal tip of the elongate needle member; and inserting the elongate needle member relative to the insertion member and tissue interface indentor member.

37 Claims, 116 Drawing Sheets

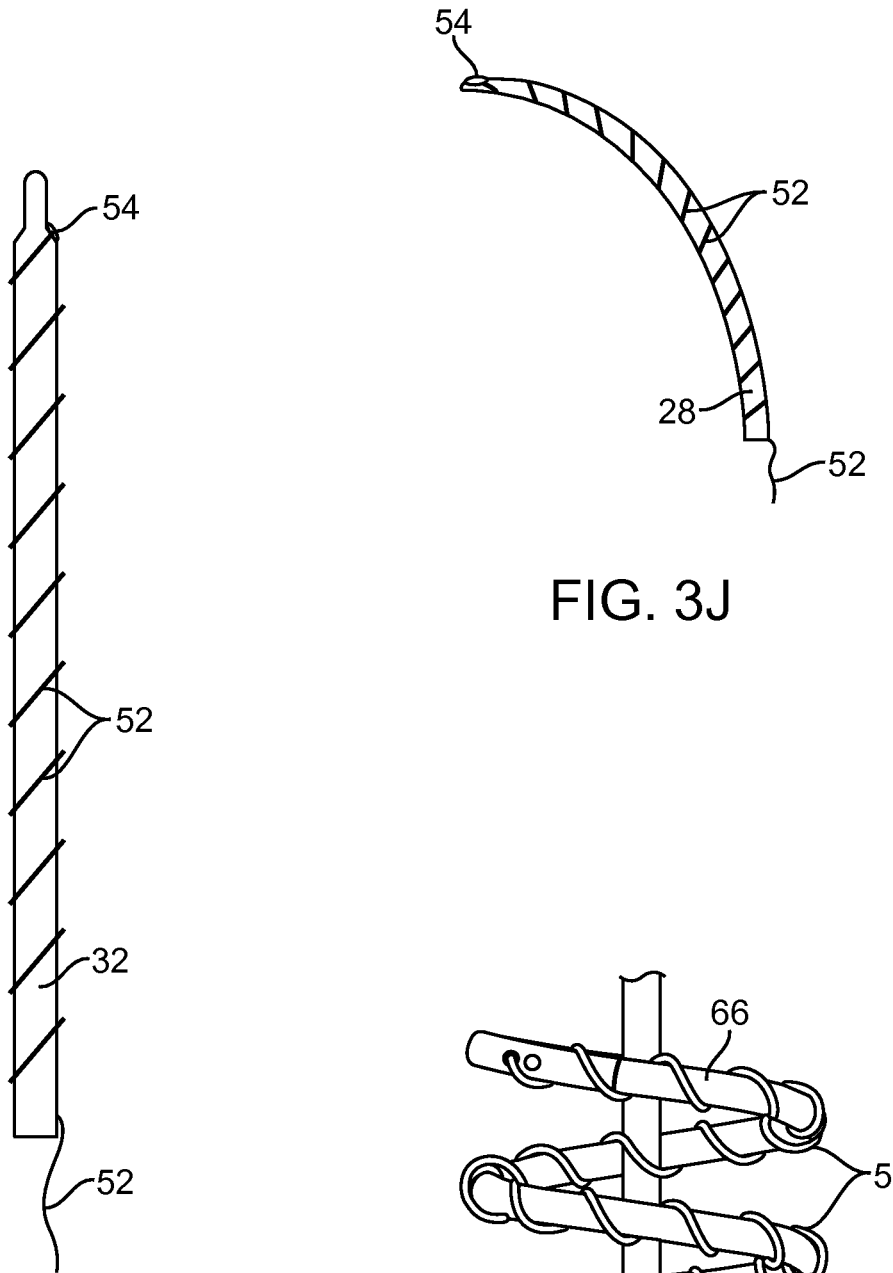

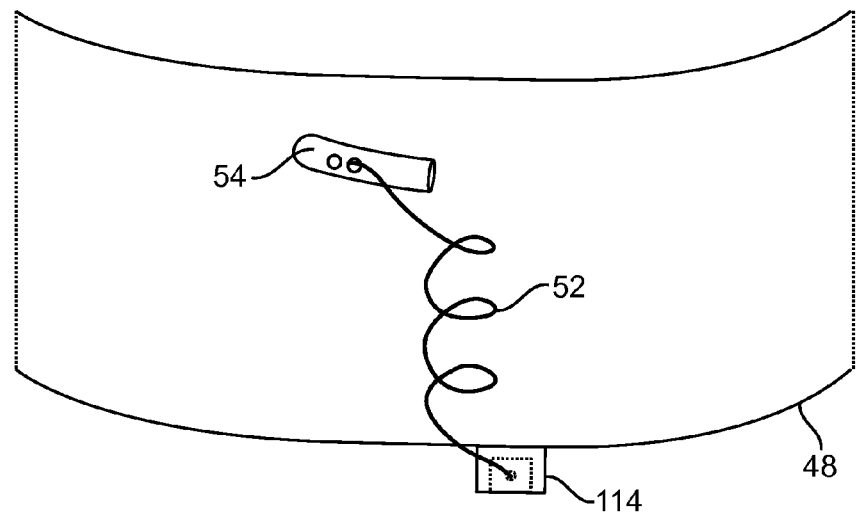
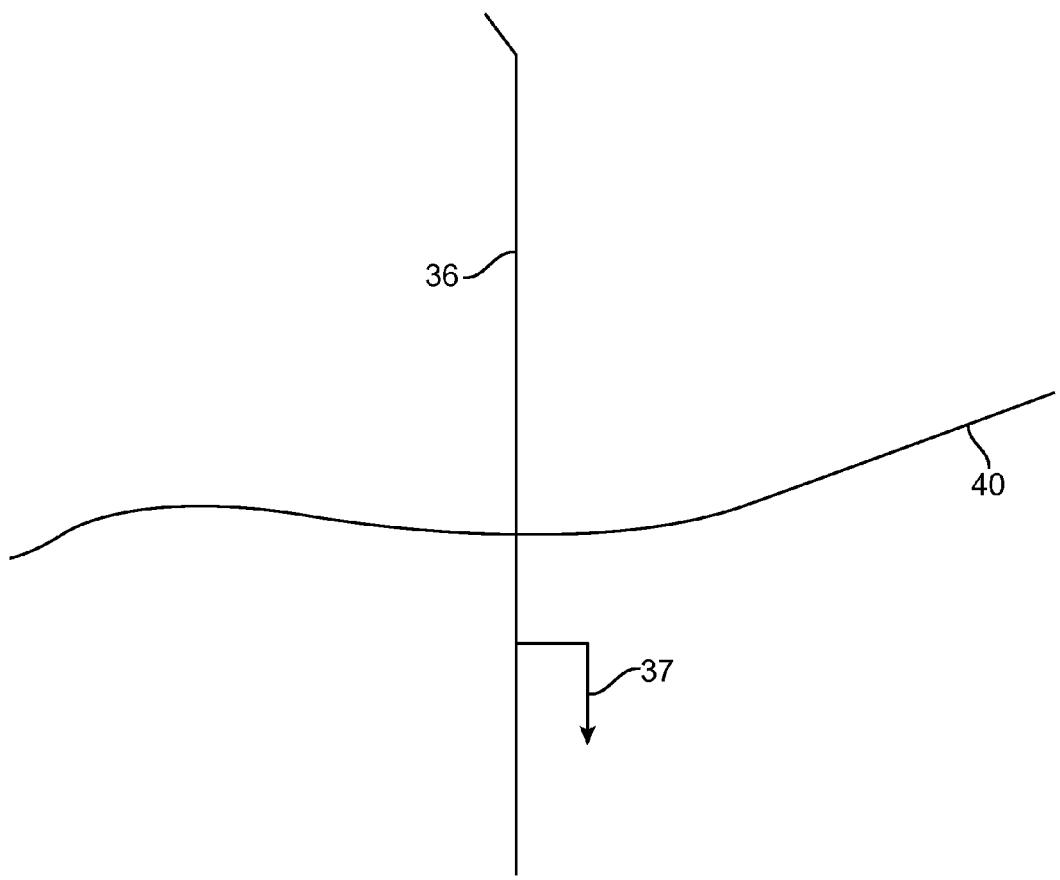
FIG. 4P

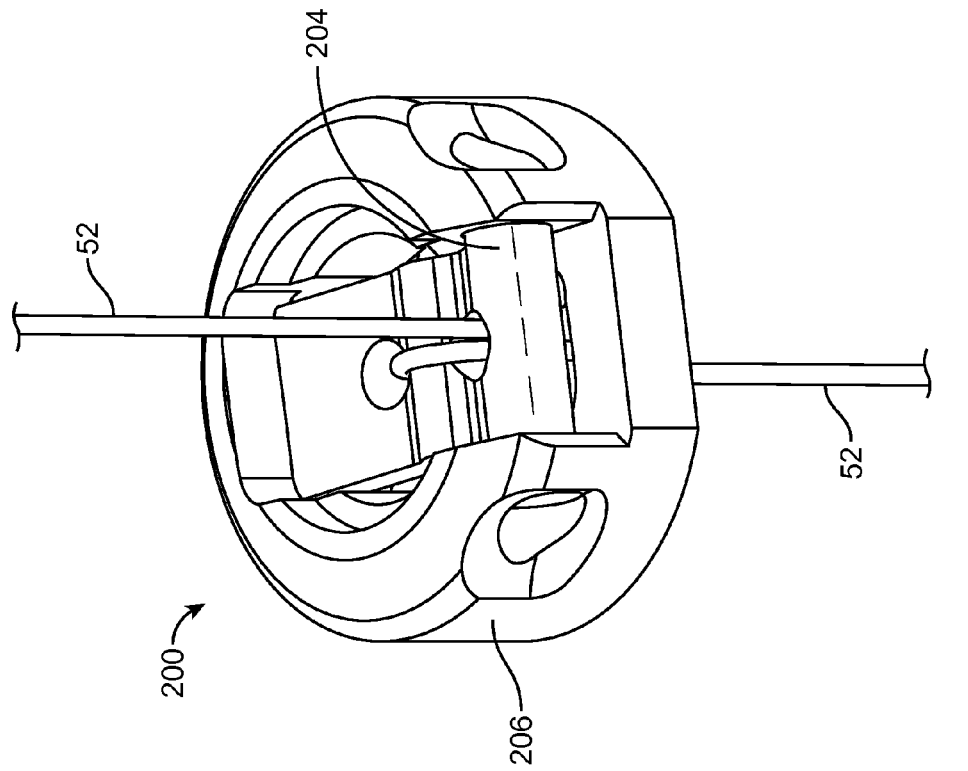
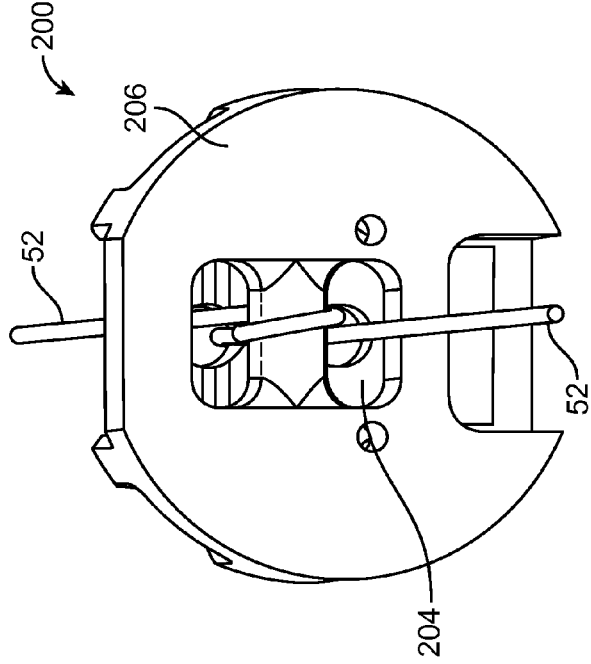
FIG. 15H
FIG. 15G

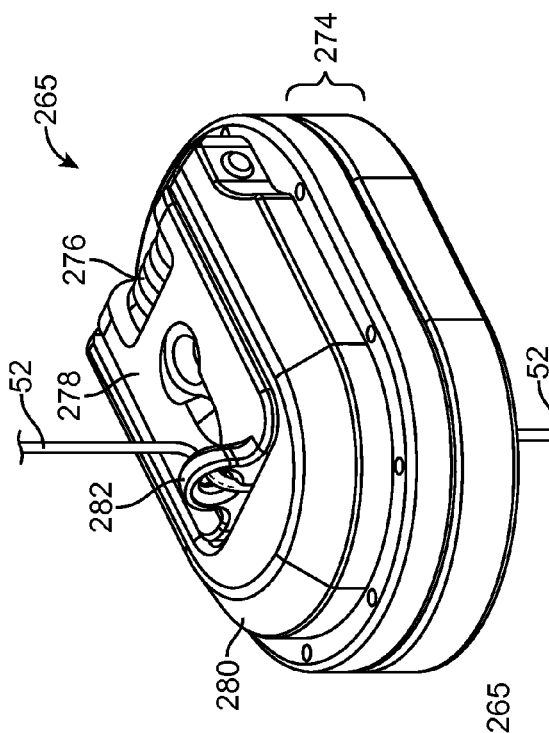
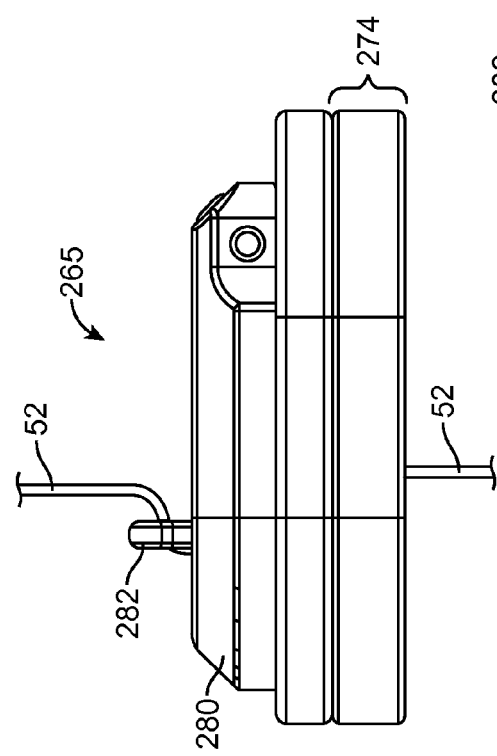
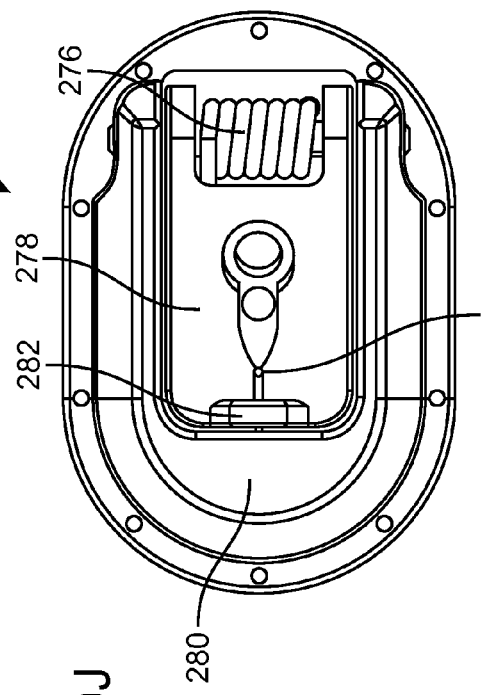
FIG. 19K
FIG. 19L
FIG. 19J

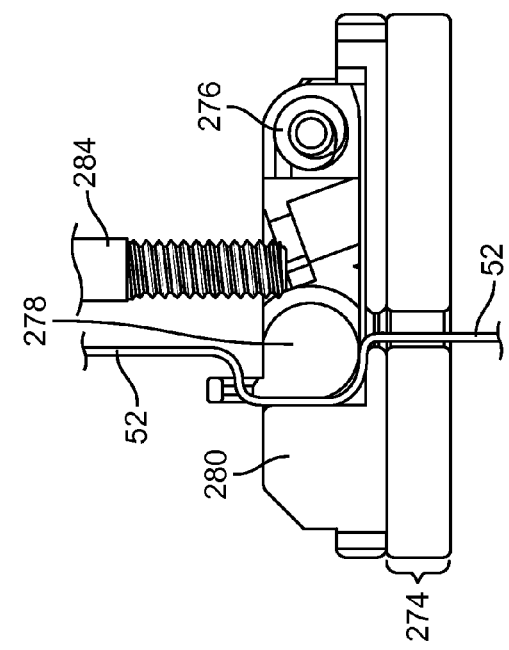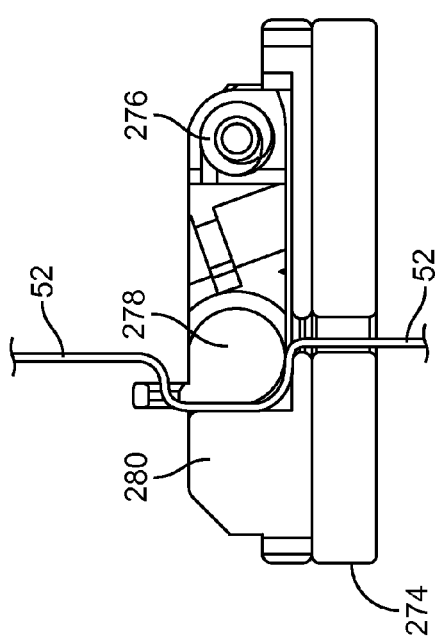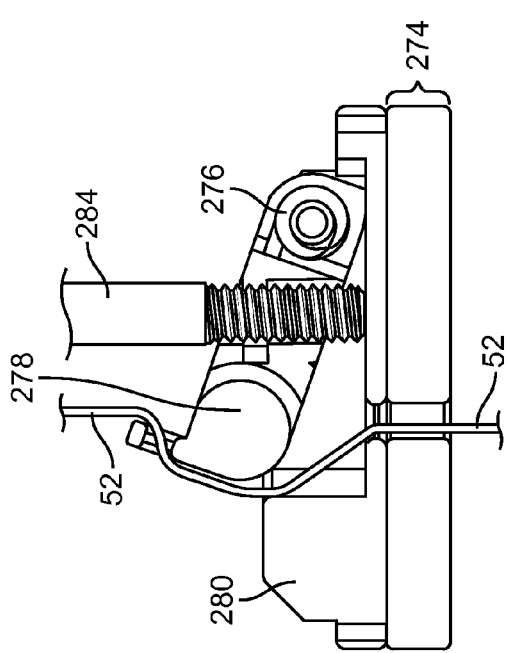

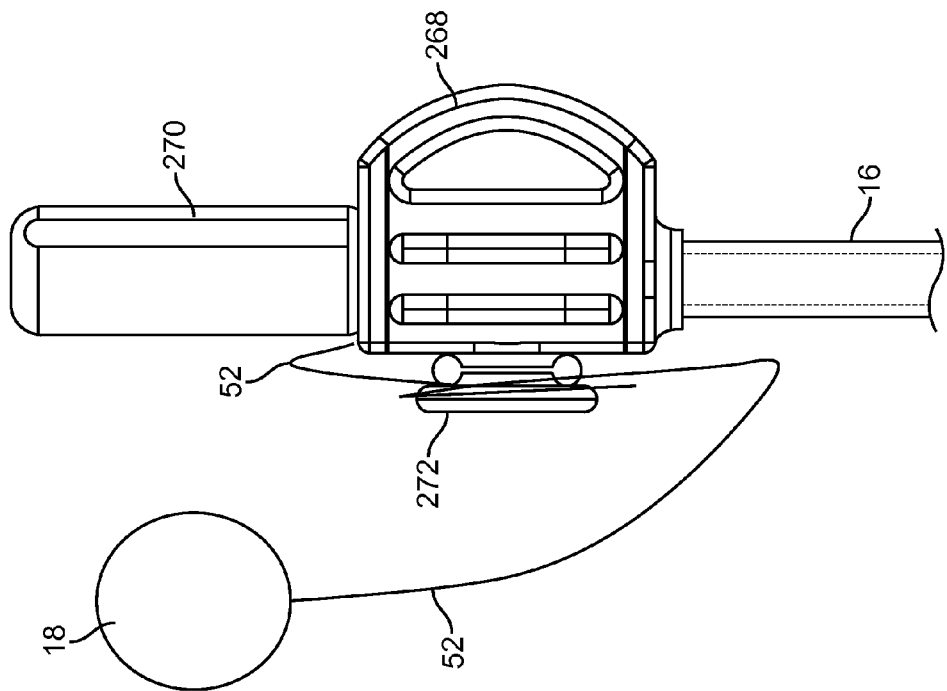
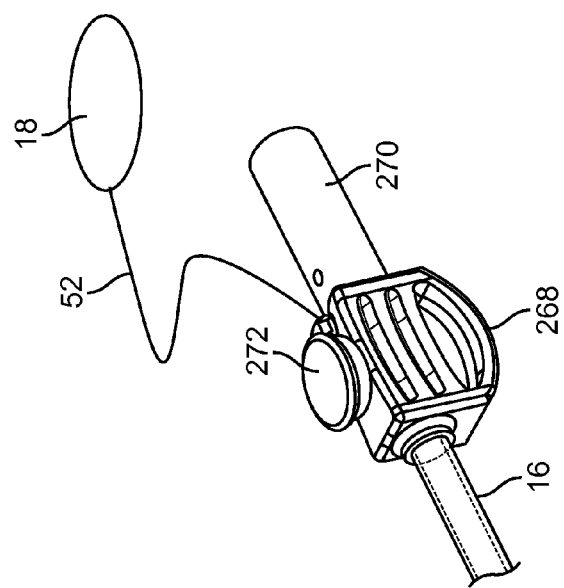
FIG. 19T
FIG. 19S

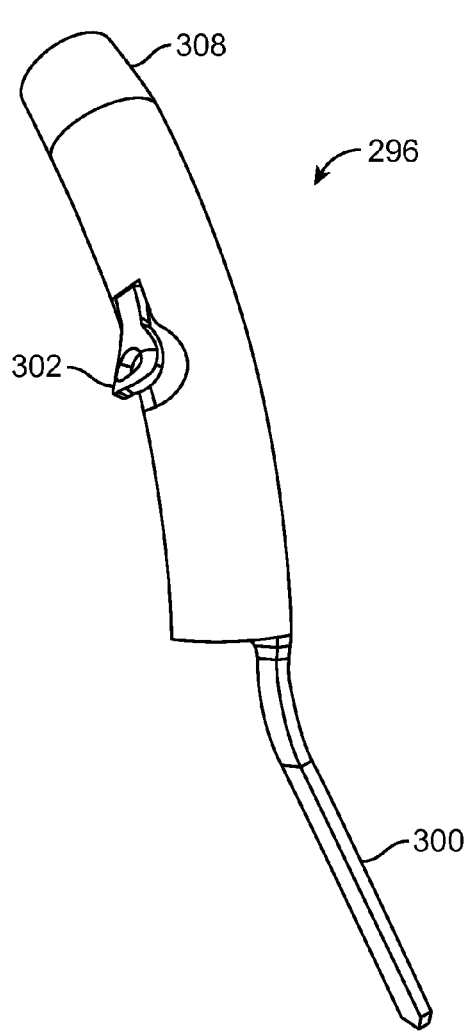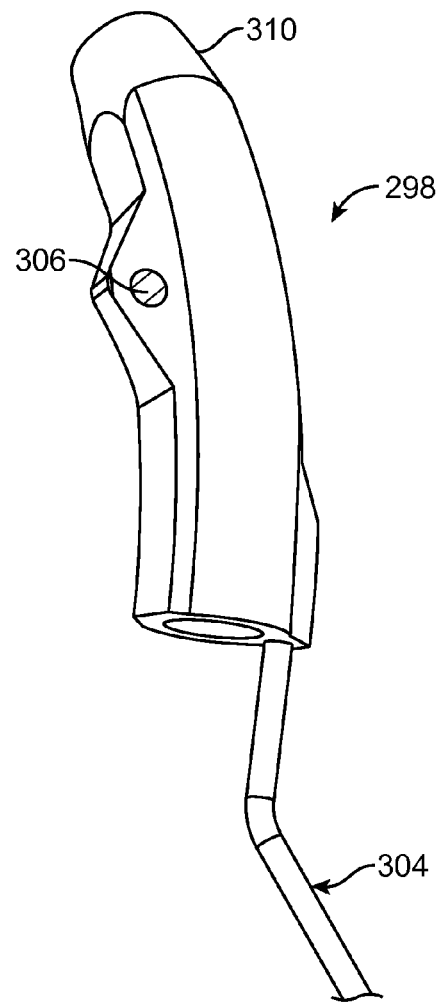
FIG. 19Z-2     FIG. 19Z-3

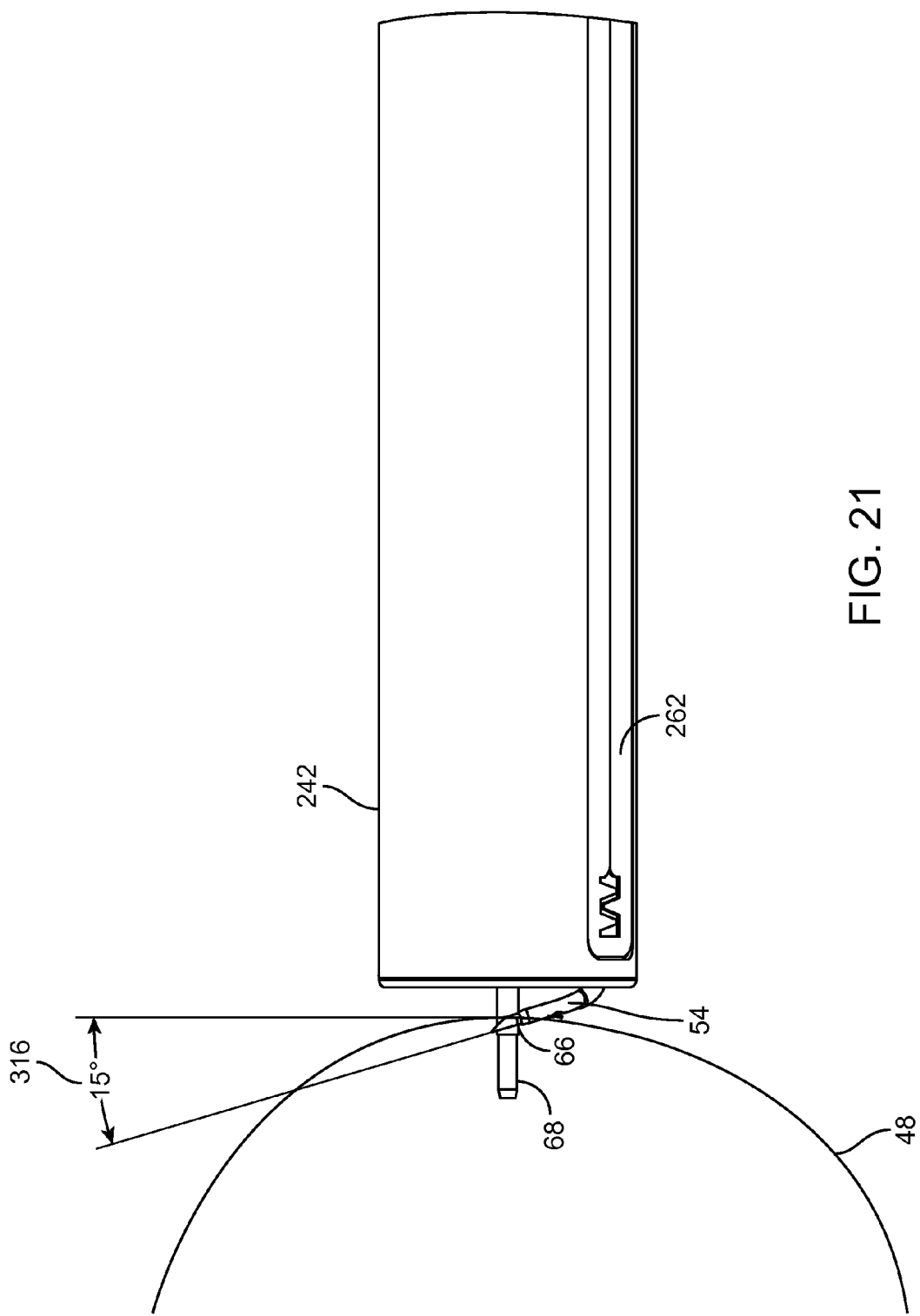

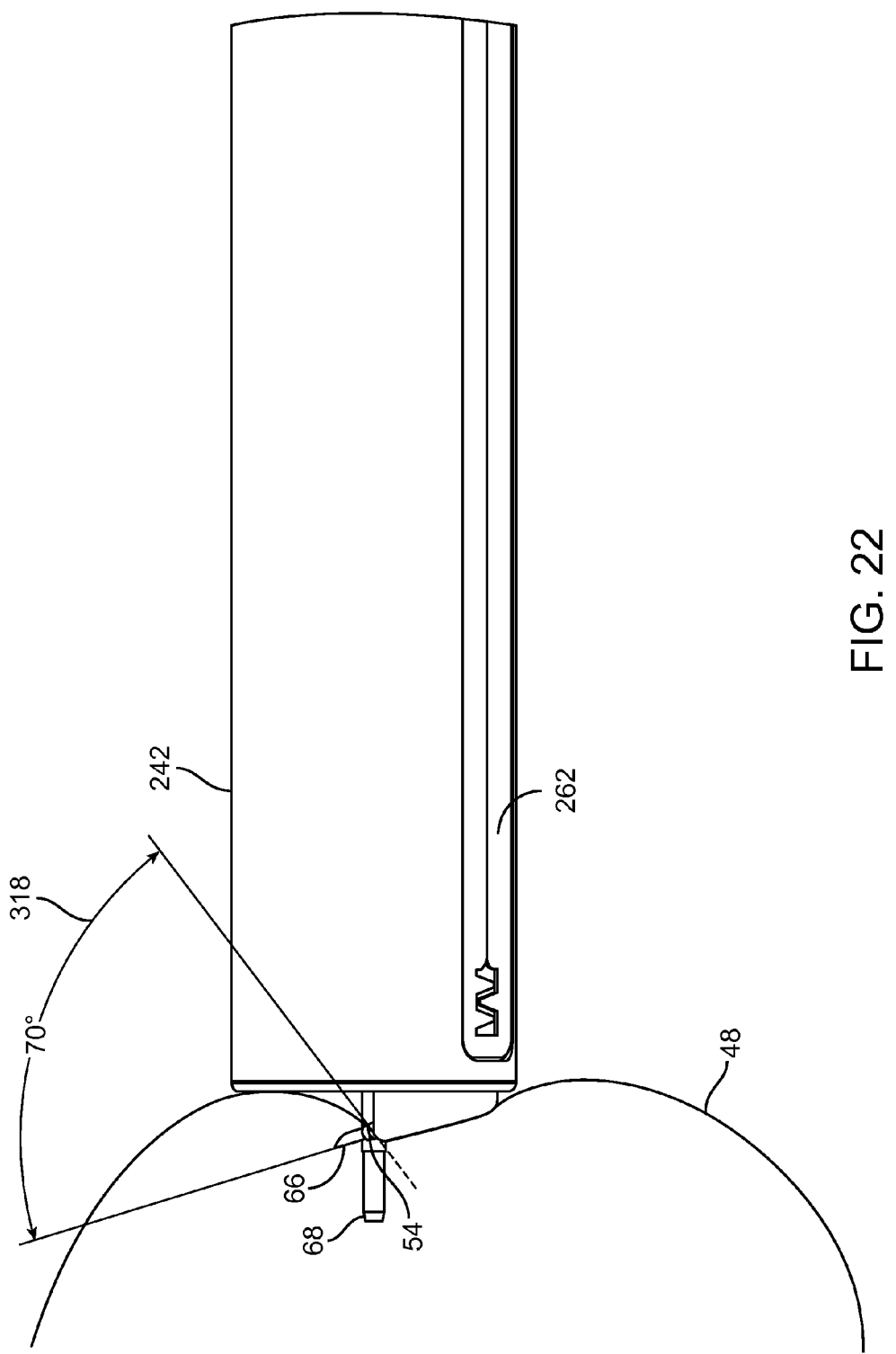

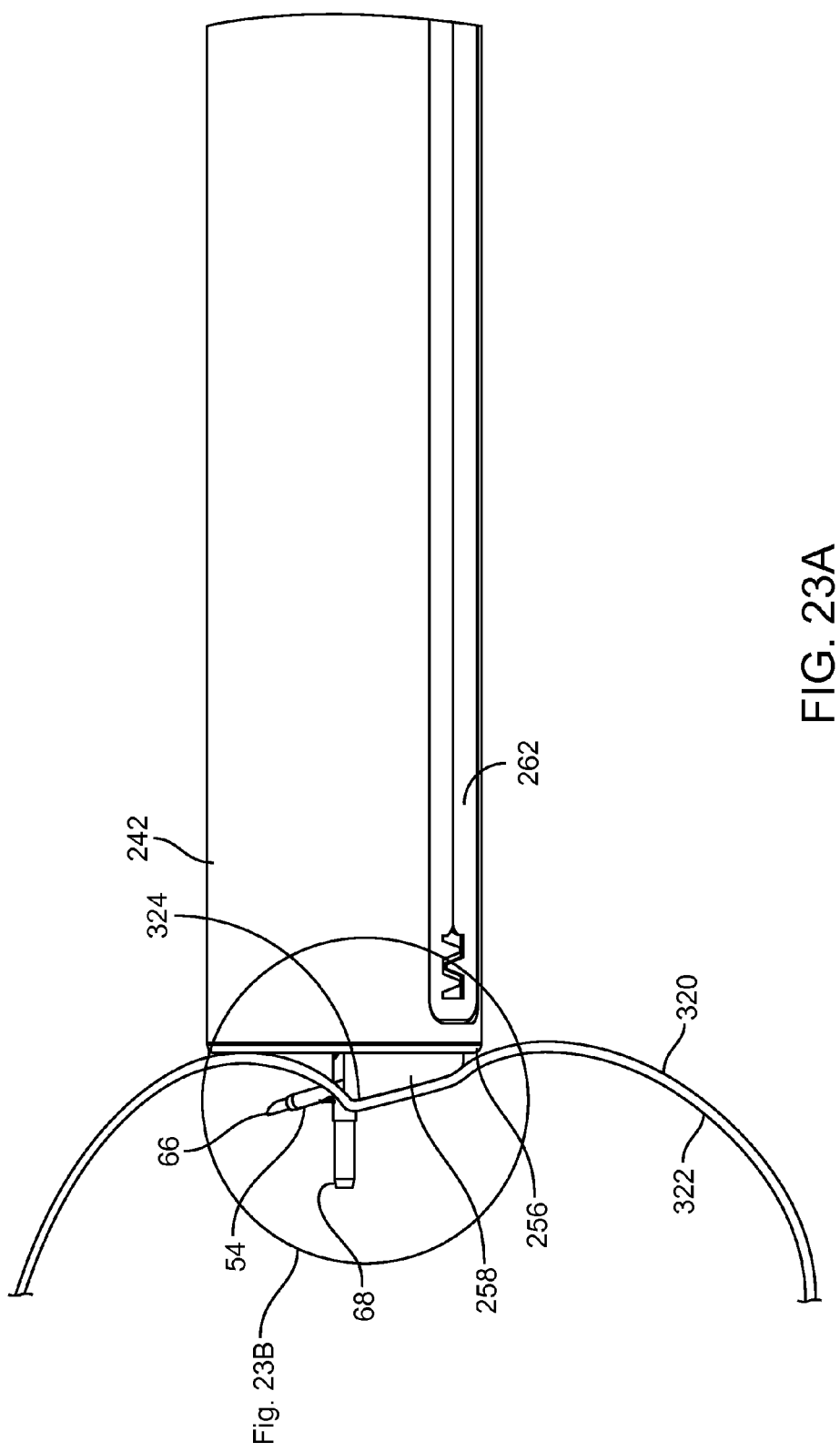

METHOD FOR PROVIDING SURGICAL ACCESS

RELATED APPLICATION DATA

The present application claims the benefit under 35 U.S.C. §119 to U.S. provisional patent application Ser. No. 61,384,659, filed Sep. 20, 2010, and No. 61/484,175, filed May 9, 2011. The foregoing applications are hereby incorporated by reference into the present application in their entirety.

FIELD OF THE INVENTION

This invention is related generally to tissue structure access and wound closure methods, and more particularly to configurations for accessing and closing walls of tissue structures, such as the walls of the cavities of the heart during a trans-apical procedure.

BACKGROUND

Minimally invasive diagnostic and interventional procedure prevalence in US and foreign hospitals continues to increase, as does the demand for certain procedures which involve placement of relatively large devices into targeted locations within tissue structures of criticality. Procedures such as aortic valve replacement conventionally have been addressed with open surgical procedures which are highly invasive. More recently, such procedures have been attempted using natural lumen (i.e., through large blood vessels after an initial surgical transcutaneous or percutaneous access to such vessels) access and delivery systems. Referring to FIG. 1, such systems typically are configured, for example, to reach the aortic valve (12) location inside of the heart (2) from an antegrade approach, which generally requires navigating instrumentation through three of the four chambers of the beating heart (the right atrium 22, left atrium 8, and left ventricle 20, by way of the mitral valve 10 and atrial septum), or from a retrograde approach, which generally requires navigating instrumentation along the aortic arch, from the descending aorta (4) to the ascending aorta (6) and adjacent the aortic valve (12). Each of these approaches presents certain clinical challenges to the surgical team, some of which may be avoided by using what is referred to as a transapical approach, whereby the surgeon creates transcutaneous access to the region around the apex of the heart (26) with a surgical thoracotomy, followed by direct access to the left ventricle (20) using a needle or other device aimed to access the left ventricle (20) around the left ventricular apex (24), which may be followed by one or more dilating instruments to create a temporary access port to the left ventricle. Aspects of a conventional access procedure are illustrated in FIG. 2, wherein a needle device (34) is puncturing the muscular heart wall (30) to gain access to the left ventricle (20) around the location of the left ventricular apex (24). Also shown is a guidewire (36) which may be advanced (38) toward and through the aortic valve (12) to assist with diagnostic and interventional aspects of the procedure. Using these and other instruments such as dilators, this left ventricular access port may be utilized, for example, to replace an aortic valve if bleeding and tissue damage around the access port can be successfully mitigated during such procedure. Subsequent to such a procedure, the instrumentation needs to be removed and the access port closed, usually leaving a prothetic valve or portion thereof behind. The successful closure of a transapical wound on a beating heart of a patient is obviously of high criticality to such a procedure, as is the minimization of loss of blood. Conventional transapical closure techniques typically involve the placement of small sutures to create a purse-string type effect to close the wound as the instrumentation is withdrawn, and it may be very difficult to repeatably create acceptable closures using these techniques without a larger thoracotomy or improved instrumentation. In other words, one of the key challenges to transapical intervention remains transapical wound closure. Indeed, it is believed that transapical access may provide enhanced stability and control during procedures such as aortic valve replacement, due to the fact that the operator may have a relatively direct mechanical connection with the pertinent instrumentation, relative to the connection that he may have using, for example, an antegrade or retrograde vascular approach with more compliant catheter type tools. For this reason, it is even more desirable to successfully address the challenges of transapical access and closure. Further, it would be desirable to have a wound or access closure technology that was applicable not only to transapical access port closure, but also other closure demands pertinent to other surgical interventions of the human body wherein wounds or ports are created, such as in gastrointestinal or gynecological surgery.

SUMMARY OF THE INVENTION

One embodiment is directed to a method for advancing a needle into a tissue structure, comprising: advancing a distal end of a needle insertion assembly, the assembly comprising an insertion member coupled to a tissue interface indentor member and movably coupled to an elongate needle member, against a targeted tissue structure such that a distally protruding shape feature of the tissue interface indentor member engages one or more portions of the targeted tissue structure adjacent a distal tip of the elongate needle member at a position at which the elongate needle member distal tip is configured to be advanced through the insertion member and into the tissue structure, and locally changes an available angle of penetration between such portions and the distal tip of the elongate needle member; and inserting the elongate needle member relative to the insertion member and tissue interface indentor member. The elongate needle member may comprise a shape selected from the group consisting of: a substantially straight shape, an arcuate shape, and a helical shape, and inserting the elongate member relative to the insertion member and tissue member may comprise manually manipulating a proximal end of the elongate needle member. The elongate needle member may comprise a first helical member that defines an inner helix diameter that is substantially constant across the length of the helical member, and manually manipulating may comprise imparting a twisting load to the elongate needle member. The elongate needle member may comprise a first helical member that defines an inner helix diameter that varies across the length of the helical member, and manually manipulating may comprise imparting a twisting load to the elongate needle member. The inner helix diameter may be between about 5 mm and about 60 mm. The inner helix diameter may be between about 10 mm and about 20 mm. The elongate needle member may comprise a first helical member that is comprised of an elongate member formed into the helical shape, the elongate member having an outer diameter. The elongate member may have a cross sectional shape selected from the group consisting of: a circular cross section, an elliptical cross section, a square cross section, and a rectangular cross section. The outer diameter may be between about 0.5 mm and about 3 mm. The helical shape may comprise a number of helical turns advanceable into tissue relative to the insertion member that is between about 1 and about 3. The helical shape may have a substantially constant helix pitch along the length of the helical shape. The helical shape may have a substantially variable helix pitch along the length of the helical shape. The helical shape may have a substantially constant helix pitch along the length of the helical shape. The helical shape may have a substantially variable helix pitch along the length of the helical shape. The helix pitch may be between about 5 mm and about 20 mm. The helix pitch may be between about 7 mm and about 13 mm. The distal end of the first helical member may comprise a sharpened tip configured to easily dive into and cross portions of the tissue structure. The elongate member may comprise a solid cross-sectional construct. The elongate member may comprise a tubular construct having an inner diameter and as well as the outer diameter. The elongate member may comprise a material selected from the group consisting of: stainless steel, nitinol alloy, titanium, cobalt chrome, and polymer composite. The elongate member may comprise a material selected from the group consisting of: stainless steel, nitinol alloy, titanium, cobalt chrome, and polymer composite. The insertion member may comprise a substantially rigid construct, and manually manipulating may comprise imparting a twisting load to the insertion member. The insertion member may comprise a flexible construct, and manually manipulating may comprise imparting a twisting load to the insertion member. Advancing the distal end of the needle insertion assembly may cause the distally protruding shape feature to concentrate interfacial stresses upon the tissue structure such that the portions of the tissue structure adjacent the distal tip of the elongate needle member become locally strained about the distally protruding shape feature as the distally protruding shape feature is advanced into contact with the adjacent tissue structure portions. At least one surface of the distally protruding shape features may comprise a surface configuration selected from the group consisting of: a portion of a spherical surface, a linear ramp surface, an arcuate ramp surface, a multi-stepped ramp surface, and a single-stepped ramp surface. The surface configuration may be helically wrapped about a longitudinal axis of the helical member. At least one surface of the distally protruding shape features may comprise a substantially perpendicular leading surface. The distally protruding shape feature may have a cross sectional profile comprising a cross sectional shape selected from the list consisting of: a rectangle, a square, a half circle, a triangle, a polygon, a rounded rectangular shape, a rounded square shape, and a multi-arcuate shape. The distally protruding shape feature and distal tip of the elongate needle member may be operatively coupled such that the distal tip is movably coupled through a portion of the distally protruding shape feature. The distal tip substantially may bisect the portion of the distally protruding shape feature. The distally protruding shape feature and distal tip of the elongate needle member may be operatively coupled such that the distal tip is movably coupled adjacent a portion of the distally protruding shape feature. The distal tip of the elongate needle member may be configured to follow a path substantially parallel to the surface configuration of the distally protruding shape feature. The distally protruding shape feature may comprise one or more tissue traction features configured to prevent relative motion between the distally protruding shape feature and portions of the tissue structure with which it may be directly interfaced. At least one of the one of the one or more tissue traction features may comprise a barb. The method may further comprise preventing movement of the tissue interface indentor member relative to the targeted tissue structure portion against which it is interfaced once a desired interfacing has been achieved by advancing the needle insertion assembly against the targeted tissue structure. Preventing movement may comprise preventing rotation of the tissue interface indentor member relative to the targeted tissue structure portion. Preventing movement may comprise preventing translation of the tissue interface indentor member relative to the targeted tissue structure portion. Advancing the distal end of the needle insertion assembly may comprise manipulating the needle insertion assembly with one hand of an operator, and inserting the elongate needle member may comprise manipulating the elongate needle member with the other hand of the operator, such that the needle may be controllably inserted by a single operator.

BRIEF DESCRIPTION OF THE DRAWINGS

FIGS. 3A to 3K illustrate various aspects of an experimental configuration.

FIGS. 15A-15J illustrate various aspects of a compound helical closure configuration featuring a single helical member and a one-way tension retainer.

FIG. 21 illustrates various aspects of one embodiment of a helical closure configuration having a relatively shallow angle of approach.

FIG. 22 illustrates various aspects of one embodiment of a helical closure configuration having a relatively large effective angle of approach.

FIGS. 23A and 23B illustrate aspects of one embodiment of a helical closure configuration having a relatively large effective angle of approach and features to decrease slipping of nearby tissue structures.

DETAILED DESCRIPTION

Figure 3A:
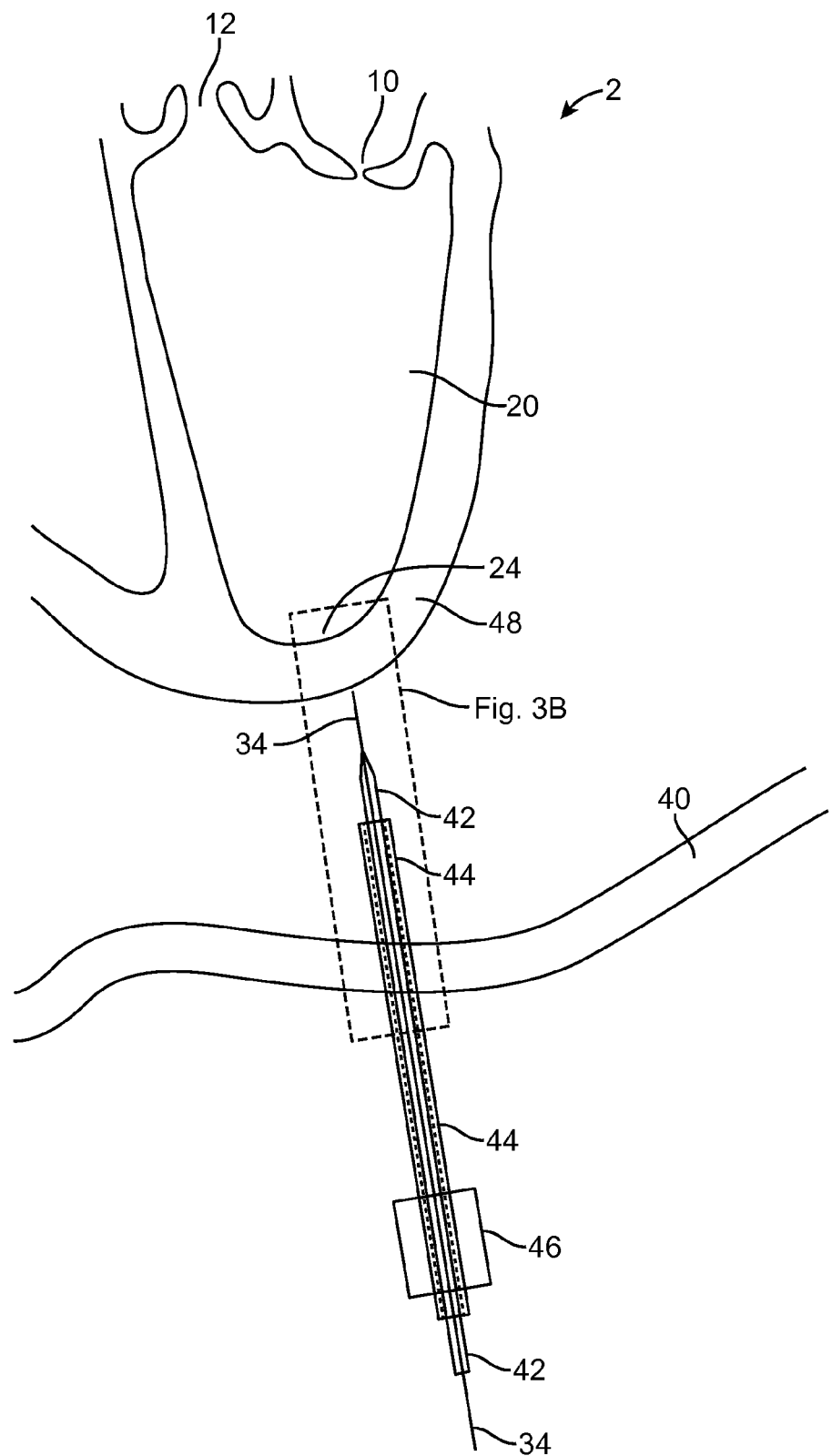
Figure 3B:
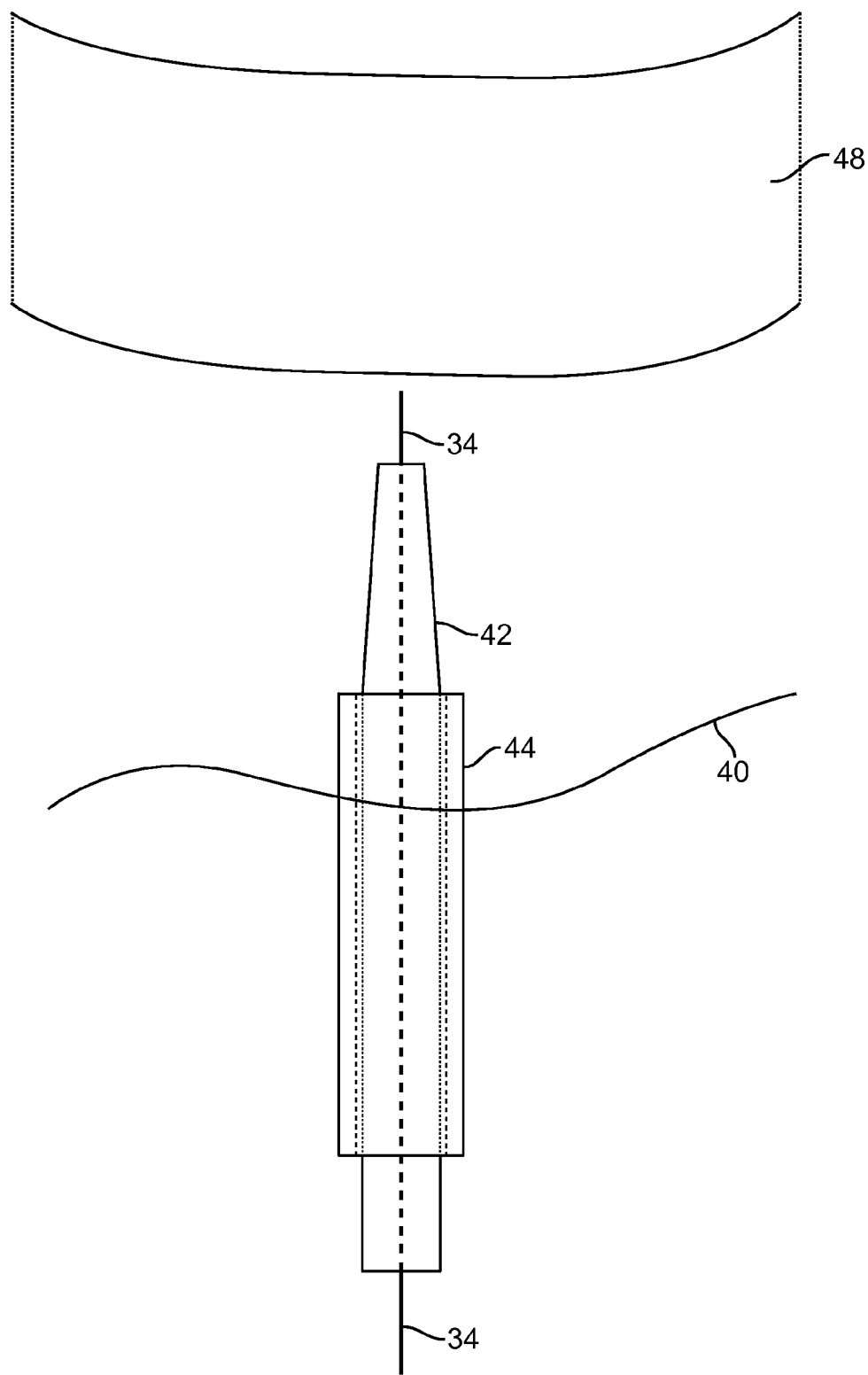
Figure 3C:
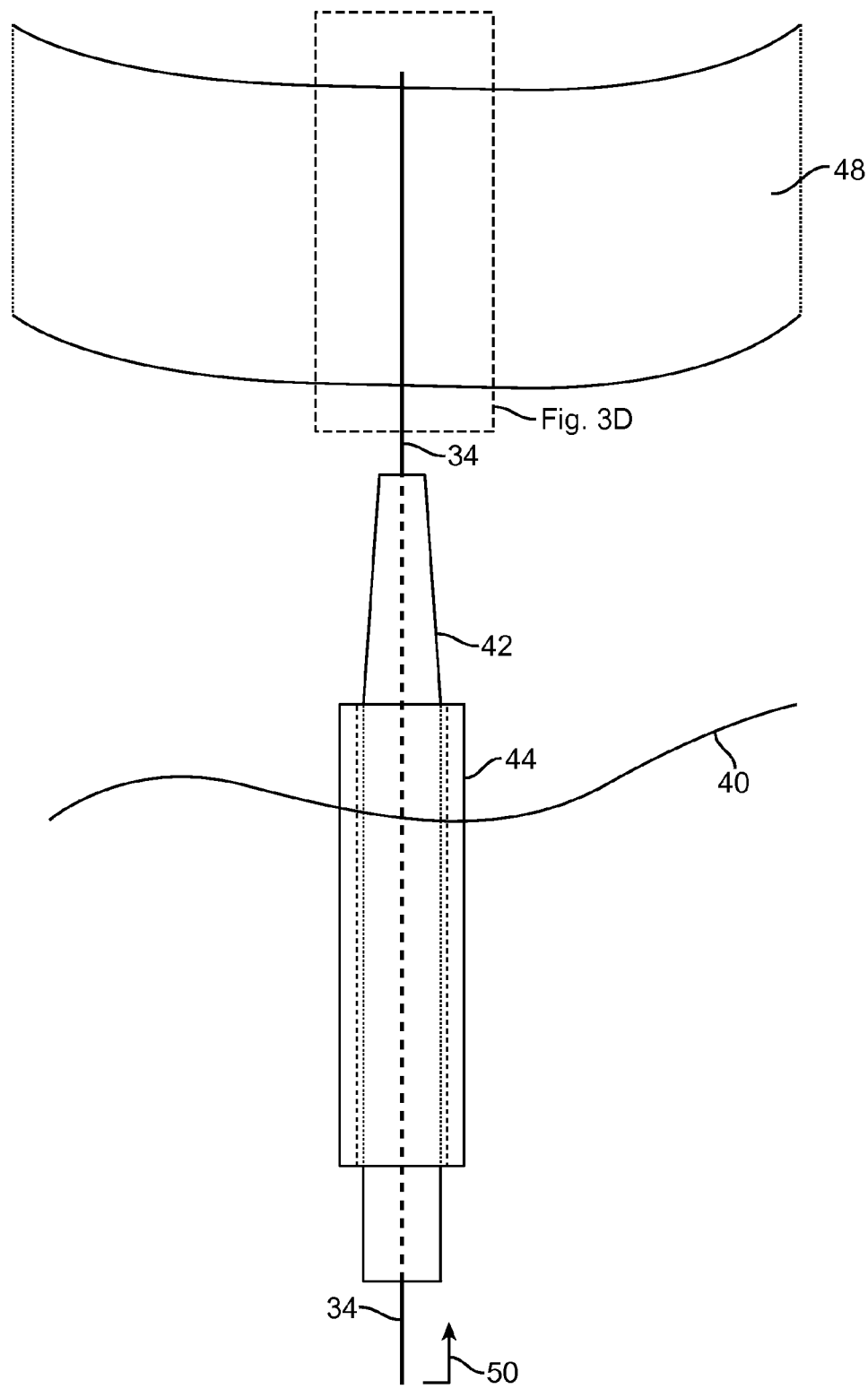
Figure 3D:
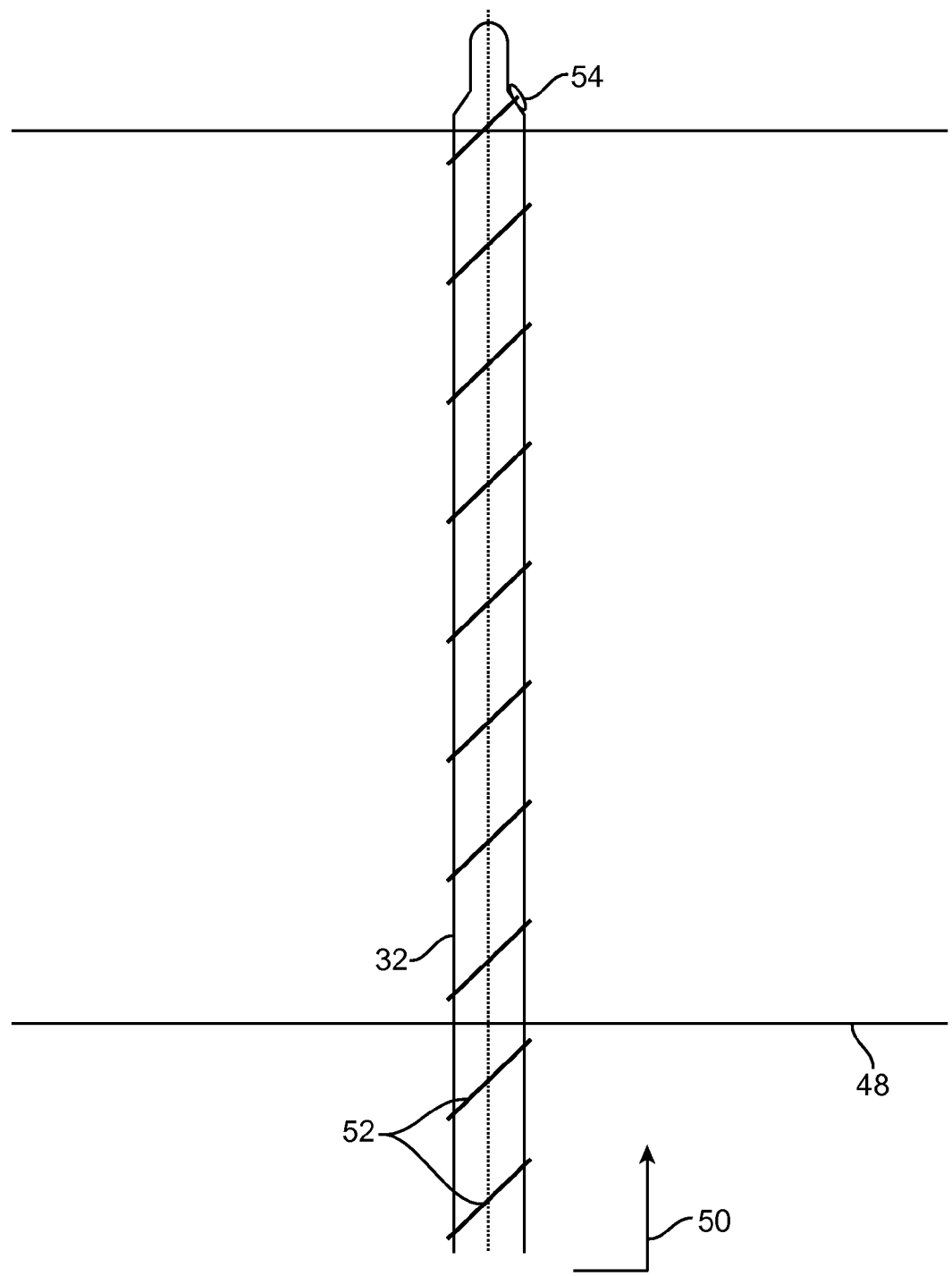
Figure 3E:
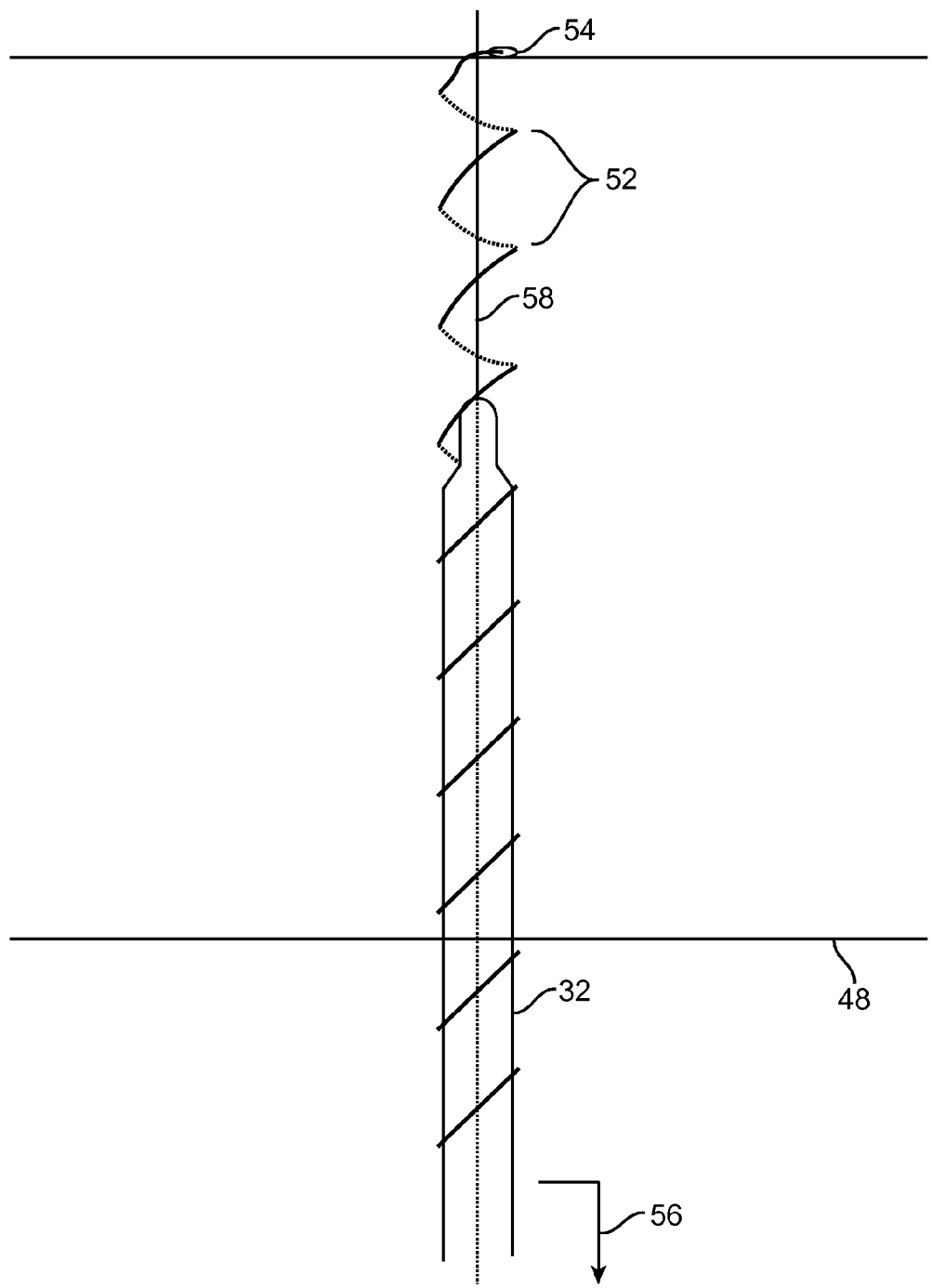
Figure 3F:
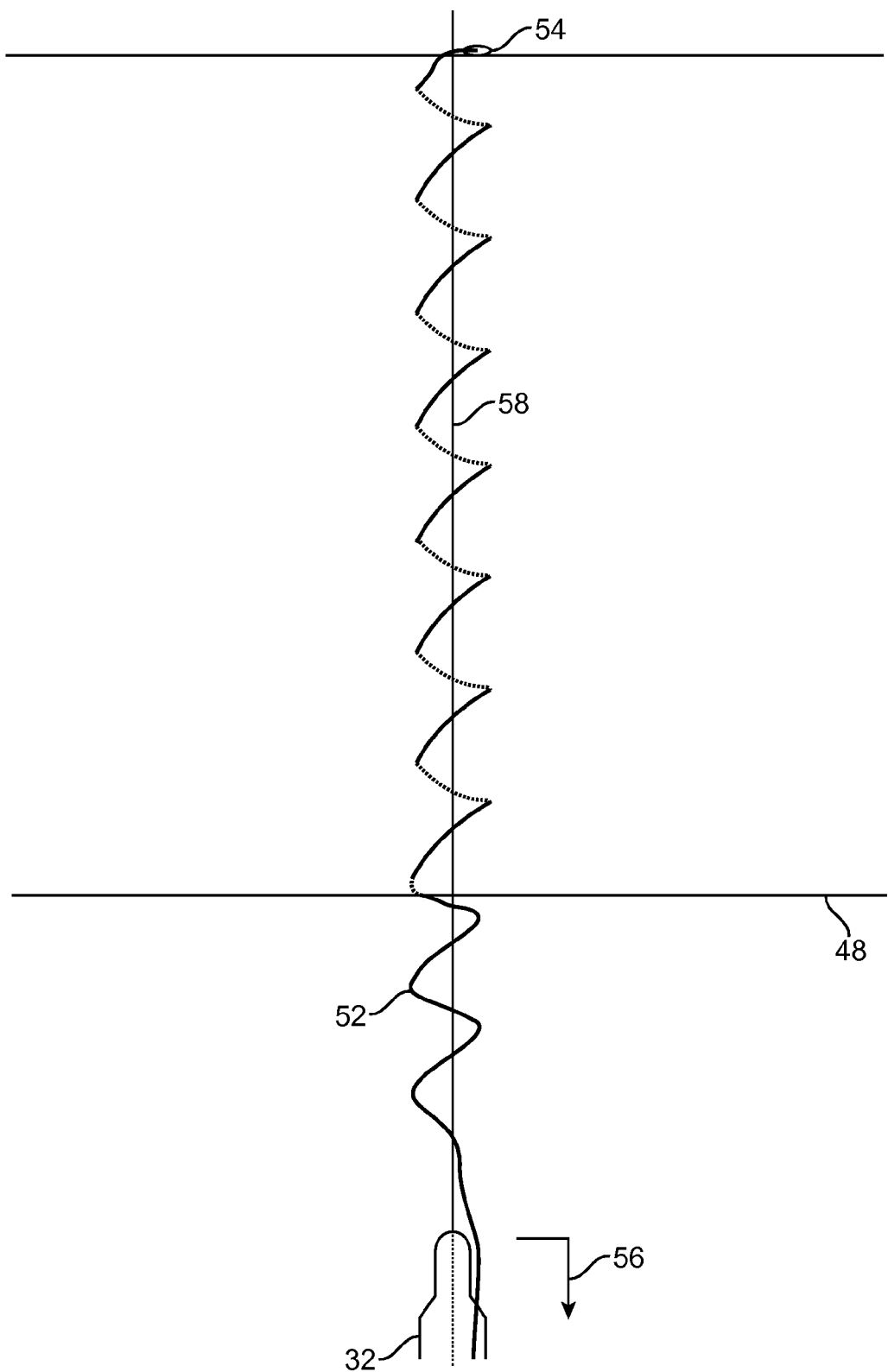
Figure 3G:
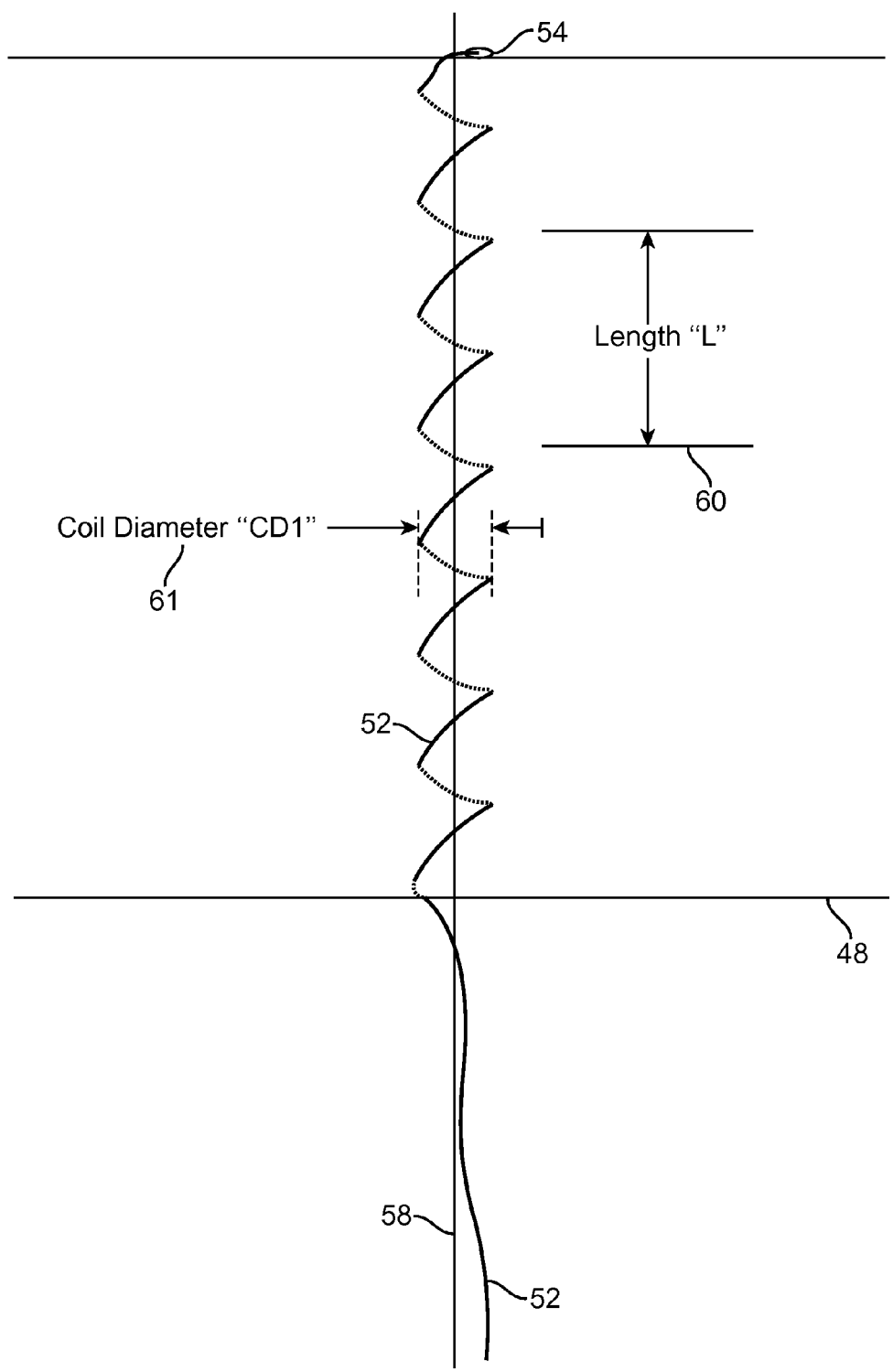
Figure 3H:
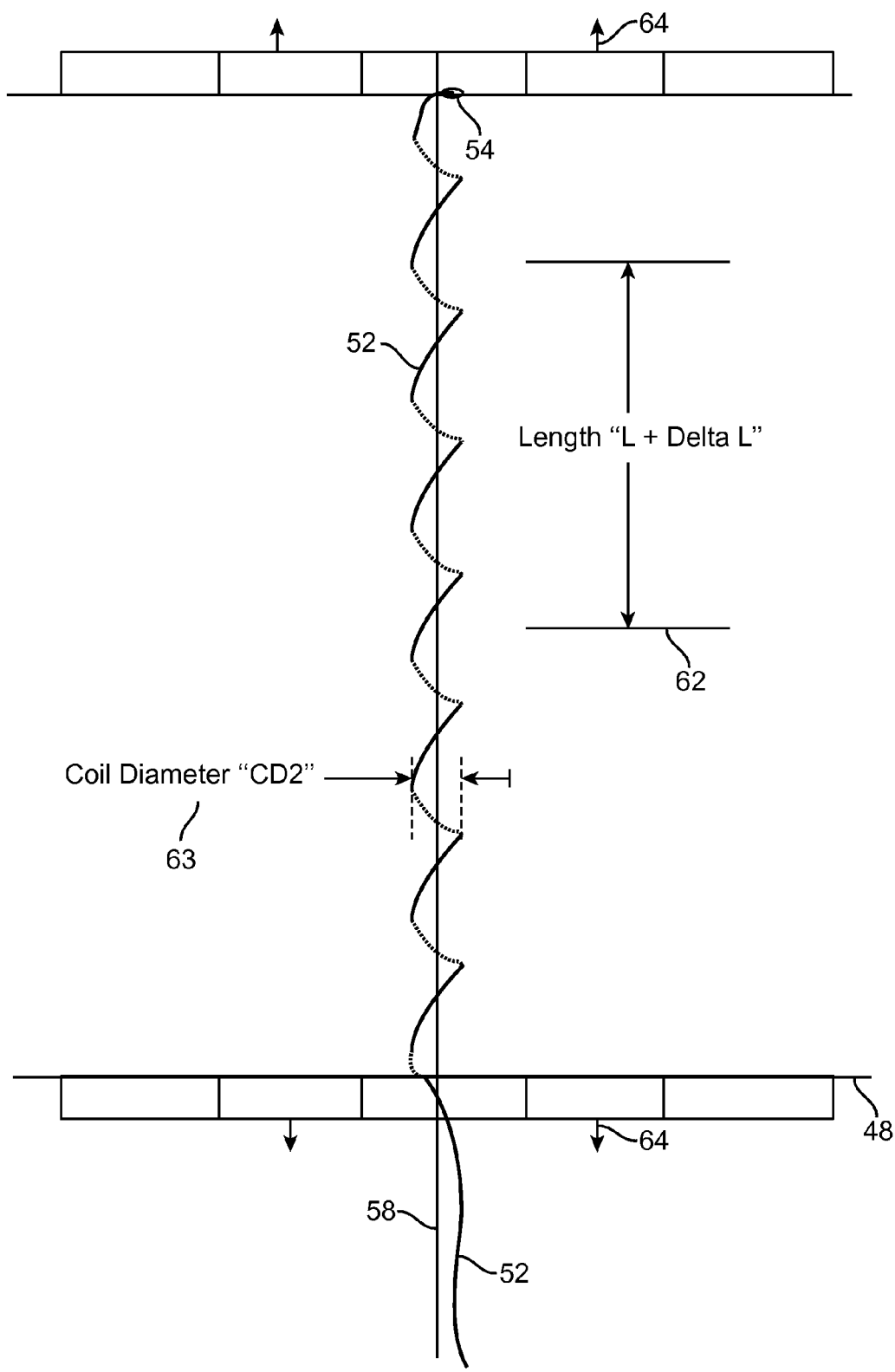

Referring to FIGS. 3A through 3H, various aspects of embodiments associated with a transapical access and closure system are depicted, including certain experimental and illustrative configurations. As shown in FIG. 3A, a transapical access assembly is depicted comprising a needle (34) placed through an elongate dilator member (42), which is slidably positioned through a working lumen of an introducer sheath (44) which may be manipulated using a proximal handle or hub (46). The assembly has been placed through a thoracotomy created in the chest wall (40) of a patient, and directed toward a location on the heart (2) that is determined to be close to the apex (24) of the left ventricle (20) using information derived from sources such as anatomic markers, preoperative diagnostic imaging information, such as radiography and/or fluoroscopy, and intraoperative imaging information derived, for example, from radiography, endoscopy, and/or fluoroscopic imaging of portions of the access assembly which may be radioopaque (or radioopaque markers which may be fastened to portions of the assembly in one embodiment). Referring to FIG. 3B, a close-up view of certain structures depicted in FIG. 3A is shown. FIG. 3C illustrates that with a transventrical, or more specifically, transapical, approach, the elongate guiding member (34), such as a needle (which may be subsequently utilized to advance a guidewire), may be the first structure advanced (50) into or across the heart wall (48). FIG. 3D illustrates a close up detail view of one embodiment wherein an elongate guiding member comprises a straight needle (32) that has been advanced (50) across the heart wall (48) with a suture (52) helically wrapped around it and terminating near the distal end of the straight needle (32) with an anchor element (54). In experiments, we have found that certain variations of such a configuration may be utilized to advance a suture (52) into a position partially or entirely across a tissue wall (48) with the spiral configuration retained on the way in (indeed, tension, friction, and pressure applied to the helically wound suture 52 tends to keep it in its helical configuration during entry; additional proximal tension on the suture 52 may also be utilized to assist in retention of the spiral configuration). Further, we have demonstrated that by withdrawing the needle (32), the anchor element (54) retains the distal suture (52) position and the suture (52) is unfurled and left behind in a substantially helical or "coiled" configuration. FIGS. 3E and 3F, for example, illustrate that upon withdrawal (56) of the straight needle (32) and release of suture tension which may be keeping the suture helically in place relative to the guiding member (34), the anchor element (54) configured to prevent withdrawal of the distal end of the suture (52) and the unfurling action of the suture leave a coiled or helical suture (52) configuration in place. We have also found that the retained helical suture (52) pattern accommodates significant longitudinal expansion (i.e., in the range of 200% to 300% strain) without applying significant slicing type loads to nearby tissue structures, as demonstrated in FIGS. 3G and 3H, wherein the helical suture (52) pattern is substantially retained as the tissue wall (48) or pertinent portion thereof is strained from an initial length of "L" to a length of "L+deltaL". Referring to FIG. 3G, with the suture in its deployed coiled configuration with adjacent tissues substantially unloaded, the coil diameter of the helical suture configuration is may be represented by "CD1" (61). Referring to FIG. 3H, with elongation (64, 62) of the nearby tissue structure (48), the localized length storage provided by the coiled configuration provides extra length fairly uniformly across the suture, which prevents cutting loads against the nearby tissue, and which results in a smaller coil diameter (63) as further length is extracted out of the coiled configuration, ultimately leading to a substantially uncoiled, or completely uncoiled, linear suture configuration without additional localized suture length storage. This notion of localized length storage may be utilized quite effectively in surgical procedures wherein it may be desirable to incrementally and efficiently close ports, wounds, and the like without laceration of nearby tissue, which may be associated with more conventional suture-tightening configurations. In other words, many conventional "purse-string" type suture configurations lead to simultaneous motion and loading at the interface between suture material and tissue, which can lead to undesirable cutting of the tissue. With adequate localized length storage, incremental tightening may be conducted with significantly reduced risk of tissue cutting due to the fact that the coiling facilitates tightening with reduced interfacial loading until the very end of the tightening range, at which point very little motion is required to complete the requisite tightening paradigm (depending upon the pertinent tissue structures, desired loading, etc). Referring to FIGS. 3I-3K, this helical configuration for localized length storage may be utilized not only with straight needle members (32), as in FIG. 3I, but also with curved needle members (28), as in FIG. 3J, and helical needle members (66), as in FIG. 3K.

Figure 4A:
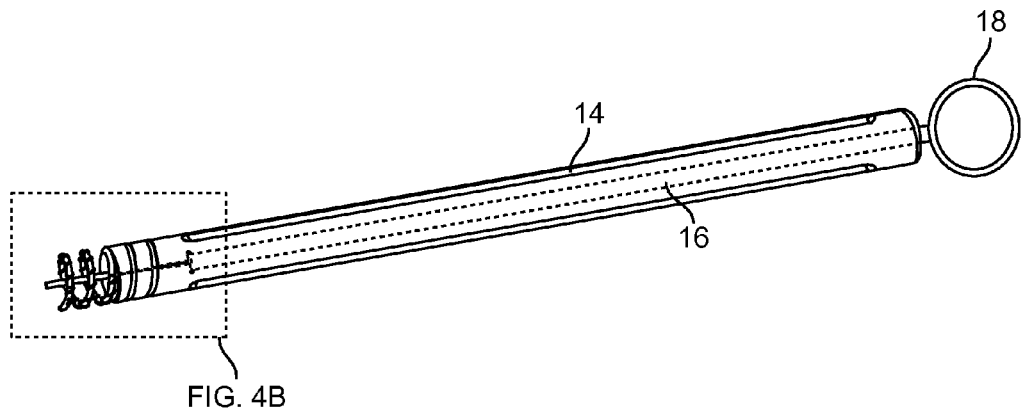
FIGS. 4A to 4P illustrate various aspects of a compound helical closure configuration featuring a single helical member.

FIGS. 4A-4P depict aspects of one embodiment of a compound helical closure configuration utilizing a suture (52) helically wound ("first" or "suture helix") around a helical needle member (66-"second" or "needle helix"), as previously shown in FIG. 3K. Further embodiments are disclosed in FIGS. 5A-9B, while FIGS. 10A-11J depict images of some of our confirming experiments, and FIGS. 12A-12C depict aspects of methods for utilizing related configurations in surgical procedure embodiments.

Figure 4B:
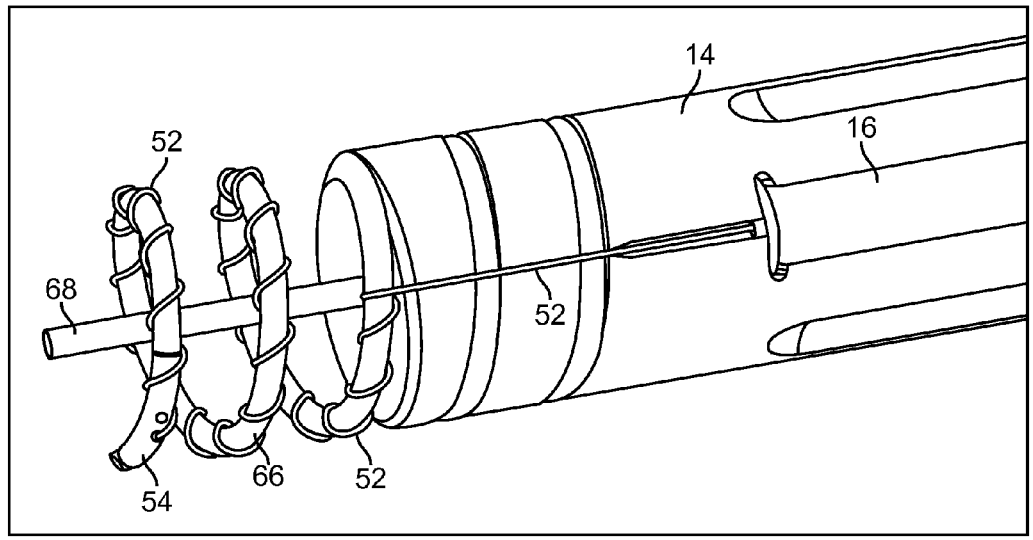

Referring to FIG. 4A, a deployment, or delivery, member (14) is shown with a compound helical configuration at its distal end, comprising a suture, or suture member, (52) helically wound around a helical member (66). A tensioning element, such as an elongate tubular member defining a lumen therethrough, (16) is proximally coupled to the suture (52), and a manual tensioning interface (18) is coupled to the proximal aspect of the tensioning element (16) to allow an operator to apply tension to the suture (52) from a proximal location. FIG. 4B shows a close-up view of the distal portion of the deployment configuration of FIG. 4A, with the compound helical suture (52) configuration, distal anchoring element (54), and elongate tracking member, or "helical member guiding member", (68) more visible. The elongate tracking member (68) may be utilized in an "over the wire" or "over the needle" configuration relative to an associated needle or guidewire, and particularly in the scenario of a guidewire (which is generally substantially more flexible than a needle), is configured to maintain the tracking of the helical needle member (66) during advancement (i.e., to prevent "walking around" of the helical needle, as may be possible with only a flexible guidewire for tracking) The distal end of the helical member guiding member (68) may be substantially straight, as depicted, and define a longitudinal axis that is substantially coincident with that of the helical member. The helical member guiding member may be coupled to the delivery member, which is coupled the helical member, as shown; the helical member guiding member may also be immediately coupled to the helical member.

Figure 4C:
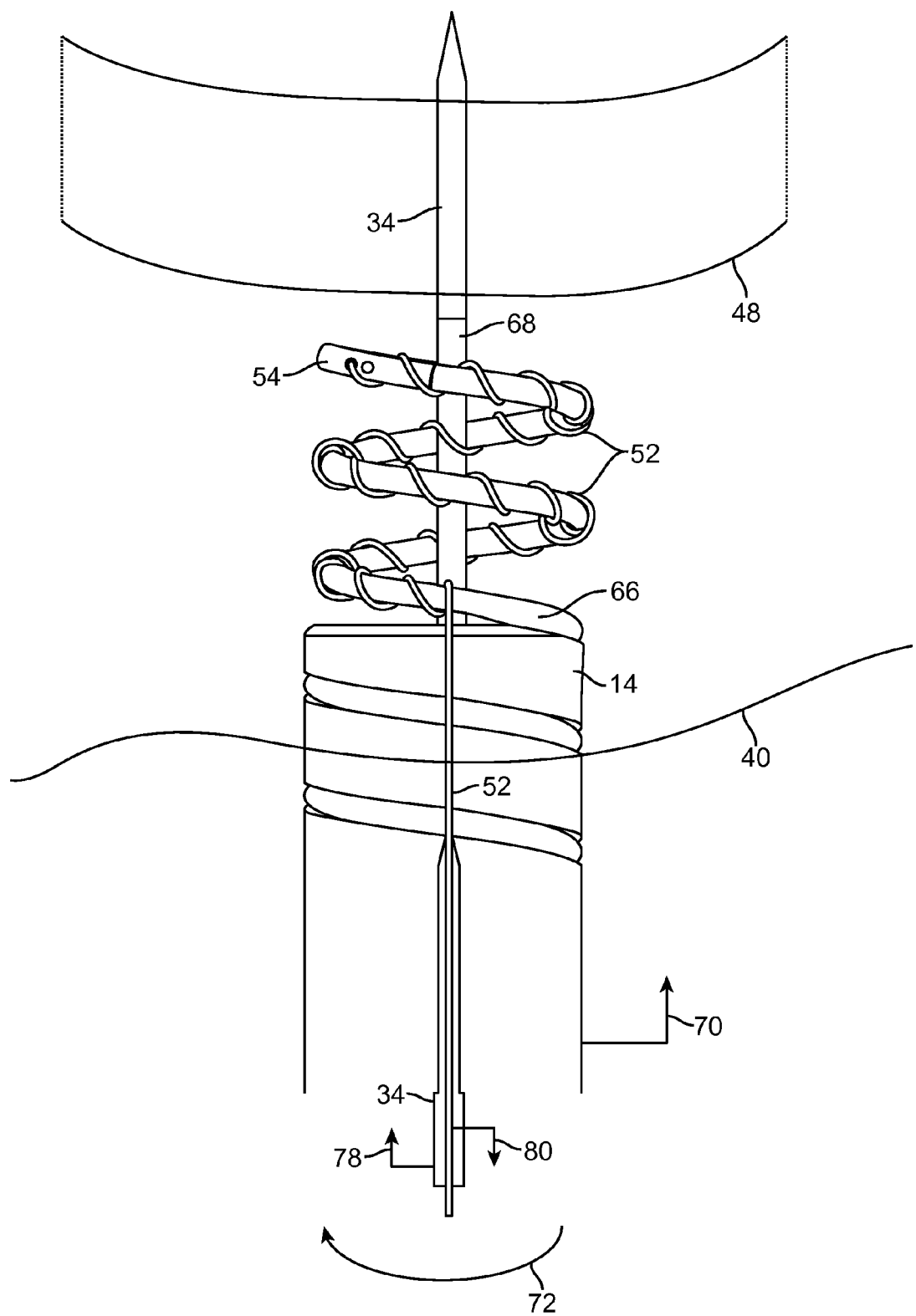

Referring to FIG. 4C, a configuration such as that depicted in FIGS. 4A and 4B may be utilized to deploy a compound helical suture across a tissue structure wall (48) or portion thereof. In the depicted embodiment, an elongate guiding member (34) such as a needle or guidewire has already been advanced across the wall (48), but in other embodiments, this need not be the case (i.e., the tracking member 68 itself may serve as a guiding member to keep the assembly on track). Indeed, one of the key advantages of the depicted configuration is that it may be deployed to pre-install a helical closure suture configuration that may be generally inspected and examined before the installation or insertion of other diagnostic and/or interventional tools. In other words, before taking the risk of installing and utilizing generally larger tools, which require a larger wound, a closure paradigm may be pre-installed and inspected beforehand, thus taking some of the risk out of the procedure.

Figure 4D:
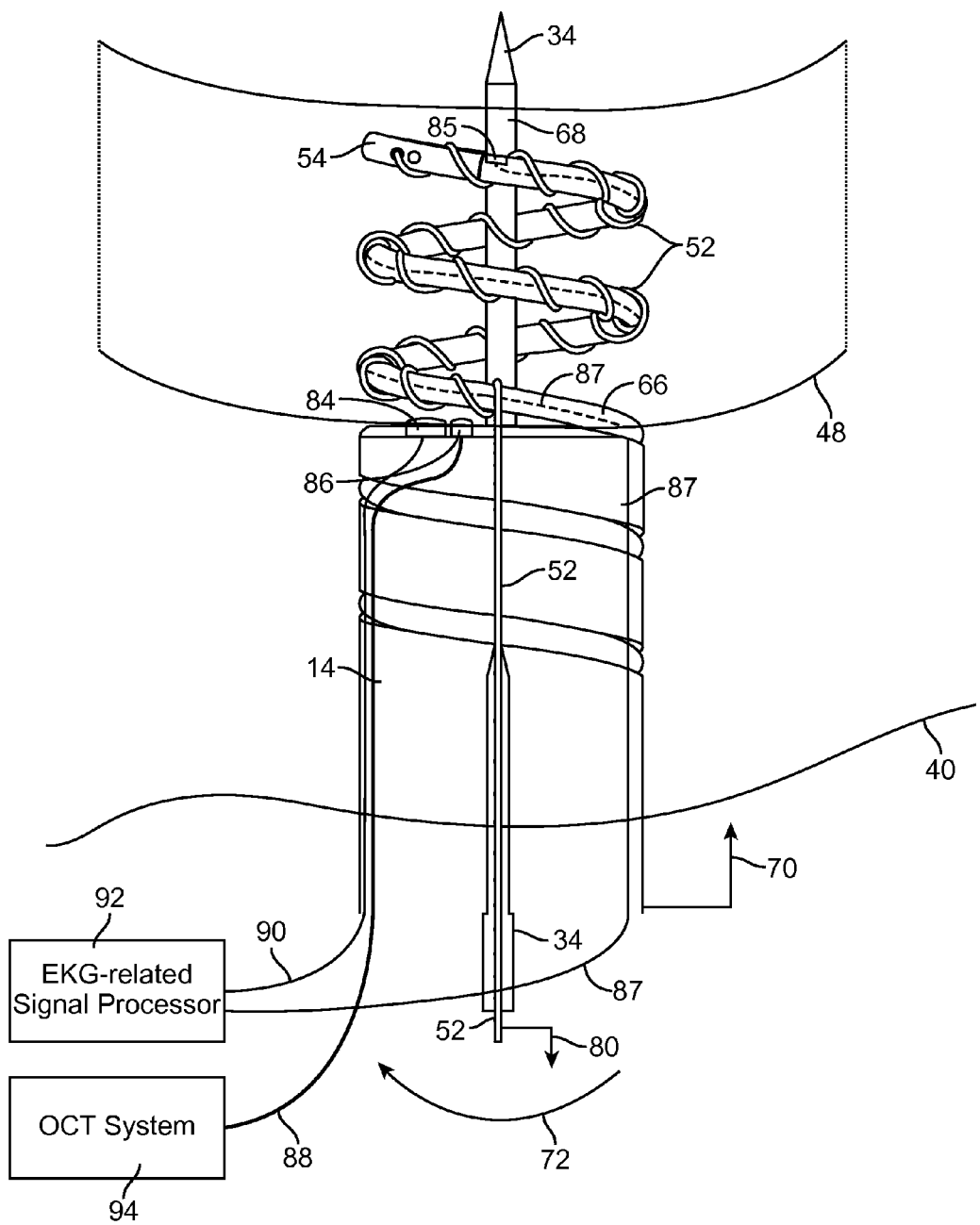

Referring again to FIG. 4C, in the depicted embodiment, an elongate guiding member (34) has been installed, and the elongate tracking member (68) is being guided in an "over the wire" form as the deployment member (14) is advanced (70) and rotated (72). Referring to FIG. 4D, with further advancement (70) and rotation (72) to rotationally advance the helical member (66), the suture (52) compound helical portion is advanced across a portion of the tissue wall (48) and the anchoring element (54) is positioned within the tissue wall (54). In one embodiment, the assembly may be loaded in both compression and rotation (i.e., both pushed and torque simultaneously); in another embodiment, only a rotational load is used to advance the assembly. Preferably the distal ends of the needle members are sharpened to easily dive into a cross portions of the subject tissue structure, and the anchor members are configured to have at least one shape feature that is configured to slide in easier than it is to slide out (i.e., it preferably will resist retraction, either through a barbed type of feature, or by changing position and/or orientation relative to the surrounding tissue, as with a toggle bolt type of configuration, as described in further detail below). Preferably a reversal in needle member direction relative to the surrounding tissue applies a reverse load on the anchor members which causes them to decouple from their insertion positions upon the helical needle members. In one embodiment, the needle member comprises an anchor coupling portion that is locally decreased in outer diameter to accommodate slidable coupling through a lumen defined through an anchor, such that the outer diameter of the anchor during advancement/delivery may be sized substantially similar to the outer diameter of the helical needle In another embodiment, the anchoring element may be advanced completely across the tissue wall (48), as illustrated, for example, in FIGS. 8A and 8B. The embodiment of FIG. 4D also features several sensors configured to facilitate an operator's awareness of the positioning of the helical member (66) relative to the subject tissue. In the depicted embodiment, a first RF sensor (85) is coupled to the distal aspect of the helical needle member (66) to capture electrocardiogram ("EKG") related signals which are detectable at the outer surface of the heart (the first RF sensor 85 may be operatively coupled via a lead 87 disposed through the needle 66 and through the proximal deployment member 14 to an EKG-related signal processing system 92, such as those available from the Prucka division of General Electric, Co.). With such a configuration, as the helical needle (66) first comes into contact with the outside of the heart, such contact may be detected. The configuration in FIG. 4D also features a similar second RF sensor (86) similarly coupled to the EKG system (92) via a lead (90) and positioned at the distal aspect of the deployment member (14) such that it will contact the outside of the heart or other tissue structure (48) when the helical member (66) is fully advanced (70, 72). The depicted embodiment also features an optical coherence tomography ("OCT") system (94) configured to use interferometry computation and an optical fiber (88) terminated at a lens (86) to compute proximity to the nearby tissue wall (48) and other structural thresholds, such as the opposite wall of the tissue structure. As described above, the suture (52) may be tensioned (80) during deployment to retain the helical interfacing of the suture (52) with the helical member (66).

Figure 4E:
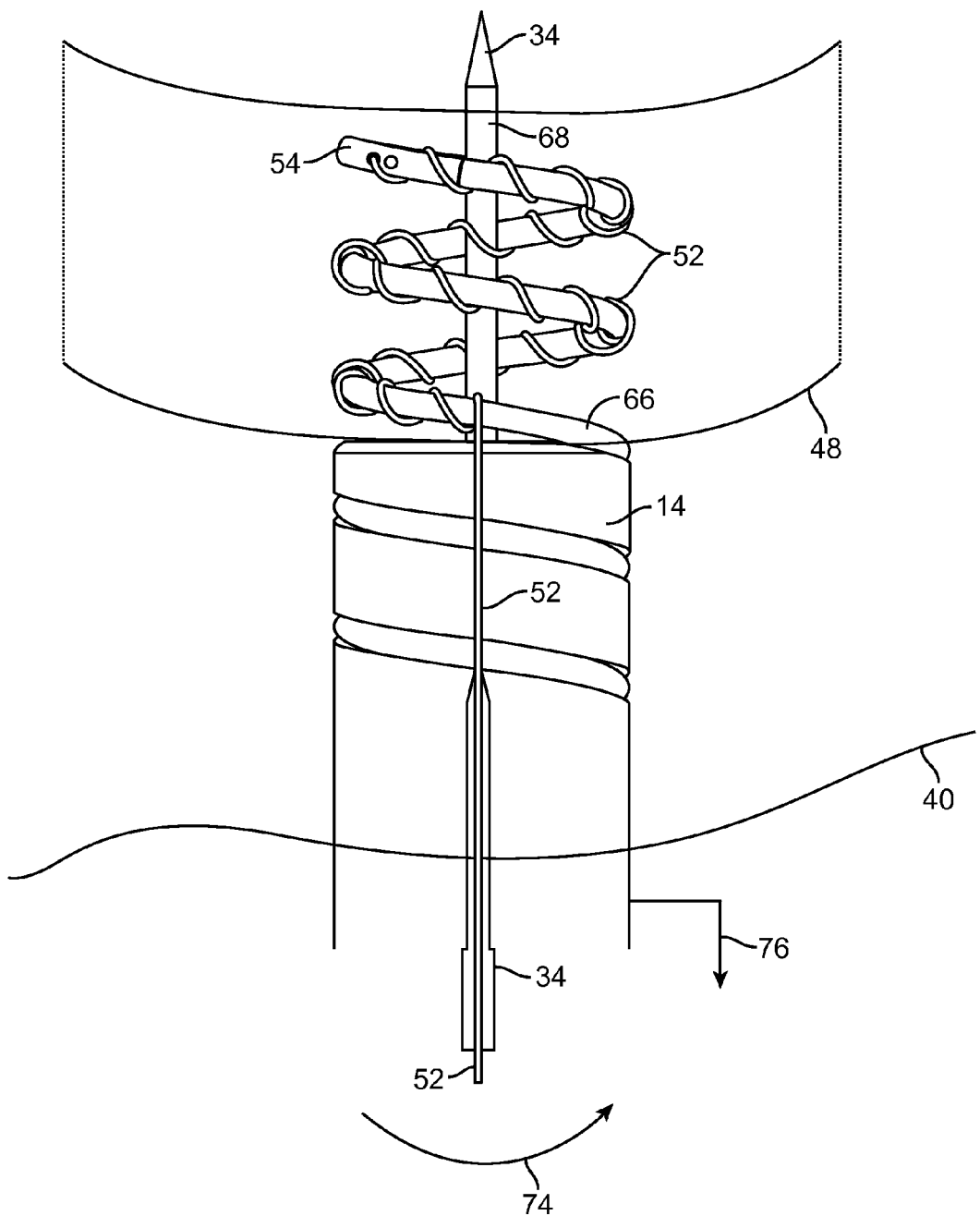
Figure 4F:
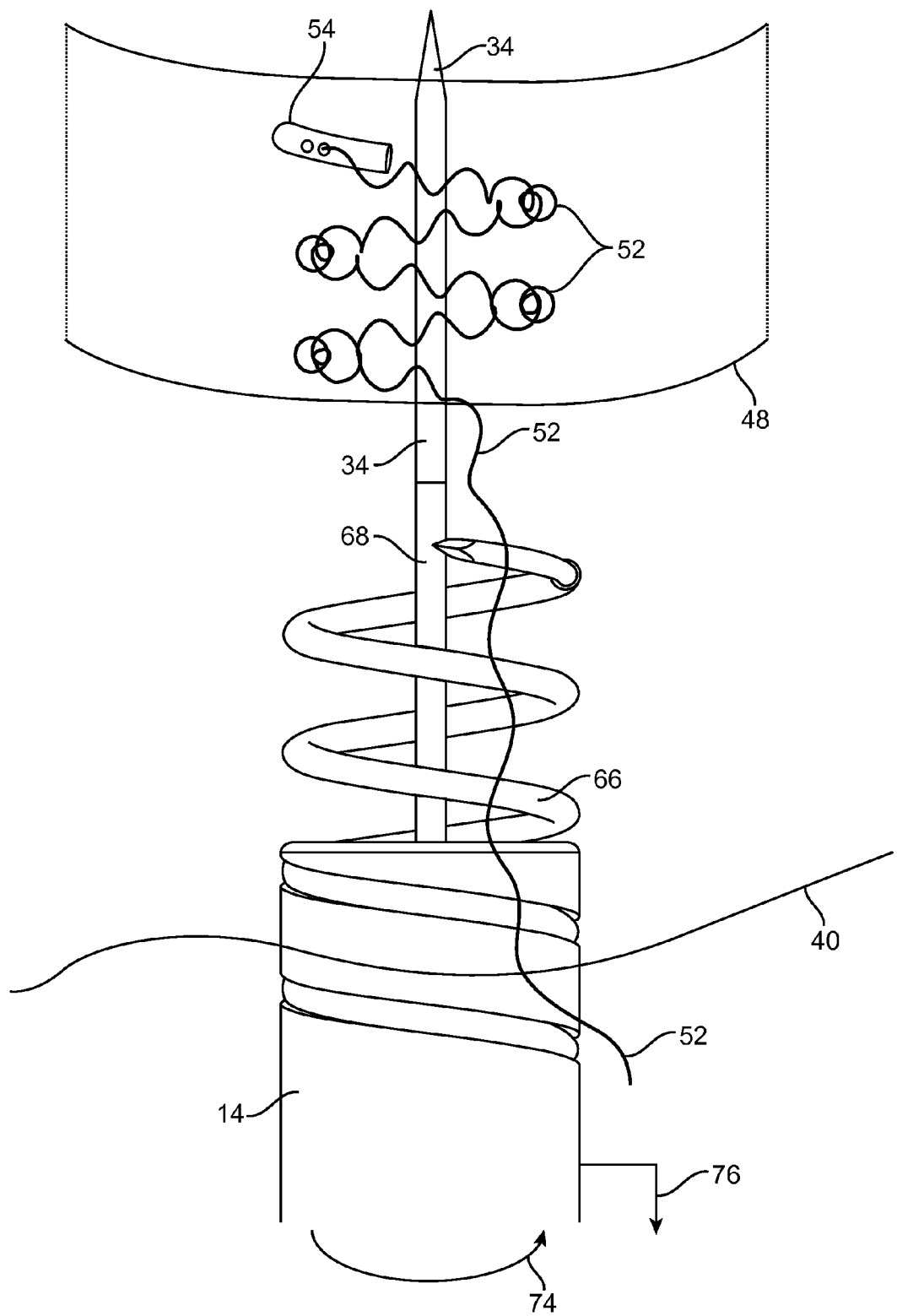
Figure 4G:
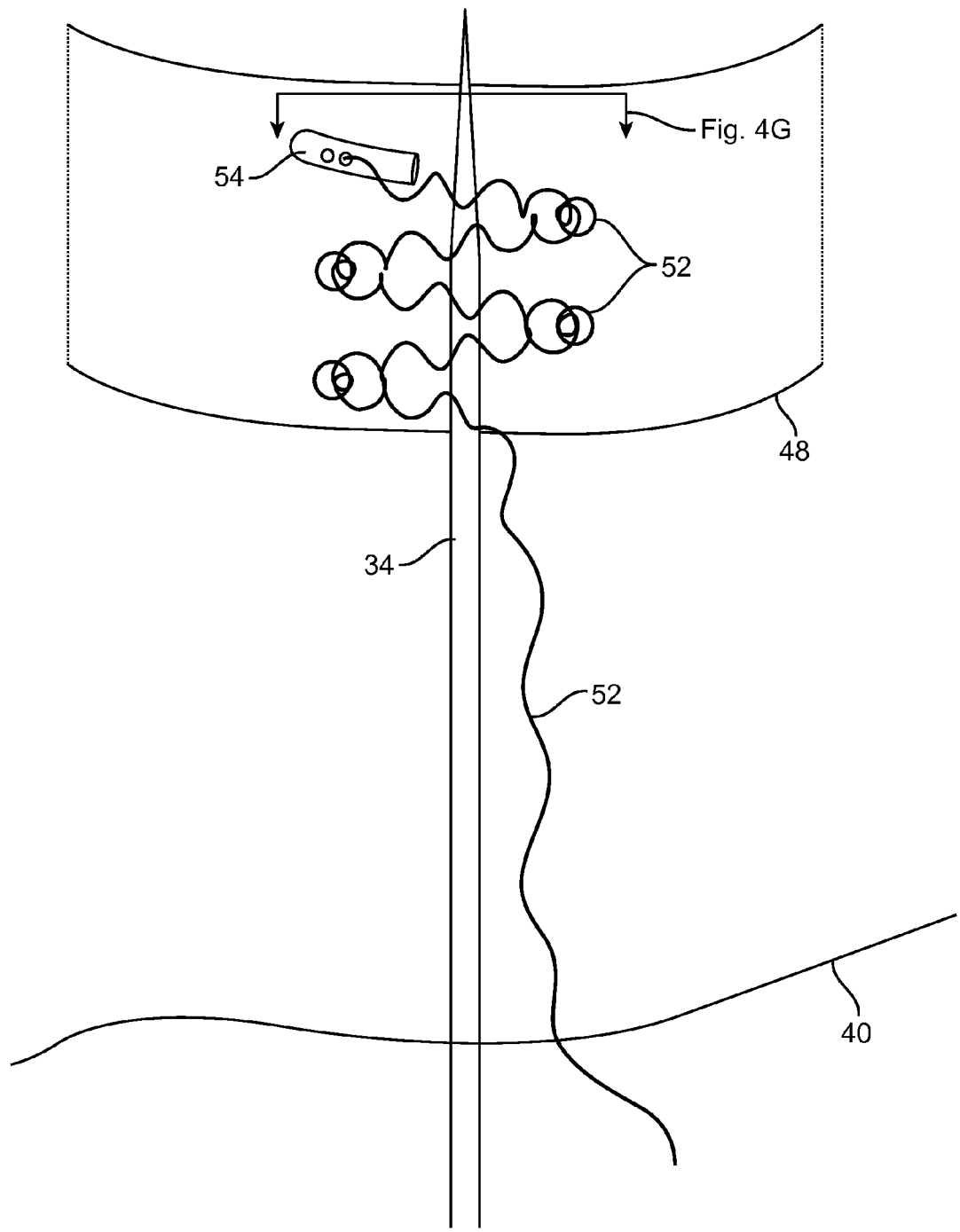

Referring to FIG. 4E, with the compound helical aspect of the suture (52) in a desired location across the tissue wall (48), the deployment member (14) may be retracted by withdrawing (76) and counterrotating (74) it (or, as discussed above, simply counterrotating) while any proximally applied tension on the suture (52) is released, thus applying a reverse load to the anchor member which causes it to become decoupled from the helical needle member (66) and assume a load resisting configuration (by rotating, expanding, loading a barb or other projecting member, etc, as described below), causing the suture (52) to separate from the needle member (66) and remain coiled in place, still coupled to the anchor member, as shown in FIG. 4F. As noted above in reference to the advancement of the helical needle assembly, the assembly may be advanced or retracted using either a combination of compressive or tensile loading (i.e., slight pulling for retraction or pushing for advancement—on a proximal manual interface) added to rotational loading (i.e., torque to a proximal manual interface either clockwise or counterclockwise)—or with only rotational loading (i.e., simply screwing the assembly in and out without concomitant tensile or compressive loading). FIG. 4F shows the deployment member (14) and helical member (66) completely withdrawn from the tissue wall (48), leaving behind the anchor element (54) and the suture (52) in a compound helical pattern ("compound" in that the suture remains helically coiled, and the coil remains in a helical configuration). FIG. 4G shows the deployment member (14) and helical member (66) completely removed, with the elongate guiding member (34) remaining in place, along with the deployed compound helical suture (52) and suture anchor element (54).

Figure 4H:
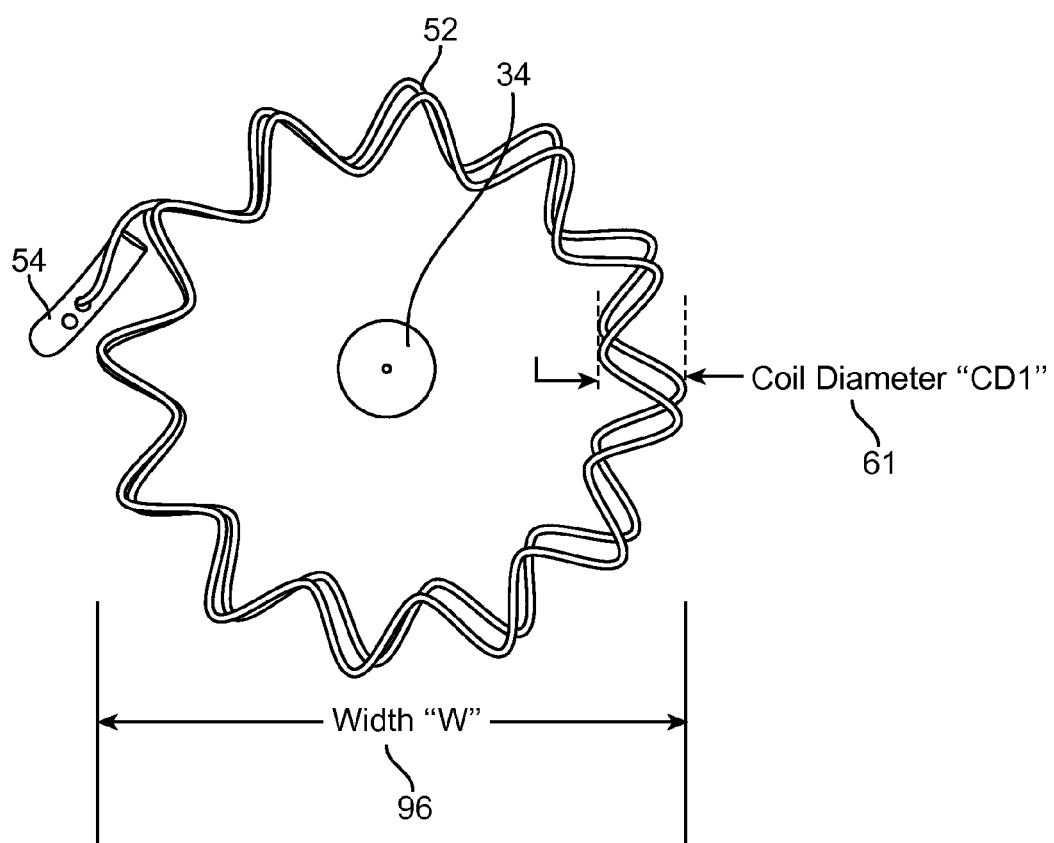
Figure 4I:
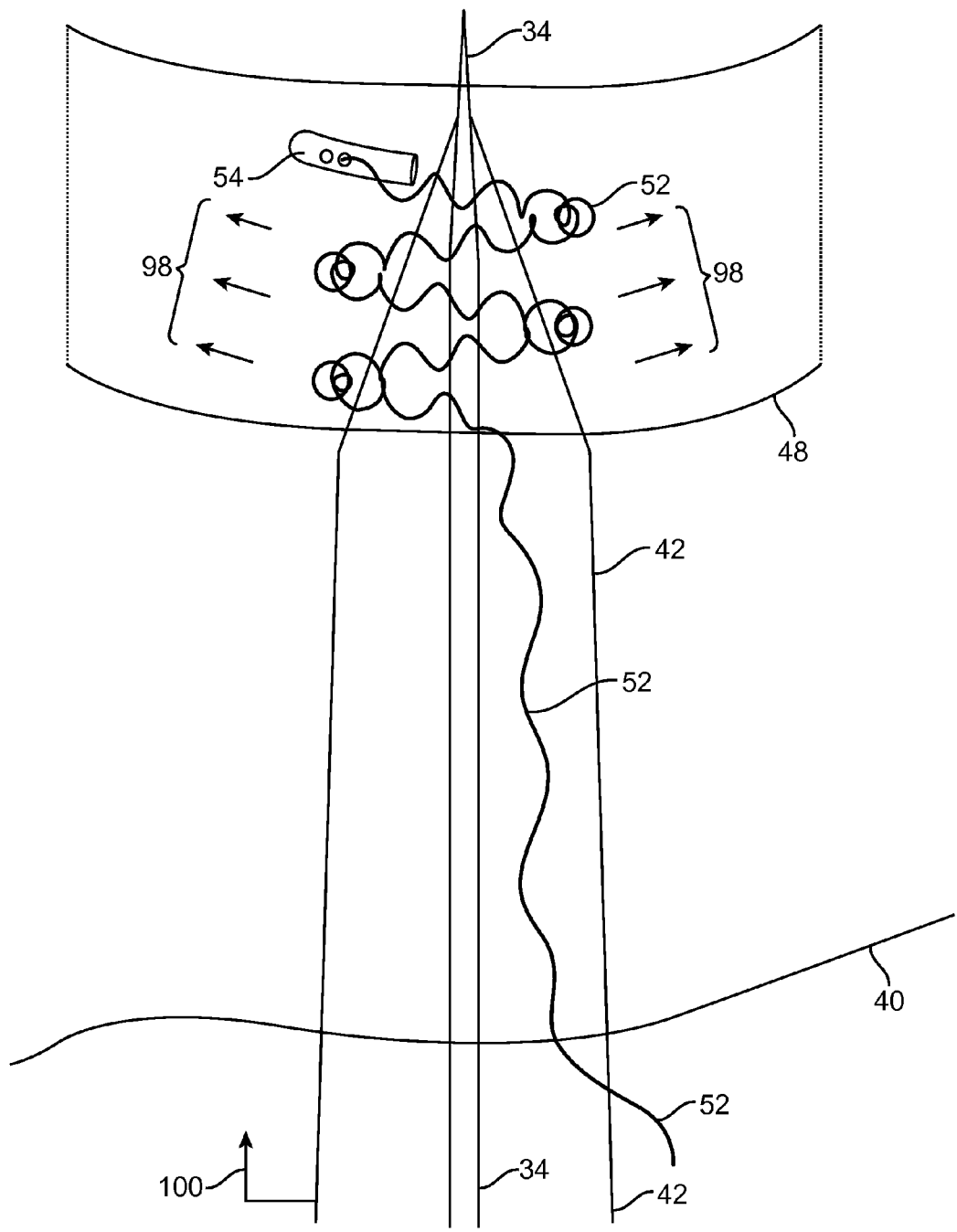
Figure 4J:
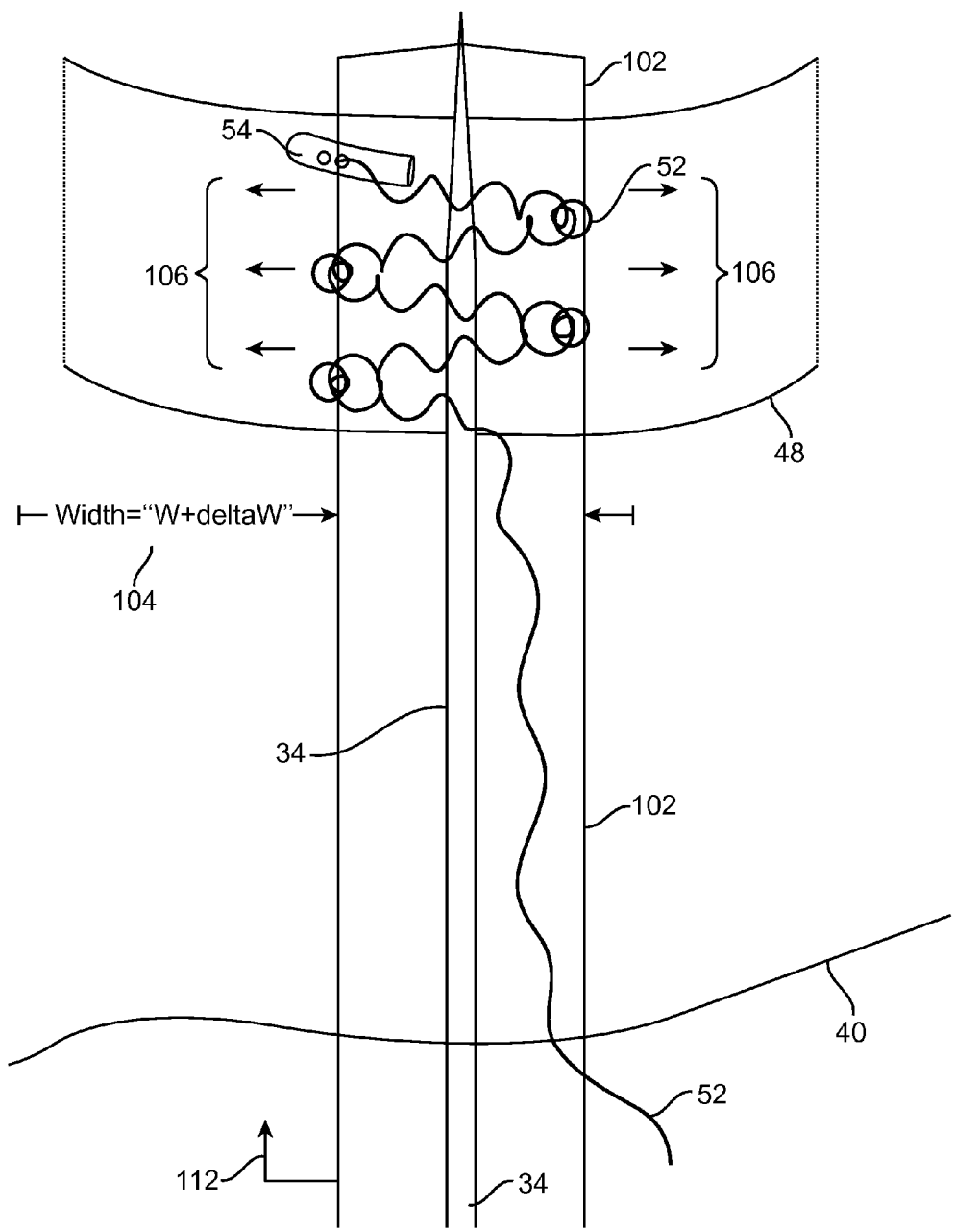
Figure 4K:
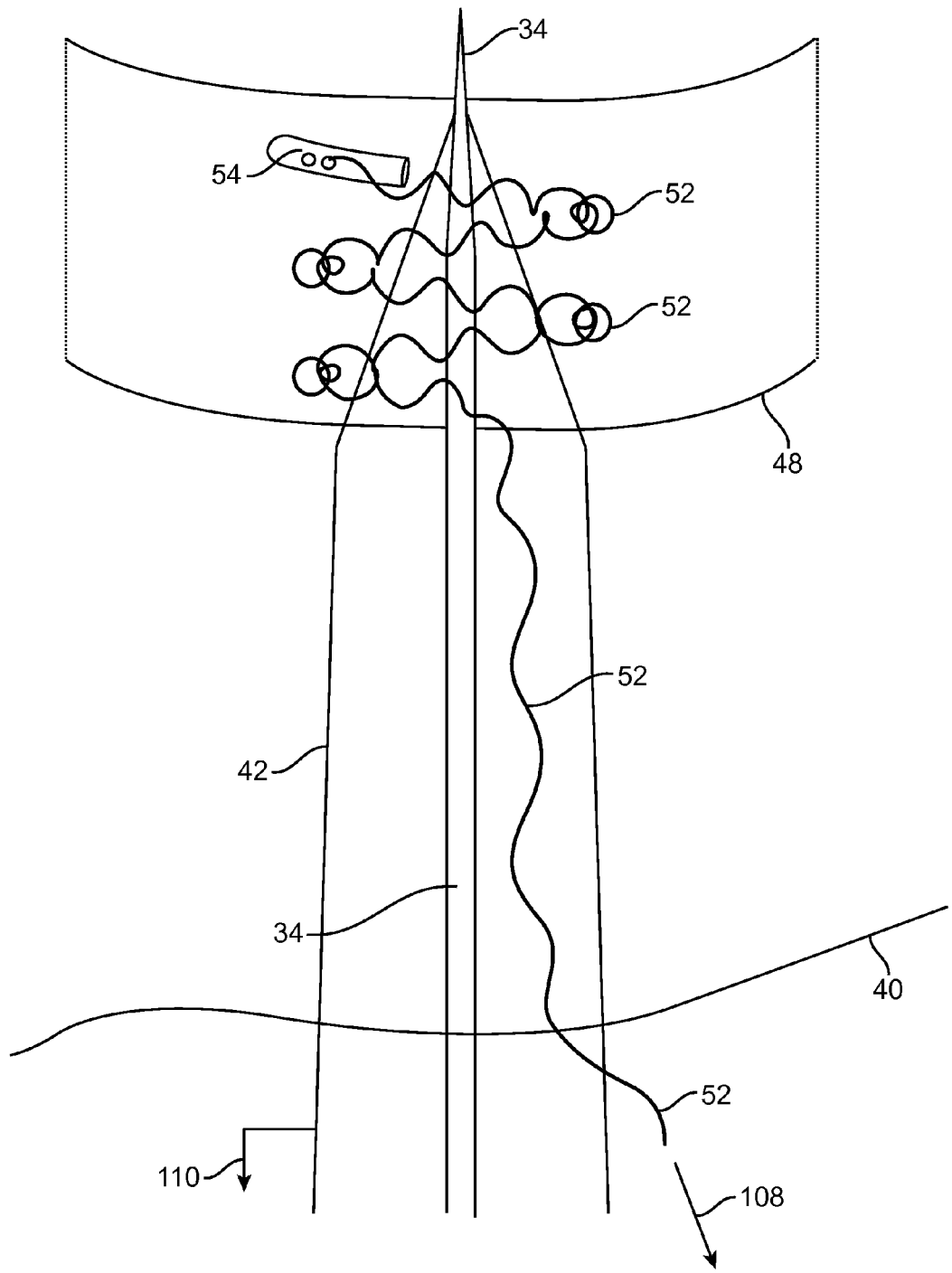
Figure 4L:
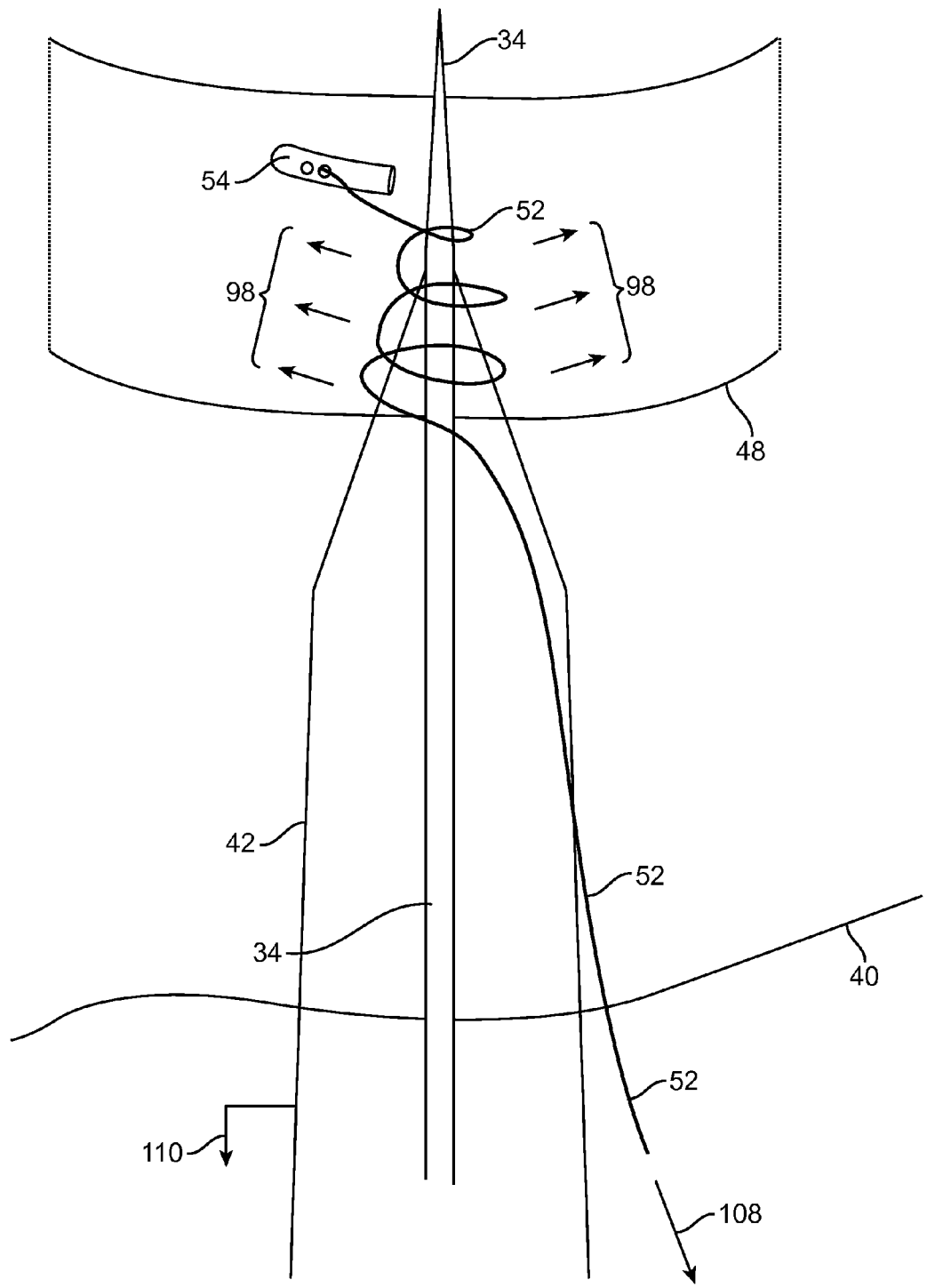
Figure 4M:
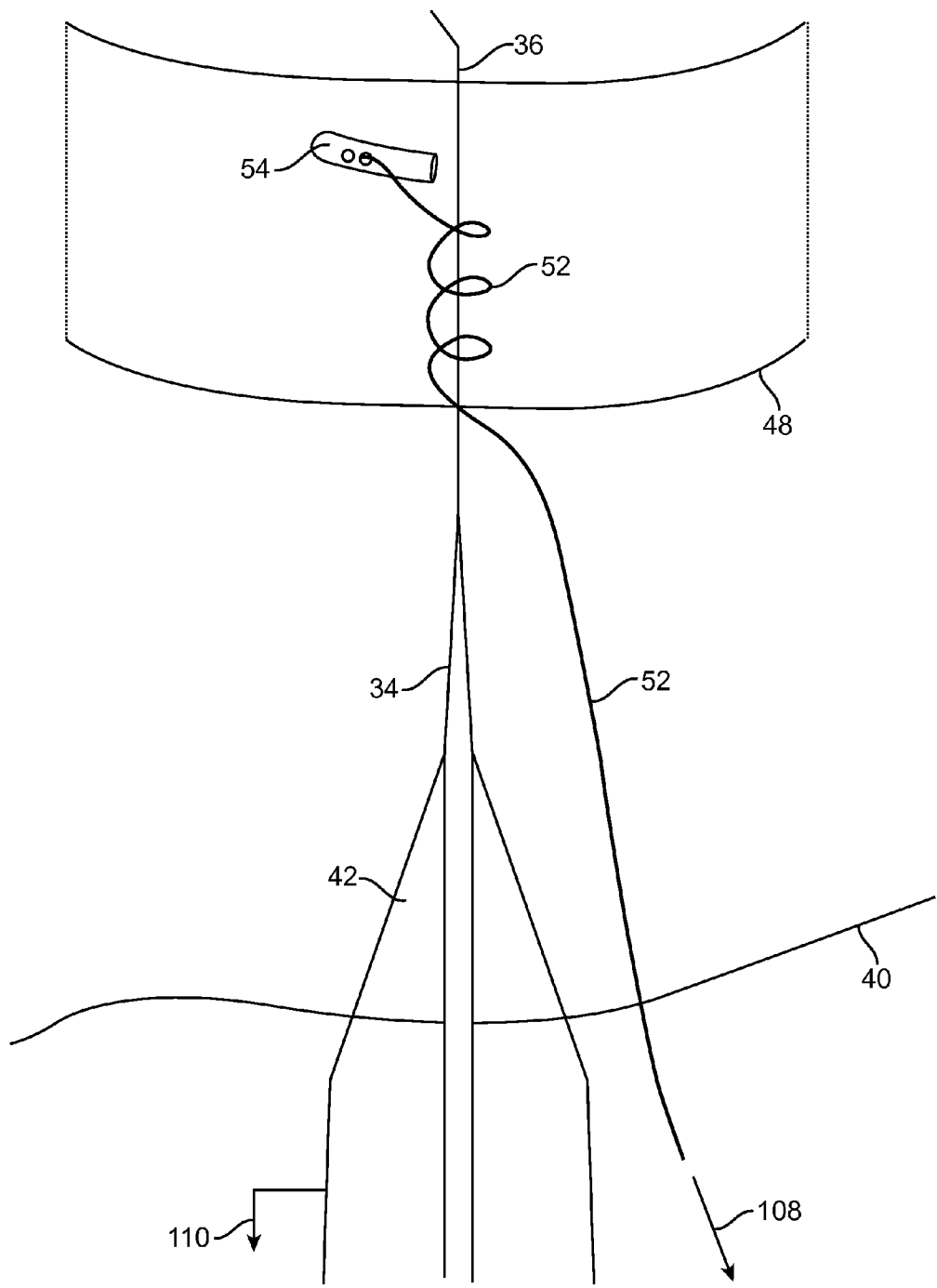
Figure 4N:
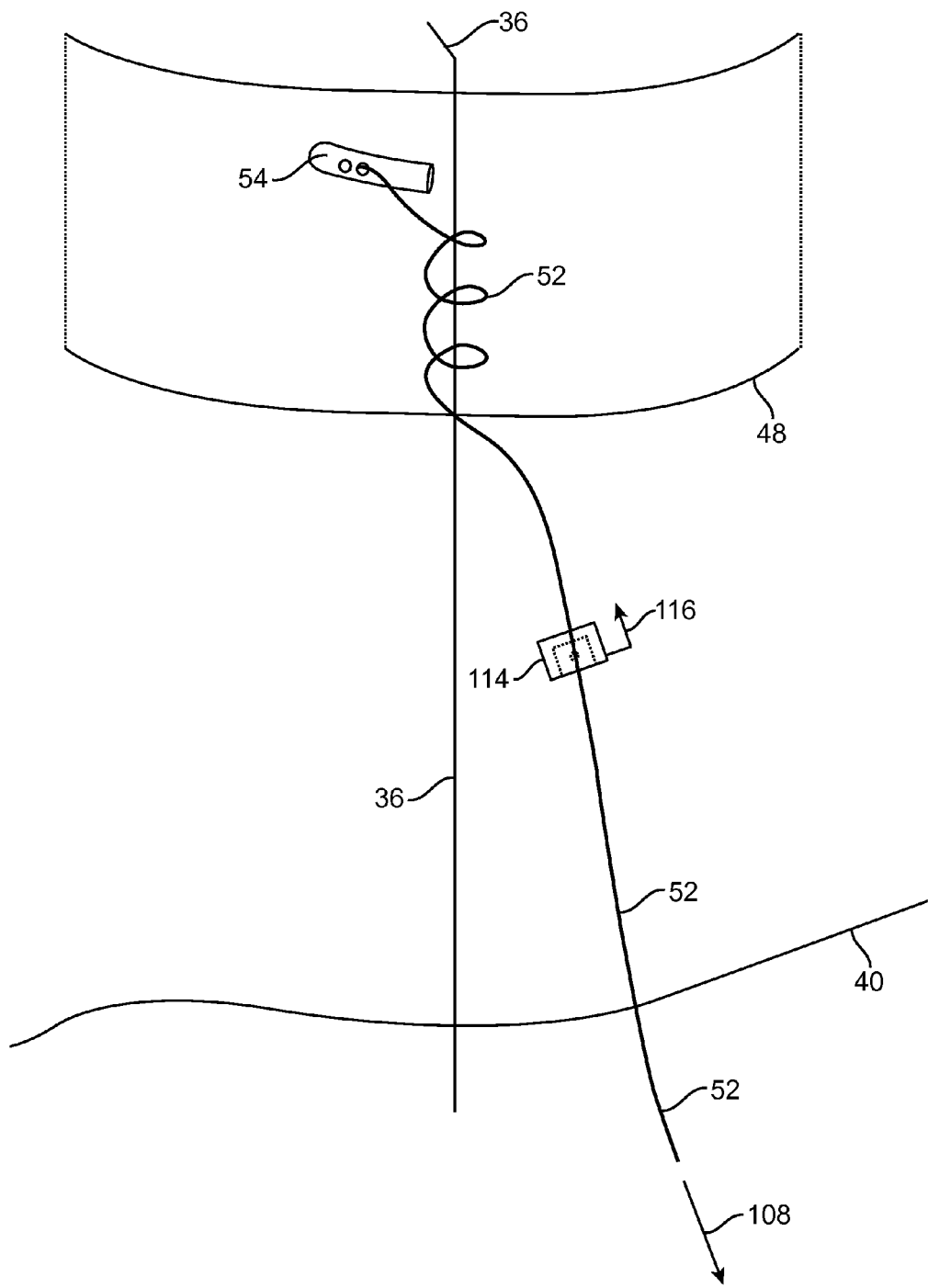
Figure 4O:
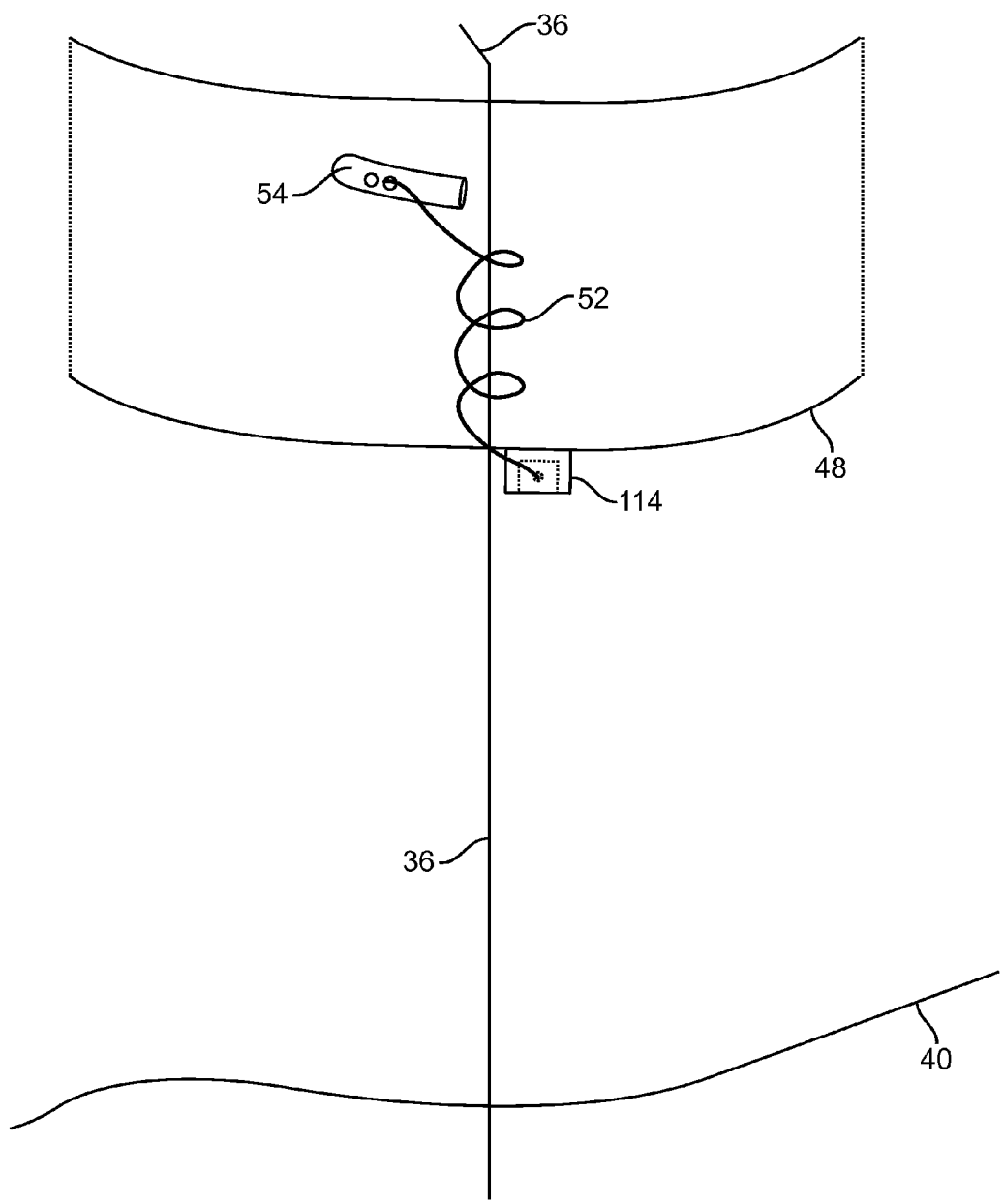

FIG. 4H depicts an orthogonal view of the deployed compound helical suture (52) and suture anchor element (54), which are configured at deployment, by virtue of the geometry of the helical member (66), to have an outer shape width that may be represented as "W" (96). The untensioned compound helical suture (52) configuration has an unloaded coil diameter of "CD1" (61). As described above in reference to our experimental findings, this deployment paradigm provides significant flexibility for diagnostic and interventional paradigms that follow, as the tissue/suture/anchor assembly may be strained in many directions quite significantly without disturbing the generally compound helical deployment of the suture, and with significantly less risk of lacerating tissue during expansion or tightening due to the localized length storage provided by the coil configuration. For example, as shown in FIG. 4I, a dilator (42) is advanced (100) over the elongate guiding member (34). The relatively large outer shape of the dilator urges (98) the surrounding tissue outward, and generally causes the orthogonal dimension of the larger suture helix to become greater than "W", but generally does not take the suture (52) out of the compound helical configuration. With the localized length storage being utilized to provide the extra length needed to increase to a larger included tool diameter, the suture (52) coil diameter decreases. Referring to FIG. 4J, an even larger tool (102), say having outer diameter of "W+deltaW" (104) may follow after the dilator (element 42 of FIG. 4H) has been proximally removed (i.e., through a sheath with hemostatic valve). This larger tool shape further locally urges (106) the tissue outward (the larger diameter causing further decrease of the coil diameter due to further take up of the localized length storage; perhaps to a new, smaller coil diameter of "CD2"), but the compound helical patterning of the suture (52) is retained while the tool (102) is in place to, for example, deploy a prosthetic heart valve, etc. Referring to FIG. 4K, when a tightening and/or closure of the wound is desired (for example, it may be desirable to tighten the wound to prevent leaks during the diagnostic and/or interventional steps using the aforementioned tool 102), the proximal aspect of the suture (52) may be tensioned (108), causing both of the involved helical shapes to shrink: the larger helical shape of the coils shrinks around the engaged tool, and the coiling helix itself shrinks away with tensioning as the localized length storage is used up. This combined helical shrinking action causes the captured wound or defect to close, as shown in FIGS. 4L and 4M, wherein the tapered shape of a dilator inserted (i.e., through a hemostatically valved sheath) after withdrawal of the tool (element 102 in FIG. 4I) may be utilized along with a successive tightening (108) interplay with the suture (52) to close the wound or defect behind the withdrawing (110) dilator (42). In other words, successive rounds of dilator withdrawal (110), then suture tightening (108) may be utilized to incrementally close the wound or defect. The suture (52) in FIGS. 4L-4P is shown with the localized length storage effected used up, and the suture forming a generally uncoiled configuration as it continues to hold the larger helical pattern around the captured wound and tools. Referring to FIG. 4M, with the needle (34) and dilator (42) retracted, a guidewire (36) may be left in place and the wound substantially closed around the guidewire (36), as shown in FIGS. 4M-4O, to provide an easy return access subsequent to a period of observation. For example, in an embodiment wherein a prosthetic valve has been placed with the aforementioned tools (102), it may be desirable to close the wound and leave a guidewire (36) in place during a few minutes of observation of the valve prosthesis in situ, to confirm adequate function while also having a fast and efficient return means (the guidewire 36) should this be required.

Referring to FIG. 4N, with only the anchor element (54), guidewire (36), and suture (52) left behind, the suture (52) may be tied into a knot and terminated at the proximal wall of the tissue structure (48), or a terminating device (114) may be advanced (116) along the suture and snugged into place against the wall (i.e., to retain a desired level of tension in the deployed suture 52), followed by cutting of the proximal un-needed portion of the suture, as shown in FIG. 4O. In another embodiment, two or more compound helical sutures may be similarly deployed in sequence before advancement of the dilator (42) and/or tool (102); for example, in one embodiment, two compound helical sutures may be sequentially deployed in different helical directions; in another embodiment, the two may be in the same helical direction but at slightly different winding offsets; many embodiments are within the scope of the invention. Referring to FIG. 4P, subsequent to confirmation that no additional intervention is necessary, the guidewire (36) may be removed (37).

Figure 5A:
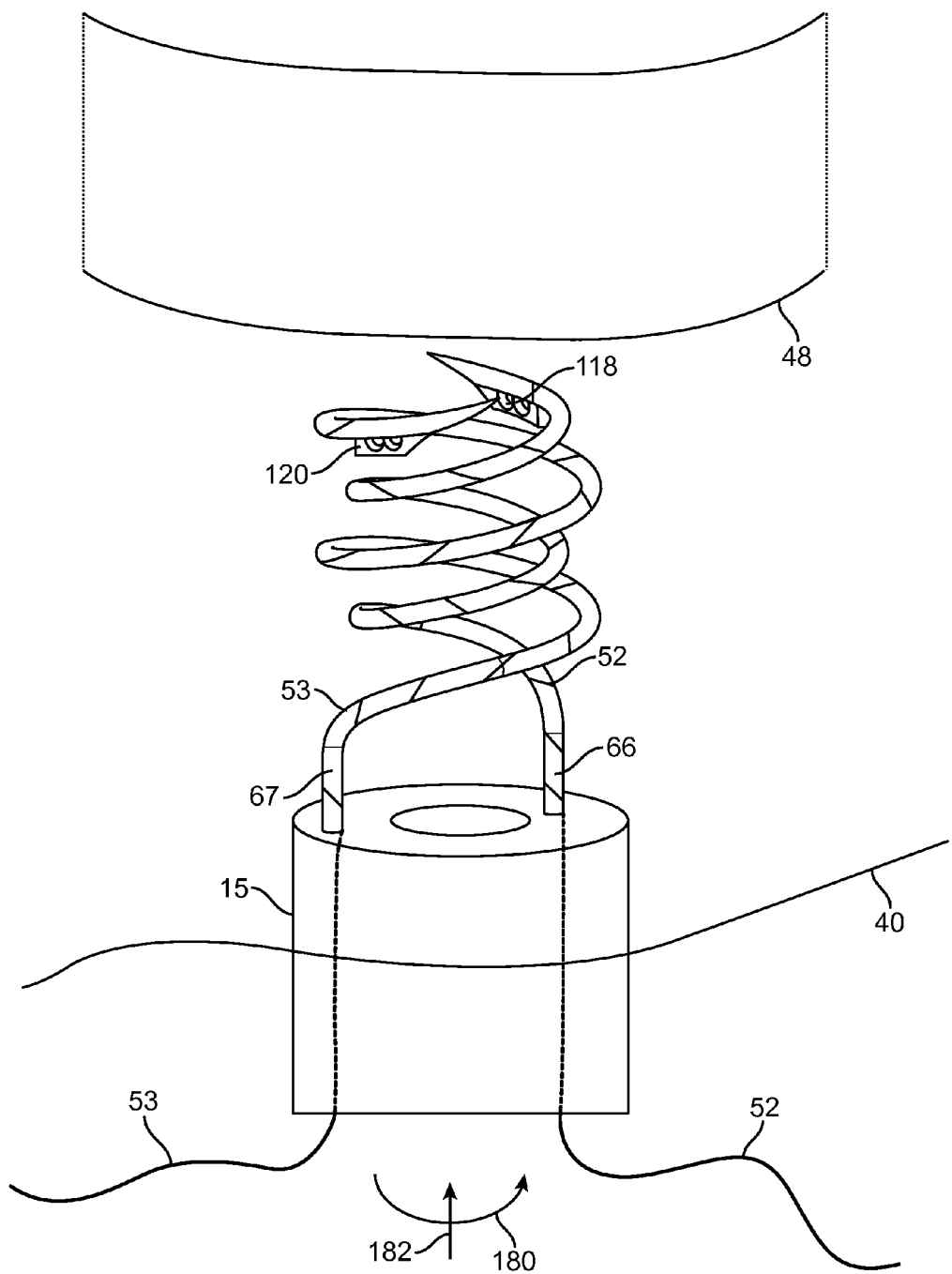
FIGS. 5A to 5I illustrate various aspects of a compound helical closure configuration featuring two helical members configured to simultaneously deploy two sutures and two anchor elements.
Figure 5B:
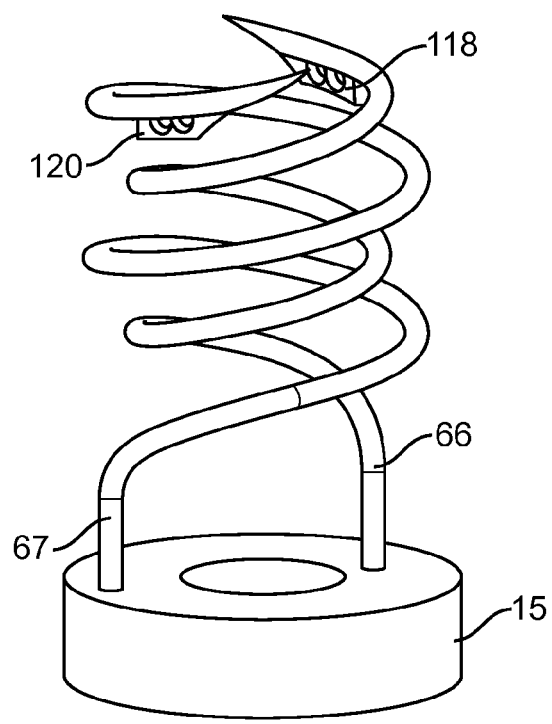
Figure 5C:
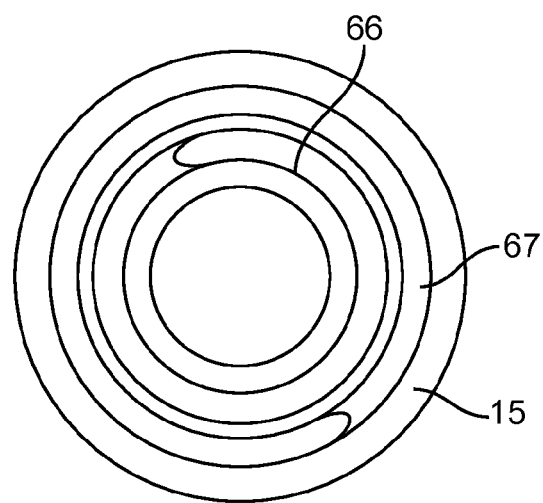
Figure 5D:
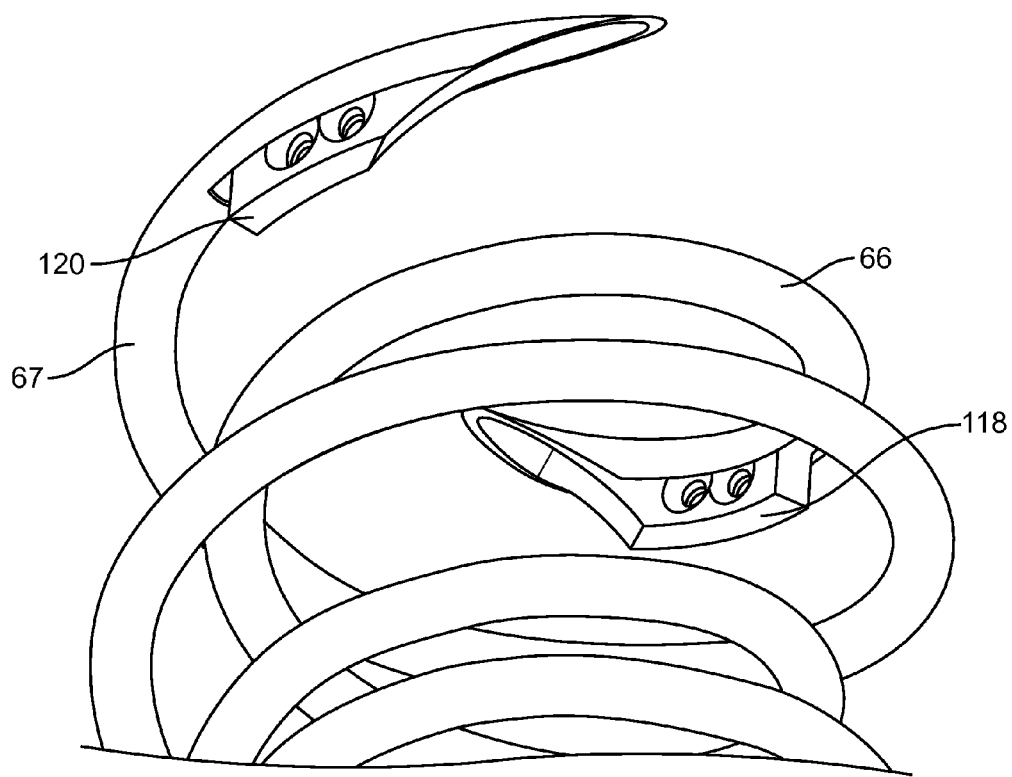
Figure 5E:
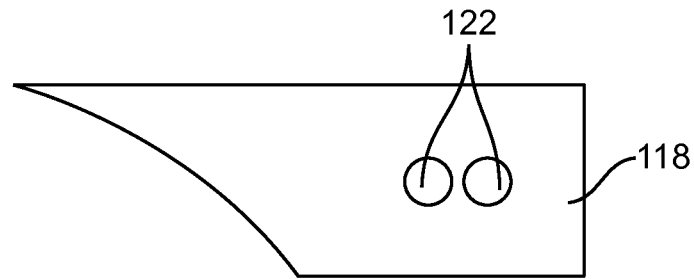
Figure 5F:
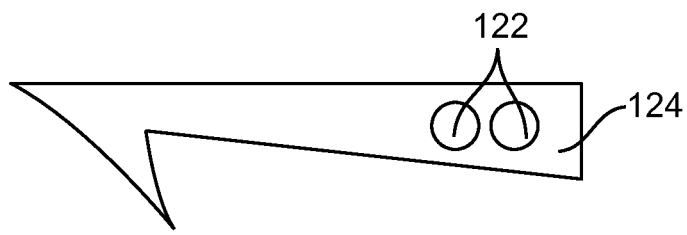
Figure 5G:
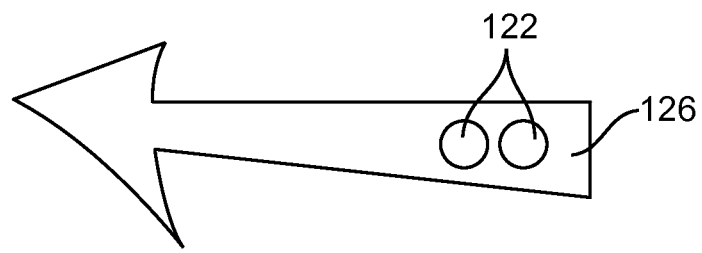
Figure 5H:
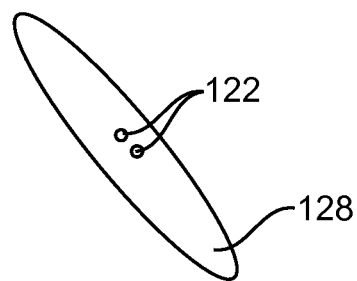
Figure 5I:
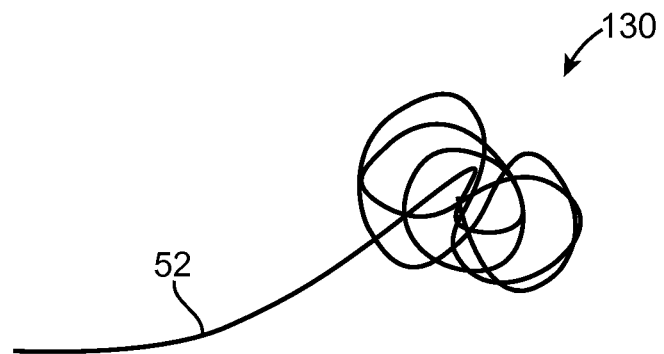
Figure 32:
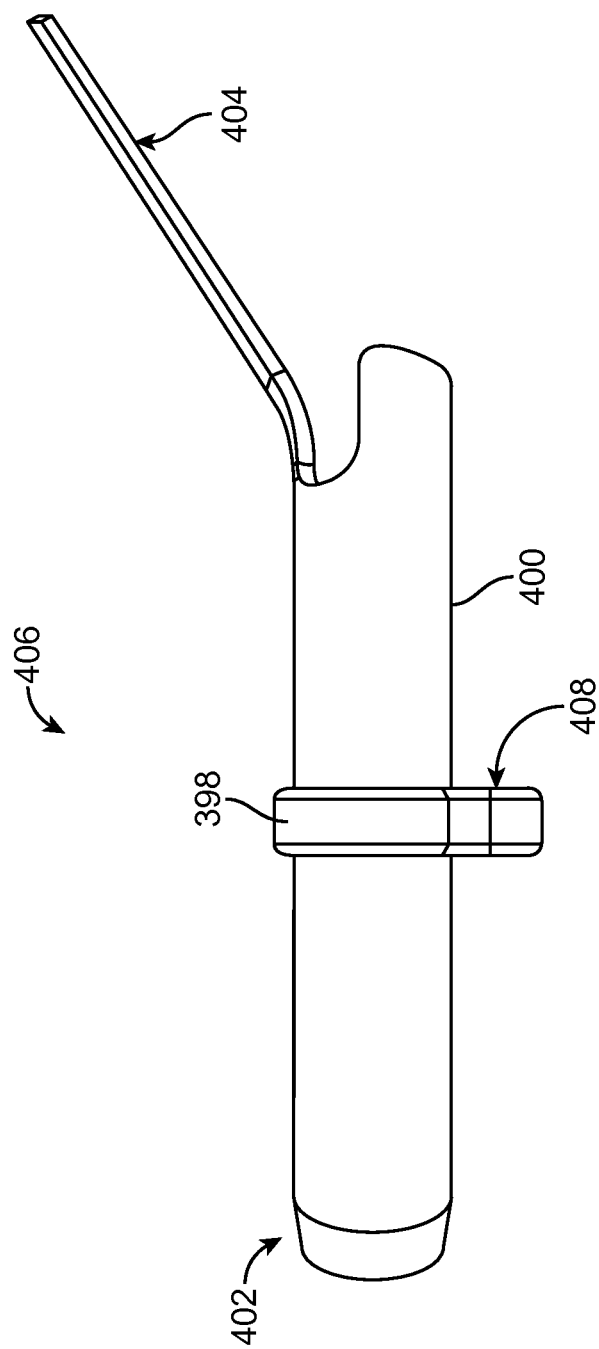
FIG. 32 illustrates an embodiment of an anchor member featuring a flex tail configuration.

Referring to FIGS. 5A and 5B, an embodiment is depicted wherein two helical members (66, 67) coupled to the same deployment member (15) but having different helical radii (see, for example, the top orthogonal view of FIG. 5C) may be utilized to simultaneously install, via rotation (180) and insertion (182), two compound helical sutures (52, 53), each having its own anchoring element (118, 120). The distal portion of such construct showing the helical members (66, 67) and anchors (118, 120), but not the compound helically wound sutures (elements 52 and 53 of FIG. 5A) is shown in orthogonal close-up view. Referring to FIGS. 5E-5I, various anchoring element configurations (118, 122, 126, 122, 130) may be utilized to retain a distal suture end within or across a tissue structure wall. Each of the configurations of FIGS. 5E through 5H has a geometry that prefers to be advanced in one direction, but resists retraction in the opposite direction when placed against viscoelastic tissue, such as that of the heart or other human tissues. Element 122 represents one or more coupling holes to facilitate coupling with the pertinent suture (52, 53). The configuration of FIG. 5I is a simple knot (130) tied in the end of the suture (52) with enough geometric bulk to prevent pullback through the subject tissue. Referring to FIG. 32, another anchor member embodiment is depicted, this one (406) comprising a tubular body comprising Nitinol superalloy heat formed in an arcuate/helical shape to match the helical needle member to which it is to be paired, with a Nitinol flex tail (404) configured to resist retraction, and a tapered leading geometry (402) configured to assist with easy insertion/advancement. A titanium suture coupling ring, or ring member, (398) defining a suture-coupling aperture (408) is coupled to the body using a press fit, welded (such as tack welded), or adhesive junction. The flex tail (404) is configured to flex inward toward the helical needle member during insertion, and to flex outward to resist retraction and assist the anchor member body (400) in rotating to an orientation approximately perpendicular to that assumed by the anchor member body (400) during insertion (i.e., toggling to a reorientation that resists retraction). Preferably the eyelet (408) is optimally positioned to urge the anchor member body into rotational movement relative to the surrounding tissue upon tensile loading of the intercoupled suture member. In the depicted embodiment, the eyelet (408) is displaced apart from a longitudinal axis of the body and approximately in the middle of the body longitudinally. Another embodiment may comprise two or more flex tails. The superalloy (such as Nitinol) flex tail, or tails, may be shape set to a projecting position (i.e., projecting out and away from the body), but configured to be delivered in an elastically compressed form (i.e., with the tail deflected toward the body of the anchor member) within the superelastic thermal range for the alloy.

The anchor may comprise a metal selected from the group consisting of: titanium, stainless steel, cobalt chrome, and alloys thereof. The anchor may comprise a durable polymer selected from the group consisting of: polyethylene tereptha-late, polyethylene, high density polyethylene, polypropylene, polytetrafluoroethylene, expanded polytetrafluoroethylene, poly (ethylene-co-vinyl acetate), poly(butyl methacrylate), and co-polymers thereof. The anchor member may comprise a bioresorbable polymer selected from the group consisting of: polylactic acid, polyglycolic acid, polylactic-co-glycolic acid, polylactic acid-co-caprolactone, poly (block-ethylene oxide-block-lactide-co-glycolide), polyethylene glycol, polyethylene oxide, poly (block-ethylene oxide-block-propylene oxide-block-ethylene oxide), polyvinyl pyrrolidone, polyorthoester, polyanhydride, polyhydroxy valerate, polyhydroxy butyrate, and co-polymers thereof. The anchor member may comprise a biological graft material, such as one that has an origin selected from the group consisting of: another human, the particular human, a non-human animal. The anchor member may comprise a bioresorbable material selected from the group consisting of: porcine collagen matrix, human collagen matrix, equine collagen fleece, gelatin, polyhyaluronic acid, heparin, poly (glucose), poly(alginic acid), chitin, chitosan, cellulose, methyl cellulose, hydroxyethylcellulose, hydroxypropylcellulose, carboxymethylcellulose; polylysine, polyglutamic acid, albumin, hydroxy apatite, cortical bone, cancellous bone, trabecular bone, bioceramic, ligament tissue, tendon tissue, dura tissue, fascia tissue, pericardium tissue, thrombin, and fibrin.

Figure 6:
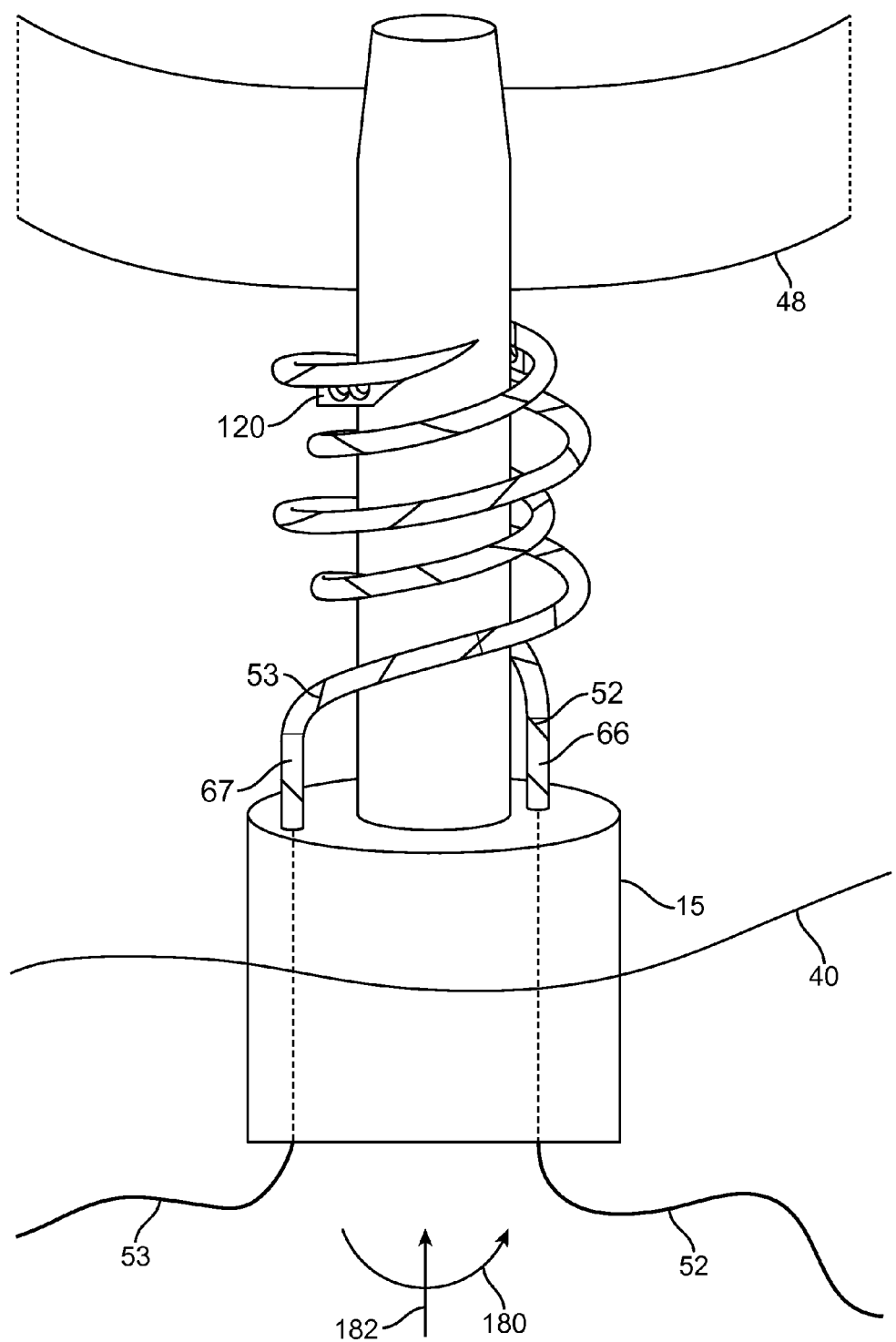
FIG. 6 illustrates an embodiment wherein one or more tools may be installed and utilized before installation of a helical closure assembly.
Figure 7A:
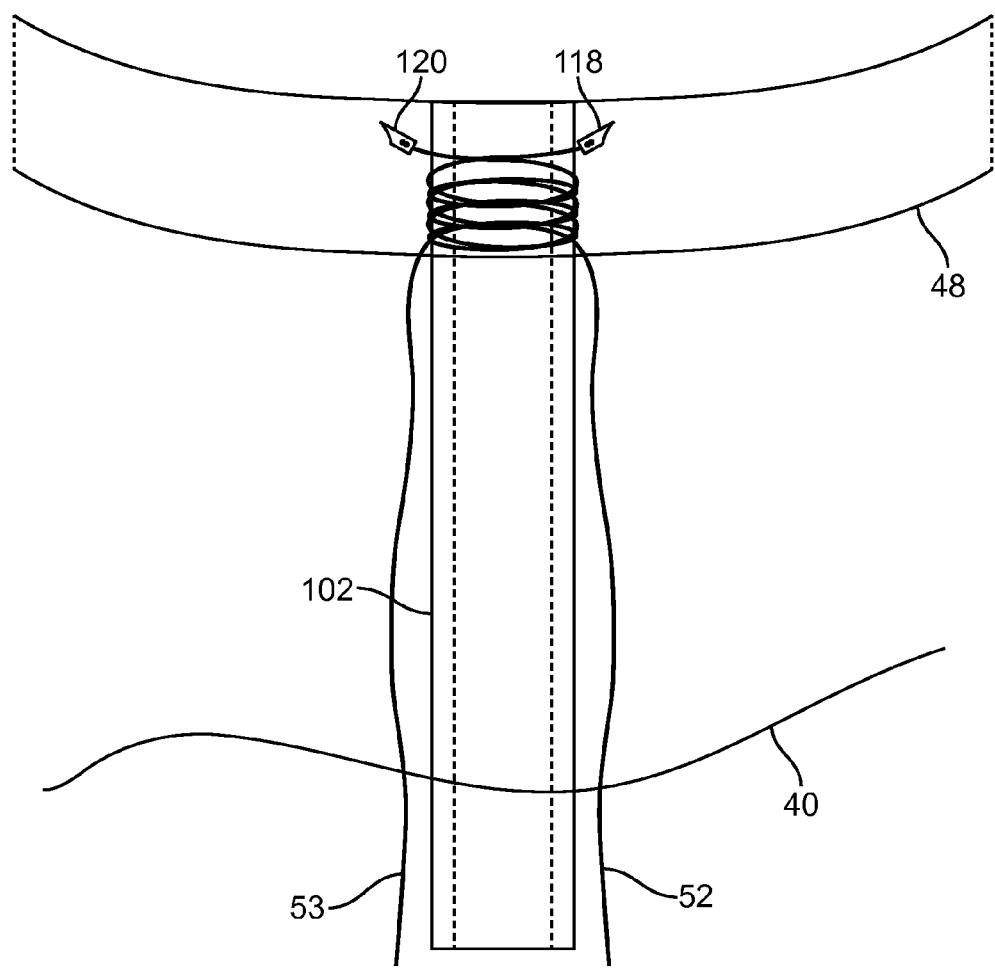
FIGS. 7A to 7B illustrate a two-suture helical closure with anchoring elements deployed partially across the subject tissue wall.
Figure 7B:
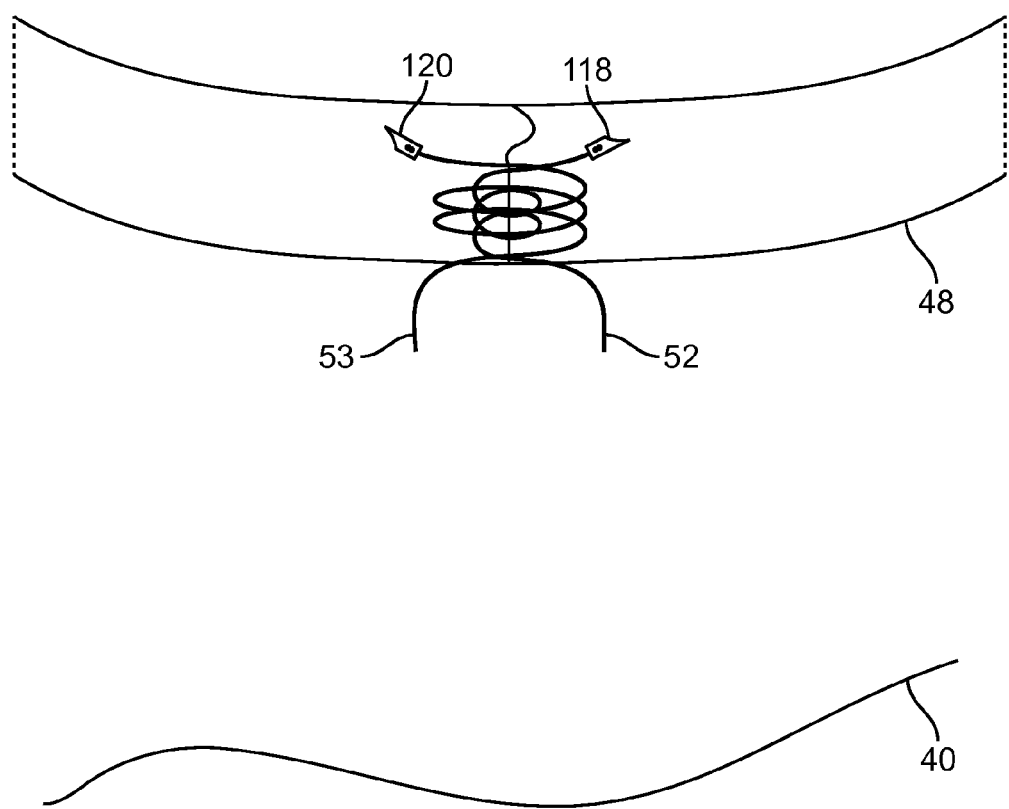
Figure 8A:
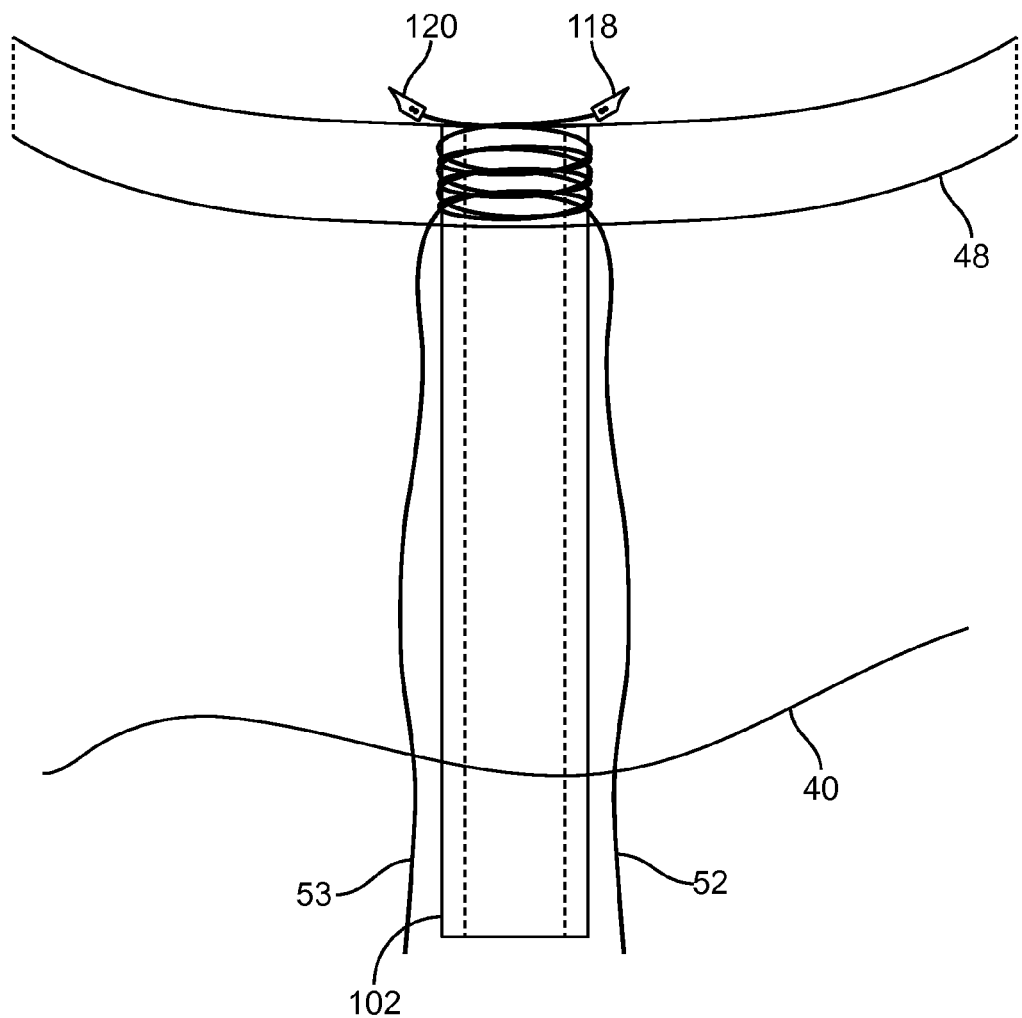
FIGS. 8A to 8B illustrate a two-suture helical closure with anchoring elements across the subject tissue wall.
Figure 8B:
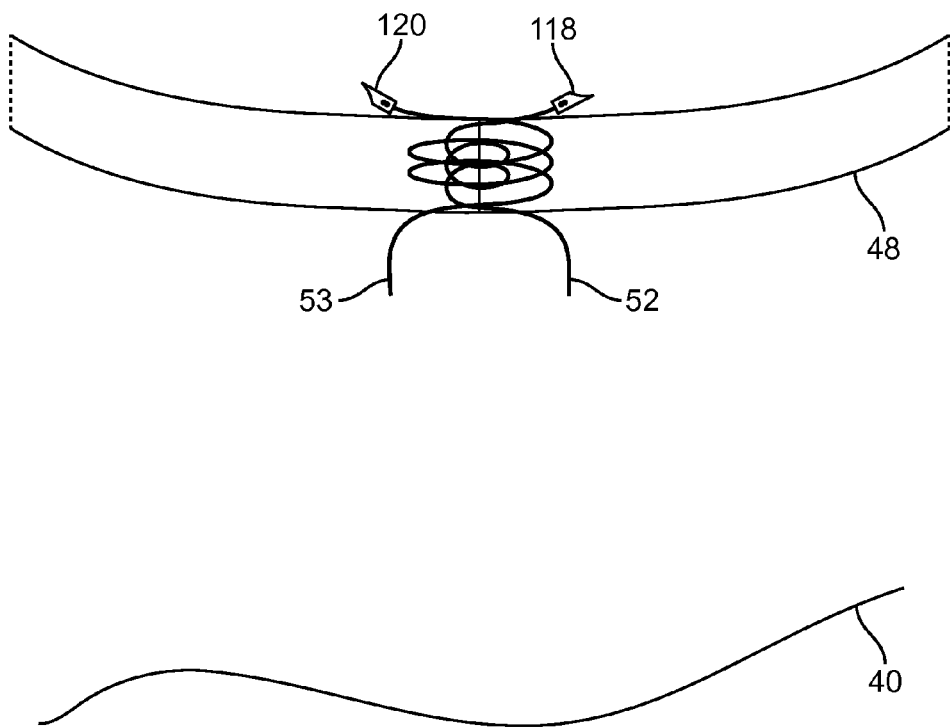
Figure 9A:
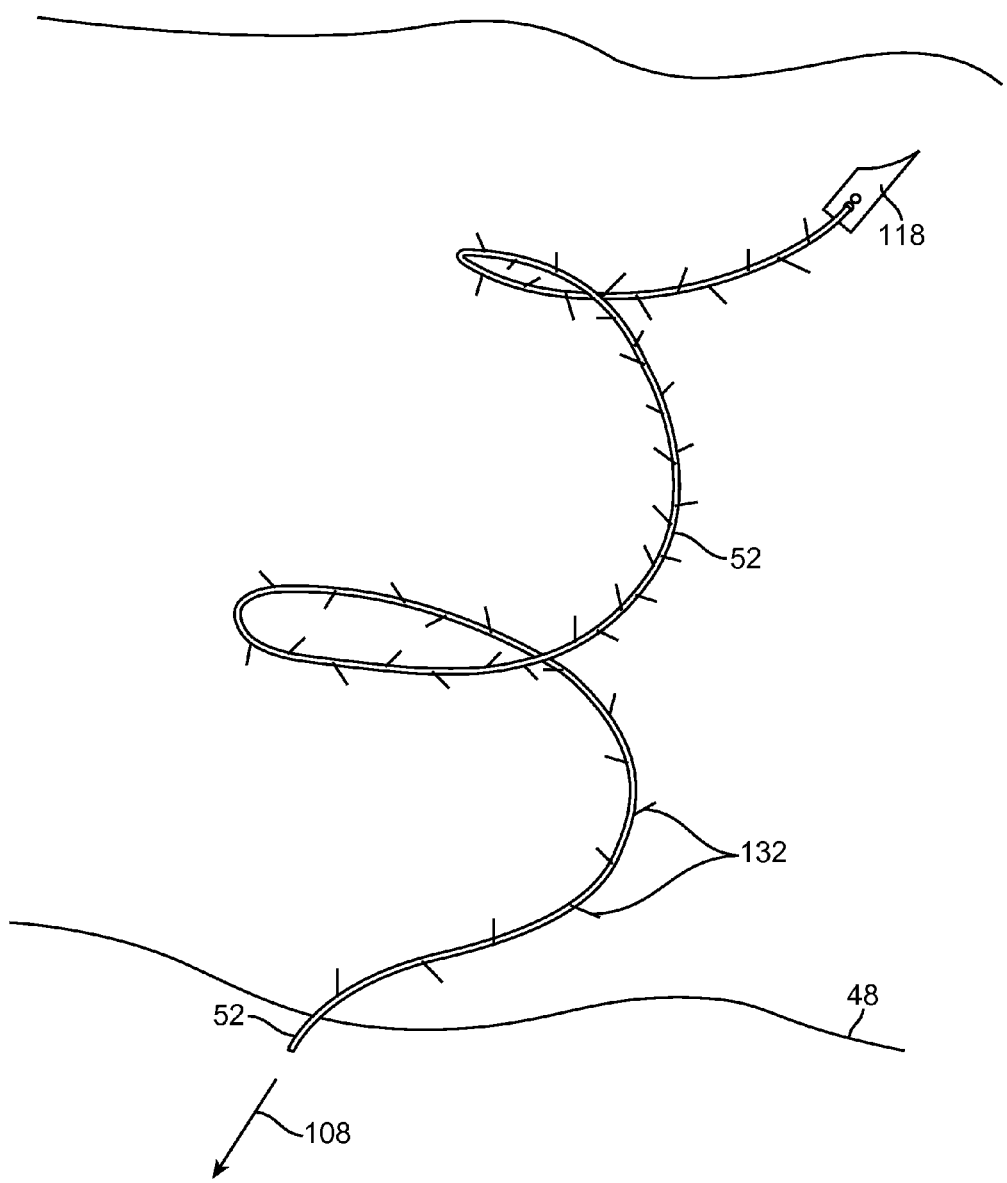
FIG. 9A illustrates a suture embodiment having barbs along a significant portion of its length.
Figure 9B:
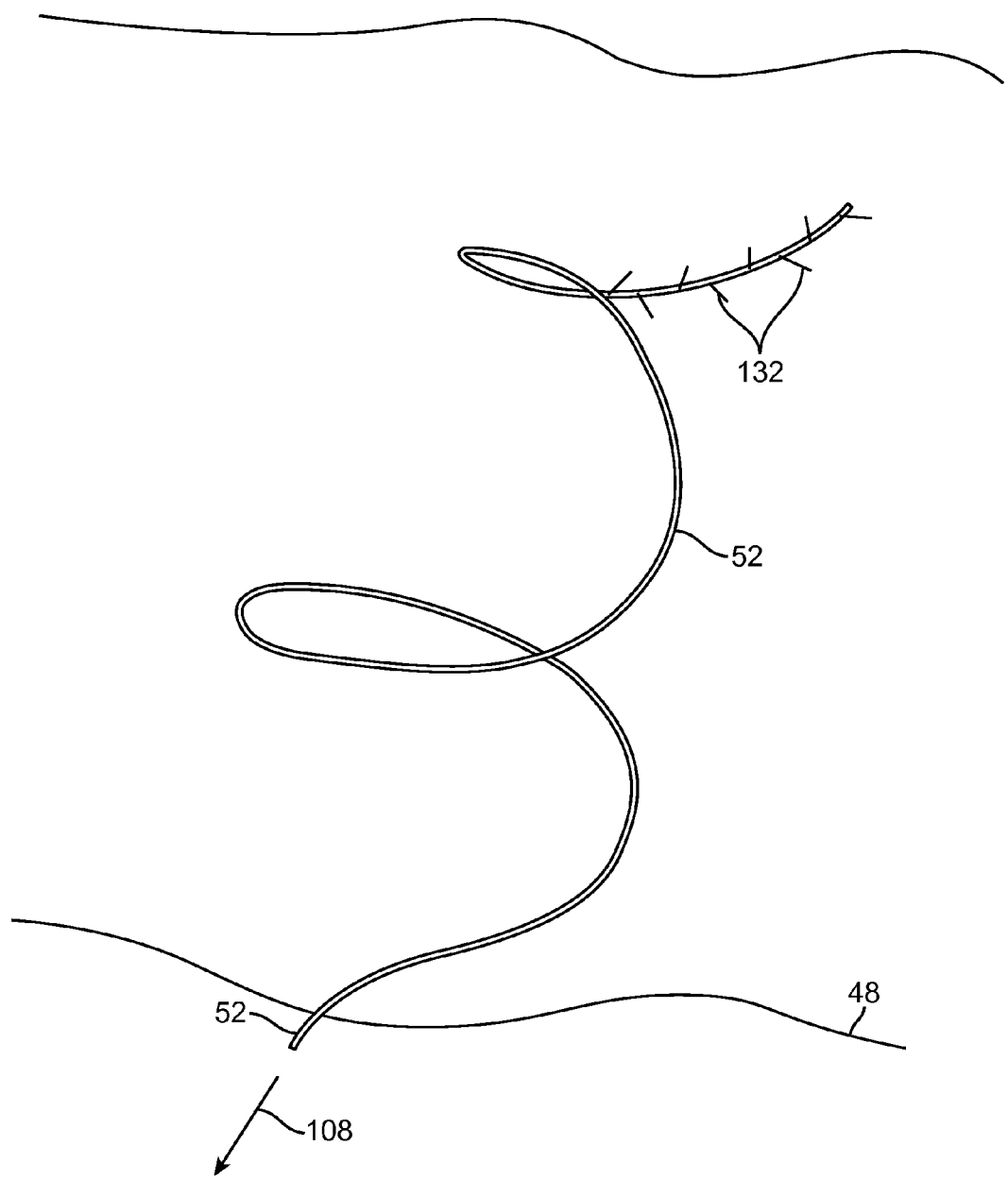
FIG. 9B illustrates a suture embodiment having barbs only on its distal portion.

Referring to FIG. 6, an another embodiment, a configuration such as those described in relation to FIG. 4A-4N or 5A-5I may be advanced into position relative to a tissue wall after a tool (102) or other structure has been deployed across the wall (48). Referring to FIGS. 7A-7B, a configuration such as those described in reference to FIG. 5A-5I or 6 may be utilized to close a wound or defect after withdrawal of a tool (102), leaving behind only sutures (52, 53) and anchoring elements (118, 120). Referring to FIGS. 8A-8B, it is important to note that the anchors need not be deployed within the midsubstance of the tissue structure to facilitate a successful closure, but may be deployed across such structure, to reside at the opposite side of the subject wall (48). Referring to FIG. 9A, in one embodiment, the suture (52) may feature barbs (132) to prevent slipping relative to the tissue structure (48) after deployment. Referring to FIG. 9B, a suture (52) embodiment is depicted wherein only distal barbs (132) are utilized, and wherein the slip prevention provided by such barbs (132) obviates the need for an anchoring element (in other words, the embodiment shown in FIG. 9B is a "suture only" embodiment).

Figure 10A:
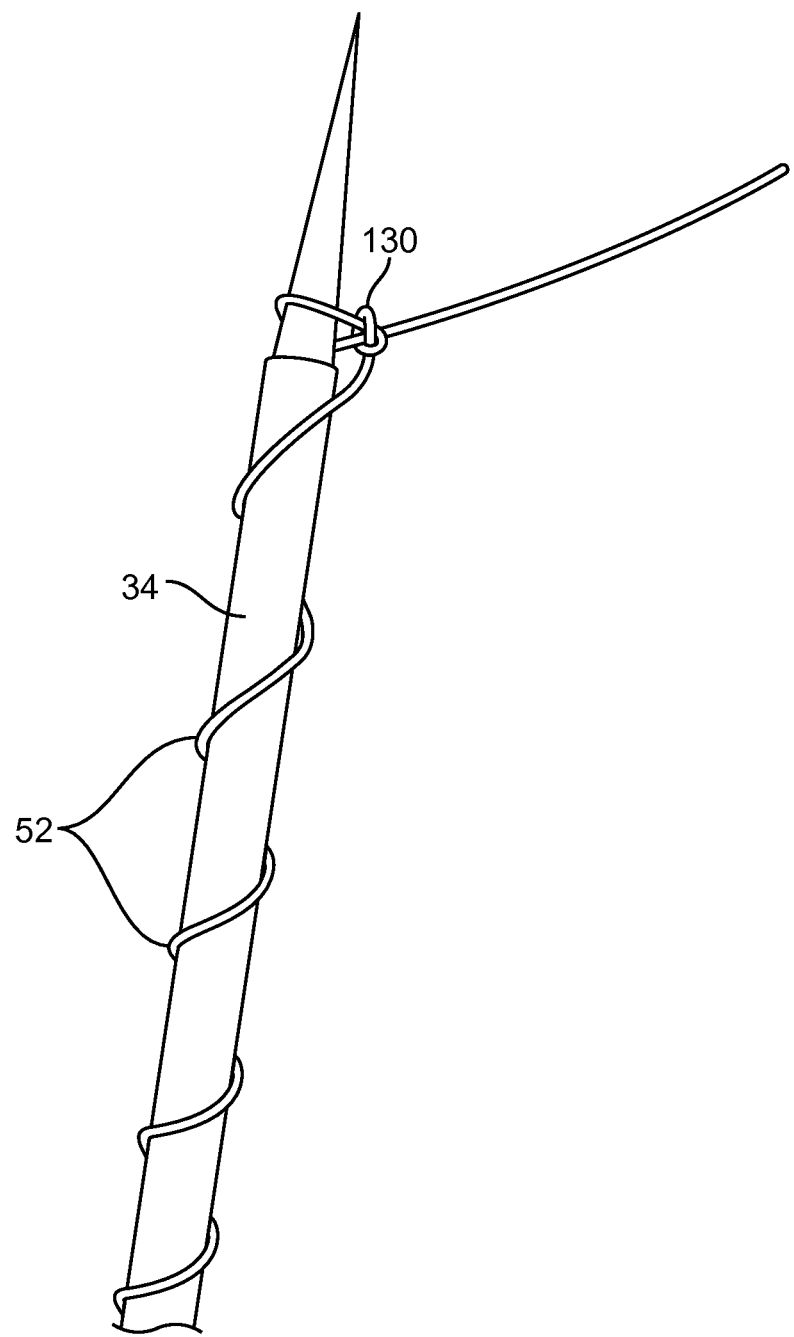
FIGS. 10A to 10F illustrate aspects of an experiment utilizing embodiments such as those shown in FIGS. 3A to 3H.
Figure 10B:
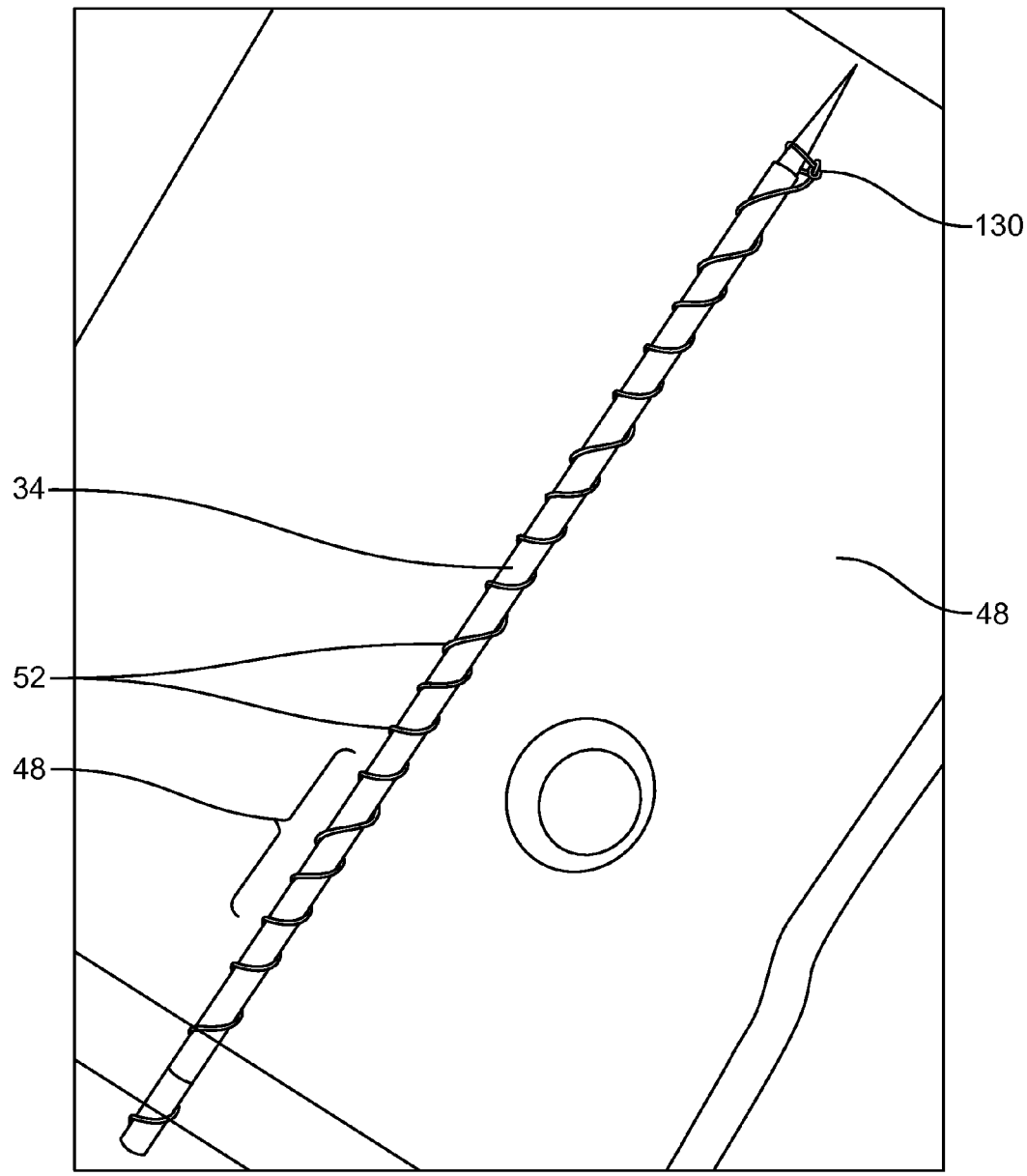
Figure 10C:
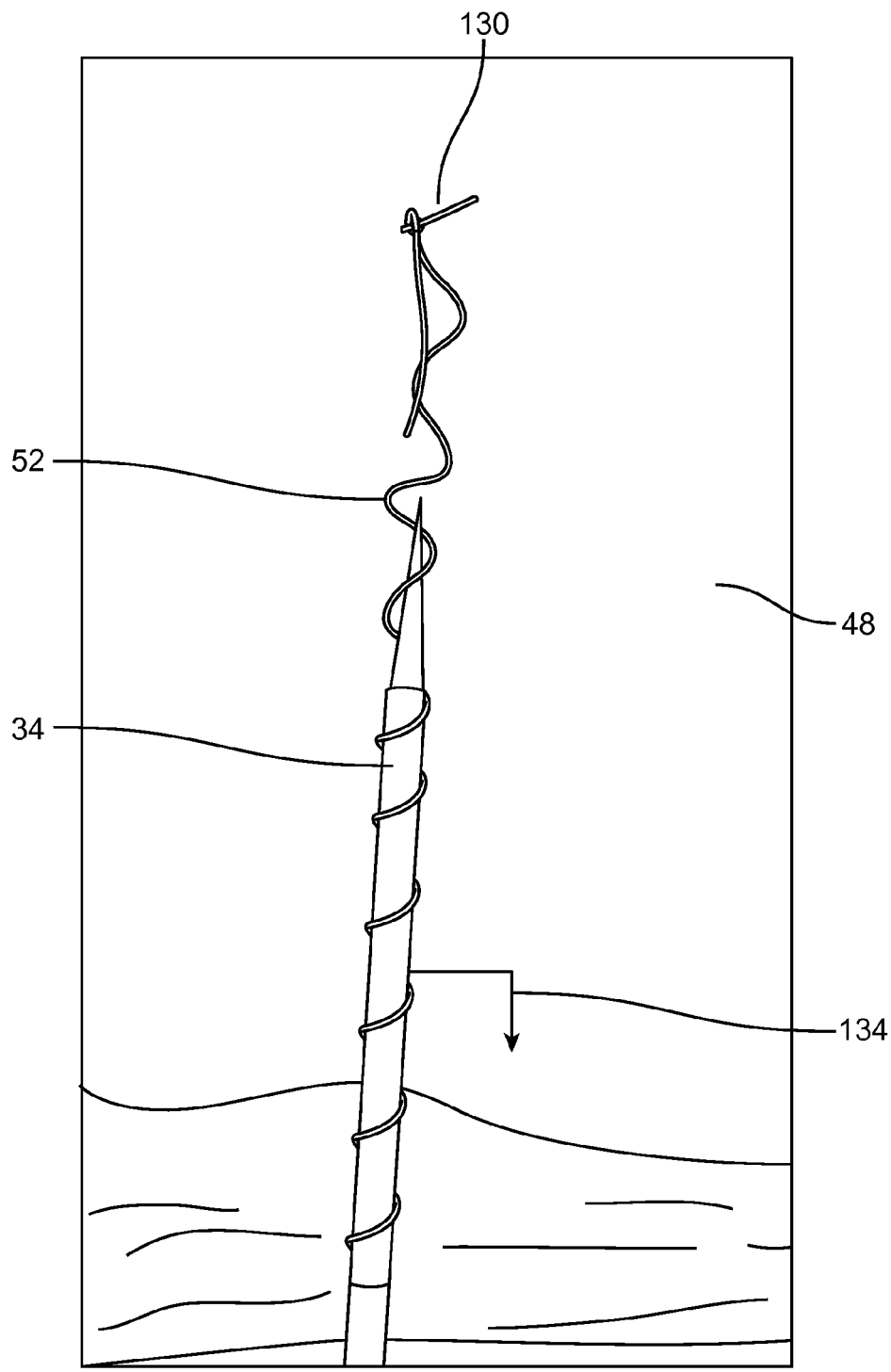
Figure 10D:
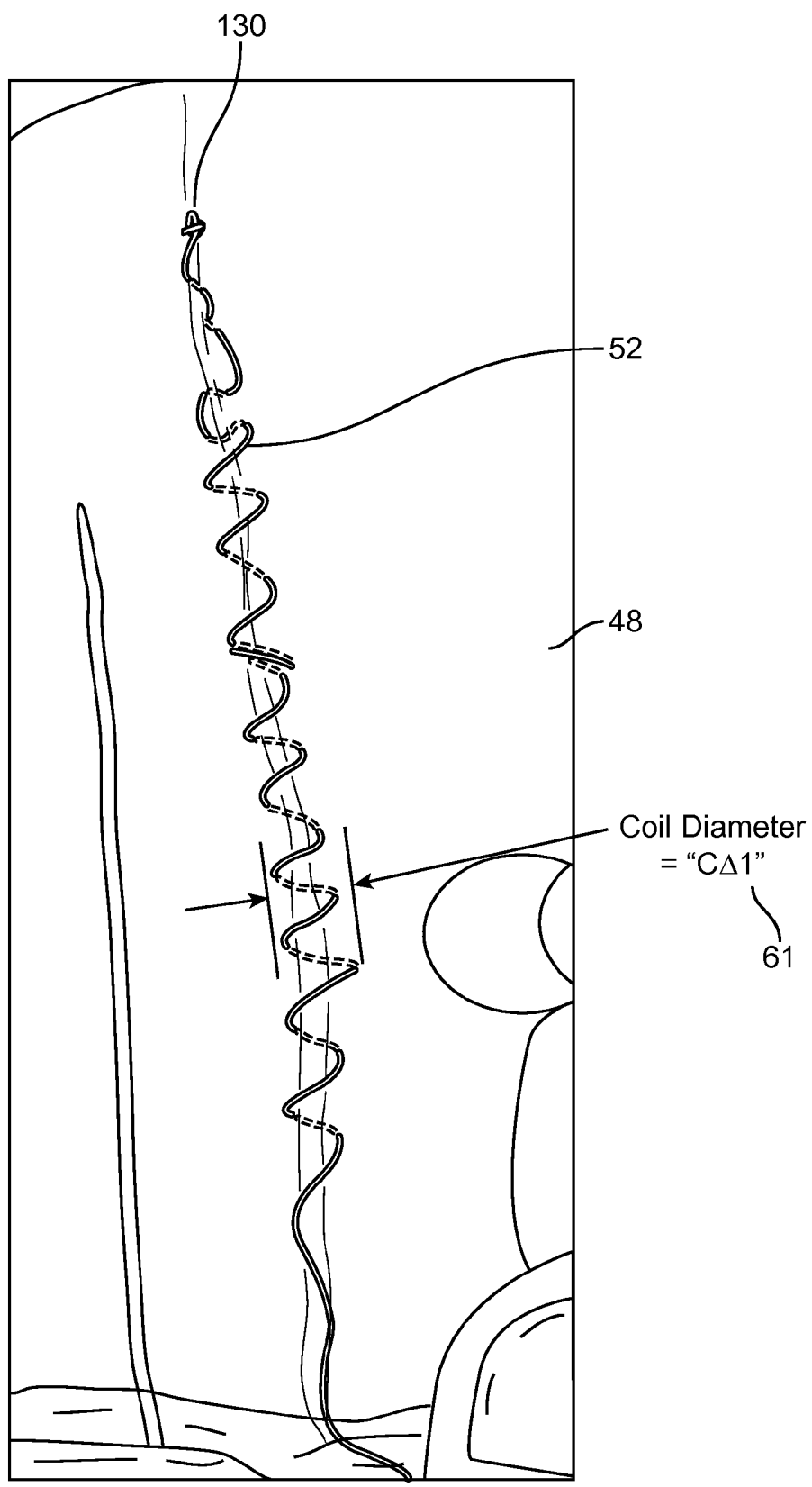
Figure 10E:
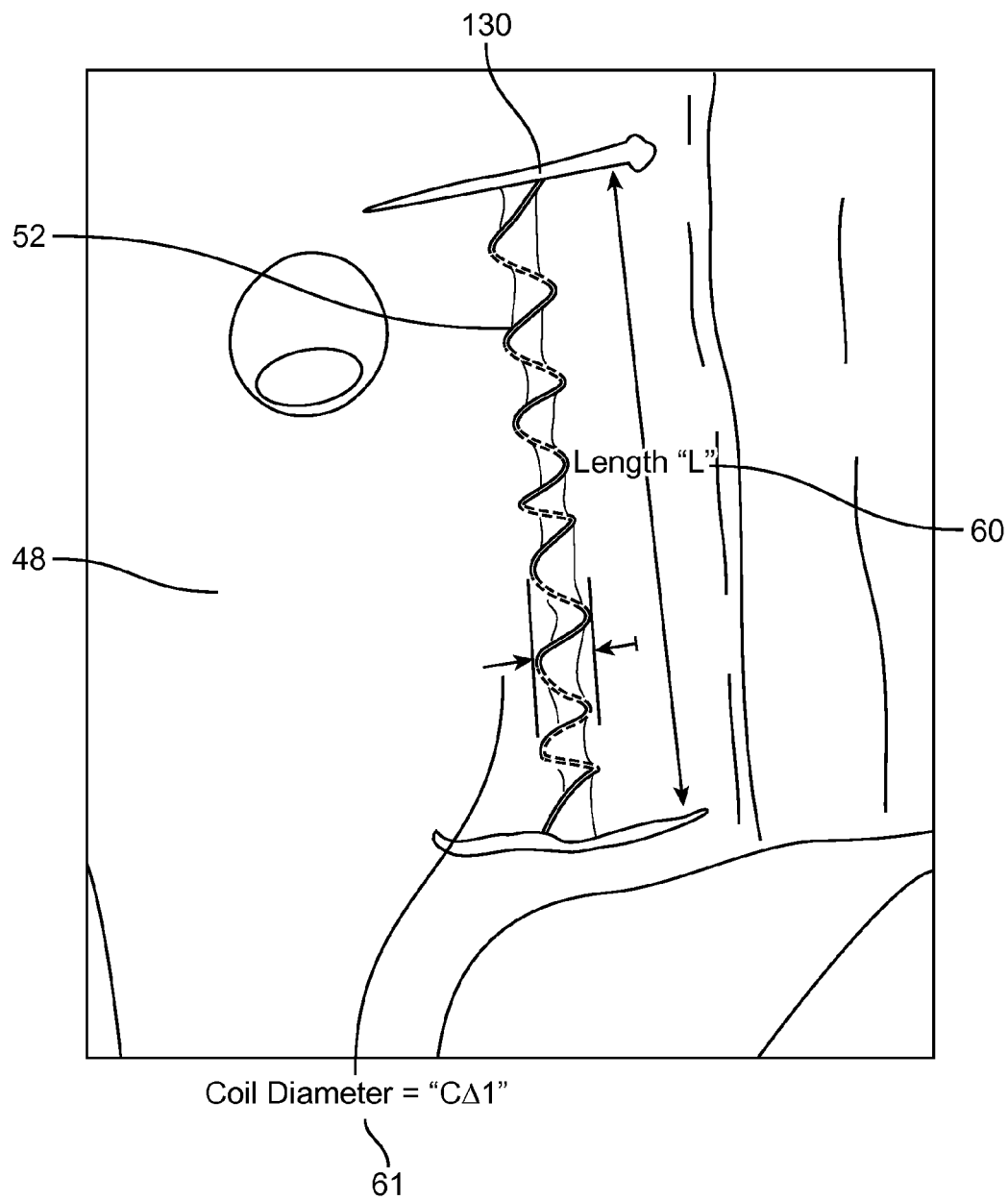
Figure 10F:
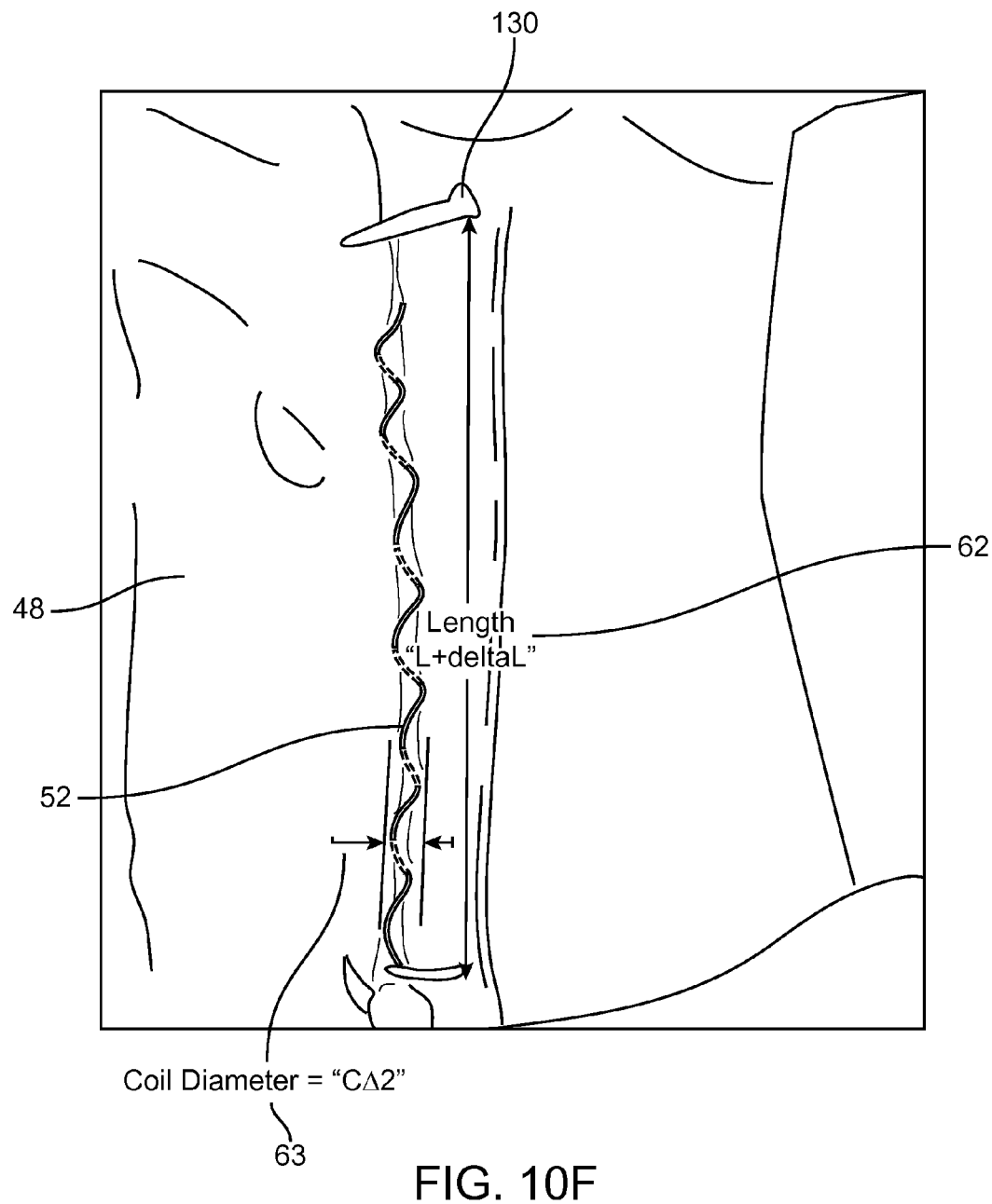

Referring to FIGS. 10A-10F, several images are depicted to illustrate the experiments we have completed to establish the flexibility and functionality of configurations such as those described in reference to FIGS. 3A-3H and 4A-4N. Referring to FIG. 10A, an elongate guiding member (34) is depicted with a suture (52) helically coupled thereto and terminated with a knot type anchoring element (130). Referring to FIG. 10B, with proximal tensioning of the suture (52) and advancement of the construct through a simulated tissue structure (48) (which happens to be conveniently translucent for experimental purposes), the helical patterning of the suture (52) relative to the elongate member (34) is retained along substantially the entire length of the elongate member (34) during insertion (i.e., there is no "bunching"). Referring to FIGS. 10C and 10D, with a release of the tensioning on the suture (52) and proximal withdrawal (134) of the elongate member (34), the suture (52) stays in place in its helical configuration. Referring to FIGS. 10E and 10F, with relatively significant strain (exemplified here by a strain from length L 60 to length L+deltaL 62; recall that strains as high as 200% to 300% or more may be accommodated), the helical patterning of the suture (52) is generally retained. With the strain applied (from FIG. 10E to FIG. 10F), the coil diameter (61) shrinks from CD1 to CD1 (63) as the localized length storage is used up.

Figure 11A:
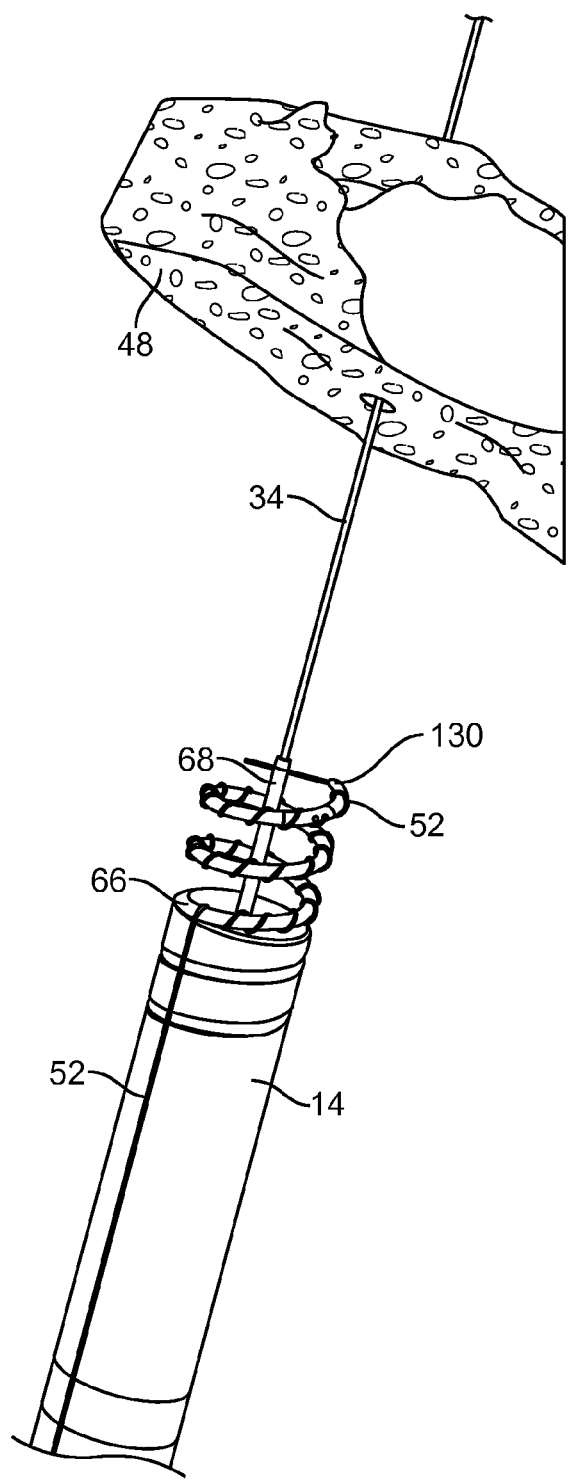
FIGS. 11A to 11J illustrate aspects of an experiment utilizing embodiments such as those shown in FIGS. 4A to 4N.
Figure 11B:
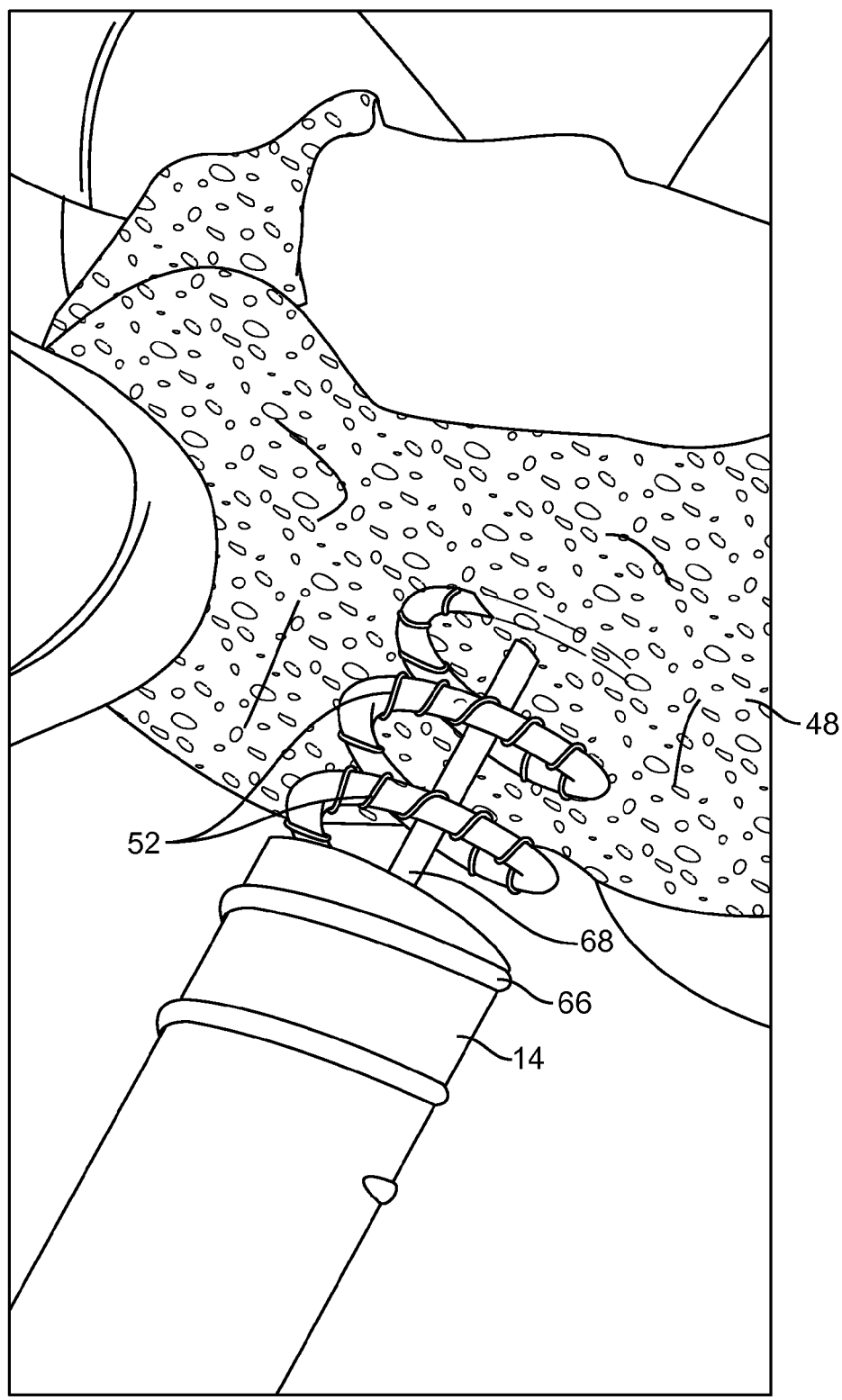
Figure 11C:
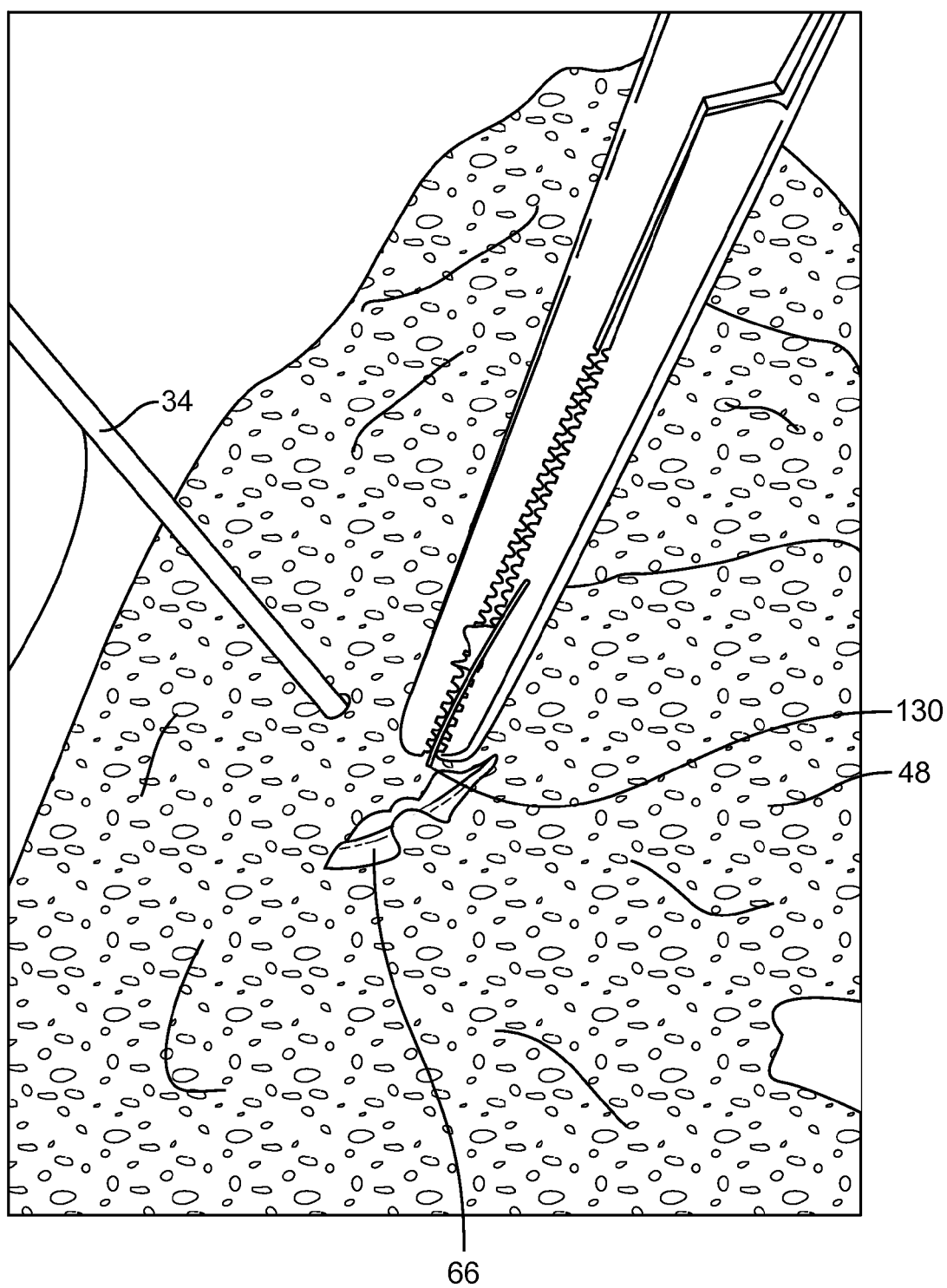
Figure 11D:
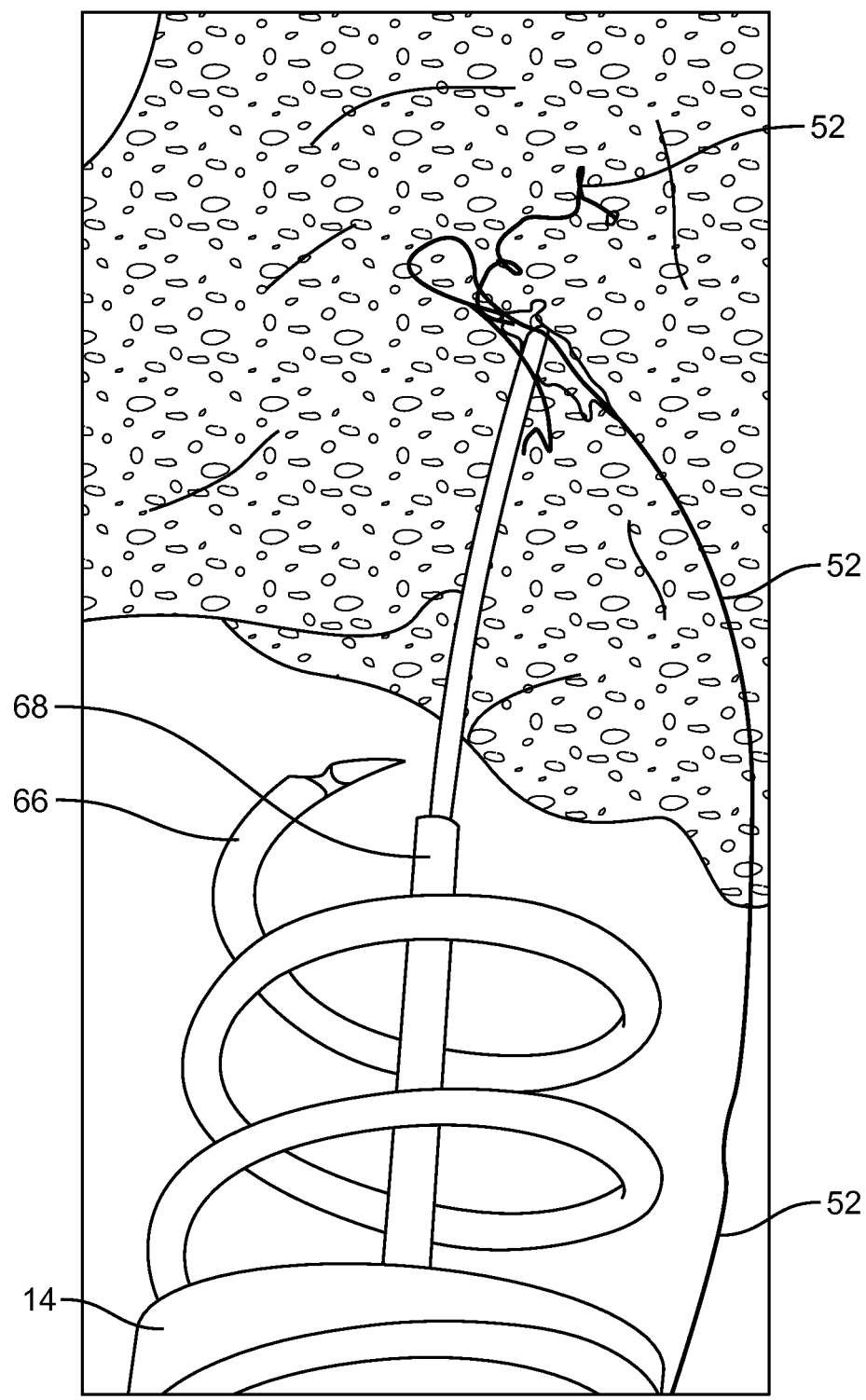
Figure 11E:
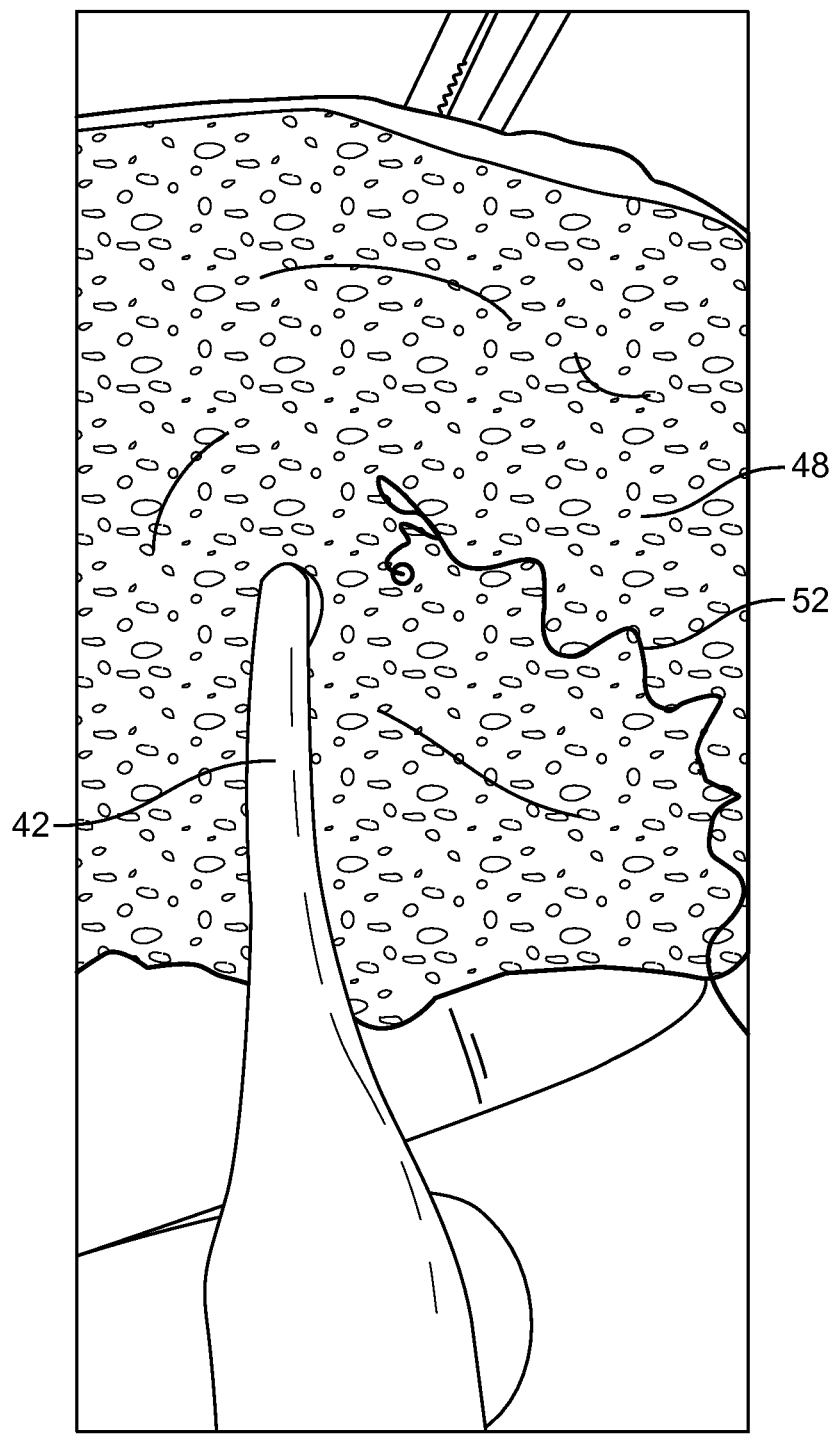
Figure 11F:
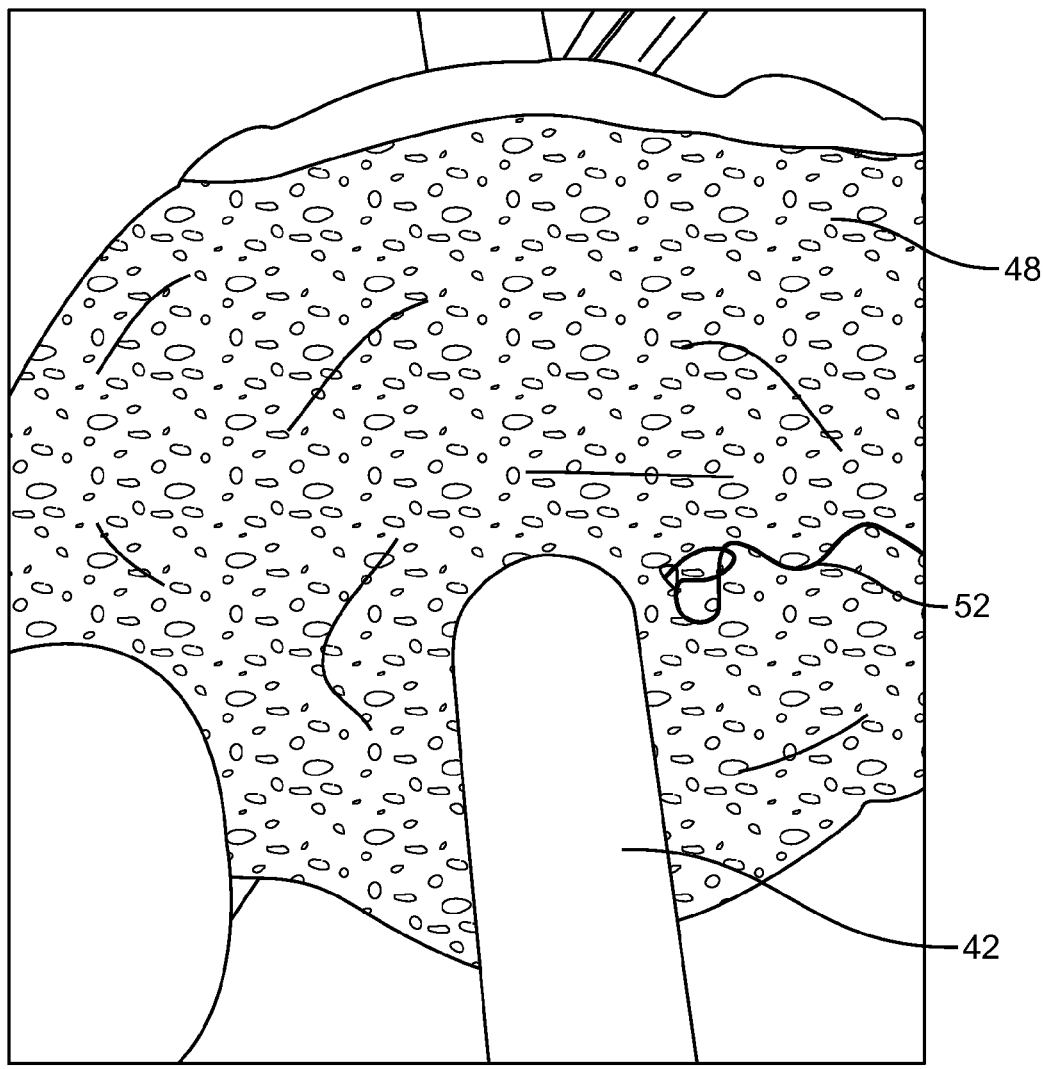
Figure 11G:
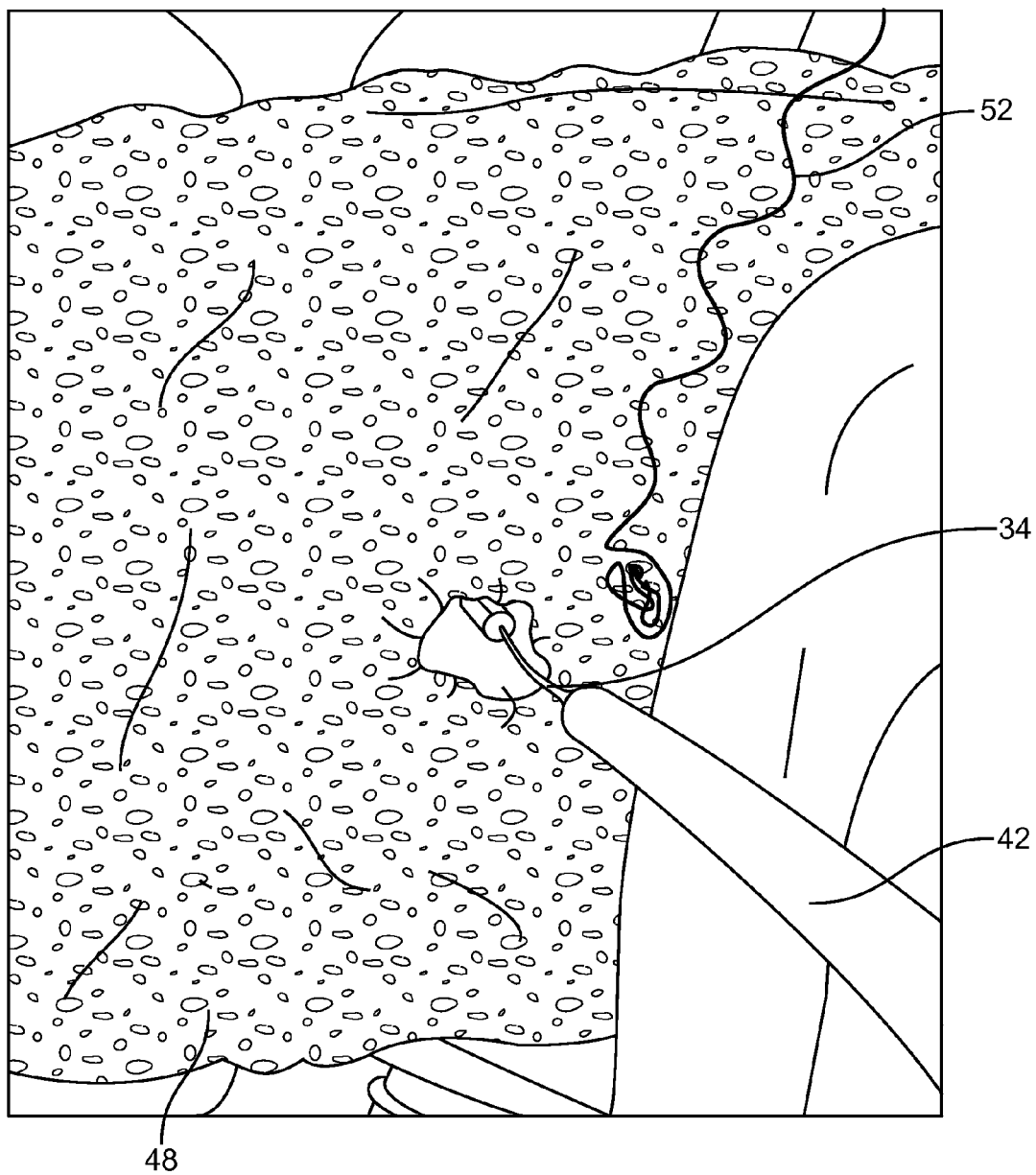
Figure 11H:
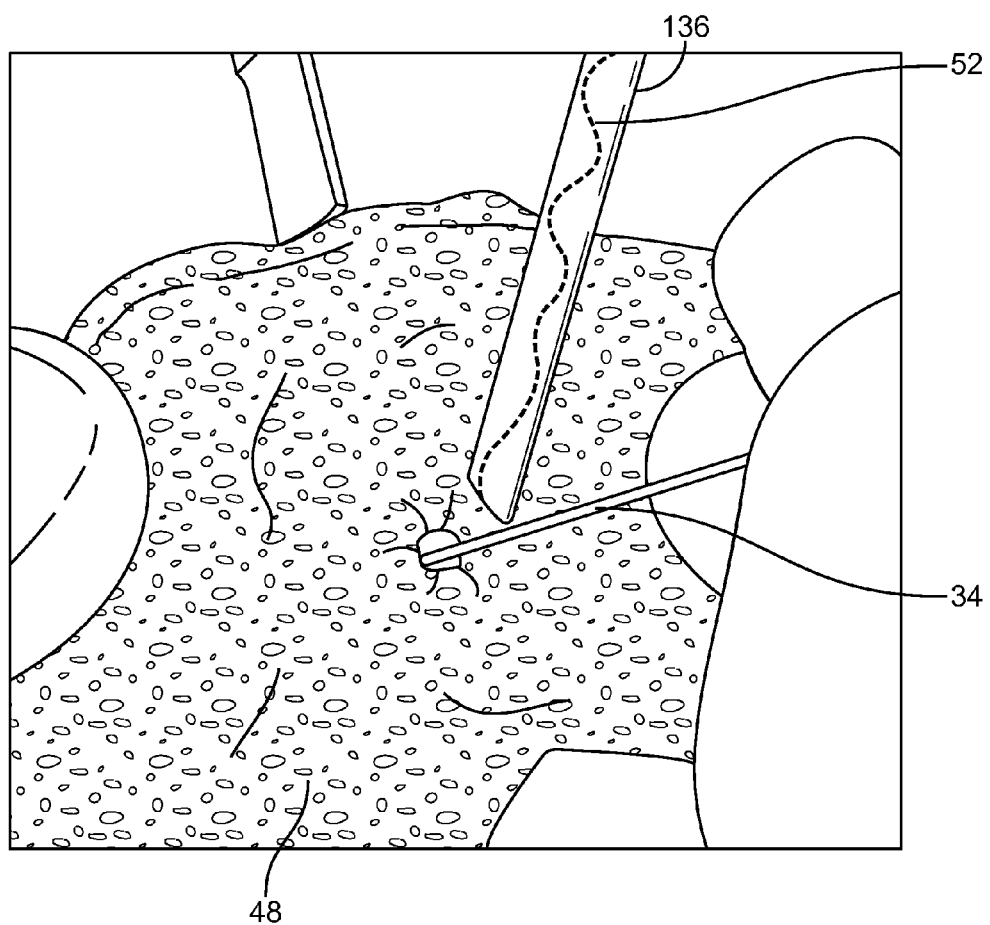
Figure 11I:
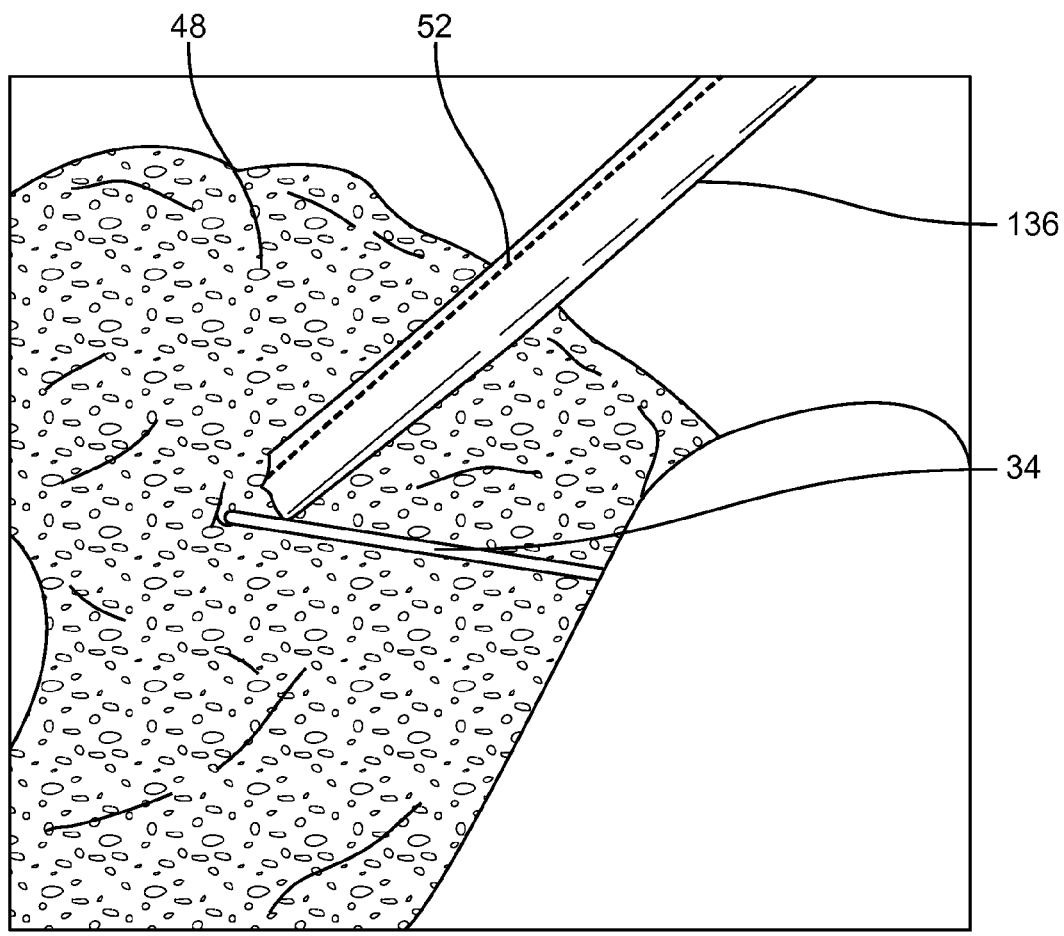
Figure 11J:
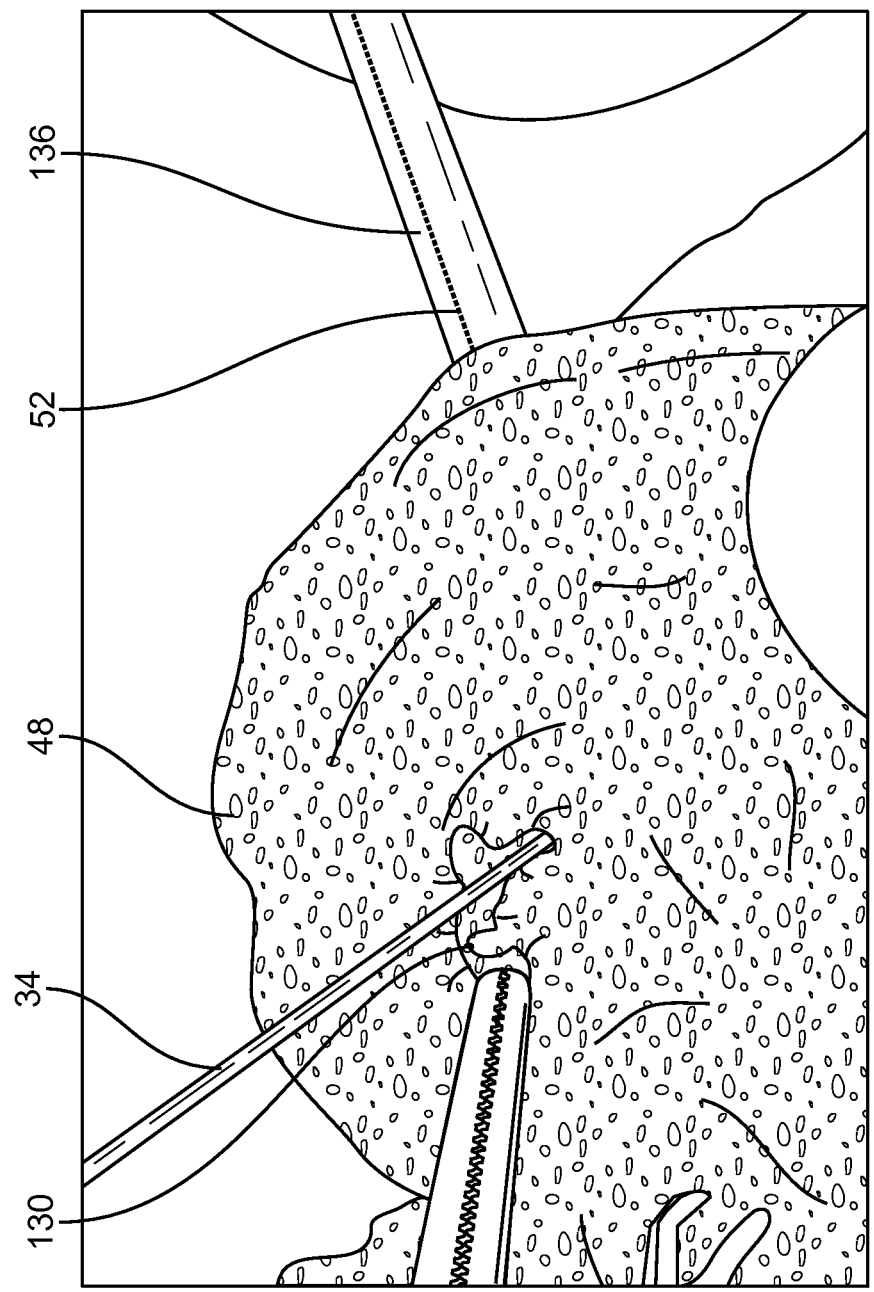
Figure 12A:
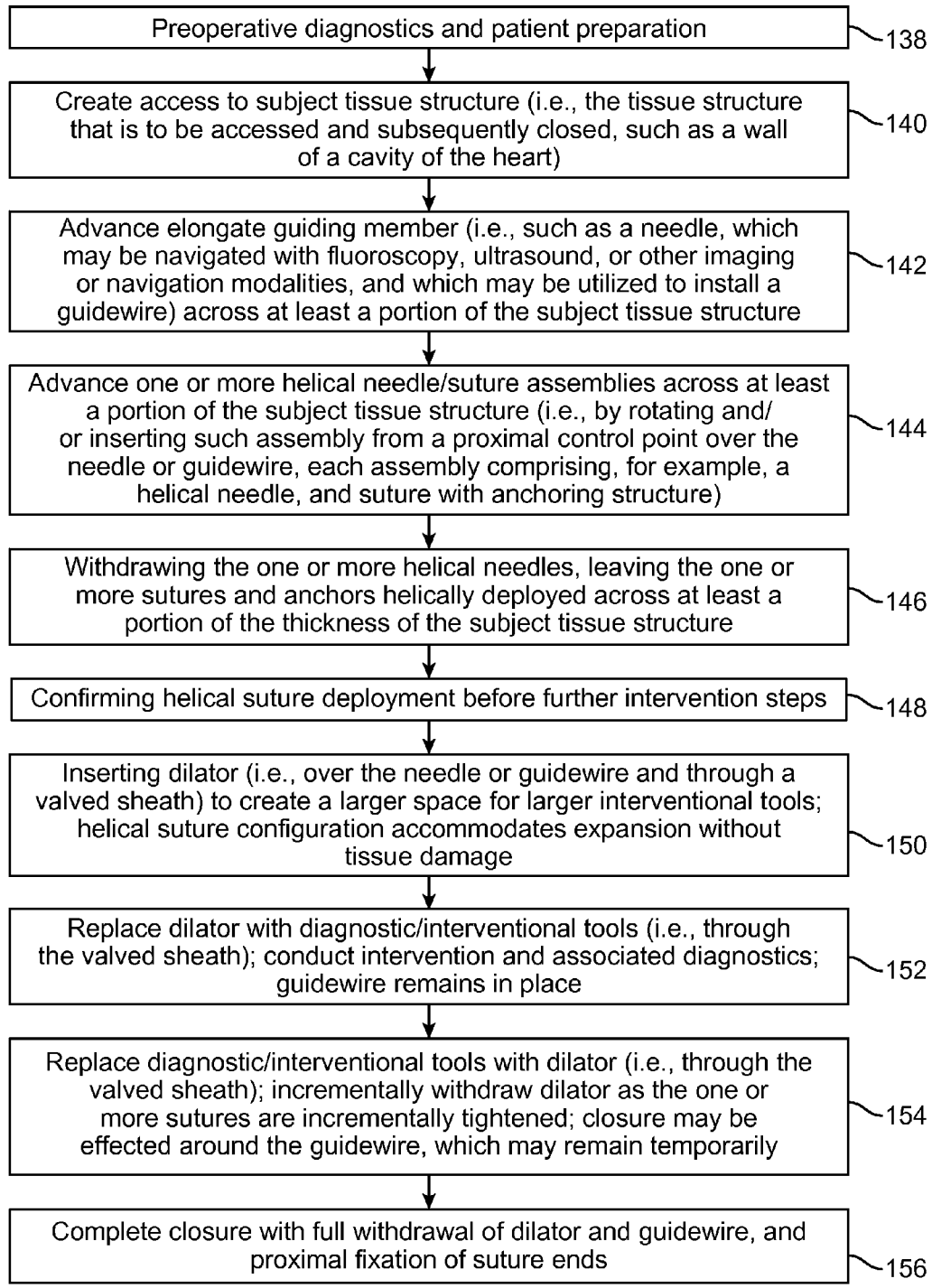
FIGS. 12A to 12C depict techniques for implementing various embodiments of the subject helical closure configurations.
Figure 12B:
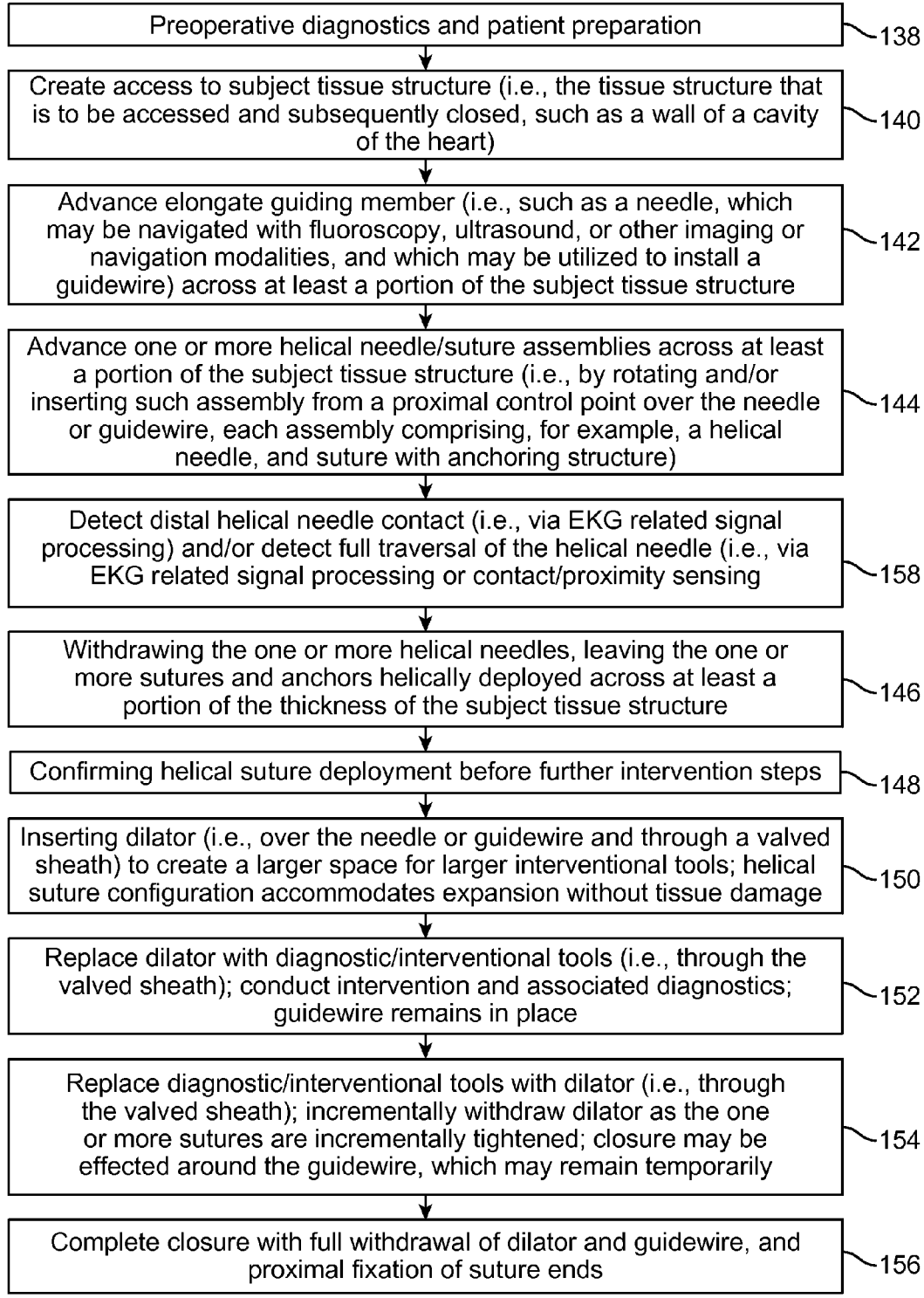
Figure 12C:
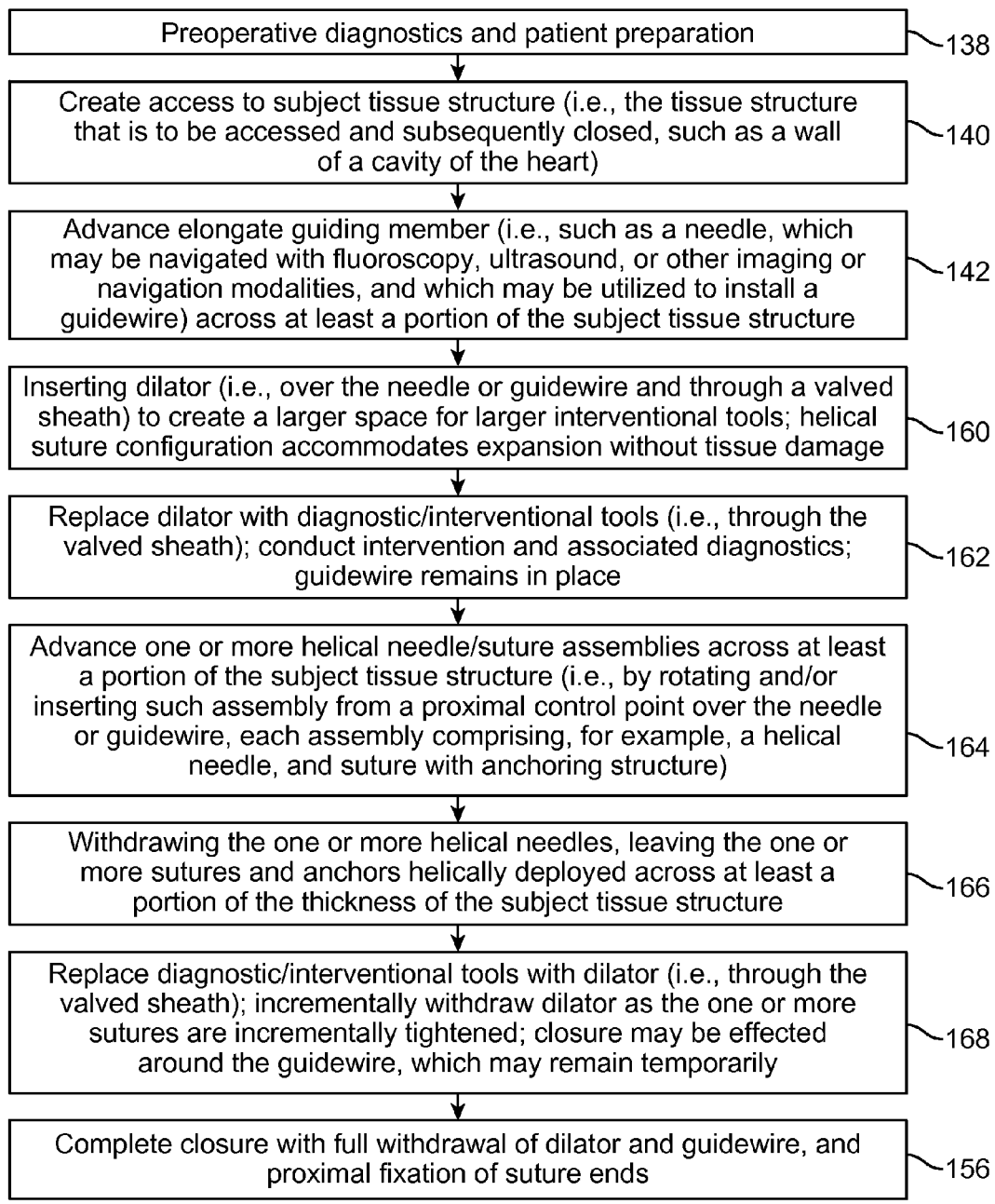

Referring to FIGS. 11A-11F, several images are depicted to illustrate the experiments we have completed to establish the flexibility and functionality of configurations such as those described in reference to FIGS. 4A-4P. Referring to FIG. 11A, a deployment member (14) coupled to a single helical member (66) and tracking member (68) is depicted, with the tracking member (68) being advanced over an elongate guiding member (34) that has been deployed across a muscle tissue wall (48). A single suture (52) is helically wound around the helical member (66) and terminated with a knot anchoring element (130). FIG. 11B shows the construct being advanced and helically rotated into the tissue wall (48) with a tension being retained on the suture (52) from a proximal location. Referring to FIG. 11C, on the opposite side of the tissue wall (48), the anchoring knot element (130) has reached the other side adjacent to the location wherein the elongate guiding member (34) passes out of the tissue wall (48). Importantly, a uniform radial margin of tissue is retained between the helical needle (66) and the center of the wound adjacent the elongate guiding member (34) (i.e., the suture is not lacerating through the tissue). Referring to FIG. 11D, with release of the tension on the suture (52) and withdrawal/counterrotation of the deployment assembly (66, 68, 14), the deployed suture (52) retains its compound helical configuration within the muscle tissue. FIG. 11E depicts a dilator (42) being advanced through the deployed suture compound helix, and FIG. 11F depicts further advancement to illustrate that relatively significant dilation may be required to accommodate various diagnostic and/or interventional tools for various procedures—and that the compound helical suture configuration is quite flexible in accommodating such large dilations, while retaining the ability to be controllably tightened from a proximal location at any time. It is worth noting that in our experiments, proximal tightening of a single helical suture configuration (i.e., deployed with a helical needle but not with helical coiling in a helical pattern) resulted in significant undesirable laceration of the tissue (particularly the tissue captured between the helical needle/suture and the wound centerpoint), something that we have not found with the compound helical deployment, due to the localized length storage provided with the coiling. FIG. 11G shows that a relatively large wound or port has been created following removal of the dilator (42). Referring to FIG. 11H, with a simple sheath (136) to isolate the free proximal portion of the suture (52), tensioning of the suture (52) to execute a closure or partial closure may be initiated. Referring to FIG. 11i, with further tensioning of the suture (52), the wound or port is closed around the elongate guiding member (34). Referring to FIG. 11J, on the opposite side of the wall, the suture (52) and anchor element (130) based closure execution is evident.

Referring to FIGS. 12A-12C, techniques for utilizing the subject configurations are illustrated. Referring to FIG. 12A, after preoperative diagnostics and patient preparation (138), access may be created (140) to the subject tissue structure (for example, a thoracotomy may be created to access the wall of the heart, the heart wall being the subject of the subsequent wall crossing and closure). The subject tissue structure may be at least partially crossed (142) using an elongate guiding member such as a needle, which may be navigated utilizing various imaging, sensing, and/or navigation modalities. The needle may be followed by a guidewire (i.e., a guidewire advanced through the needle). One or more helical needle/suture assemblies may be advanced (144) across a portion of the tissue wall following the elongate guiding member (or in another embodiment, without the assistant of a guiding member); then the helical member may be axially and rotationally withdrawn to place an anchoring element and compound helical suture into a configuration wherein they may be subsequently utilized to effect a closure (146), and such configuration may be confirmed (148) before further interventional steps. Subsequent to confirmation that a closure configuration appears to be ready, a dilator (150) and/or other tools (152) may be advanced through the suture helix, thereby expanding the suture helix so that pertinent diagnostic and/or interventional steps may be accomplished, such as the installation of a heart valve. Subsequently, the dilator may be re-inserted (i.e., using a hemostatically-valved sheath) in place of the diagnostic and/or interventional tools (154), and the tapered outer shape of the dilator may be utilized to effect an incremental tightening of the wound or port. A guidewire may be left in place as a "test closure" is accomplished around the guidewire to permit observation of the intervention while also permitting easy re-access. The closure may be completed with full withdrawal of the dilator, needle, and guidewire, and proximal fixation of the suture end or ends to retain tension (156).

Referring to FIG. 12B, an embodiment similar to that of FIG. 12A is depicted, with the exception that traversal of the deployment assembly may be detected using sensors such as an EKG (electrocardiogram) electrode or a proximity/contact sensor, such as an ultrasound transducer and analysis system and/or an OCT fiber and signal processing system (158). In another embodiment such as that described in reference to FIG. 4D, another EKG-signal related sensor coupled to a distal portion of the needle may be utilized to detect initial contact of the needle and heart wall.

Referring to FIG. 12C, an embodiment similar to that of FIG. 12A is depicted, with the exception that after crossing the subject tissue structure with an elongate guiding member (142), a dilator and other tools are advanced into place and utilized (160, 162) before deployment of any compound helical sutures through advancement of pertinent helical members/sutures/anchors (164) and withdrawal (166) of the helical members to leave the sutures and anchors behind. With one or more compound helical sutures and anchor elements in place, the tools may be withdrawn, and an incremental tightening/closure effected (168), followed by completion of the closure and fixation of the pertinent proximal suture ends (156).

Figures 13, 14:
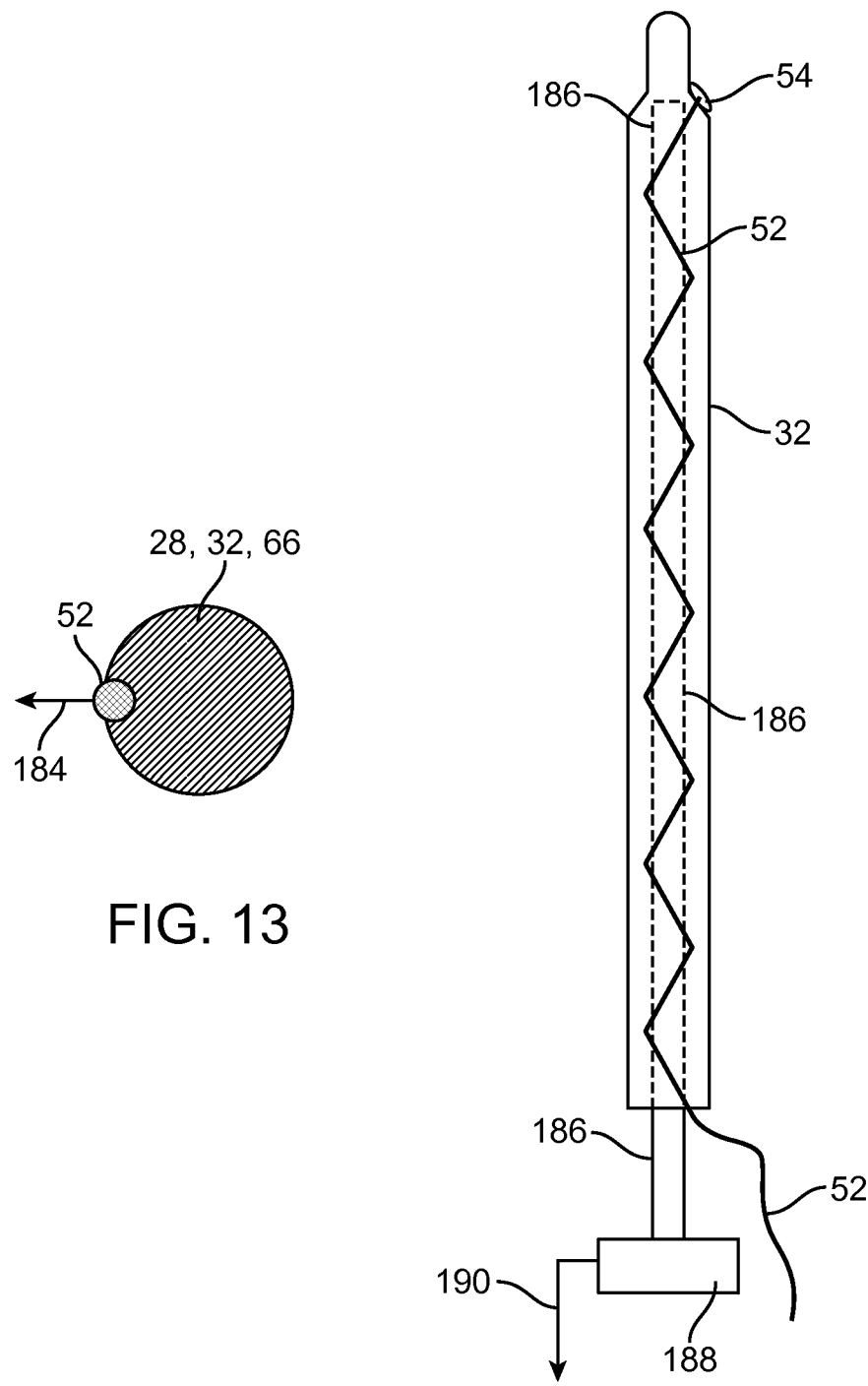
FIG. 13 illustrates one needle structure embodiment having a channel formed therein for localized suture storage.
FIG. 14 illustrates one needle and suture arrangement wherein a sawtooth pattern is utilized for localized length storage functionality.

Referring to FIG. 13, localized length storage of suture material (52) relative to a needle structure (28, 32, 66) may be facilitated wherein the needle structure (28, 32, 66) defines a channel into which the suture material (52) may be fitted during deployment; preferable the fit with such channel is loose enough that the suture material (52) will deploy (184) easily out of the channel as the needle structure (28, 32, 66) is withdrawn.

Various suture (52) materials may be utilized in accordance with the subject invention, including resorbable and nonresorbable polymeric sutures, woven sutures, highly stretchable sutures (the "stretch" of which may be utilized to facilitate localized length storage functionality), and metallic sutures or suture-like structures, such as fine gauge nitinol wire configured to form a compound helix as described above. Referring to FIG. 14, a sawtooth pattern of a suture (52) may be utilized for localized length storage functionality in relation to a needle device (32). In the depicted embodiment, after insertion, a proximal tag (188) coupled to a removable coupling member (186) that temporarily holds a "zig zag" or "sawtooth" suture length storage pattern in place may be pulled (190), allowing the suture (52) to uncouple from the needle (32), akin to the unfurling action of the aforementioned compound helical configurations.

Figure 15A:
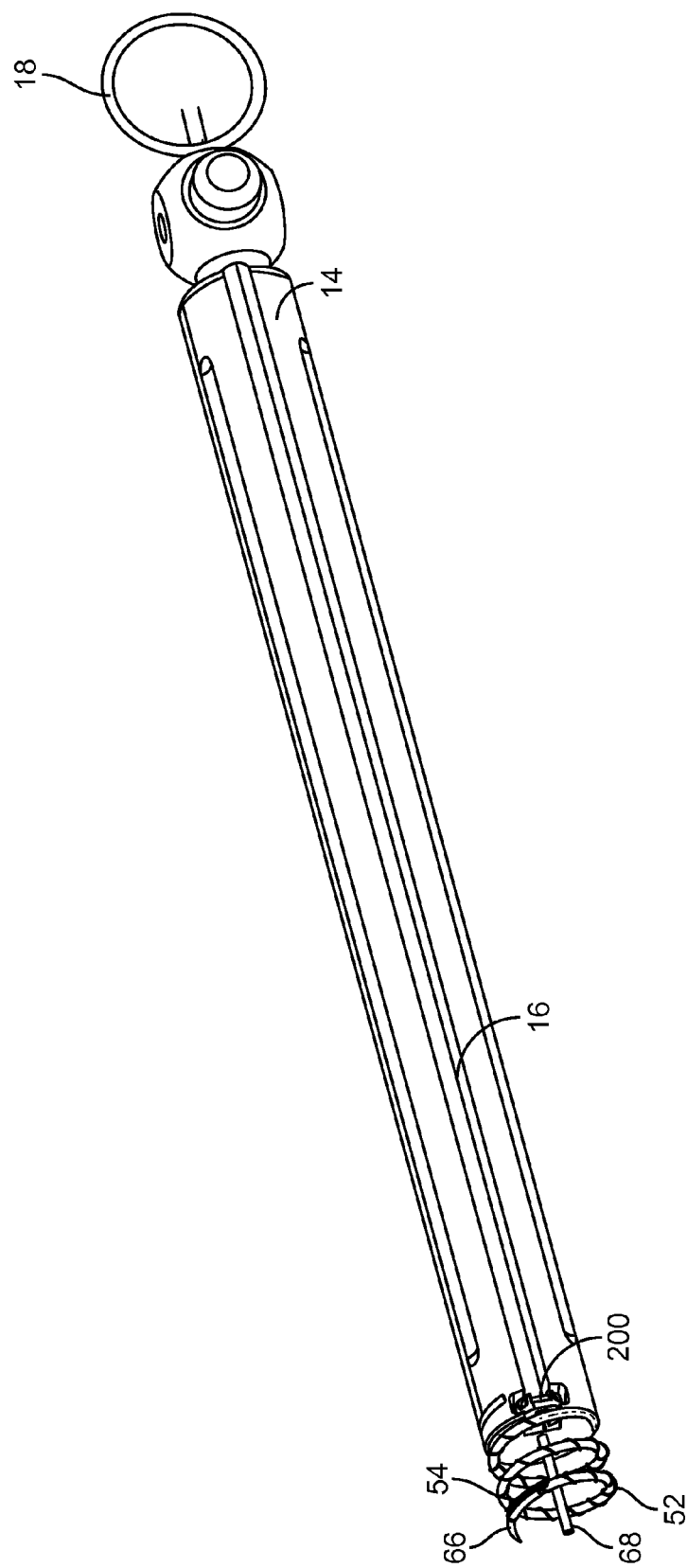
Figure 15B:
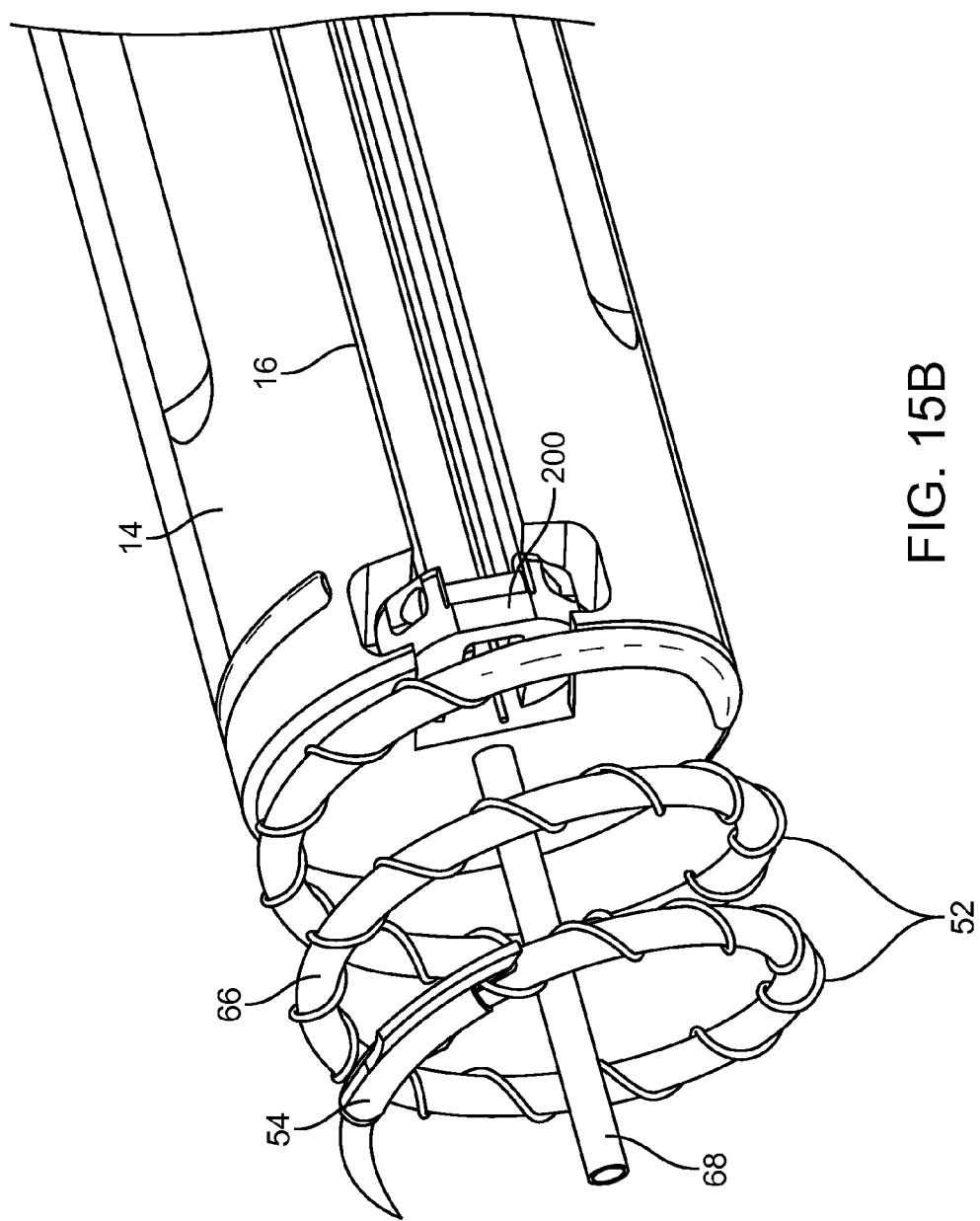
Figure 15C:
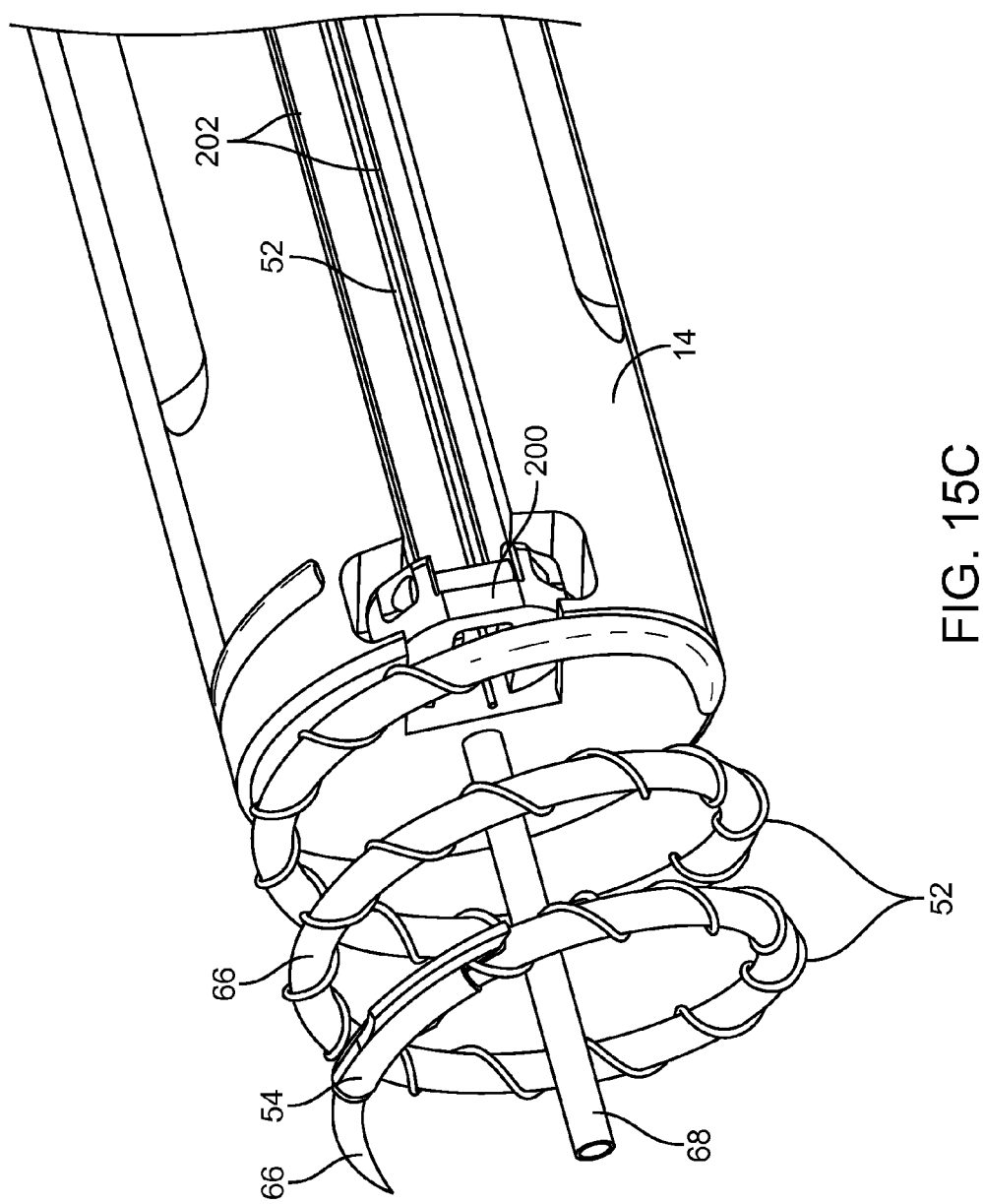
Figure 15D:
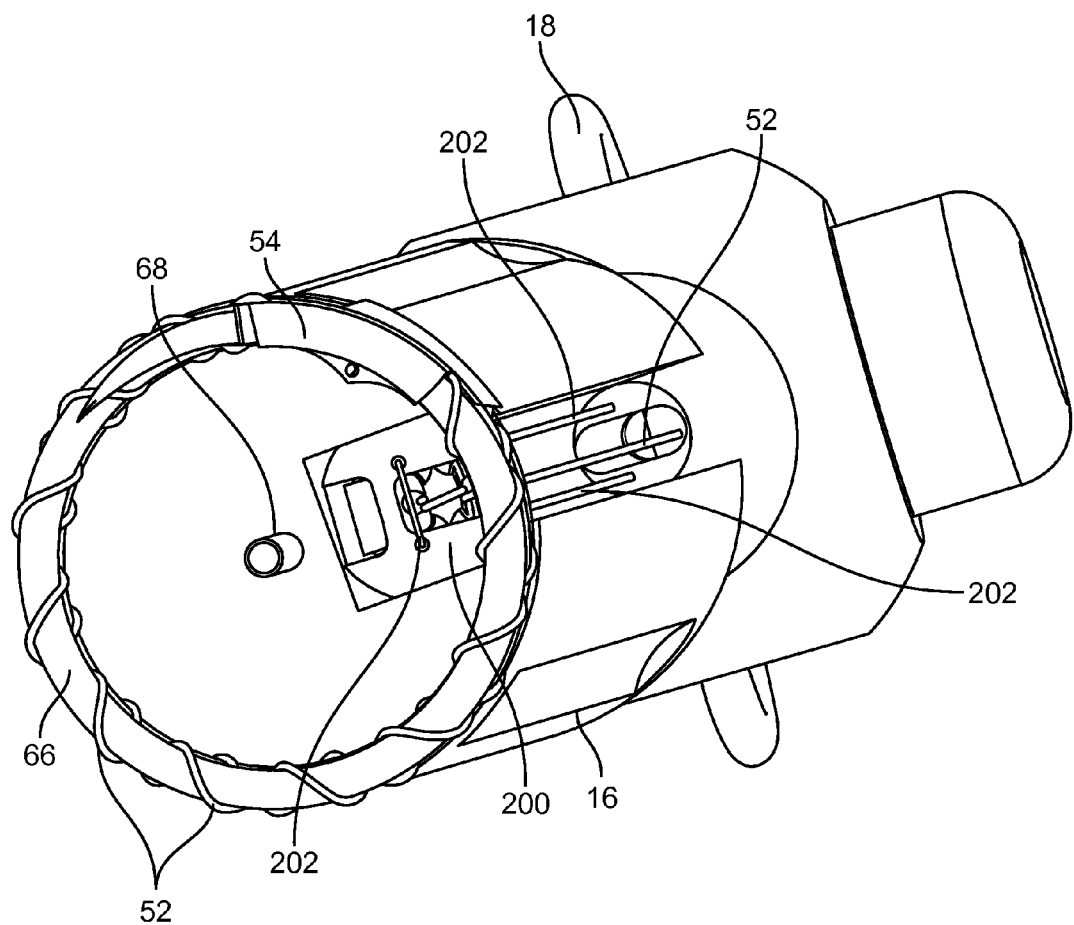
Figure 15E:
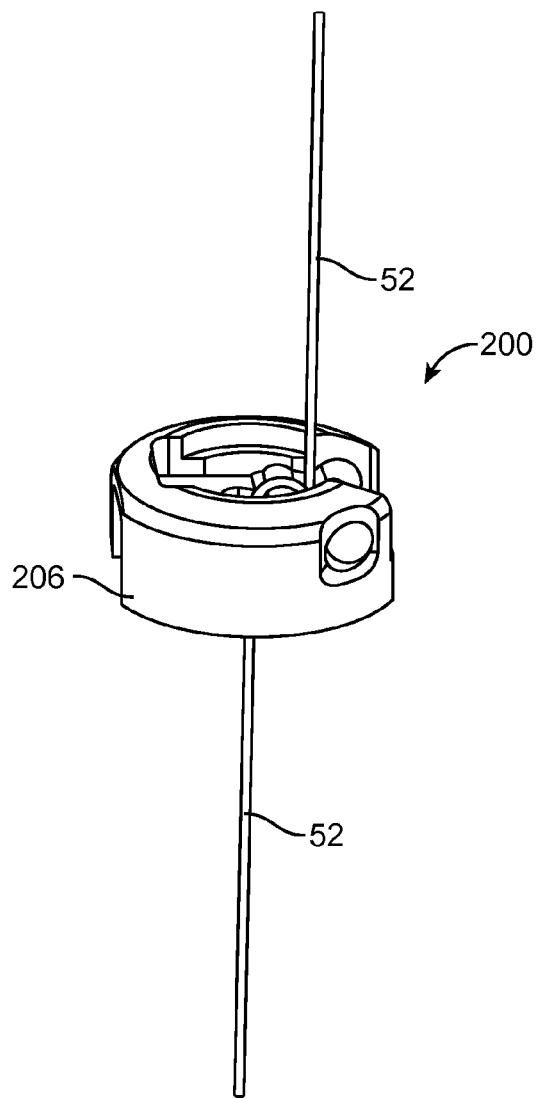
Figure 15F:
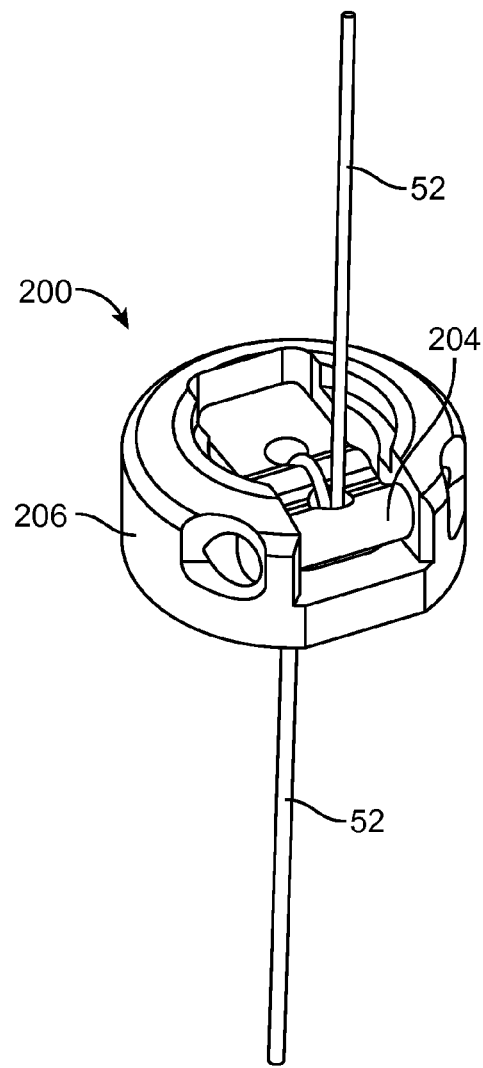
Figure 15J:
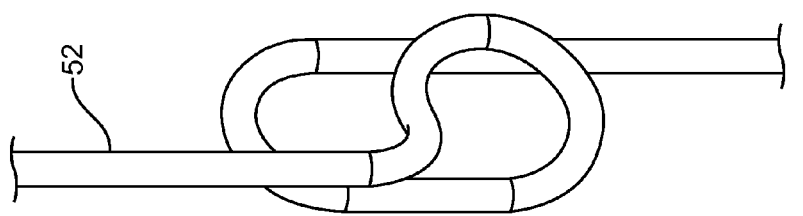
Figure 15I:
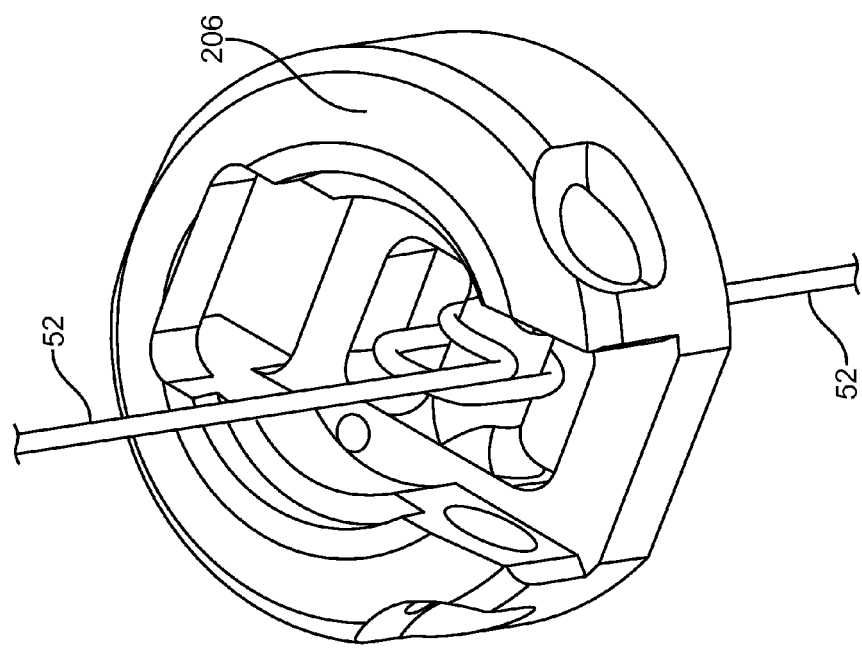
Figure 16:
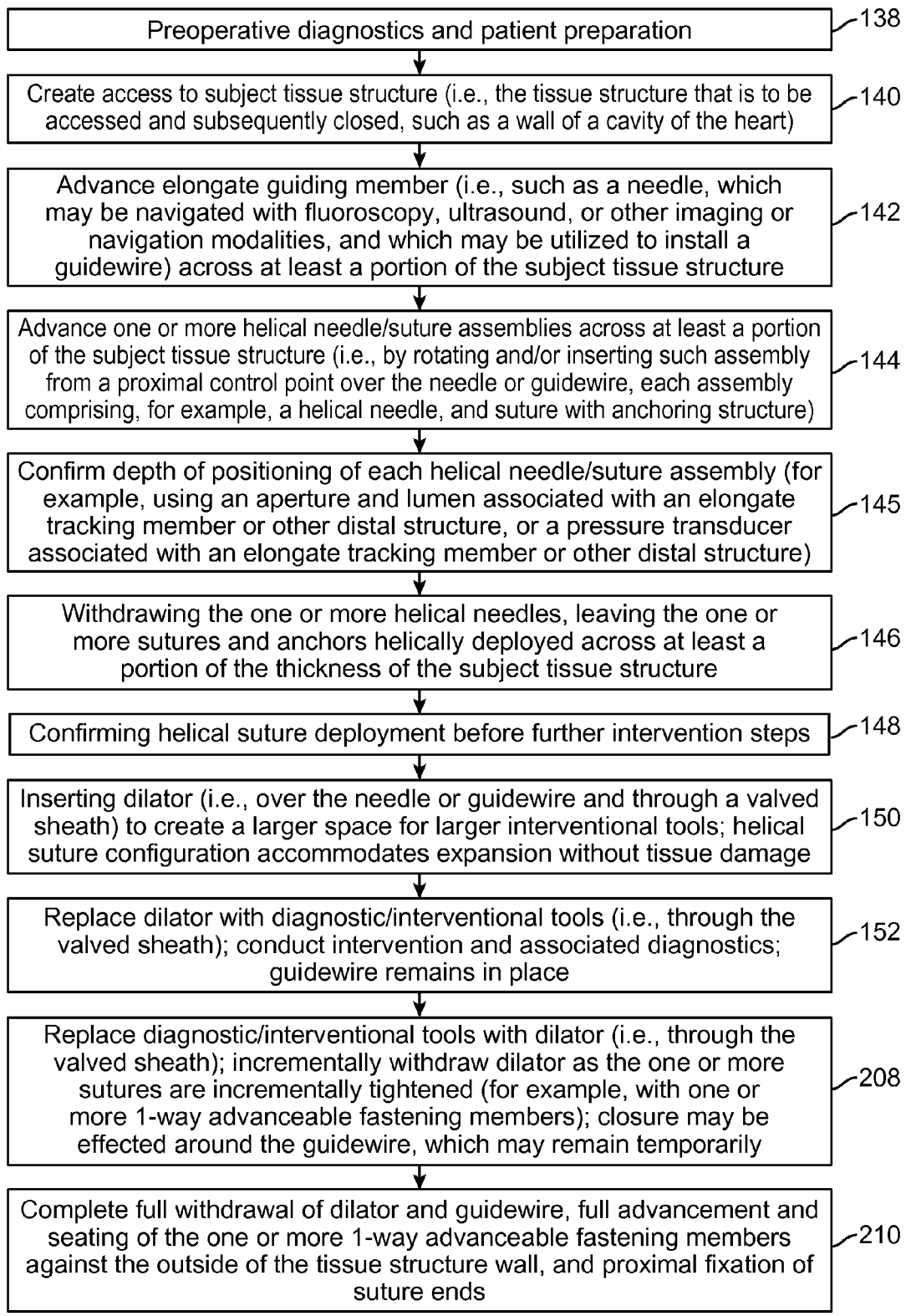
FIG. 16 illustrates a technique for implementing various embodiments of the subject helical closure configurations.
Figure 17A:
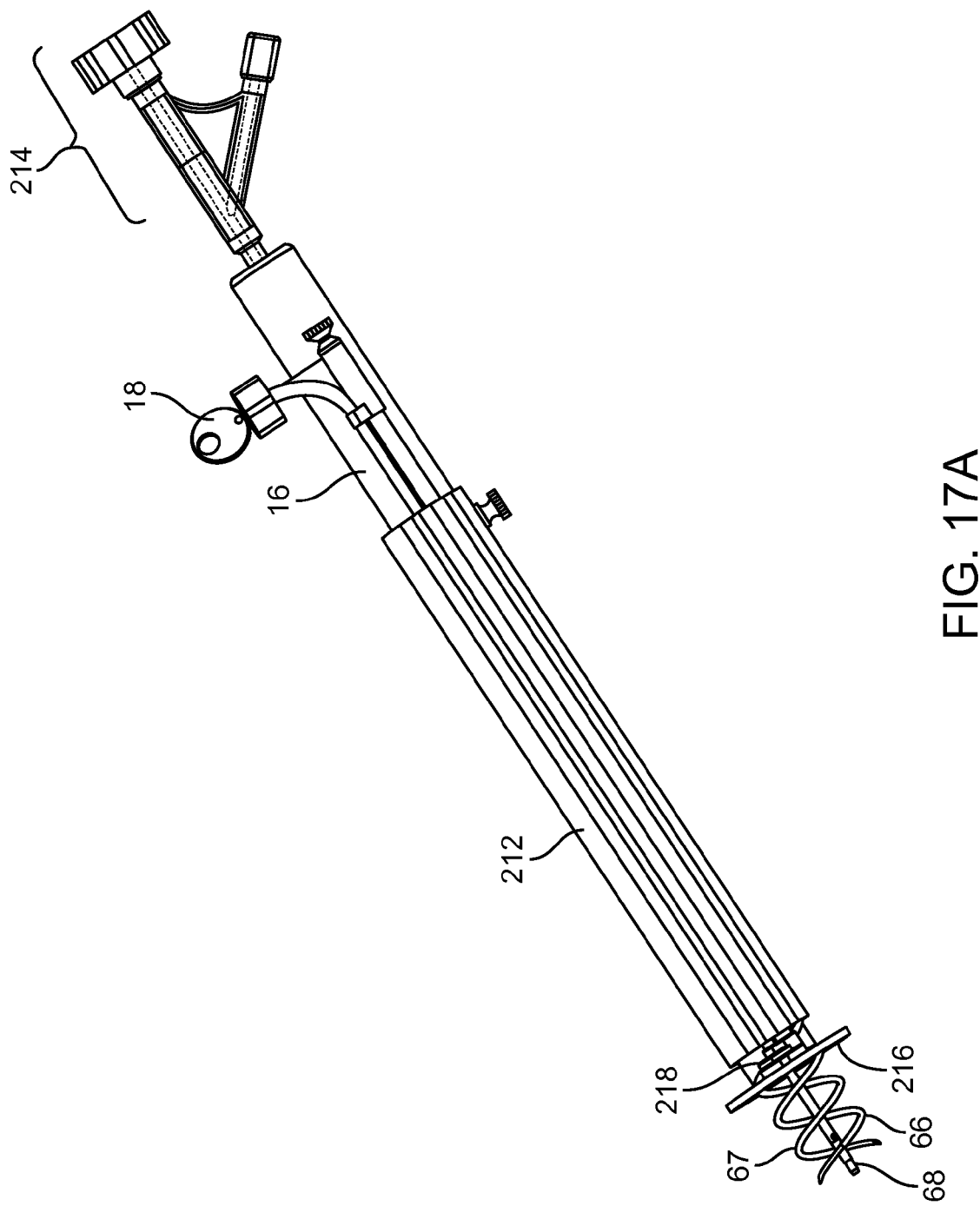
FIGS. 17A-17F illustrate various aspects of a compound helical closure configuration featuring a pair of helical members and a controllably-locking tension retainer.
Figure 17B:
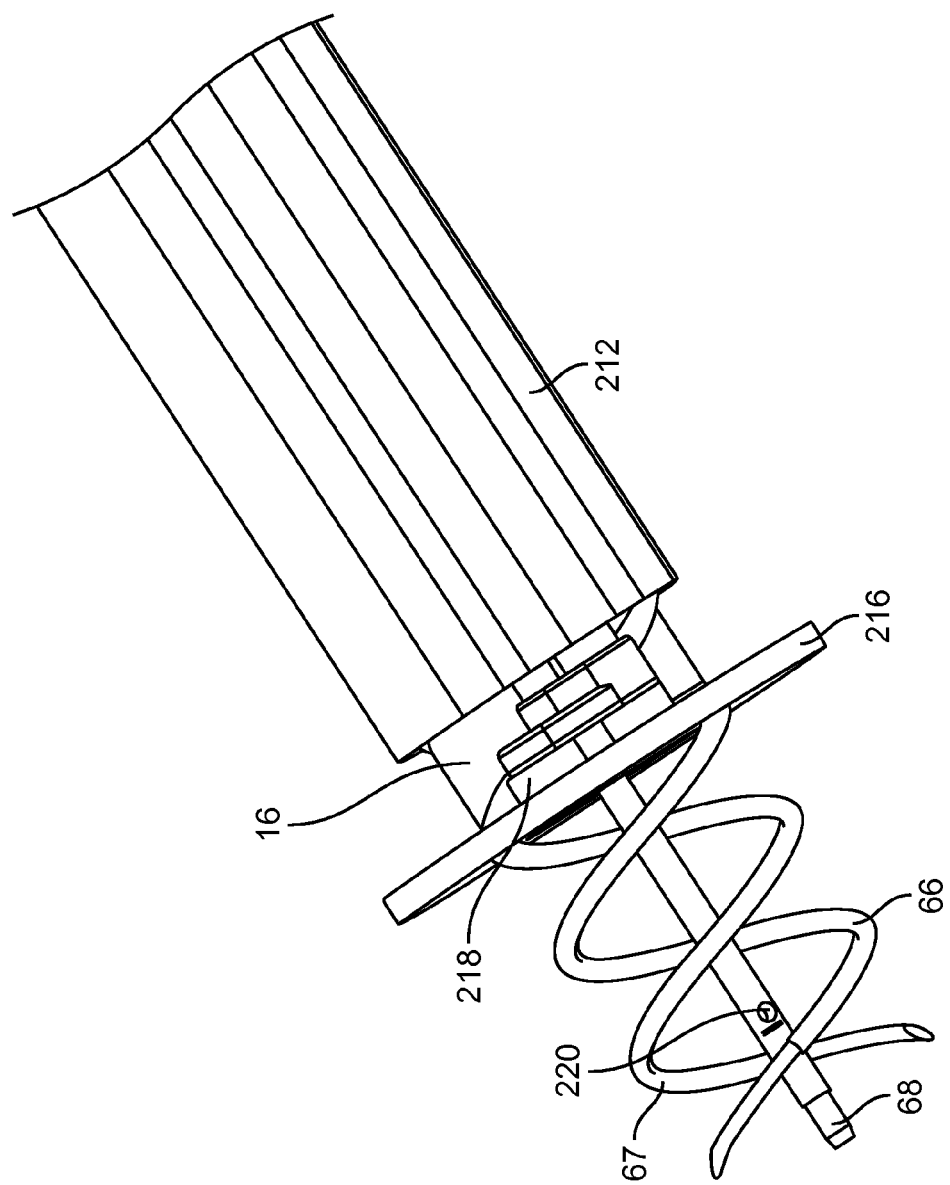
Figure 17C:
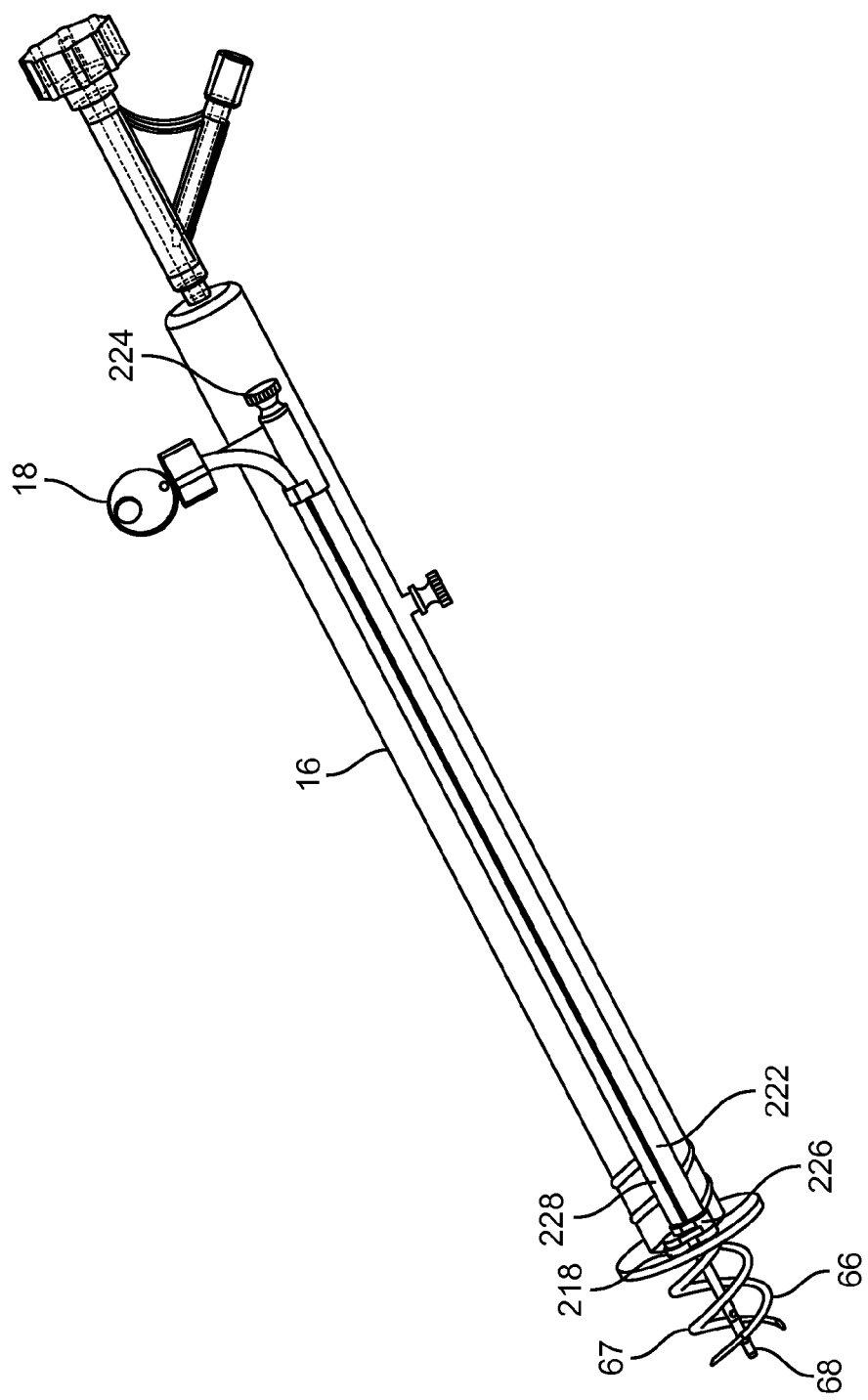
Figure 17D:
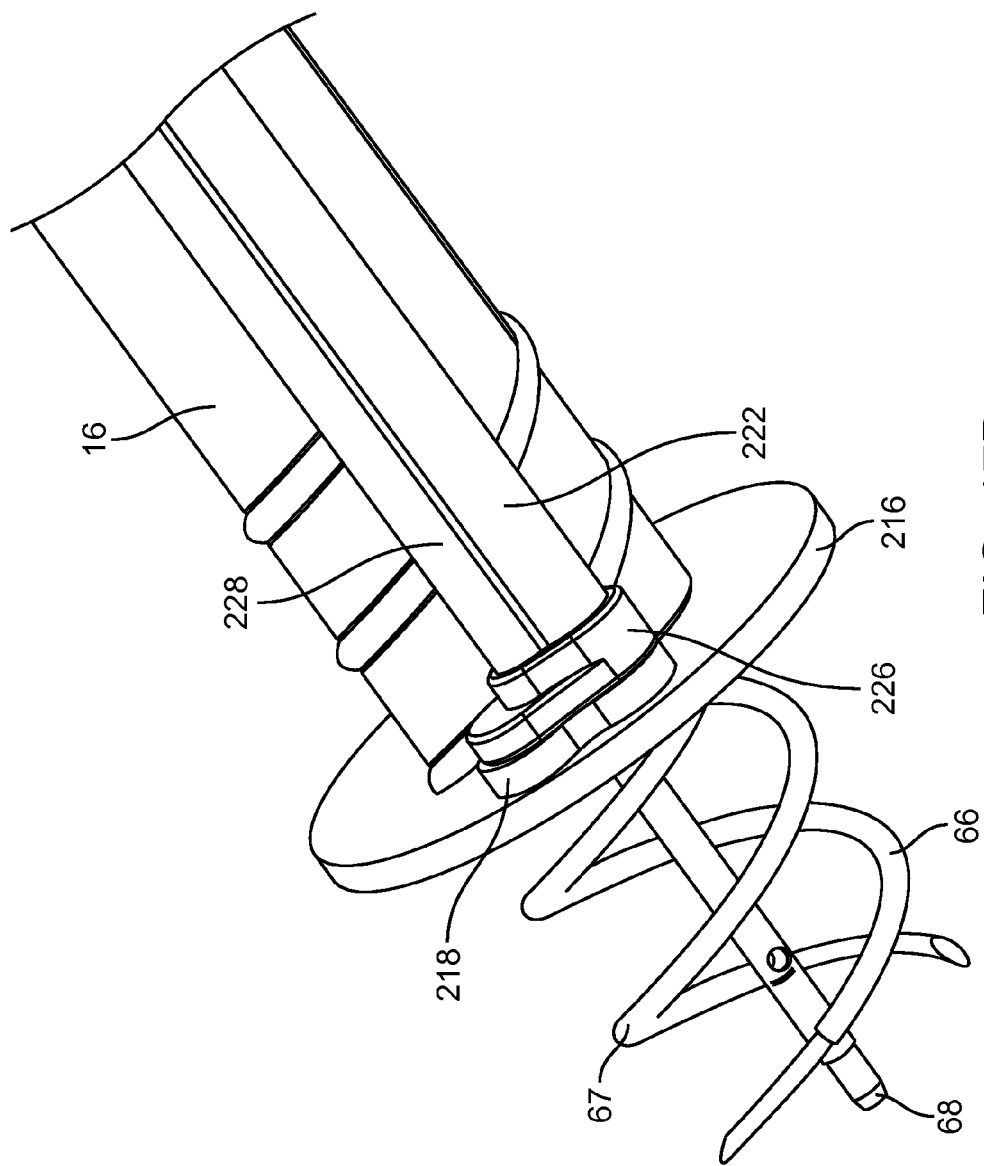
Figure 17E:
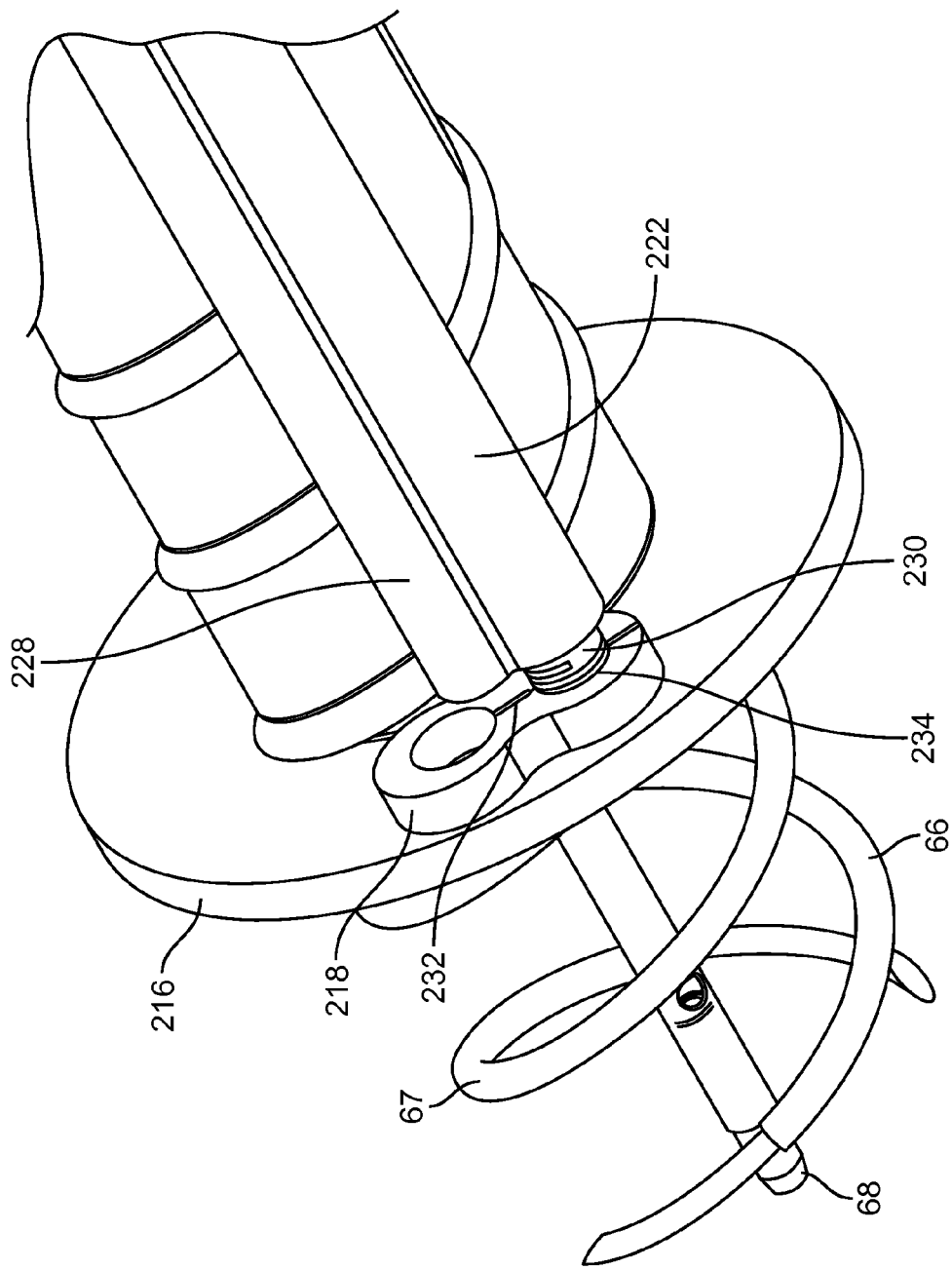
Figure 17F:
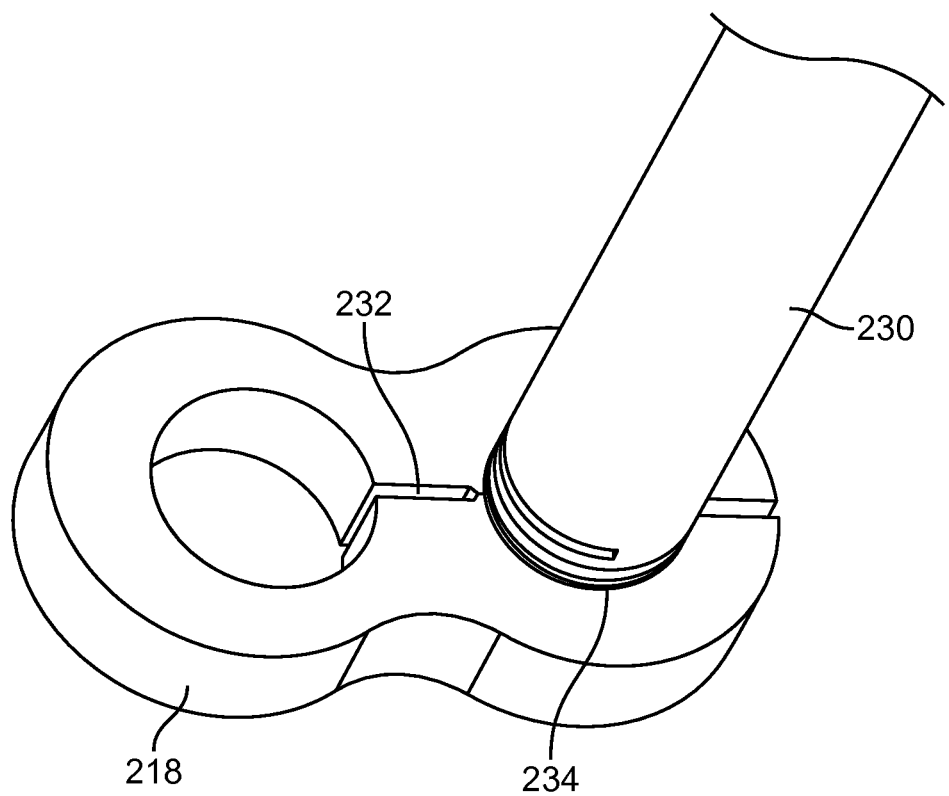
Figure 18:
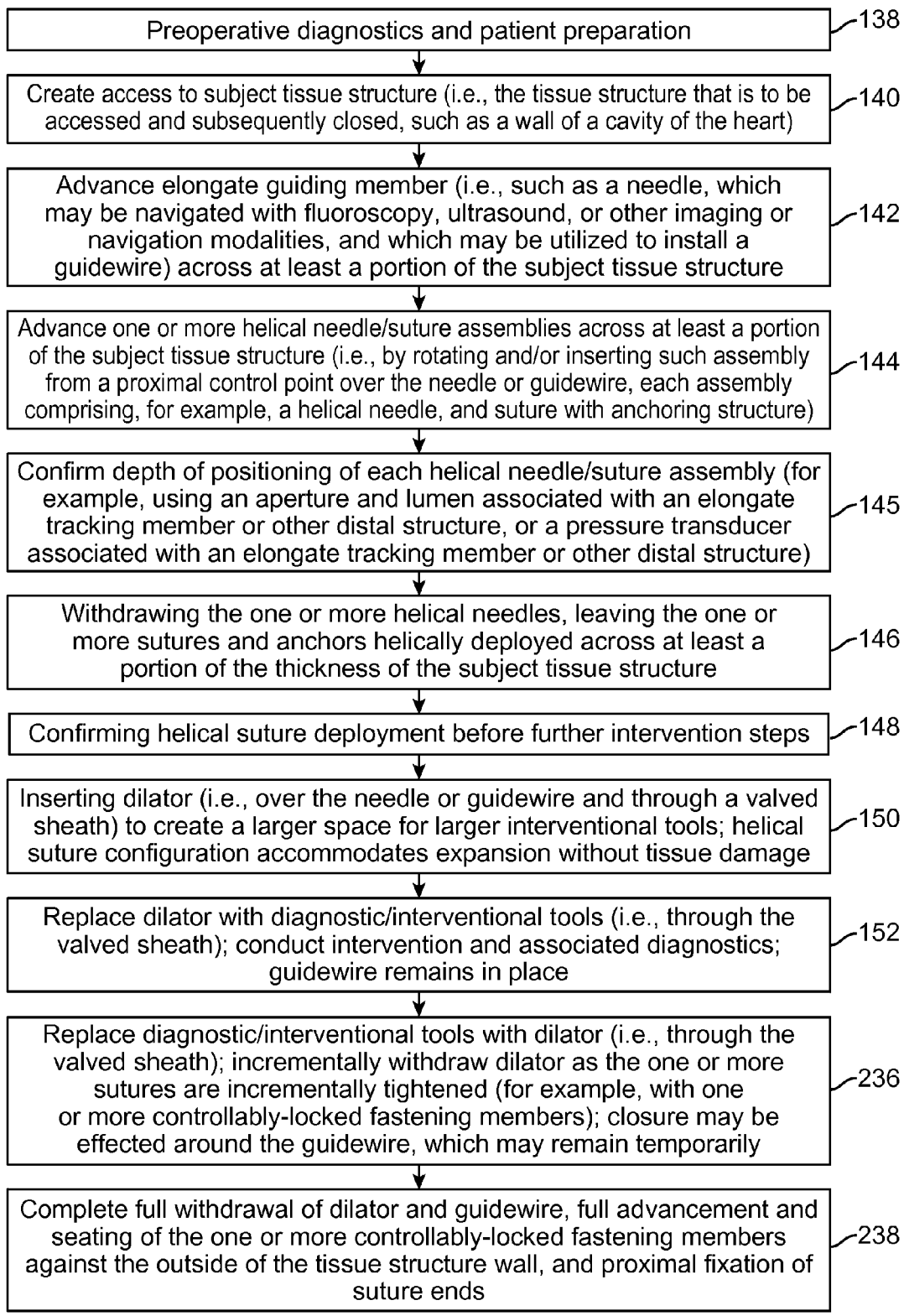
FIG. 18 illustrates a technique for implementing various embodiments of the subject helical closure configurations.
Figure 19A:
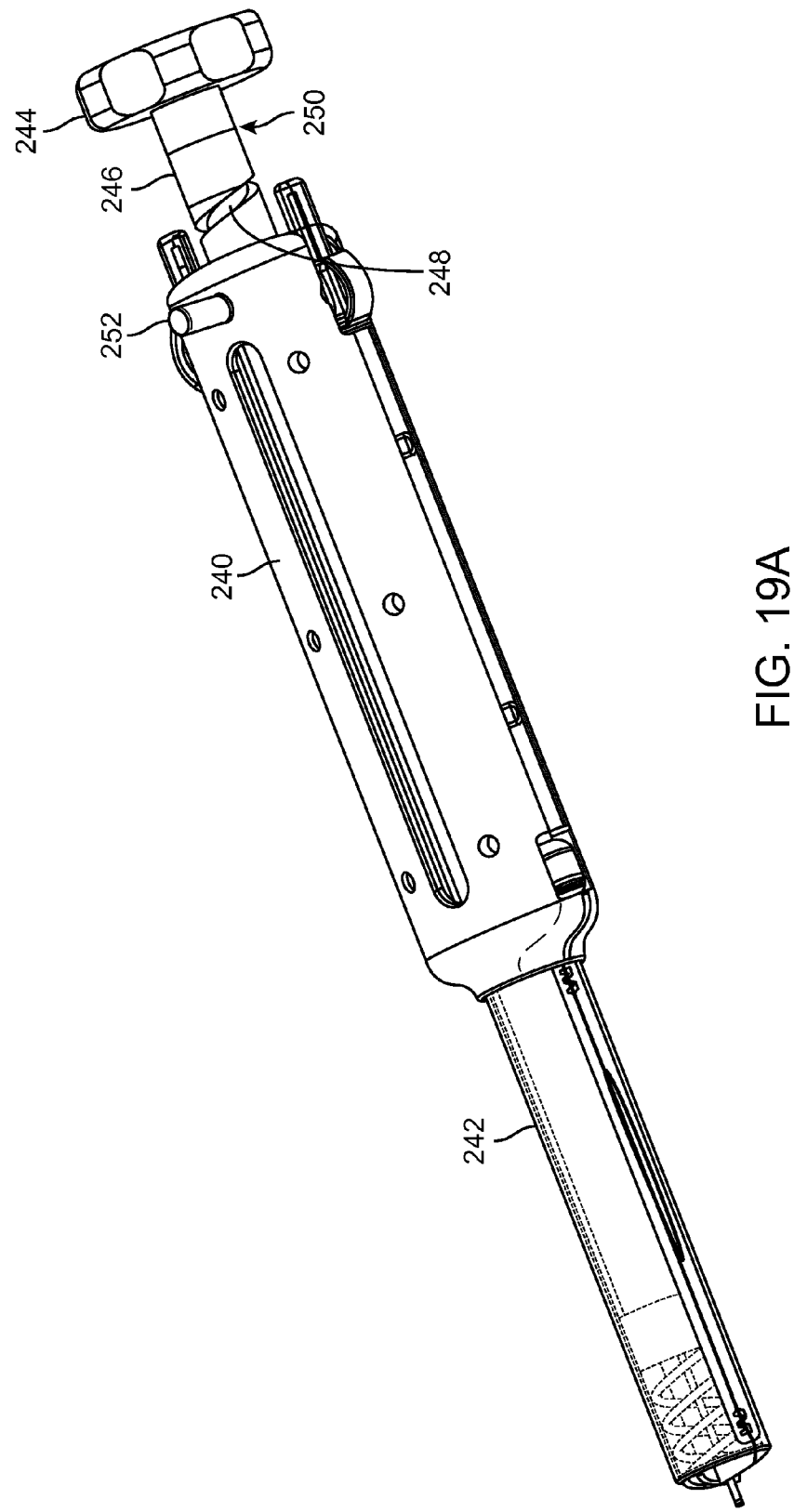
FIGS. 19A-19Z-8 illustrate various aspects of a compound helical closure configuration featuring a pair of helical members and a two-way/one-way controllably-advanceable tension retainer.
Figure 19B:
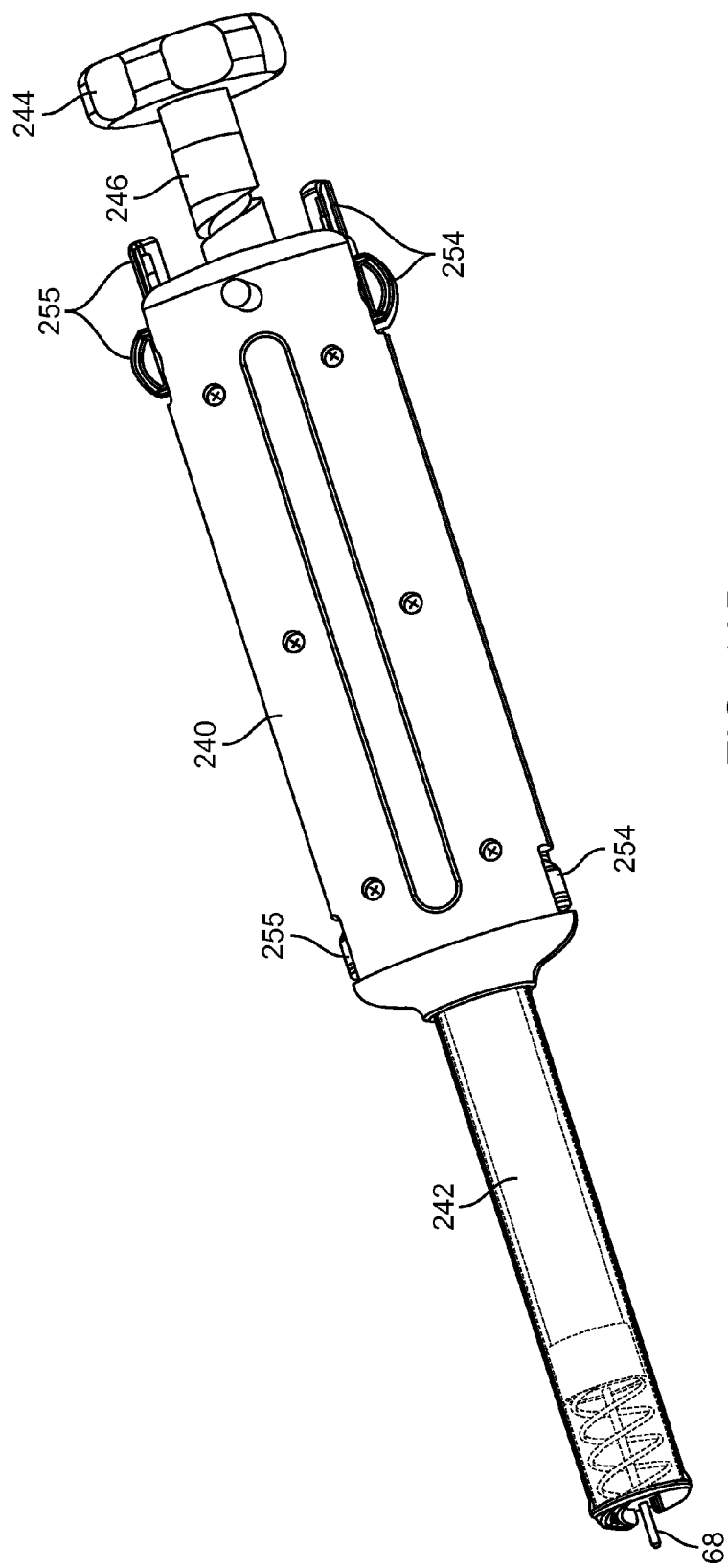
Figure 19C:
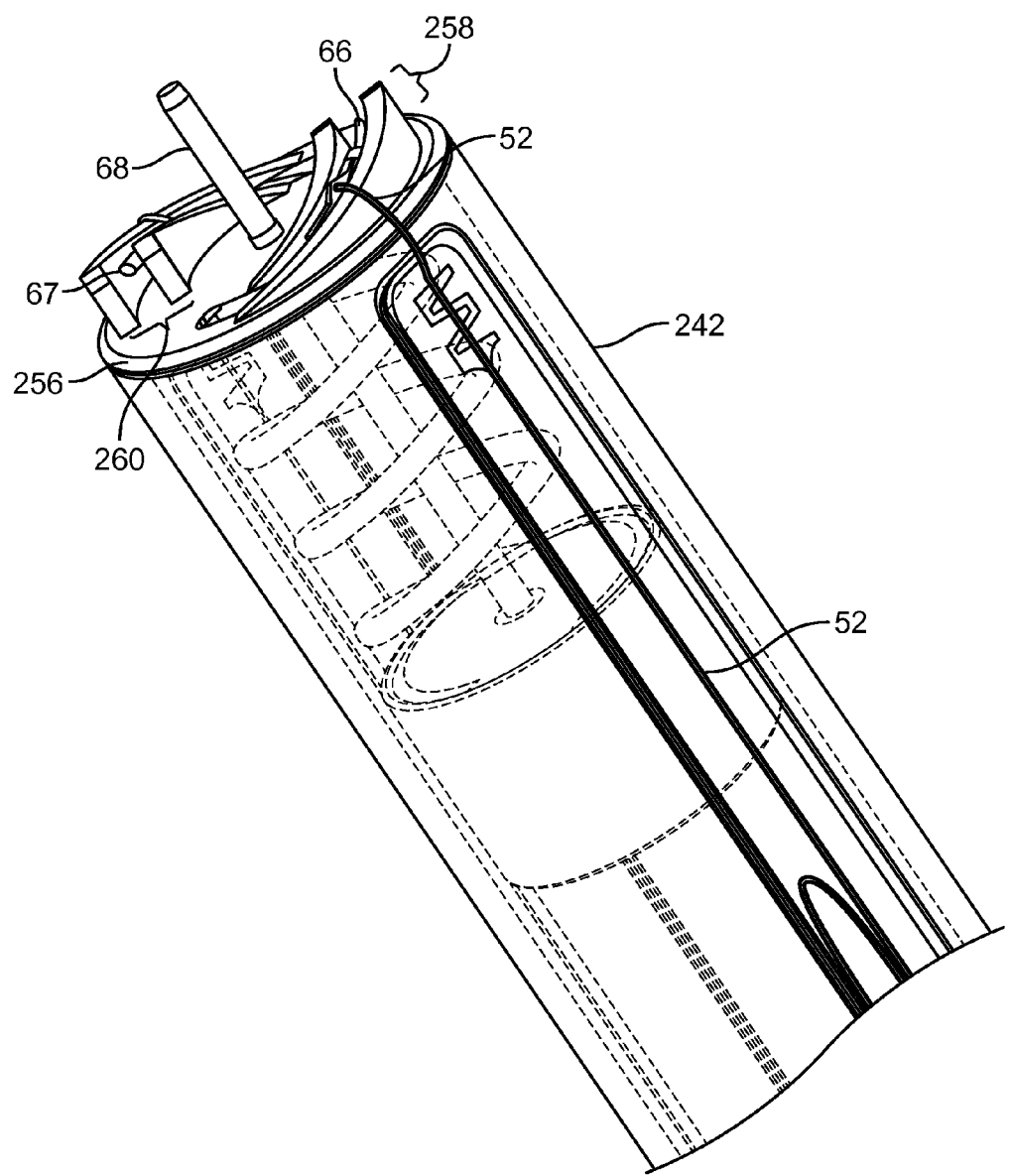
Figure 19D:
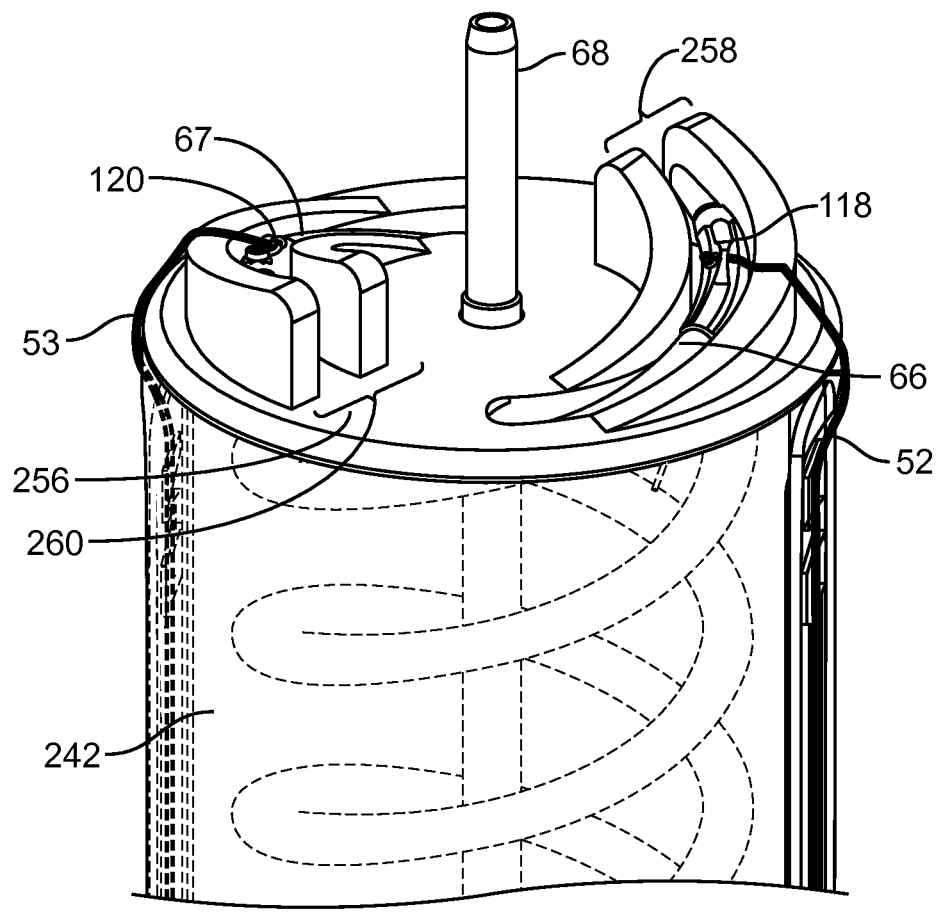
Figure 19E:
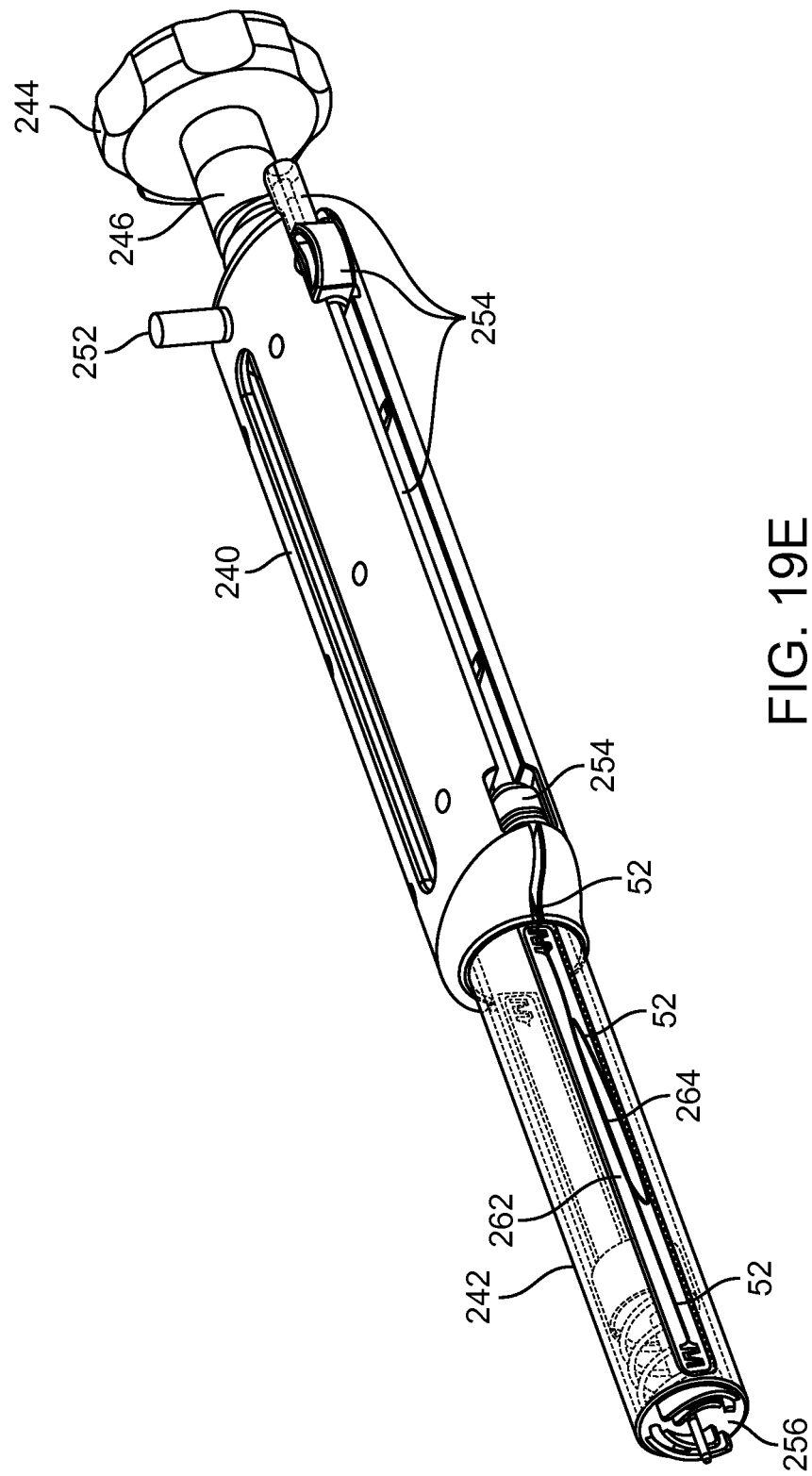
Figure 19F:
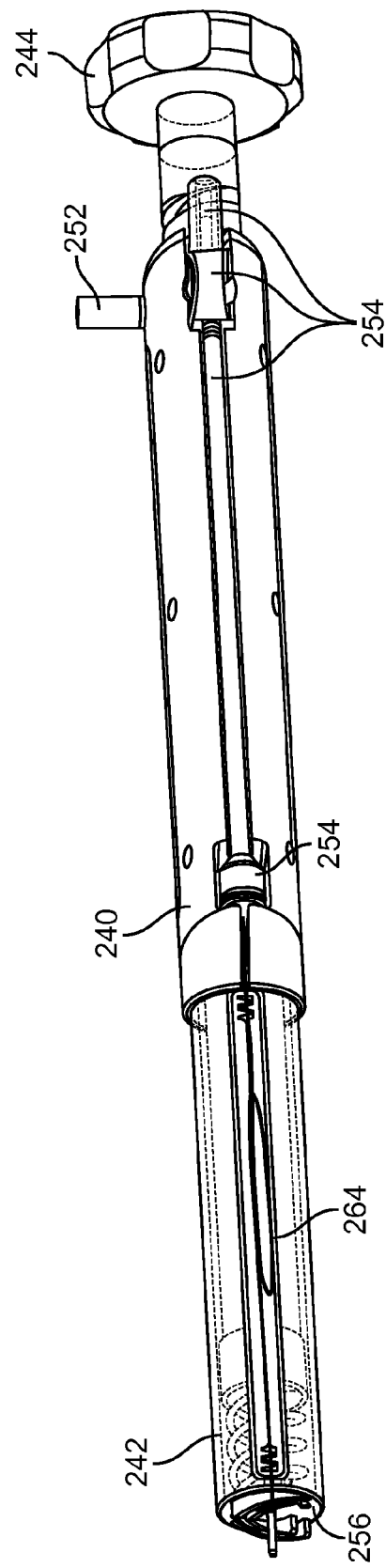
Figure 19G:
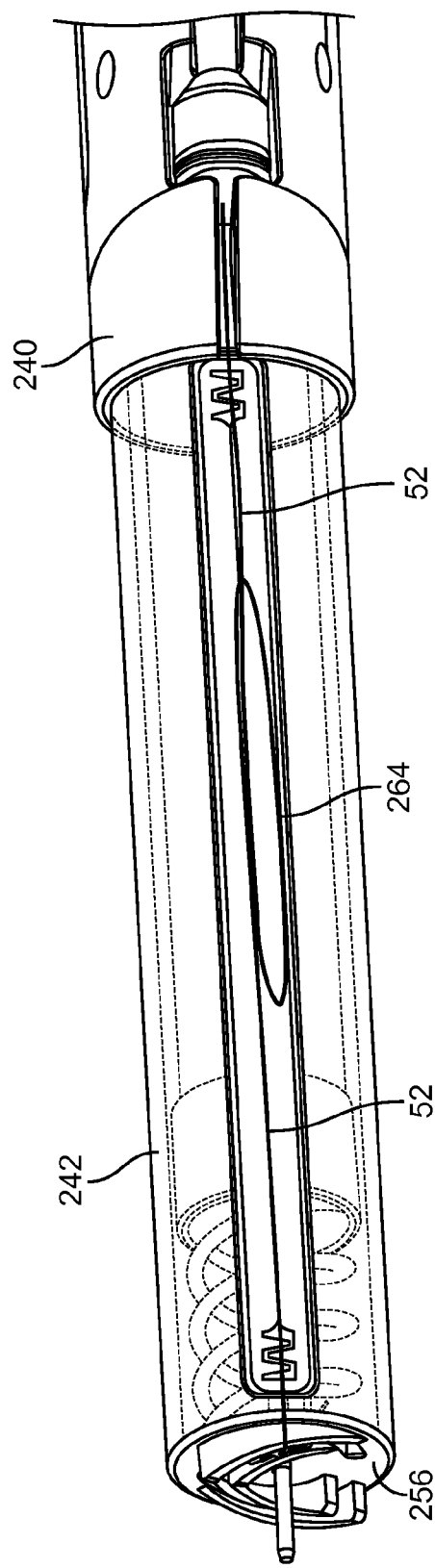
Figure 19H:
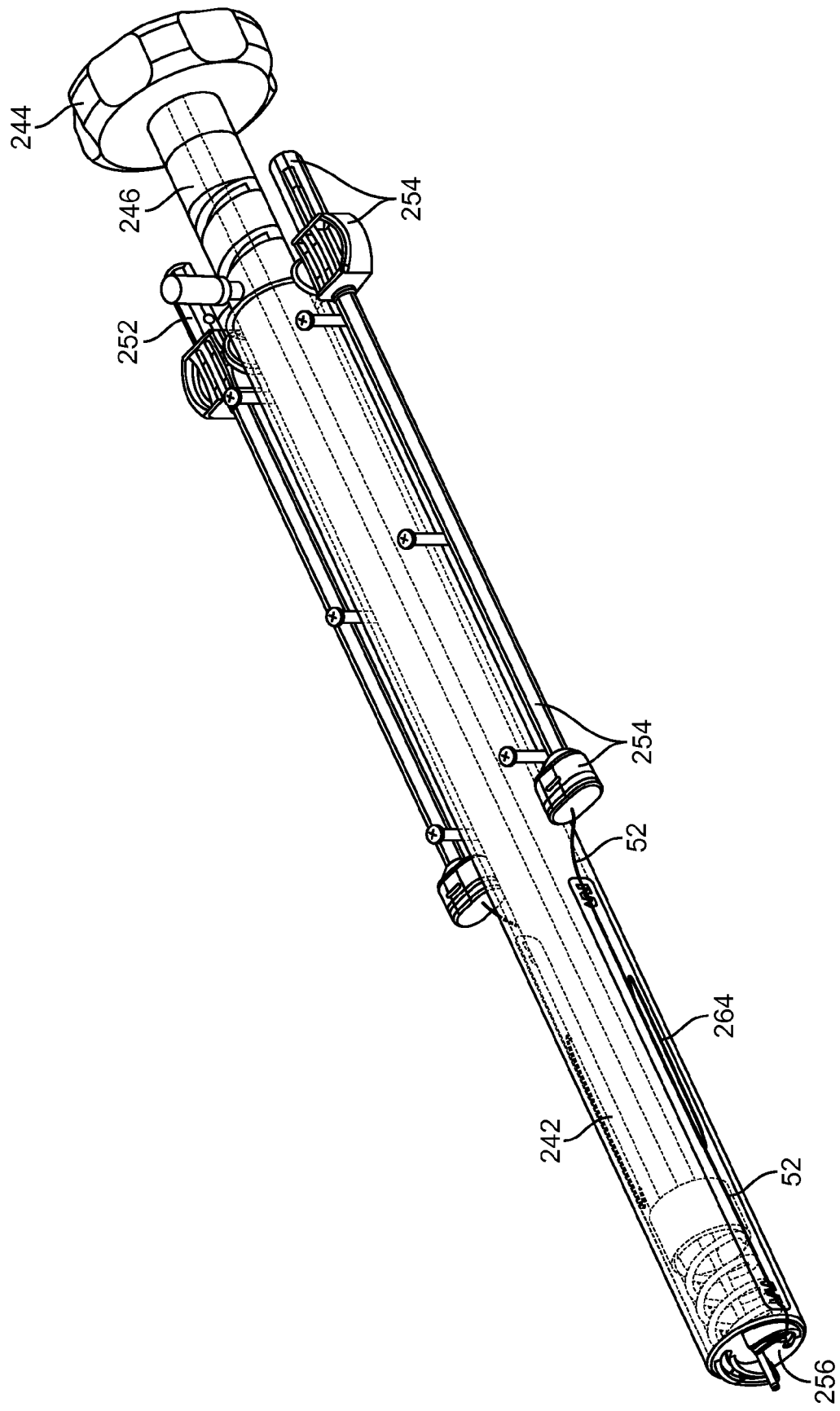
Figure 19I:
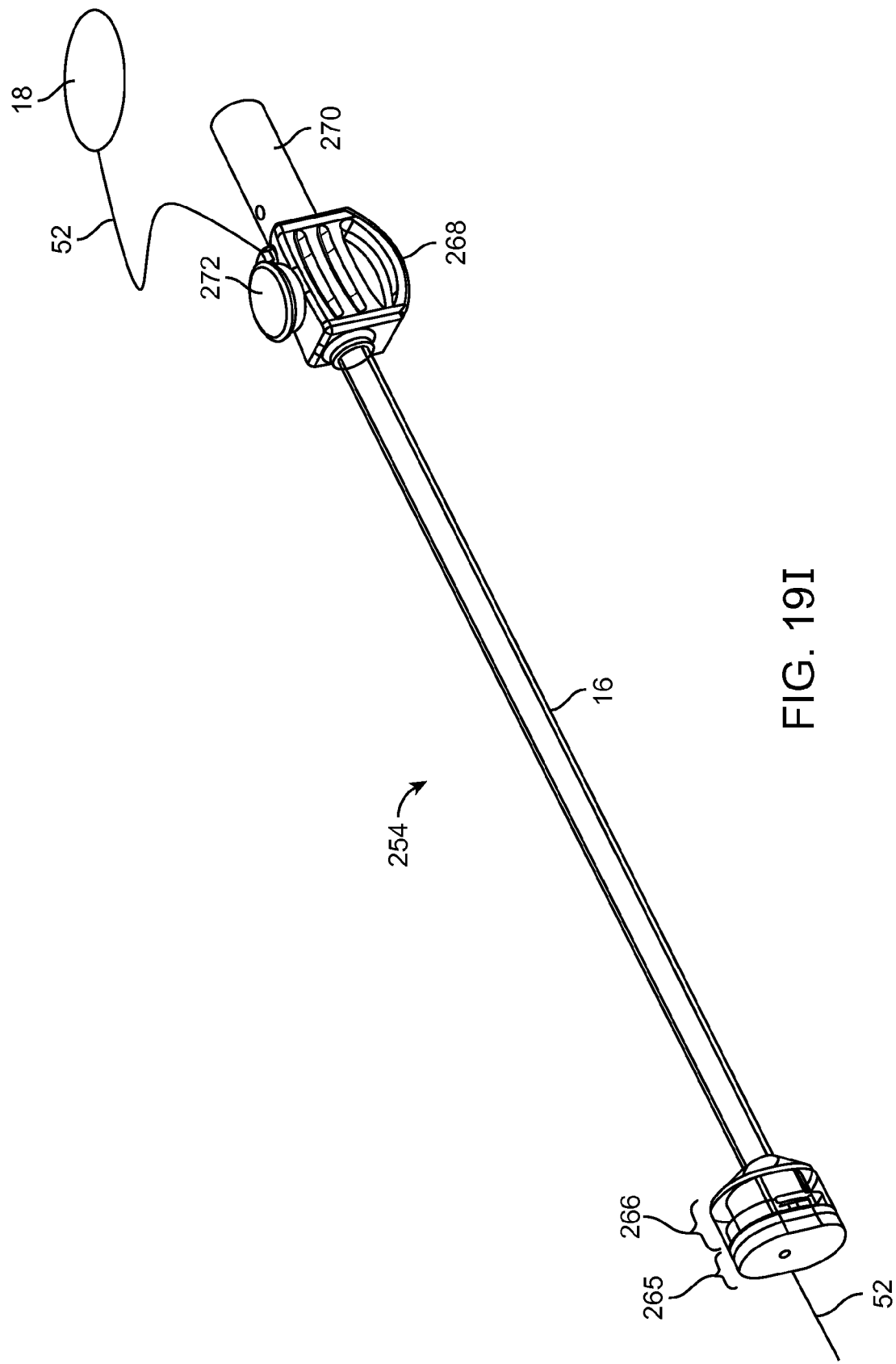
Figures 19P, 19Q:
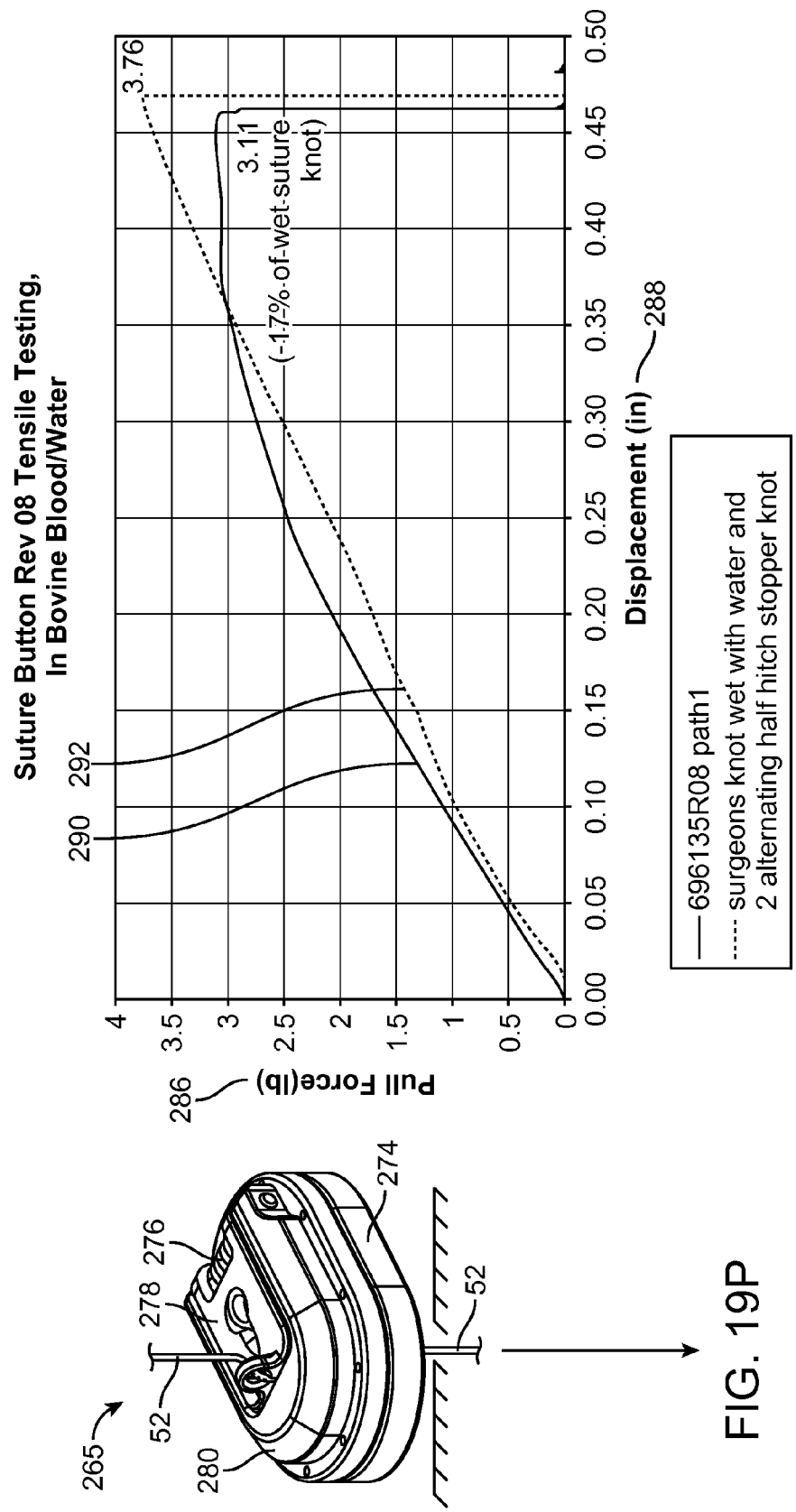
Figure 19R:
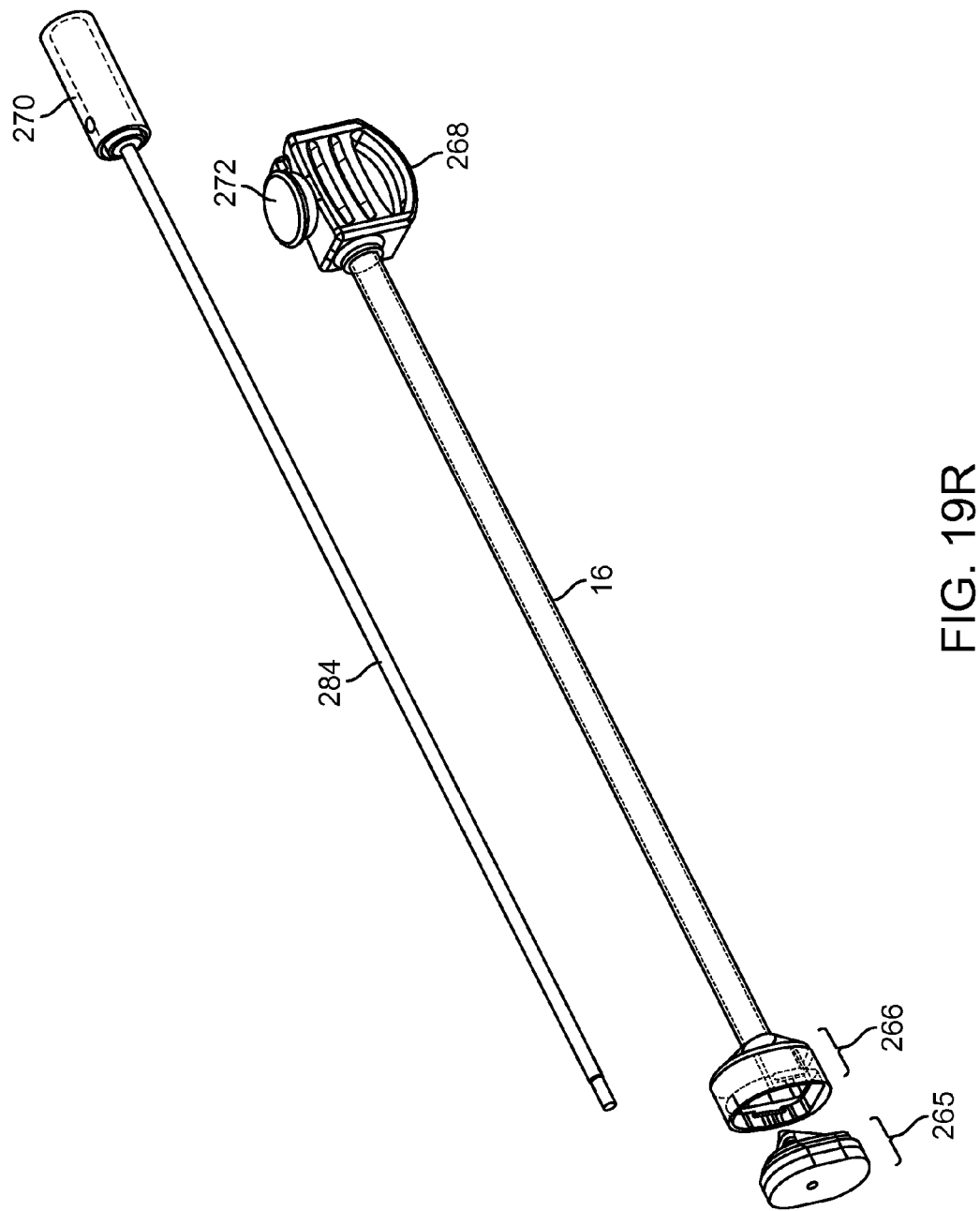
Figure 19U:
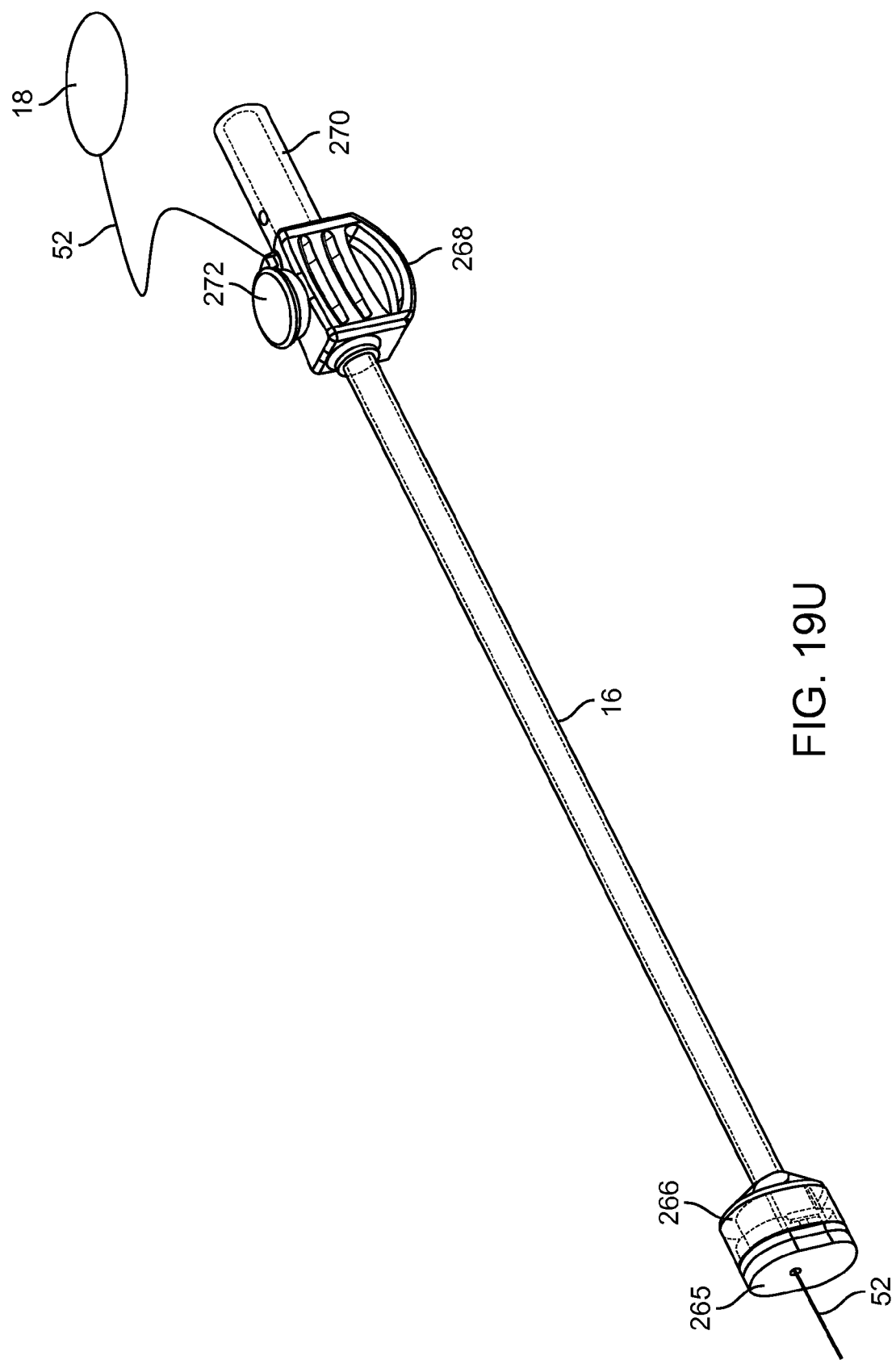
Figure 19V:
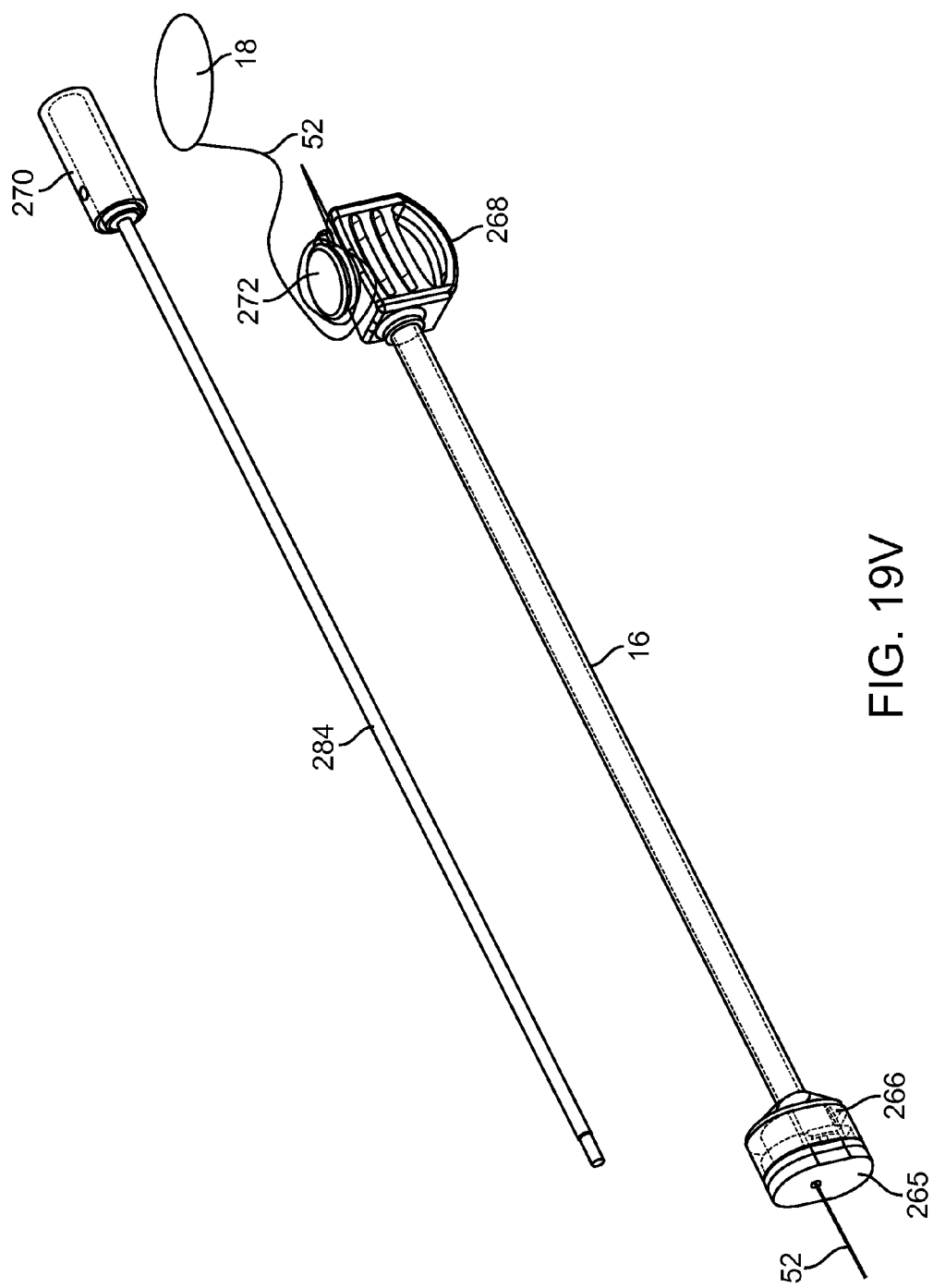
Figure 19W:
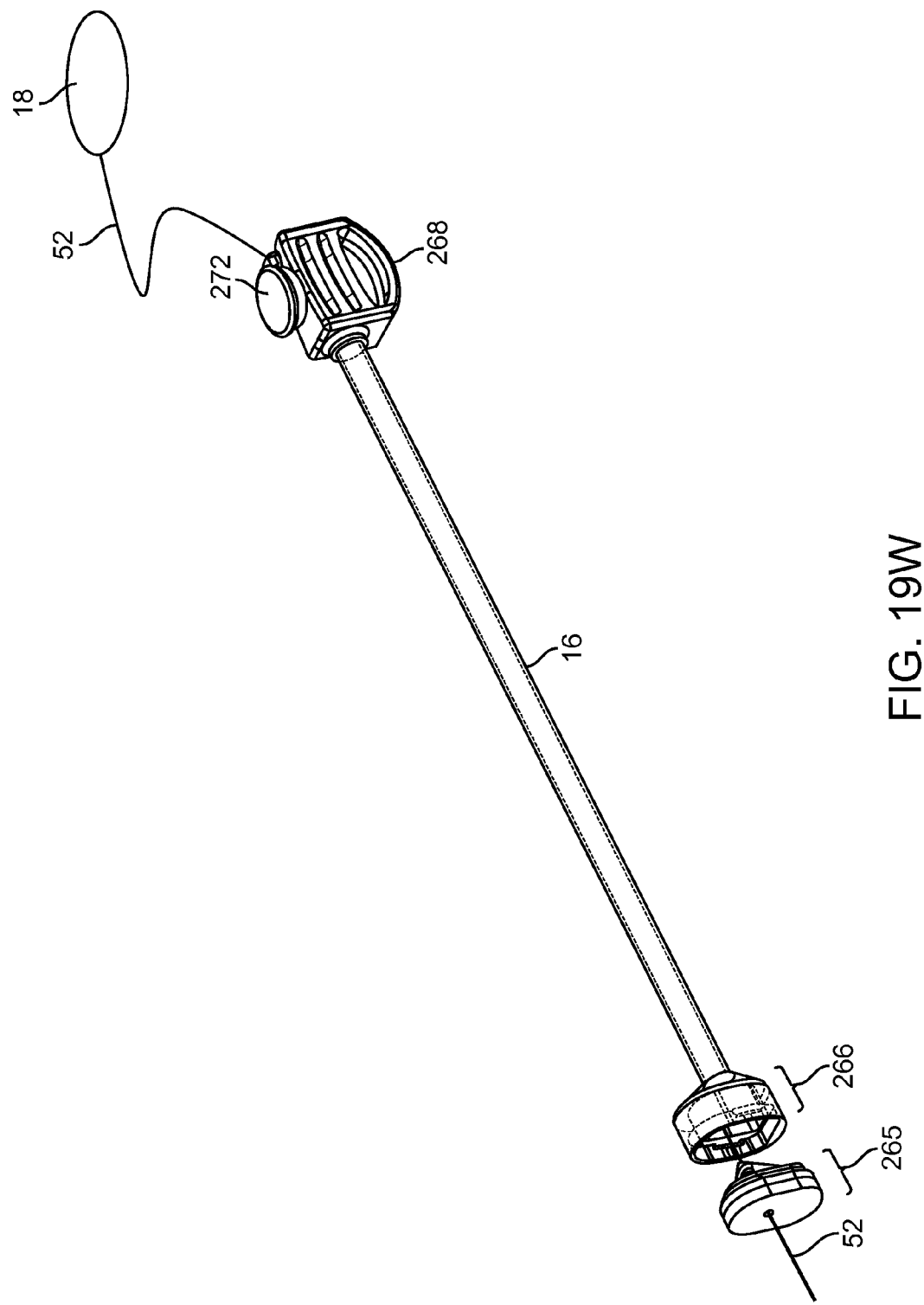
Figure 19X:
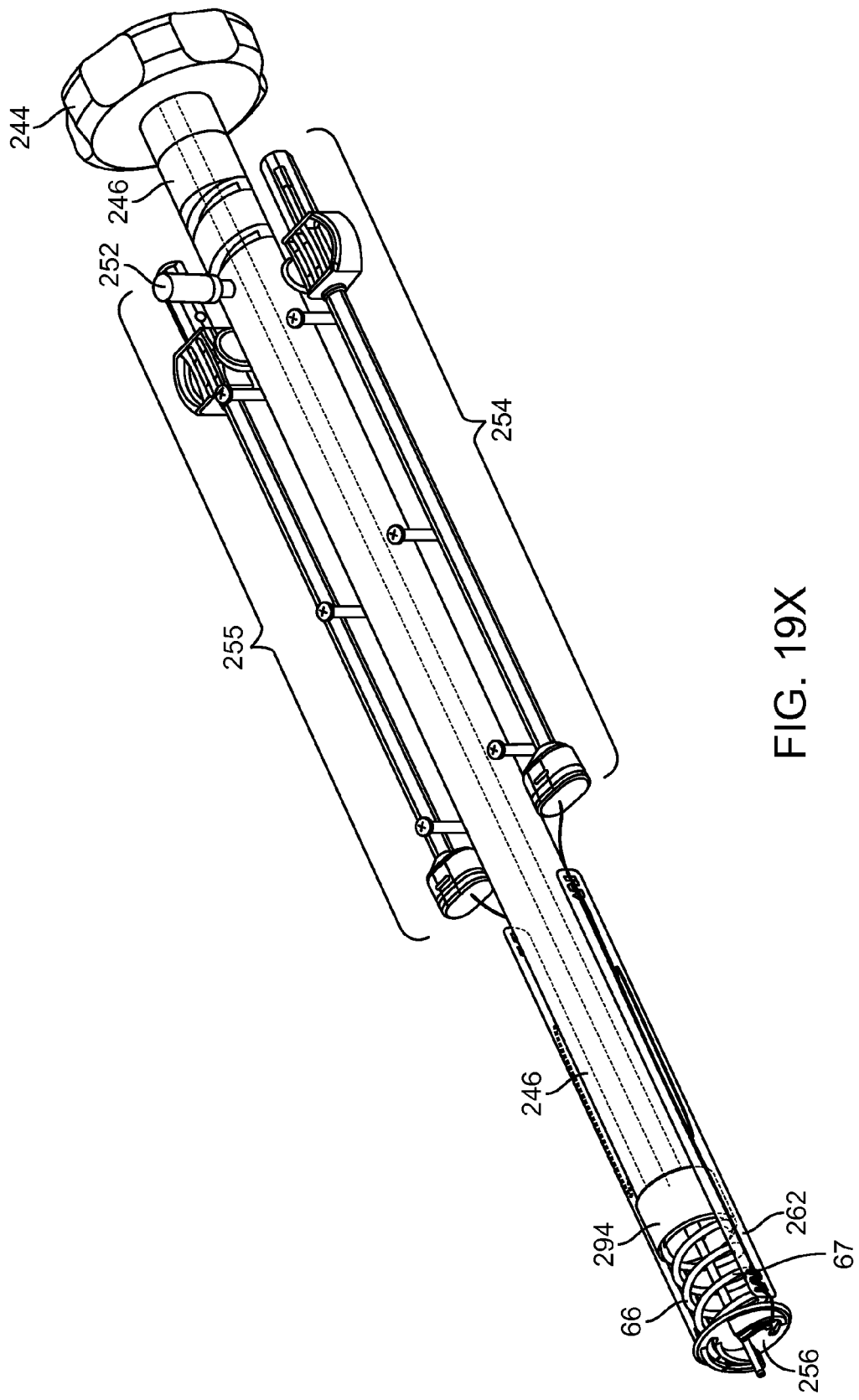
Figure 19Y:
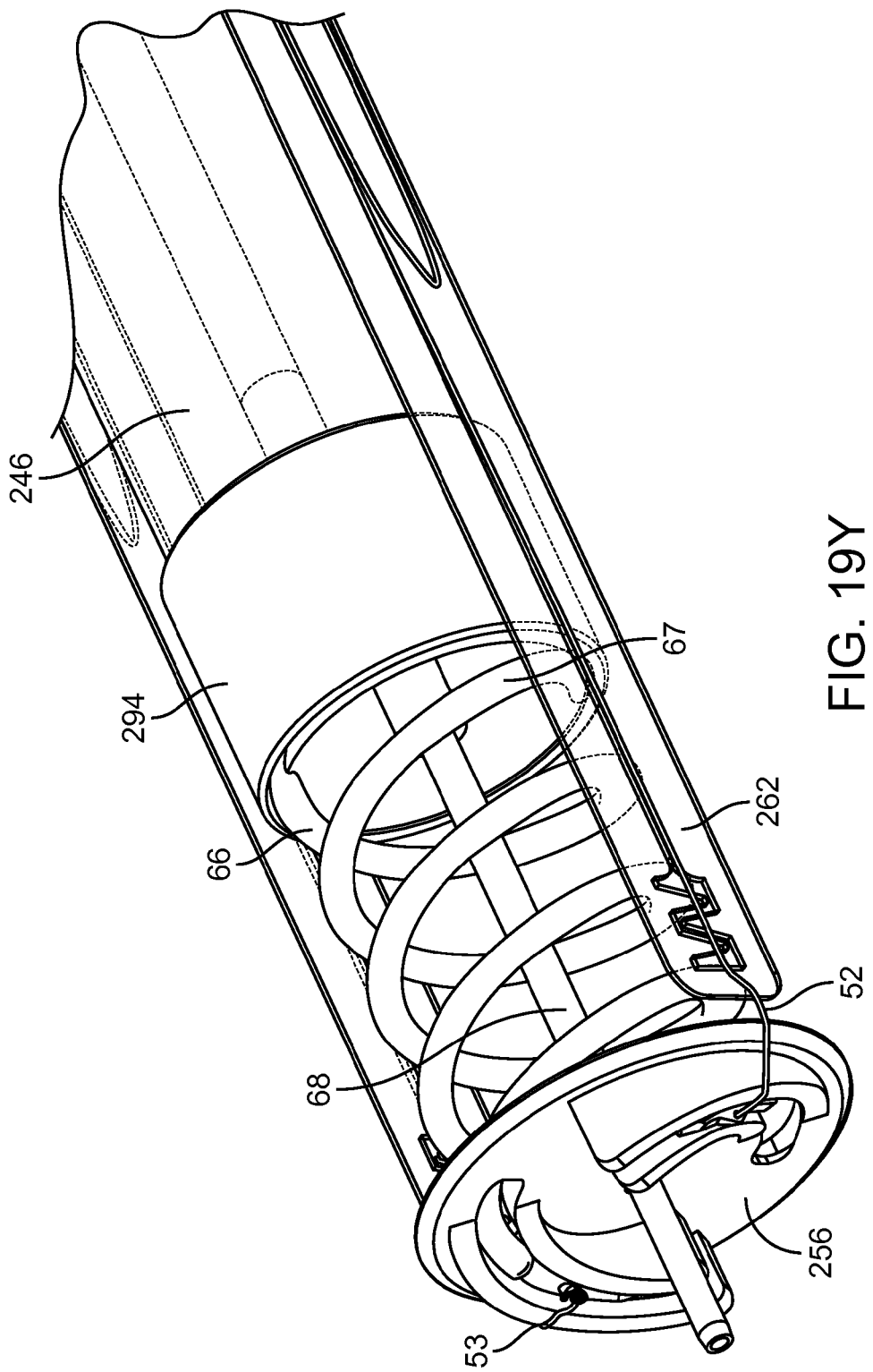
Figure 19Z:
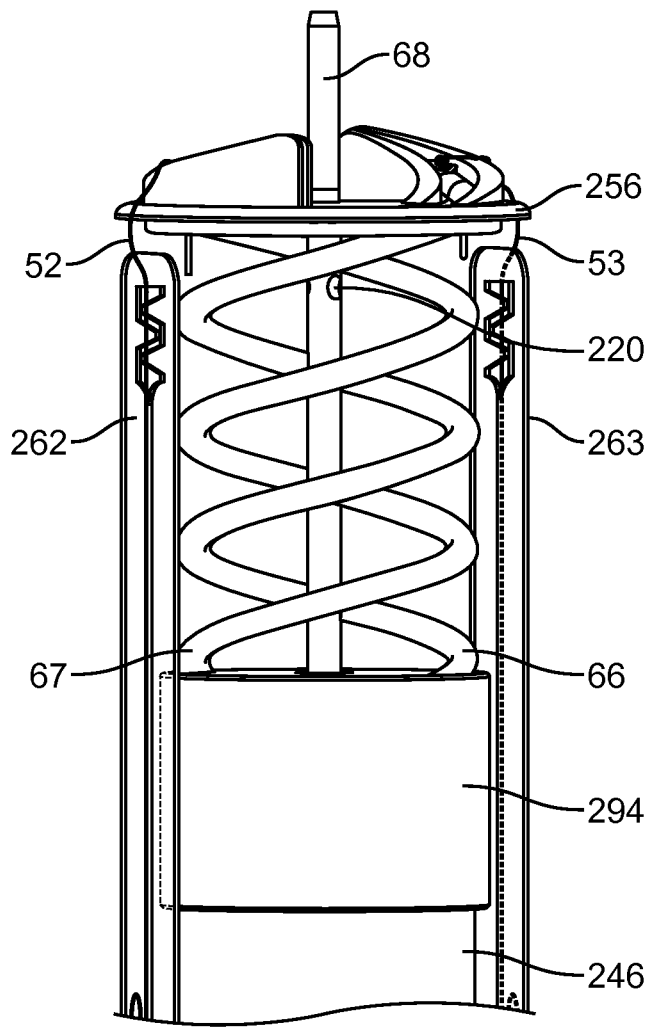
Figures 1, 19Z:
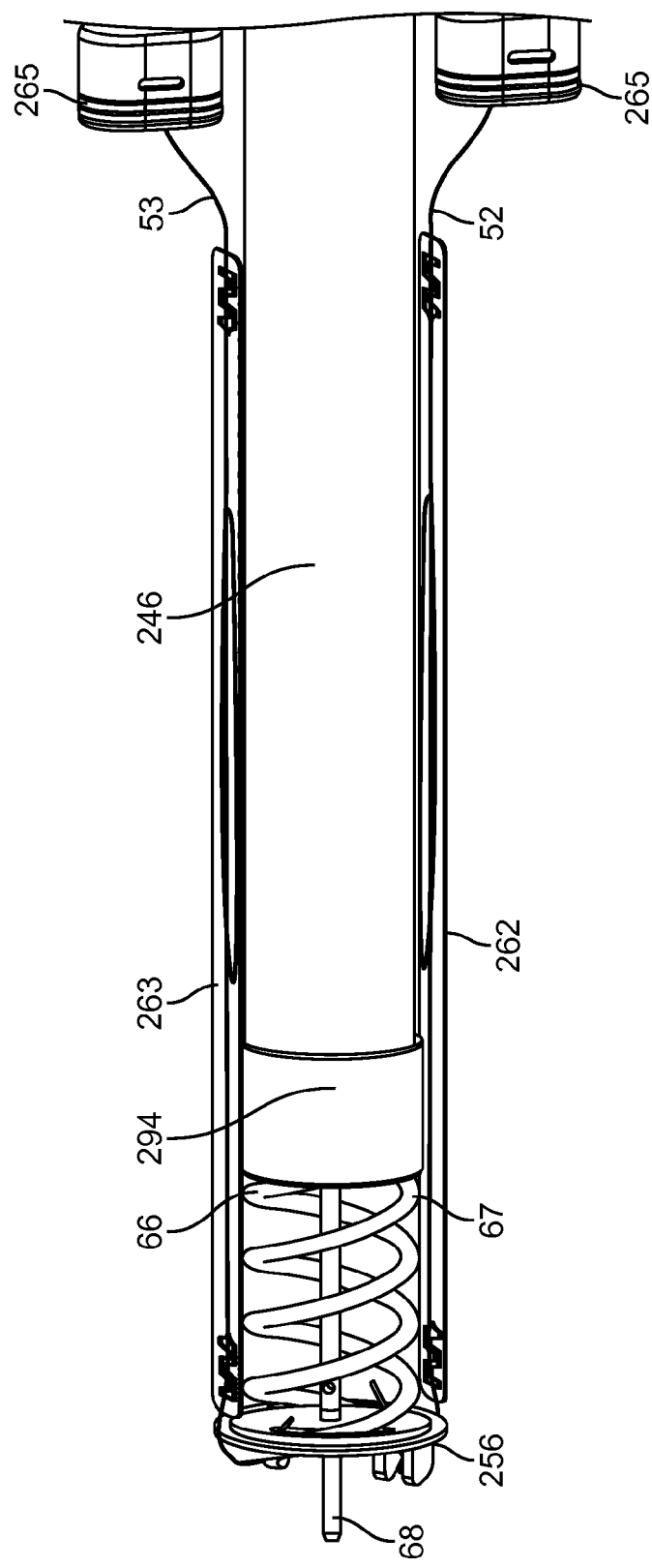
Figures 4, 19Z:
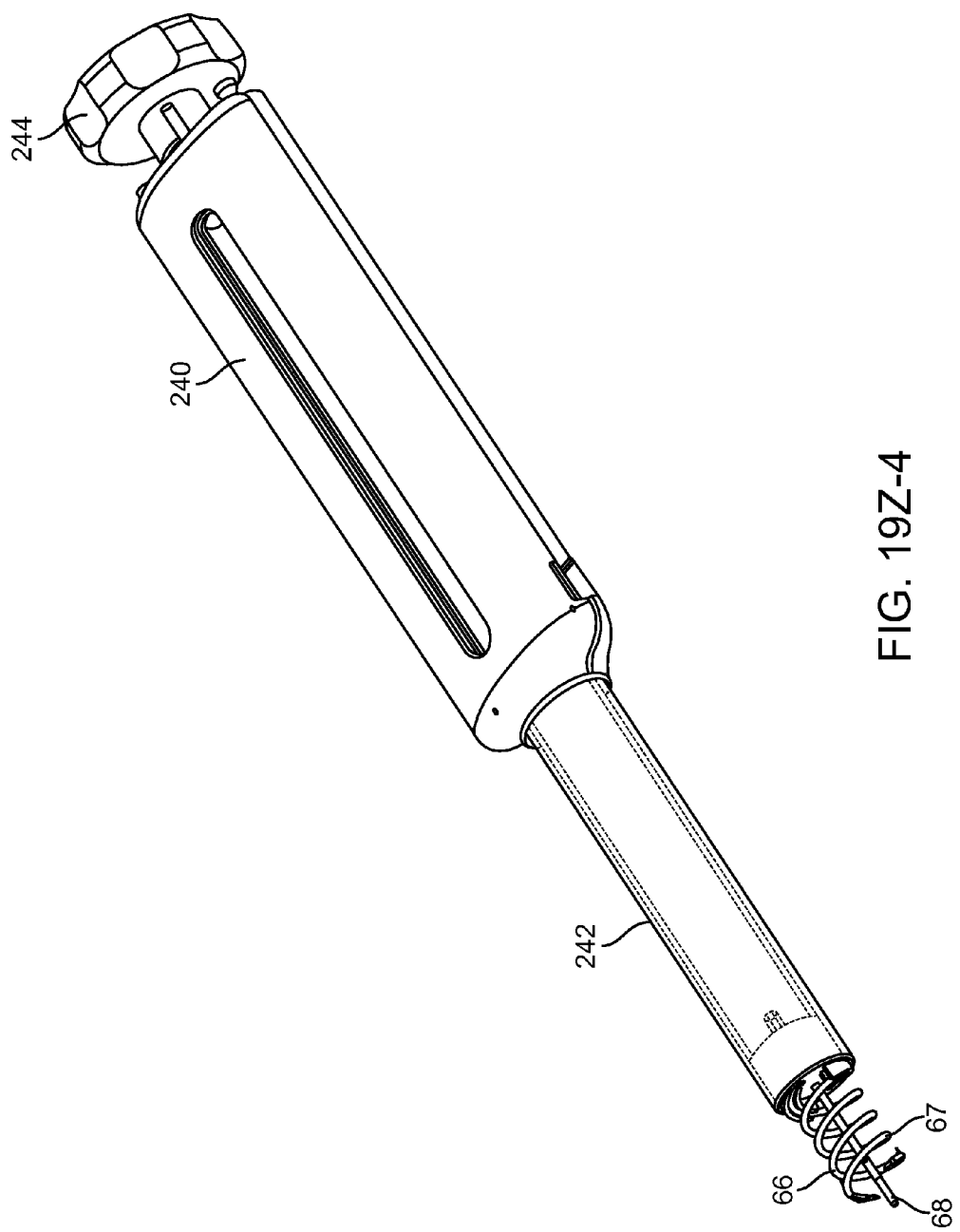
Figures 5, 19Z:
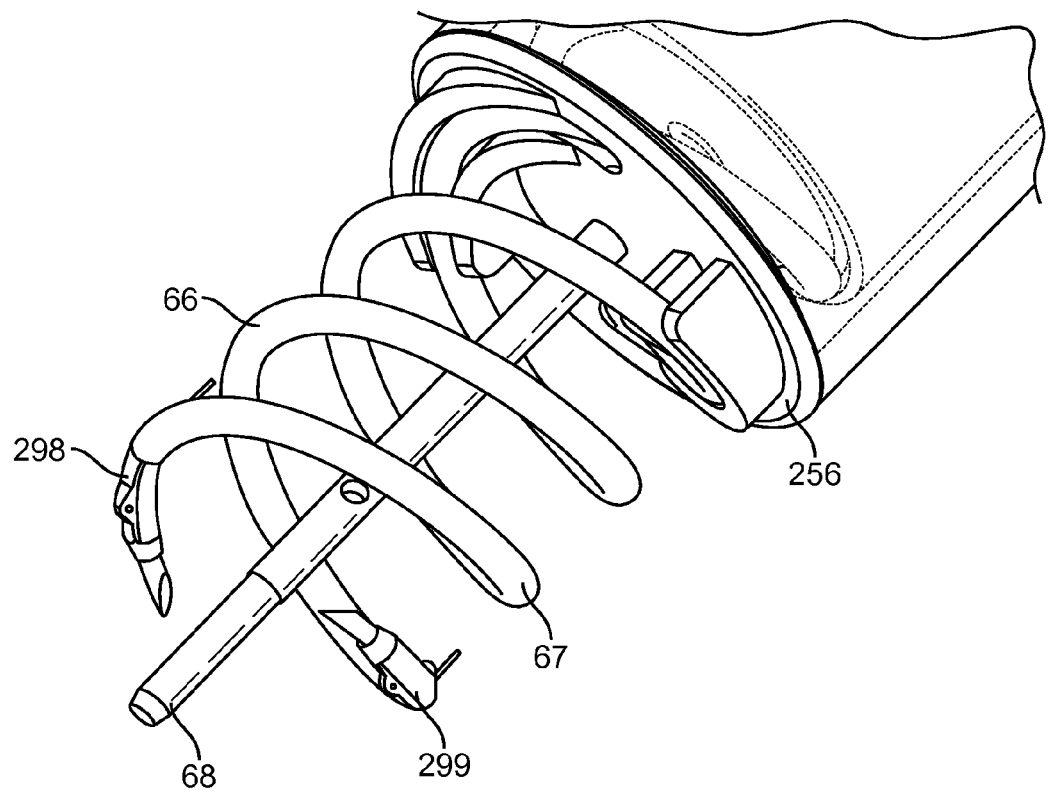
Figures 6, 19Z:
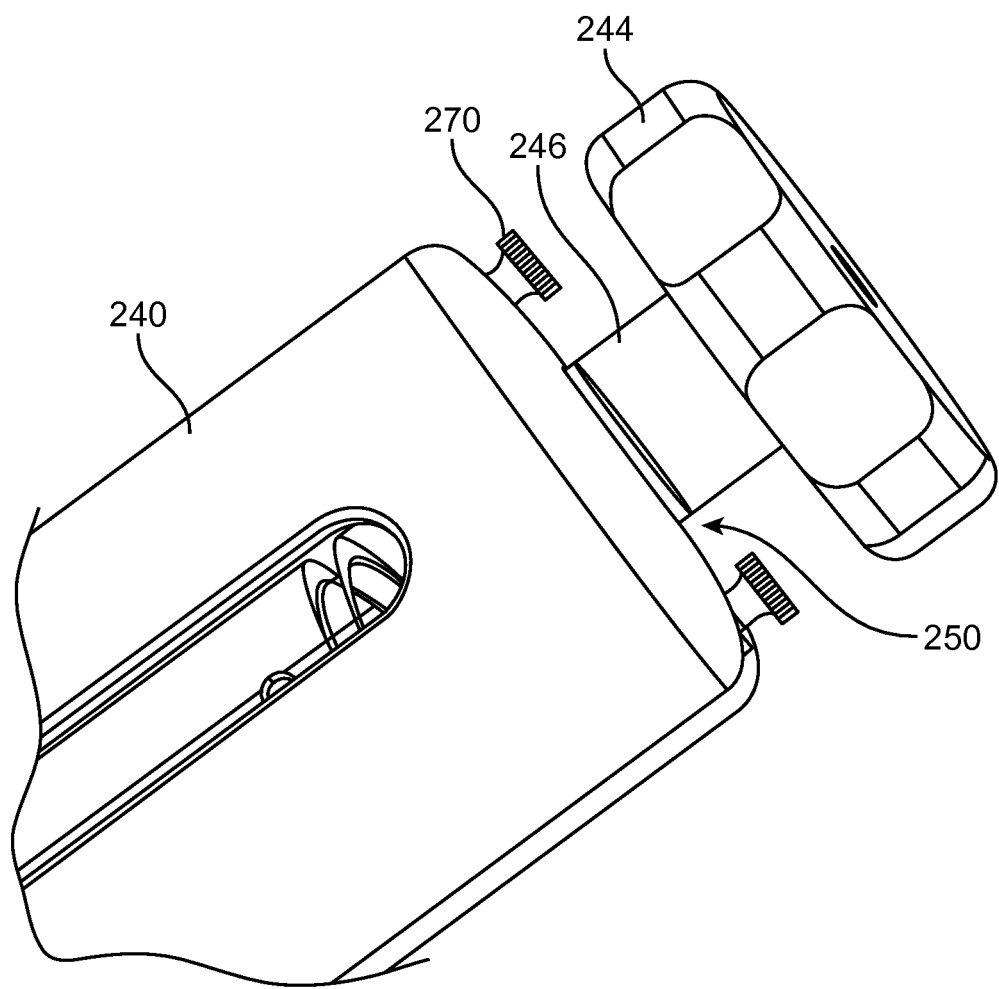
Figures 7, 19Z:
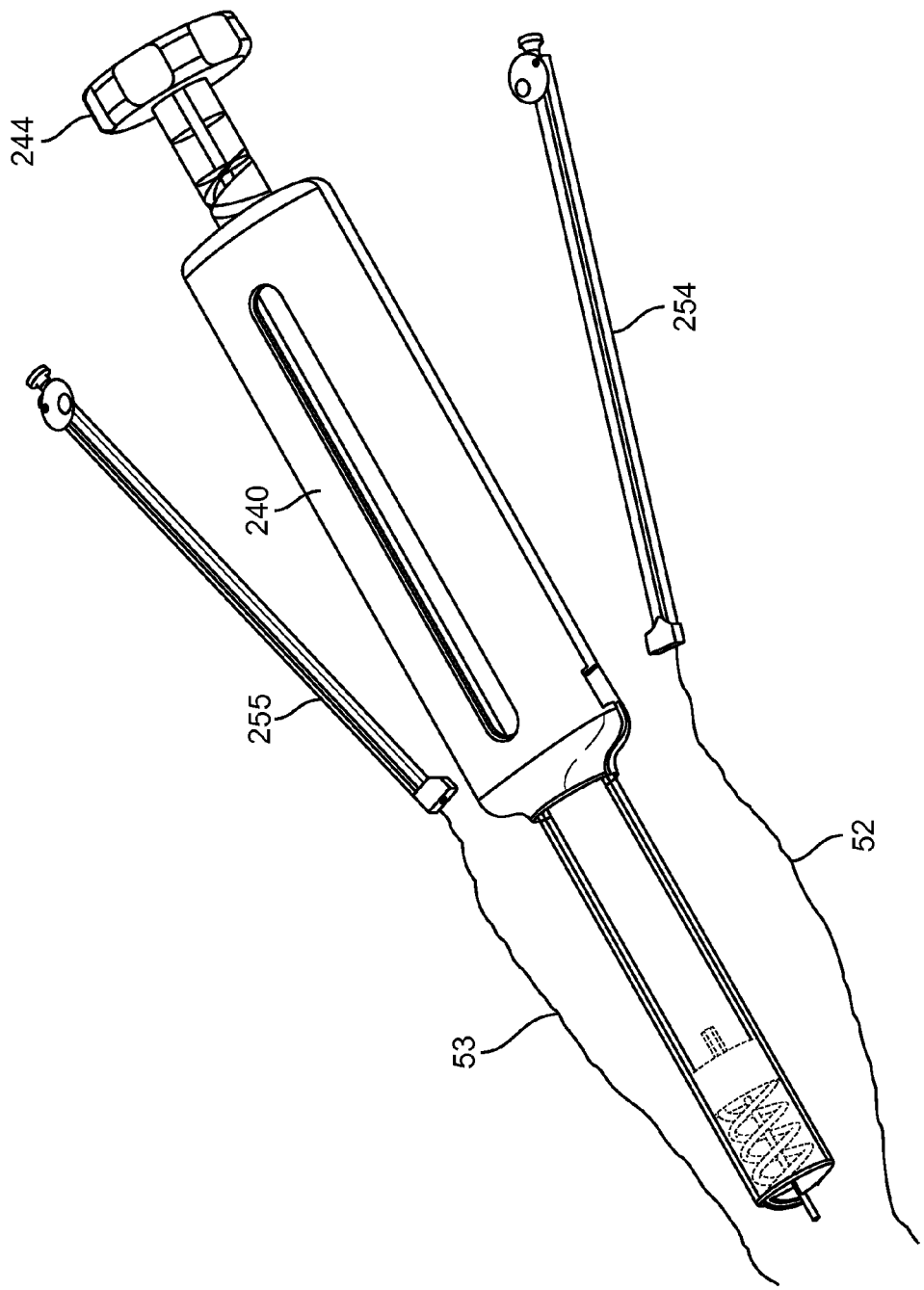
Figures 8, 19Z:
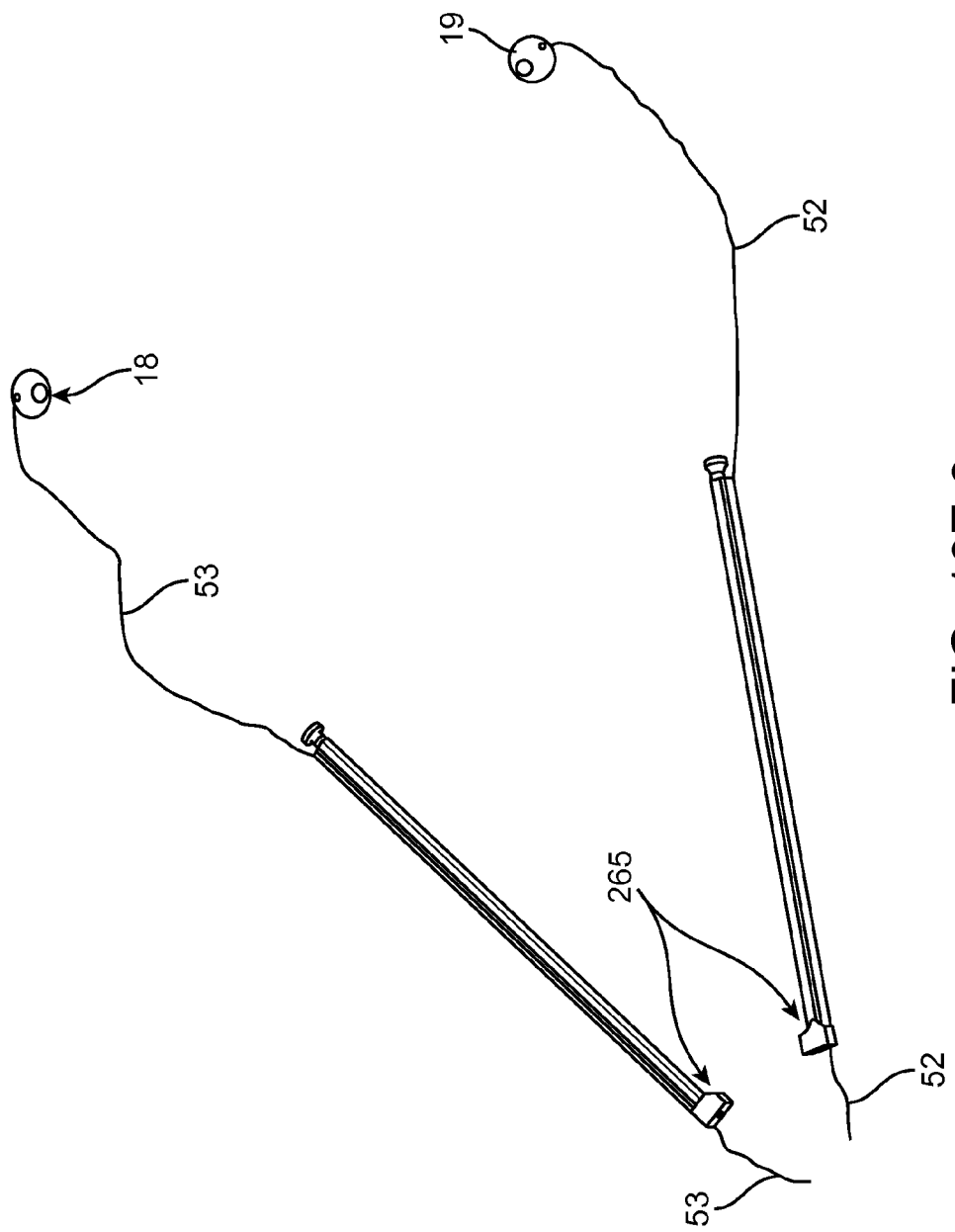
Figure 20:
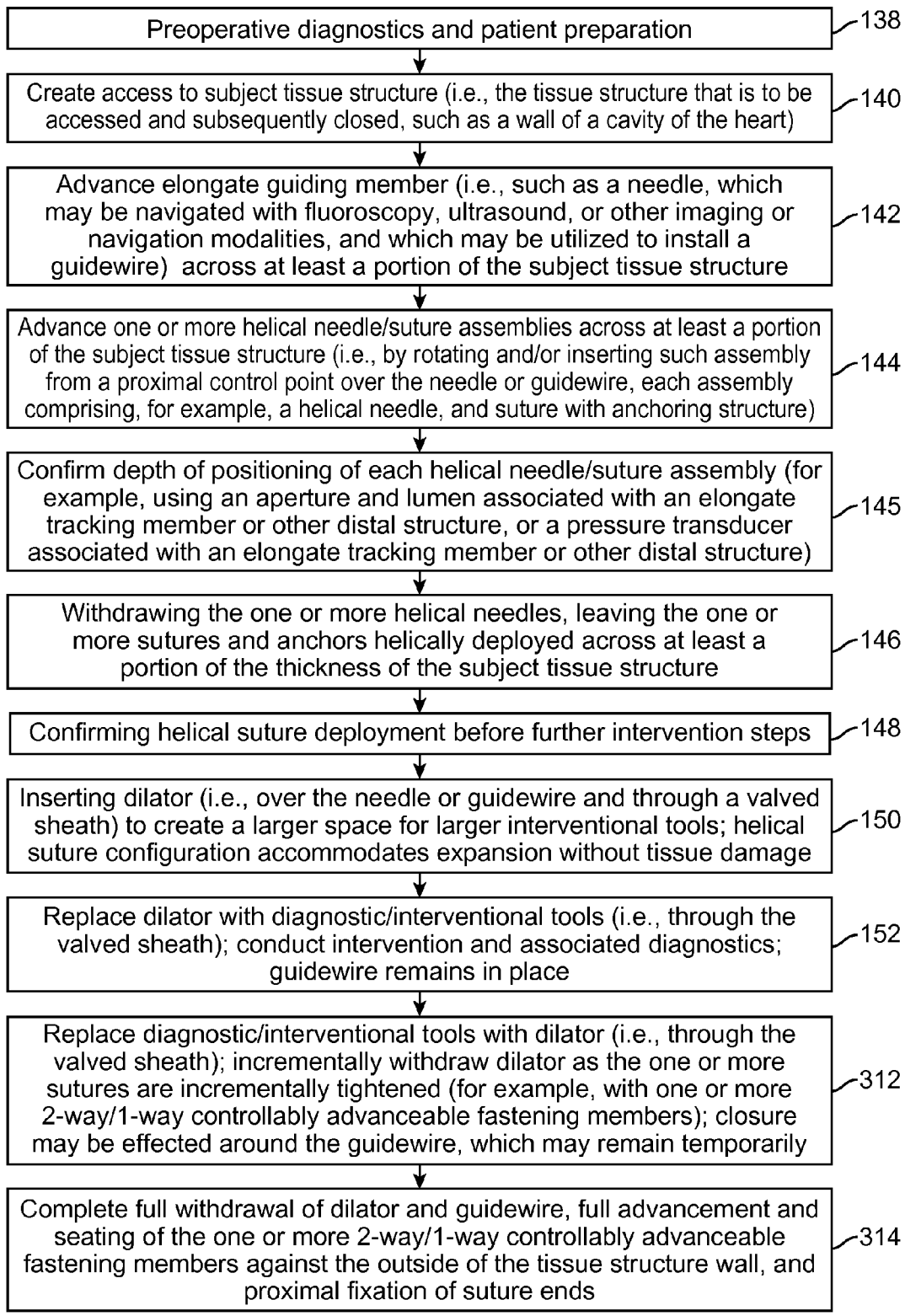
FIG. 20 illustrates a technique for implementing various embodiments of the subject helical closure configurations.

Referring to FIGS. 15A-20, various aspects of additional embodiments of helical needle configurations for effecting suture-based closure procedures are illustrated. FIGS. 15A-16 illustrate aspects of a configuration wherein a single helical needle member may be utilized to advance a suture, and wherein a 1-way tension retainer may be separated from a deployment assembly to become a suture-tension-retaining prosthesis against the outside of the subject tissue structure. FIGS. 17A-18 illustrate aspects of a configuration wherein a twin helical needle configuration may be utilized to advance two suture members, and wherein a pair of implantable controllably-locking tension retainers may be used in concert with a pair of load-spreading engagement members to retain tension and/or positioning of the suture members in situ. FIGS. 19A-20 illustrate aspects of a configuration wherein a twin helical needle configuration may be utilized to advance two suture members, and wherein a pair of implantable 2-way/1-way controllably-advanceable tension retainers may be used in concert with a pair of thrombogenic members to retain tension and facilitate biological fixation of the suture members in situ.

Referring to FIG. 15A, an assembly is depicted for deploying a single suture member (52) with a distally affixed anchor member (54) coupled to a helical needle member (66) in manner similar to those described above, with the exception that the proximal portion of the suture member (52) is configured to lead away from the proximal end of the exposed helical needle member (66), into an implantable 1-way tension retainer (200), through a tubular elongate tensioning element (16) removably housed within a slot formed in the elongate deployment member (14), and to a manual tensioning interface (18), such as the small finger handle configuration shown in FIG. 15A. Referring to FIG. 15B, a close-up view of the configuration of FIG. 15A is shown to further illustrate the relationship of the suture member (52) to the tubular elongate tensioning element (16) and implantable 1-way tension retainer (200), both of which are temporarily and removably housed within portions of the elongate deployment member (14). The distal portion of the suture member (52) is shown in a compound helical configuration (i.e., the suture member 52 is helically wrapped around a helical needle member 66), but as described above, this suture may also be deployed in a single helical configuration, wherein the distal suture member (52) portion is simply aligned with the helical winds of the helical needle member (for example, using a suture-retaining slot formed in the helical needle member 66) to form a single helical suture pattern very similar to the helical pattern of the helical needle member (66). For illustrative purposes, compound helical configurations are shown in the embodiments of FIGS. 15A-15J, 17A-17F, and 19A-19Z-8.

Referring again to FIG. 15B, after the helical needle member (66) and associated anchor member (54) and distal portion of the suture member (52) have been driven at least part of the way across the subject tissue structure, as described above, the deployment member (14) may be backed off in a reverse rotational direction to leave behind the anchor member (54) and distal portion of the suture member (52). When ultimate closure of the associated wound is desired, an assembly comprising the manual tensioning interface (18), elongate tensioning element (16), and implantable 1-way tension retainer (200) may be manually separated away from the handle-like body of the elongate deployment member, and the manual tensioning interface (18) may be pulled relative to the somewhat flexible, yet somewhat stiff in column compression tubular structure of the elongate tensioning element (16) to push the implantable 1-way tension retainer (200) down the suture distally toward the exposed outer wall of the subject tissue structure where it may be cinched into place and left to retain tension on the implanted portion of the suture member (52), after which the elongate tensioning element (16) and manual tensioning interface (18) maybe removed away proximally so that any remaining proximal ends of the suture member (52) may be clipped or tied off, similar to the scenario described above in reference to FIGS. 4N and 4O.

FIGS. 15C through 15J illustrate some of the complexities of the 1-way tension retainer (200) and its association with the helical needle member (66), elongate deployment member (14), and suture member (52). Referring to FIG. 15C, the elongate tensioning element (item 16 of FIG. 15B) has been removed to show the pathway of the suture element (52) proximal of the 1-way tension retainer (200), as well as an additional looped tension element (202) configured to assist with the application of compressive loads to the elongate tensioning element (item 16 of FIG. 15B). FIG. 15D shows an end view depicting the same structure as shown in FIG. 15C, to illustrate the pathways of the suture member (52) and additional looped tension element (202). Referring to FIGS. 15E and 15F, two different views of a 1-way tension retainer (200) are shown along with an associated suture member (52). As shown in FIG. 15E, the 1-way tension retainer (200) comprises an assembly of a housing and a movable door member (204) configured to hinge about a pivot. With the suture member (52) threaded around the door member (204) in a pattern as illustrated in a close up and partial views of FIGS. 15G-15J, the configuration allows for the suture member to be pulled tight in one direction, but not in the other direction, because the other direction causes the door to pivot down into a clamping configuration versus one portion of the suture member (52) such that the suture member becomes immobile relative to the door member (204) or housing (206). In one embodiment, the door member (204) may be biased to close against the housing (206) with a spring, such as a cantilever or coil type spring, such that a level of compression is always applied upon the portion of the suture member (52) passing through the interface of the door member (204) and housing (206). In other words, in such a configuration, the door member (204) and housing (206) may be biased to clamp down upon the suture member (52).

Referring to FIG. 16, a process for utilizing technology such as that depicted in FIGS. 15A-15J is illustrated. As shown in FIG. 16, after preoperative diagnostics and patient preparation (138), access may be created (140) to the subject tissue structure (for example, a thoracotomy may be created to access the wall of the heart, the heart wall being the subject of the subsequent wall crossing and closure). The subject tissue structure may be at least partially crossed (142) using an elongate guiding member such as a needle, which may be navigated utilizing various imaging, sensing, and/or navigation modalities. The needle may be followed by a guidewire (i.e., a guidewire advanced through the needle). One or more helical needle/suture assemblies may be advanced (144) across a portion of the tissue wall following the elongate guiding member (or in another embodiment, without the assistant of a guiding member); depth of positioning (145) of one or more of the pertinent structures (such as the distal needle tips, anchor member positions, or the like) may be monitored (using an aperture 220 and associated lumen such as that described below in reference to FIG. 17B—or a pressure transducer configured to sense pressure at a chosen distal location, the transducer preferably operatively coupled to a means for signaling an operator, such as a small proximally-positioned light that toggles between red and green colors when the given pressure threshold for completed insertion/deployment has been reached); with full insertion/deployment completed, the helical member may be axially and rotationally withdrawn to place an anchoring element and compound helical suture into a configuration wherein they may be subsequently utilized to effect a closure (146), and such configuration may be confirmed (148) before further interventional steps. Subsequent to confirmation that a closure configuration appears to be ready, a dilator (150) and/or other tools (152) may be advanced through the suture helix, thereby expanding the suture helix so that pertinent diagnostic and/or interventional steps may be accomplished, such as the installation of a heart valve. Subsequently, the dilator may be re-inserted (i.e., using a hemostatically-valved sheath) in place of the diagnostic and/or interventional tools (208), and the tapered outer shape of the dilator may be utilized to effect an incremental tightening of the wound or port, using, for example, one or more 1-way tension retainers (200). A guidewire may be left in place as a "test closure" is accomplished around the guidewire to permit observation of the intervention while also permitting easy re-access. The closure may be completed with full withdrawal of the dilator, needle, and guidewire, tightening of the one or more 1-way tension retainers (200), and proximal fixation of the suture end or ends to retain tension (210).

Referring to FIGS. 17A-20, another embodiment is shown wherein a two needle (66, 67) configuration may be utilized to simultaneously insert two suture members and two associated anchor members. The assembly depicted in FIG. 17A includes a sleeve (212) slidably coupled over the elongate delivery member (16). The sleeve (212) may be freely rotatable and longitudinally slidable to assist with atraumatic interfacing of the instrumentation versus nearby tissue structures such as a chest wall wound and nearby calcified tissue. A manual tensioning interface (18) is coupled to the proximal end of one or more of the suture members, and a touhy assembly (214) may be configured to allow for valved switching of tools and elongate members, such as a guidewire and various catheters. A relatively large surface engagement member (216) is configured to be urged against the subject tissue wall between the tissue and a suture tensioning structure, such as a 1-way tension retainer as described above in reference to FIGS. 15A-16, or such as the controllably-locking tension retainer (218) shown in greater detail in FIGS. 17B-17F.

Referring to the close-up orthogonal view of FIG. 17B, the relatively flat engagement member (216) and controllably-locking tension retainer (218) are shown, along with an aperture (220) which may be present in any of the aforementioned or depicted variations of the elongate tracking member (68). The aperture may be fluidly coupled to a lumen down the center of the elongate tracking member, and such lumen may become proximally exposed (for example, by a simple exit from the deployment member 14, or via exposure to a window within the deployment member 14 or other associated member, the window being configured to assist an operator in visualizing blood or other fluid that may bleed back through the lumen, indicating that the aperture has been exposed to such relatively high pressure fluid), so that an operator can see if blood or other pressurized fluids are coming through the aperture and through the lumen, as a signal that such aperture has been exposed to such pressurized fluids. Two or more apertures may be similarly used in the embodiments depicted here in FIGS. 17A-17F, and also the embodiments described in reference to FIGS. 19A-19Z-8, with each aperture fluidly connected to a lumen, which is connected either to a detection window or lumen for viewing a flash of fluid to which the aperture has been exposed—or coupled to a sensor configured to detect the fluid immersion of the aperture, such as an OCT sensor, an ultrasound sensor, an RF impedance sensor, a partial pressure of oxygen sensor, and/or a pressure sensor. One or more apertures and/or sensors may be geometrically keyed to (i.e., configured to indicate protrusion to the level of): the distal end of a helical needle member, the distal end of an anchor member, the proximal end of an anchor member (i.e., to confirm that the anchor has, for example, crossed a threshold of a distal tissue wall). In one embodiment, for example, the aperture (220) may be longitudinally positioned more distally along the elongate tracking member (68) relative to the longitudinal positions of the distal ends of the needle members (66, 67) to provide an operator with a clear indication that the needle ends are a known distance from pressurized fluid on the other side of the subject tissue wall. In another embodiment, such as that depicted in FIG. 17B, the aperture (220) may be positioned with a known distance proximal to the distal ends of the needle members (66, 67) to provide a signal to an operator that the distal ends of the needle members (66, 67) and associated anchor members should be past the threshold of the recently crossed tissue structure wall, and have reached pressurized fluid on the other side of the wall (i.e., such as in the case of crossing a heart wall into one of the cavities of the heart). In another embodiment, multiple apertures may be present to signal various things to an operator. For example, in one embodiment, a small aperture may be positioned most distally to signal that a first longitudinal position of the elongate tracking member and associated needle complex (66, 67) has been achieved, while a larger aperture (providing a noticeably larger flow rate proximally observed by the user) may be located at another known and more proximal location as another signal to the user. In another embodiment, two or more apertures may be associated with two or more unique lumens to provide clear and distinguished signaling.

Referring to FIG. 17C, the movable sleeve member has been removed to more clearly show the elongate deployment member (16) as it is coupled to a lock actuation member housing (222) and a suture conduit housing (228). In the depicted embodiment, both of these housings (222, 228) are distally coupled to a lock actuation distal housing shoe (226) which is coupled to the controllably-locking tension retainer (218). Referring to FIG. 17D, the controllably-locking tension retainer (218) is positioned adjacent the engagement member (216), which may comprise a thrombogenic material to function somewhat like a surgical pledget to spread out loads and promote clotting and tissue encapsulation. Referring to FIG. 17E, the lock actuation housing shoe (226 in FIG. 17D) has been removed to reveal the interfacing (234) of the threaded distal portion of the lock actuation member (230) with the controllably-locking tension retainer (218). A simplified orthogonal view is shown in FIG. 17F to illustrate that a length of suture may be passed freely through the slot (232) in the spring-biased (i.e., biased to close and thereby close the slot) tension retainer (218) until the lock actuation member (230) is threaded out (i.e., by manually threading it out using a proximal manipulation interface placed proximal of the proximal end of the lock actuation member housing (222) (see, for example, FIG. 17C)), after which the close closes upon the captured suture portion, causing a locking of the suture relative to the tension retainer (218). Thus, in operation, the suture member may be proximally tightened using the manual interface (18), after which the lock actuation member (230) may be threaded out to capture a portion of the suture in the slot (232), thereby locking the tension retainer (218) in place, presumably in a configuration wherein it will apply a load to be spread on the nearby tissue structure by the engagement member (216).

In another embodiment, an active compression locking configuration may be used to allow both relative slideability between the locking configuration and interfaced suture material, and conversion (i.e., subsequent to application of a load) to a fixed relationship wherein relative motion is not allowed. In one embodiment, such an active compression locking configuration may comprise a coupled assembly of two portions that may be compressed against each other to convert to a fixed relationship (i.e., akin to a "split shot" that may be moved or slid along a suture line, then clamped into a fastened position relative to the suture line with a pliers or the like). In another embodiment, two movably coupled—or decoupled—members may be compressed or otherwise loaded together (for example, with a crimping tool) to convert from a relative movement configuration between the fastener and suture line, to a clamped configuration that disallows relative motion. Certain medical grade type crimping fasteners are available from the orthopaedics division of Smith & Nephew, Inc., of Memphis, Tenn.

Referring to FIG. 18, a process for utilizing technology such as that depicted in FIGS. 17A-17F is illustrated. As shown in FIG. 18, after preoperative diagnostics and patient preparation (138), access may be created (140) to the subject tissue structure (for example, a thoracotomy may be created to access the wall of the heart, the heart wall being the subject of the subsequent wall crossing and closure). The subject tissue structure may be at least partially crossed (142) using an elongate guiding member such as a needle, which may be navigated utilizing various imaging, sensing, and/or navigation modalities. The needle may be followed by a guidewire (i.e., a guidewire advanced through the needle). One or more helical needle/suture assemblies may be advanced (144) across a portion of the tissue wall following the elongate guiding member (or in another embodiment, without the assistant of a guiding member); depth of positioning (145) of one or more of the pertinent structures (such as the distal needle tips, anchor member positions, or the like) may be monitored (using an aperture 220 and associated lumen such as that described above in reference to FIG. 17B—or a pressure transducer configured to sense pressure at a chosen distal location, the transducer preferably operatively coupled to a means for signaling an operator, such as a small proximally-positioned light that toggles between red and green colors when the given pressure threshold for completed insertion/deployment has been reached); with full insertion/deployment completed, the helical member may be axially and rotationally withdrawn to place an anchoring element and compound helical suture into a configuration wherein they may be subsequently utilized to effect a closure (146), and such configuration may be confirmed (148) before further interventional steps. Subsequent to confirmation that a closure configuration appears to be ready, a dilator (150) and/or other tools (152) may be advanced through the suture helix, thereby expanding the suture helix so that pertinent diagnostic and/or interventional steps may be accomplished, such as the installation of a heart valve. Subsequently, the dilator may be re-inserted (i.e., using a hemostatically-valved sheath) in place of the diagnostic and/or interventional tools (236), and the tapered outer shape of the dilator may be utilized to effect an incremental tightening of the wound or port, using, for example, one or more controllably locking tension retainers (218). A guidewire may be left in place as a "test closure" is accomplished around the guidewire to permit observation of the intervention while also permitting easy re-access. The closure may be completed with full withdrawal of the dilator, needle, and guidewire, tightening of the one or more controllably locking tension retainers (218), and proximal fixation of the suture end or ends to retain tension (238).

Referring to FIGS. 19A-20, various aspects of another embodiment for utilizing a twin helical needle (66, 67) configuration to install two or more suture members (52, 53) with anchors (54, 55) are depicted. The assembly of FIG. 19A includes a proximal housing assembly (240) configured to be comfortably handled and/or held in place by an operator while a manual rotation interface (244) is turned clockwise or counterclockwise (with the other available hand, for example) to advance a coupling member (246) coupled to one or more (in the depicted embodiment a pair of two) helical needle members carrying suture and anchor elements. The proximal portion of the coupling member (246) may have slots or threads (248) formed therein that are configured to mechanically and movably interface with one or more pins (252). The coupling member (246) is configured to advance or retract relative to the proximal housing assembly (240) in response to rotation of the manual rotation interface (244) coupled to the coupling member (246). A distal housing, or sleeve member, (242) guides the distal portion of the coupling member (246), provides a mechanical platform for a specialized end geometry (as described below), and provides a platform for storing additional suture length locally (also as described below). The coupling member (246) may comprise one or more graduation marks (250) to establish how far the coupling member (246) has been inserted relative to the proximal housing assembly (240). In one embodiment, such graduation marks may be utilized as indicators that the needle members (66, 67) have been inserted into the subject tissue wall by a distance equivalent to the typical thickness of a heart wall, or by some other predetermined amount.

Referring to FIG. 19B, a different orthogonal view is illustrated to show that the assembly comprises two suture members (52, 53) and two associated suture tensioning assemblies (254, 255) that may be removably coupled to the proximal housing assembly (240). In the depicted embodiment, they (254, 255) are configured to temporarily reside within slots or recesses formed within the proximal housing assembly (240).

Referring to FIG. 19C, an orthogonal view of the distal end of the assembly of FIG. 19A or 19B is shown to illustrate a distal interface member (256) that comprises one or more ramp members (258, 260) configured to locally stretch and reorient tissue that is encountered near the distal tips of the needle members (66, 67), to facilitate capture of such tissue by such needle tips, as opposed to laceration of the tissue when the needle tips are dragged along without capturing, puncturing, and protruding into such tissue. In other words, these ramp members locally increase the angle of approach of the needle tips versus the tissue to increase the odds of capture, puncture, and protrusion of the needle tips into the tissue without laceration or scarification. The depicted embodiment shows two ramp members on each side of the needle member (66, 67) tip such that each needle member (66, 67) tip is nearly encapsulated by the associated pair of ramp members (258, 260). In another embodiment, only one ramp member may be used for the same function adjacent each needle member (66, 67). In use, an operator may manually grasp the proximal (240) and/or distal housing, or sleeve member, (242), push the distal interface member (256) against the targeted tissue structure—thus causing the ramp members (258, 260) to engage, locally stretch, and locally reorient nearby tissue structure subportions, and turn the coupling member (246) with the manual rotation interface (244) to advance the helical needle members (66, 67) and the associated anchors (118, 120; or 54, 55, etc) and suture members (52, 53) into the targeted tissue structure in a predictable format.

Also shown in the close-up views of FIGS. 19C and 19D is the proximal extension of the suture members (52, 54) from the associated anchor members (118, 120) into a local suture length storage membrane or reservoir (262).

Referring to FIG. 19D, each of the ramp member pairs (260) may also be referred to as an indentor member comprising one or more distally protruding shape features (in this embodiment the distally protruding shape features are two ramp members; also viewable as one ramp member that is bisected by the emerging helical needles and associated anchor members). These distally protruding shape features are configured to concentrate interfacial stresses upon the tissue structure such that the portions of the tissue structure that are adjacent to the distal ends of the needle/anchor assemblies become locally strained about the distally protruding shape features as these shape features are advanced into contact with the adjacent tissue structure portions. It is this contact configuration that locally increases the effective angle of penetration between the anchor/needle assemblies and the tissue structure. Various embodiments may include one or more distally protruding shape features or surfaces that comprise portions of a spherical surface, a linear ramp surface (as shown in FIG. 19D, for example, wherein the ramping up along each ramp is substantially linear), an arcuate or nonlinear ramp surface (wherein the ramping is nonlinear), or a single or multiple stepped ramp surface (wherein the ramping comprises discrete steps). The ramping angle in the depicted embodiment is generally parallel to the angle formed as the helical needle and associated anchor emerge from the distal interface member (256), but in other embodiments these geometries may not match. The non-ramped aspect of the depicted embodiment comprises a substantially perpendicular leading surface (i.e., perpendicular to the surface of the distal interface member (256) and generally aligned with a longitudinal axis of the helical needle assembly. The depicted ramp members are bisected by the needle members; in another embodiment, the needle members emerge adjacent to, but not directly through the middle of, the ramp members or other protruding shape features. The shape features in the embodiment of FIG. 19D are helical wrapped about approximately the same longitudinal axis as the helical member. In other embodiments, they may be wrapped about a different axis. As described below in reference to FIG. 23B, the distally protruding shape features may comprise one or more tissue traction features (such as the barbed features 324 depicted in FIG. 23B) configured to prevent relative motion between the distally protruding shape feature and portions of the tissue structure with which it may be directly interfaced.

Referring to FIG. 19E, this membrane (262) has a slot or cut defined therein that allows additional suture length to be pulled out of the relatively flat membrane reservoir (262), which may be configured initially to contain a few additional loops worth (264) of length of suture material (52). For example, in one embodiment, a local suture length enclosure, such as one comprising a membrane material with one or more access apertures or slots for the suture member to be drawn out and tensioned proximally, may have one or more loops of suture providing an additional length of between about 20 millimeters and about 500 millimeters that may be pulled out, for example, under tensile loading from associated anchor and helical members advancing into a tissue structure relative to the location of the reservoir, which is generally configured to somewhat fixed relative to the position of the proximal wall of the tissue structure in one embodiment. Thus the suture is coupled distally to an anchor member (118, 120), then is routed through the membrane reservoir (262), into a slot in the proximal housing member (240) to enter a suture tensioning assembly (254, 255), the subportions of which are described below. A different orthogonal view of the assembly of FIG. 19E is shown in FIG. 19F. A close view of one of the membrane reservoirs (262) and associated suture member (52) pathways is depicted in FIG. 19G.

Referring to FIGS. 19H and 19X, with the proximal housing member (240) hidden away, the suture tensioning assemblies (254, 255) are more clearly visible. FIG. 19X also has the distal housing member, or sleeve member, (242) hidden to show the underlying coupling member (246) extending distally to a sleeved (294) coupling with the helical needle members (66, 67), which are configured to rotatably extend out of the apertures in the distal interface member (256), through the ramp members (258, 260) as described above.

Referring back to FIGS. 19I-19W, aspects of and operation of the suture tensioning assemblies (254, 255) are depicted. Referring to FIG. 19I, a suture tensioning assembly is shown comprising a manual tensioning interface (18) coupled to a distal end of the suture member (52). The suture member extends distally from the manual tensioning interface (18), around a length storage and fixation spool fitting (272), through a lumen formed in a small handle member (268), into a lumen formed through the tubular suture tensioning element (16), through a locking member shoe housing (266) coupled to the distal end of the tubular suture tensioning element (16), into a two-way/one-way controllably advanceable tension retainer (265), and out toward the membrane reservoir (not shown in FIG. 19I; element 262 in FIG. 19H, for example).

FIGS. 19J-19L show three different orthogonal views of the same two-way/one-way controllably advanceable tension retainer (265) assembly, which comprises a main housing member (280), a door member (278) rotatably coupled to the main housing member (280), a spring (276) configured to bias the door member (278) closed against the main mousing member (280), as in FIGS. 19J-19L. The suture member (52) is routed through an alignment aperture (282) in the door member (278) such that it is caught, or "grasped", between the closed door member (278) and the associated surface of the main housing member (280). The bottom of the tension retainer (265) assembly may be coupled to a pad (274) which may be configured to de-concentrate interfacial loads between the bottom surface of the main housing member (280) and nearby tissue structures against which the main housing member (280) may be advanced by virtue of suture member (52) tightening. The pad (274) may comprise a material such as Dacron®, or a nonthrombogenic material treated with a thrombogenic chemical agent or medicine, to assist with clot formation and biological fixation and incorporation. As shown in FIGS. 19M-19O, an actuation member (284) may be temporarily threaded into the door member (278) to urge (i.e., against the spring 276 load biasing the door member to shut) the door member (278) open relative to the main housing member (280), thus leaving the suture member (52) relatively unconstrained and free to move in both directions relative to the main housing member (280). By backing out (i.e., by threading out in reverse) the actuation member (284), the door becomes unconstrained by the actuation member, and is urged shut by the spring (276), thus capturing the suture member (52) between the door member (278) and the main housing member (280). With the door member (278) shut, the suture member (52) may still be pulled in an upward (i.e., toward the top of the illustration page containing FIGS. 19M-19O) to cause further tensioning of the assembly against a subject tissue structure wall, because this 1-way directional tensioning urges the door to slightly open and allow motion of the suture member (52) relative to the door member (278) and main housing member (280); on the contrary, tension downward on the suture member when the door member (278) is shut against the suture member (52) only causes the door to shut even tighter, by virtue of the cam-like geometry of the interface between the door member (278) and suture member (52), as shown, for example, in FIGS. 19N and 19O. Thus, the assembly is controllably switcheable: from a state of two-way movability of suture (52) relative to locking member (265), to a state of one-way movability (i.e., tightening only) of the suture (52) relative to locking member (265)—and this switching from one mode to another mode is conducted by threading in the actuation member (284) to essentially jack open the door to temporarily have the two-way movability mode. Referring to FIGS. 19P and 19Q, an experimental loading configuration and data related thereto are illustrated. FIG. 19Q features two plots (290, 292) of pull force (286) versus suture displacement (288) to show that the two-way/one-way switcheable locking member is capable of holding significant loads when in the one-way mode with the door member (278) in a shut position against the subject suture member (52).

Figure 1:
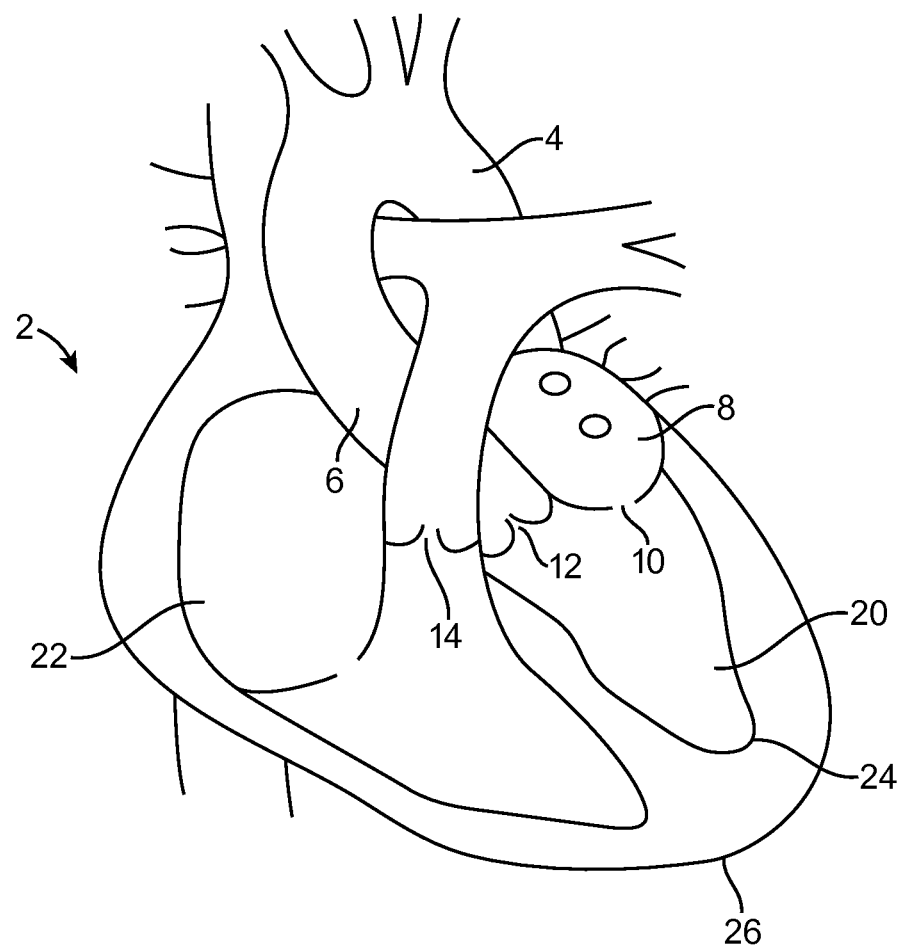
FIG. 1 illustrates aspects of the human heart anatomy.

Referring to FIG. 19R, the various portions of the suture tensioning assembly embodiment are shown in a somewhat deconstructed view. In an assembled configuration, the actuation member (284) may be inserted through a lumen formed by the tubular tensioning element (16) and twisted (i.e., using a proximal manual gripping interface 270) to thread the distal portion of the actuation member (284) into the door member (278) of the two-way/one-way controllably advanceable locking member (265). FIGS. 19S and 19T show close-up views of the interaction of the proximal portions of the suture member (52) with the spool member (272). FIGS. 19U-19W show other orthogonal views of various states of assembly of the subject suture tensioning assembly (254, 255) embodiment. FIG. 19Y-19Z-1 illustrate various orthogonal views of partial assemblies of the distal end of the subject access and closure instrument to show the positions of the needle members (66, 67), suture members (52, 53), distal interface (256), suture length storage membranes (262, 263), and elongate tracking member (68) aperture (220) relative to each other.

In one embodiment, the spool member (272) may be utilized to transiently lock down a given length of suture into a tensile state, and subsequently to adjust the length to establish a different tensile state. For example, during a process such as that described above in reference to FIG. 12A (element 154 in particular) wherein a dilator or other member is incrementally withdrawn as the one or more sutures are incrementally tightened, the spool member (272) may be utilized to temporarily retain various tensile states during such a process. In another embodiment, a releasable pinching clamp may be utilized to have the same function as described herein for the spool member (i.e., to temporarily retain a given tensile state, while also providing relatively easy releasability for repositioning).

Figure 2:
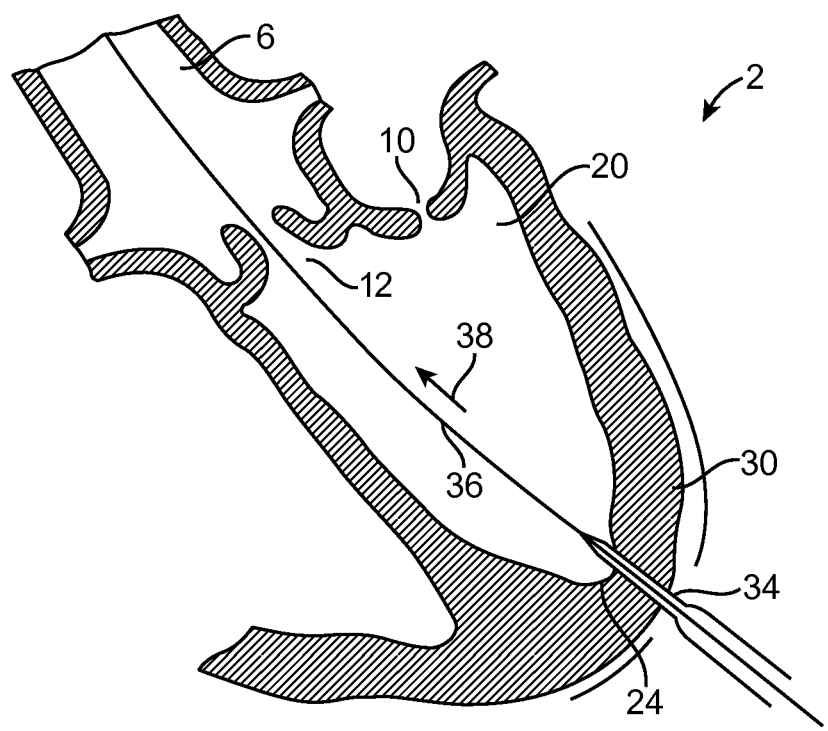
FIG. 2 illustrates a conventional transapical access procedure.

Referring to FIGS. 19Z-2 and 19Z-3, two embodiments of anchor members (296, 298) are depicted. The embodiment in FIG. 19Z-2 may be created from a single piece of tubing using, for example, a laser cutter. An eyelet or suture fastening interface (302) comprises a cut-out portion, as does a tail (300), which is configured to rotate the anchor (296) and grab onto nearby tissues when a suture coupled to the eyelet is pulled from a direction toward the tail (300)—somewhat akin to the action of a toggle bolt. FIG. 19z-3 depicts a machined version of a similar structure, created from two parts in one embodiment (the tail 304 being a separate part that is fused with the body); the eyelet (306) may be machined. Either embodiment may have a tapered forward geometry (308, 310), formed, for example, by laser cutting or grinding. Referring to FIGS. 19Z-4 to 19Z-8, in use, an assembly such as that depicted in FIG. 19A may be advanced against a targeted tissue structure wall, and when in an appropriate position, the positioning of the proximal and distal housing members (240, 242) may be maintained while the manual rotation interface (244) is utilized to rotate the needle members (66, 67) distally out through the distal interface member (256) and into the subject tissue wall (not shown), along with the elongate tracking member (68), which, as described above, may assist in preventing "walking" of the needles relative to the targeted portion of the tissue wall, and/or undesirable localized overstraining of the nearby tissue. FIG. 19Z-5 shows a close up view of the needles extended out through the distal interface member into what could be a targeted tissue structure, the needles carrying two machined anchor members (298, 299) which may be coupled to two suture members (not shown). As described above, one or more apertures or sensors on various portions of the distal hardware, along with one or more graduation marks (250) on the proximal coupling member (246) hardware, may assist in providing an operator with precision feedback as to how many turns have been made with the manual rotation interface (244), and how deep the distal hardware is into the nearby tissue. Referring to FIG. 19Z-7, with an adequate depth of anchor members and associated suture members achieved, the main bulk of the instrument assembly may be removed by reversing out the helical needle members and withdrawing the proximal instrument housings (240) and associated hardware—while the suture tensioning assemblies (254, 255) are decoupled from such proximal instrument housings (240) and associated hardware, as shown in FIG. 19Z-7, to leave behind only the anchors, sutures, and suture tensioning assemblies (254, 255). The sutures (52, 53) may be tightened onto the tissue structure using the associated locking members (such as two-way/one-way controllably advanceable locking members described above), tubular tensioning elements (16), and tensioning of the manual tensioning interfaces (18).

Referring to FIG. 20, a process for utilizing technology such as that depicted in FIGS. 19A-19Z-8 is illustrated. As shown in FIG. 20, after preoperative diagnostics and patient preparation (138), access may be created (140) to the subject tissue structure (for example, a thoracotomy may be created to access the wall of the heart, the heart wall being the subject of the subsequent wall crossing and closure). The subject tissue structure may be at least partially crossed (142) using an elongate guiding member such as a needle, which may be navigated utilizing various imaging, sensing, and/or navigation modalities. The needle may be followed by a guidewire (i.e., a guidewire advanced through the needle). One or more helical needle/suture assemblies may be advanced (144) across a portion of the tissue wall following the elongate guiding member (or in another embodiment, without the assistant of a guiding member); depth of positioning (145) of one or more of the pertinent structures (such as the distal needle tips, anchor member positions, or the like) may be monitored (using an aperture 220 and associated lumen such as that described above in reference to FIG. 17B—or a pressure transducer configured to sense pressure at a chosen distal location, the transducer preferably operatively coupled to a means for signaling an operator, such as a small proximally-positioned light that toggles between red and green colors when the given pressure threshold for completed insertion/ deployment has been reached); with full insertion/deployment completed, the helical member may be axially and rotationally withdrawn to place an anchoring element and compound helical suture into a configuration wherein they may be subsequently utilized to effect a closure (146), and such configuration may be confirmed (148) before further interventional steps. Subsequent to confirmation that a closure configuration appears to be ready, a dilator (150) and/or other tools (152) may be advanced through the suture helix, thereby expanding the suture helix so that pertinent diagnostic and/or interventional steps may be accomplished, such as the installation of a heart valve. Subsequently, the dilator may be re-inserted (i.e., using a hemostatically-valved sheath) in place of the diagnostic and/or interventional tools (312), and the tapered outer shape of the dilator may be utilized to effect an incremental tightening of the wound or port, using, for example, one or more controllably locking two-way/one-way tension retainers (265). A guidewire may be left in place as a "test closure" is accomplished around the guidewire to permit observation of the intervention while also permitting easy re-access. The closure may be completed with full withdrawal of the dilator, needle, and guidewire, tightening of the one or more controllably locking two-way/one-way tension retainers (265), and proximal fixation of the suture end or ends to retain tension (314).

Figure 23B:
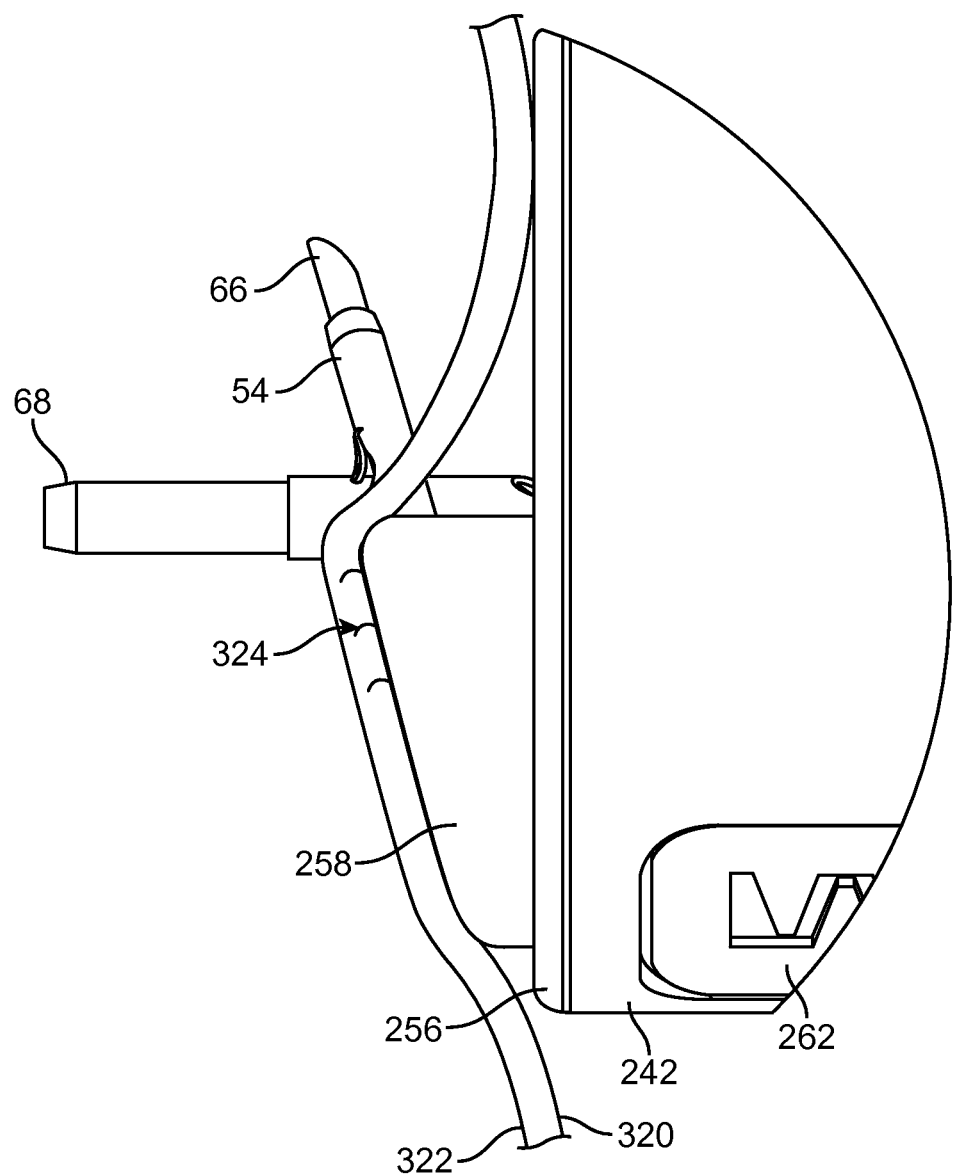

In the aforementioned illustrations and examples, one or more helical needle members have been discussed. We have discovered that there are various important relationships involved in selecting an optimal helical needle member and suture configuration. For example, referring to FIG. 21, we have shown that a very slight angle of approach (316), i.e., with a needle member tip only a few degrees from a tangential relationship relative to a point of entry into a targeted tissue structure (48) (in the depicted configuration, the angle of approach 316 is about 15 degrees) may result in some amount of relative motion between the tissue structure (48) and needle member (66) tip before the tip actually dives across the surface of the tissue structure (48). Such relative motion generally is not desirable, as it may result in relative motion and possible undesirable loading between the pericardium, epicardium, suture member, and needle member. Referring to FIG. 22, with a helical needle member (66) having the same helical pitch, one or more ramp members (258) may be utilized to locally reorient the tissue structure (48) at the point of entry of the helical needle member (66), such that the effective angle of approach (318) resulting from the combination of the ramp member (258) reorientation and the orientation of the needle based upon the associated helical pitch is relatively large (in this embodiment, about 70 degrees); we have found that such a relatively large effective angle of approach generally causes the needle member (66) to dive directly into and across the targeted tissue structure (48), as would be desired. Referring to FIGS. 23A and 23B, in another embodiment, the one or more ramp members (258) may be coupled to one or more traction features (324) (shown best in the close up view of FIG. 23B) to further assist in preventing relative sliding motion between the pericardial membrane (320), epicardial surface (322) and aspects of the tool assembly during insertion. In one embodiment, the one or more traction features (324) comprise one or more barbs or hooklike projections from the ramp member (258) surface. In a heart wall crossing scenario, with the deployment assembly pressed against the pericardial membrane (320) and the elongate tracking member (68) pressed across the pericardial membrane (320) and epicardial surface (322) into the wall of the heart, the ramp member (258) assists with locally adjusting the tissue orientation immediately adjacent the helical member (66) point of entry, as described above, and the one or more traction features press through at least a portion of the pericardial membrane (320)/epicardial surface (322)/heart wall composite to assist with a clean and relatively load-free passage of the needle member (66) tip across the pericardial membrane (320) and epicardial surface (322), and into the wall of the heart. Thus we have created configurations and techniques for successfully advancing one or more helical needle structures into a substantially slippery and viscoelastic tissue structure.

One of the other challenges in effecting an adequate closure when the procedure has been completed is assuring that proximal tensioning of the one or more deployed suture members will indeed effect a closure of the wound through the length of the wound. We define a term "helical turn" to represent the number of full turns a suture or needle travels within a subject tissue structure when viewed from a perspective coaxial to the axis of the helical winding (i.e., one helical turn would be where the needle and/or suture traveled a pathway that appears to create a full 360 degree circle when viewed down the longitudinal axis of the helix; one-half helical turn would appear like a half-circle, or 180 degrees of arcuate travel around the outer shape of the helix). We have found that with myocardial tissue and conventional suture materials, there is an optimal number of helical turns of deployed suture material; below this number, there is not enough suture helically deployed within the tissue structure to pull shut the wound; above this number, there is too much suture deployed into the tissue structure from a friction perspective, such that pulling proximally on the suture member to tension it and close the wound only tensions the proximal few helical wraps, and leaves the distal helical wraps only partially tightened due to the well known "flat belt" power transmission relationship (the ratio of belt type tensions on the tighter side, to those on the more slack side, are equivalent to e to the mu*theta, wherein mu is the friction coefficient and theta is the angle subtended by the contact surface at the pulley) described, for example, at http.//en.wikipedia.org/wiki/Belt_(mechanical), which is incorporated by reference herein in its entirety—and potentially in a configuration wherein an adequate closure may not be created. Again, with myocardial tissue and conventional suture materials, we have found the ideal number of turns for good closure performance to be between about one-half helical turn and about three helical turns, and more preferably between about 1 helical turn and about 2 helical turns.

Another factor coming into play in selecting the instrumentation configuration is the notion that the anchor may be left distally within the tissue wall, as in the embodiments of FIG. 4N or 7B, or distally past the opposite margin of the subject tissue wall, as in the embodiment of FIG. 8B. In the latter scenario, there is some slack material left unconstrained with the anchor, while in the former scenarios, there is no unconstrained slack. With dilation of the helical configuration, slack at both sides assists with the flat belt issue (i.e., in accordance with the aforementioned flat belt relationship, the ratio of tensions is equivalent to e to the mu*theta, and if you cut theta in half, you have cut the force required down by e to that factor—quite a significant nonlinear relationship). But note—upon closure, in most configurations (i.e., absent some means for also tensioning from the anchor side of the suture member), the operator is still dealing with a single-sided tensioning flat-belt scenario, and there is an important desire to effect a solid closure at the end of the procedure by tensioning only the proximal end.

Thus there is a confluence of factors at play that result in the hardware configuration selection, including but not limited to: 1) given the thickness of the wall to be crossed, we want to get between one half and two and a half helical turns through that thickness, and more preferably between one and two helical turns; 2) we would prefer to have the needle dive straight into the tissue structure without significant non-puncturing motion before entry; this can be complicated by too shallow an angle of entry; 3) we need to provide enough cross sectional area with the helical windings to accommodate the pertinent interventional hardware, dilation therefor, and helical suture closure thereof without coring out, lacerating, or necrosing the subject tissue; 4) we would prefer to use conventional materials for the suture member and needle members; 5) we will be dealing with a viscoelastic and potentially nonhomogeneous material (tissue). It is worth noting that this challenge is very different from the challenge of helically winding a running stitch along a tissue surface such that the needle tip is constantly diving and exiting the tissue surface—the flat belt friction issues there are completely different (i.e., there is no helix of suture material that is fully encapsulated by the tissue and thus subject to the flat belt relationship issues when tensioned). As described above, the second challenge may be addressed with the inventive ramp members described herein. The remaining challenges may be addressed by processing the scenario as shown in FIG. 24.

Figure 24:
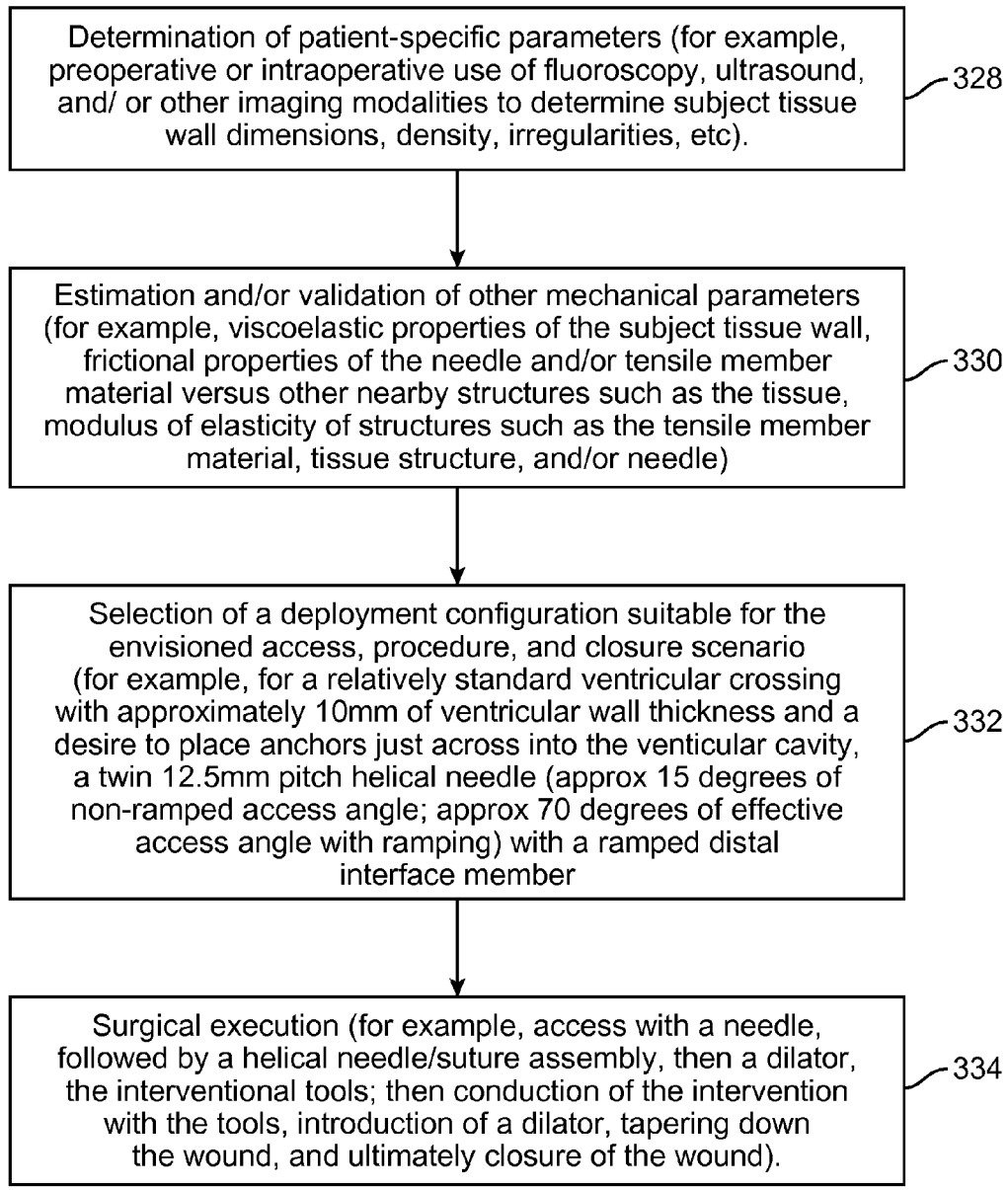
FIG. 24 illustrates a technique for implementing various embodiments of the subject helical closure configurations.

Referring to FIG. 24, after determination of patient-specific parameters, such as subject tissue wall dimensions, density, and irregularities (328), and examination of other mechanical parameters, such as estimated viscoelastic, frictional, and mechanical modulus properties of the subject tissue and instrumentation (330), a deployment configuration may be matched to the scenario (332) to address the aforementioned challenges, and the surgery may be executed (334). Heart walls, for example, may range anywhere from about 8 mm in thickness to about 25 mm in thickness. For a relatively thick targeted tissue structure crossing (for example, in the wall of a congestive heart failure patient with an enlarged heart), a relatively large helix pitch may be utilized to cross the appropriate thickness and still place between about one-half and two and a half helical turns, or more preferably between about one and two helical turns, of suture in place for closure. For a relatively thin targeted tissue structure crossing (for example, through a previously infracted area of a ventricle wall of a heart), a more shallow pitch may be utilized to ensure that enough helical turn is placed in the relatively small thickness of the targeted wall tissue to effect a closure. In one embodiment, for a heart wall of average thickness, about 12 mm in wall thickness, a twin helical needle configuration comprising two stainless steel needles with a helix pitch of about 8 mm, a helix diameter of about 15 mm, and an angle of entry (not accounting for ramping members) of about 10 degrees based upon the helical pitch may be utilized to accommodate typical valve replacement interventional tools and effect a closure. Other useful embodiments for thinner heart wall crossing include a 5 mm helical pitch (6 degree angle of entry not accounting for ramping members); and a 10 mm helical pitch (12 degree angle of entry not accounting for ramping members). For a thicker heart wall, a 13 mm pitch provides approximately one to three full helical loops with an approximate 15 degree angle of entry. Each of these embodiments would preferably incorporate one or more ramping members to address the angle of entry challenge, as described above. Other embodiments may include varied needle member helix radii (for example, one 10 mm radius helical needle may be paired with one 20 mm radius helical needle, both needles carrying a suture member and anchor member).

Yet further embodiments may include helical needle members with inner or outer helical diameters that vary or do not vary relative to length along a longitudinal axis through the center of the helical formation (i.e., such as a tapered helix with a varied inner helix diameter), helical needle members with varying, or not varying, pitch relative to length along the longitudinal axis. Further, helical needle members may be formed from solid versus tubular members formed into helical shapes, and these helical members may have various cross sectional geometries (i.e., a tubular helical member material may have a generally hollow-circular cross section, or a hollow square, rectangle, elliptical, or other cross section; a nontubular, or solid, helical member material may have a generally circular cross section, or a solid square, rectangle, elliptical, or other cross section). All of these variables may be utilized to form many permutations and combinations of suitable helical members. For example, a nontapered helix may have a constant helical pitch along its length (say, for example, a pitch between about 5 mm and about 20 mm, or more preferably between about 7 mm and about 13 mm)—or a variable helical pitch along its length; a tapered helix may have a constant helical pitch along its length—or a variable helical pitch along its length. In one embodiment, an inner helix diameter is between about 5 mm and about 60 mm, and more preferably between about 10 mm and about 20 mm. In one embodiment, an outer diameter of a wire or tube (tubular or nontubular/solid) used to form a helical member may have an outer diameter of between about 0.5 mm and about 3 mm. The helix may comprise materials such as stainless steel, Nitinol alloy, titanium, cobalt chromium, and various polymers and composites.

Further, as depicted in several of the figures associated hereto, two or more helical needle members may be utilized in various access and closure embodiments. In one embodiment, each helix may be geometrically matched to each other in the set, with substantially coaxial longitudinal axes. In other embodiments, as in the embodiment of FIGS. 5A-5D, for example, helical needle members may have different radii. Further helical needle members may have different helical pitches, different materials, different contructs (as discussed above—solid versus tubular, various cross sectional shapes, variable pitches or helix diameters with length position, etc.).

Figure 25:
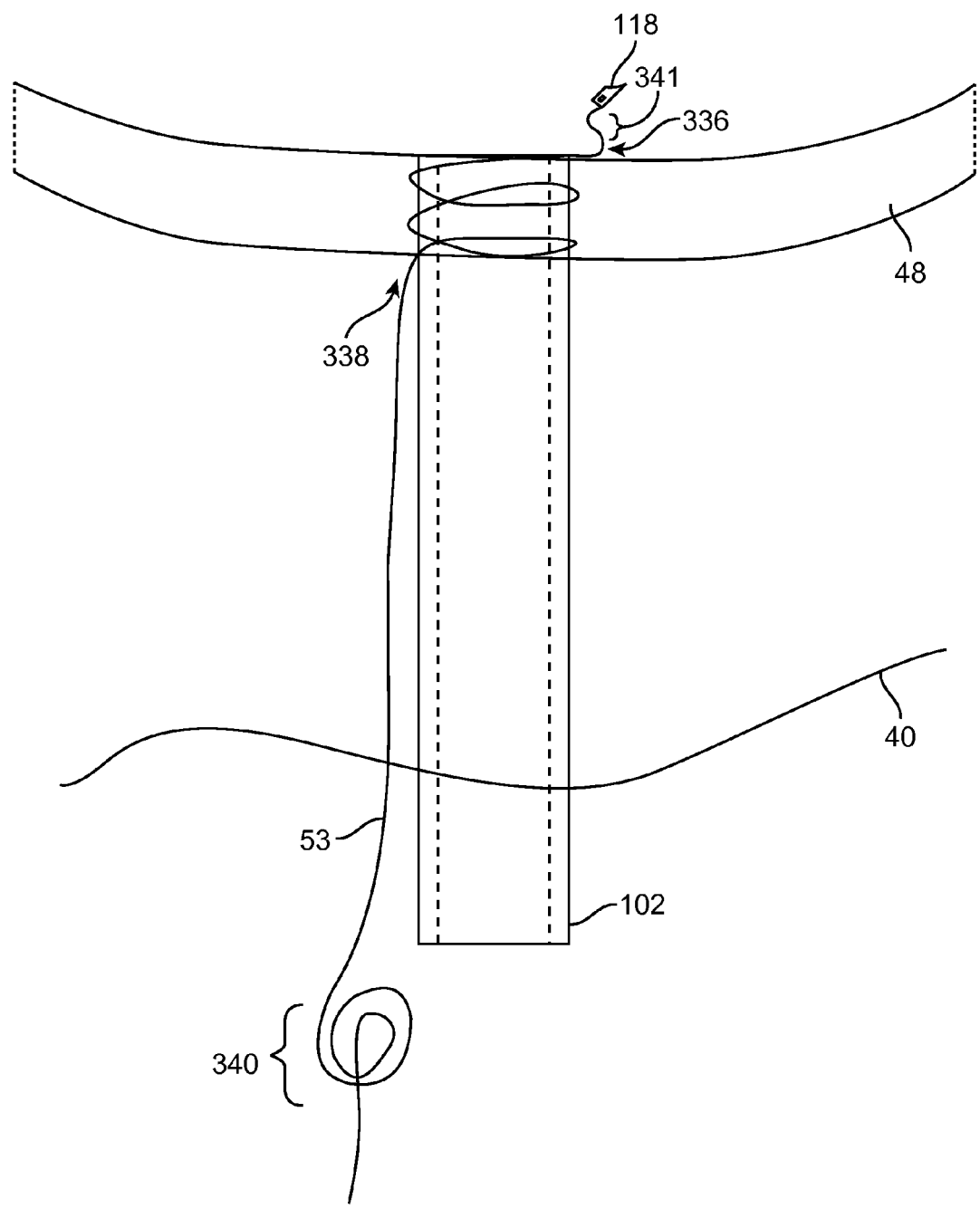
FIG. 25 illustrates a configuration wherein slack is utilized both proximally and distally to a deployed helical suture pattern.

Referring to FIG. 25, an embodiment similar to that depicted in FIG. 8A is shown. The embodiment of FIG. 25 features the deployment of extra slack suture length not only available proximally to the deployed helical suture pattern (which in the depicted embodiment comprises about two full helical loops substantially encapsulated by the midsubstance of the tissue structure 48), but also distally (i.e., on the opposite side of the targeted tissue structure wall 48). As one or more elongate tools or instruments (102) are passed through the helical suture pattern, slack may be pulled in not only from the proximal side (338), but also from the distal side (336), providing a significant advantage in view of the mechanical overconstraint issues described above in reference to the "flat belt" equation. In other words, in certain embodiments wherein it is possible to provide slack distally as well as proximally (340) in the form of localized length storage or simply some additional length (341), such as between about 3 millimeters and about 48 millimeters, provided distally by advancing the anchor by an additional distance past the threshold of the subject tissue wall before retracting the needle member, such extra distal slack can provide an additional advantage in avoiding flat belt overconstraint, and thus subsequently tensioning of the helically-deployed suture pattern may be more uniform. A preferred amount of available proximal slack, using some free length of suture member, a localized length storage structure, or otherwise, is between about 5 millimeters and about 24 millimeters.

Figure 26:
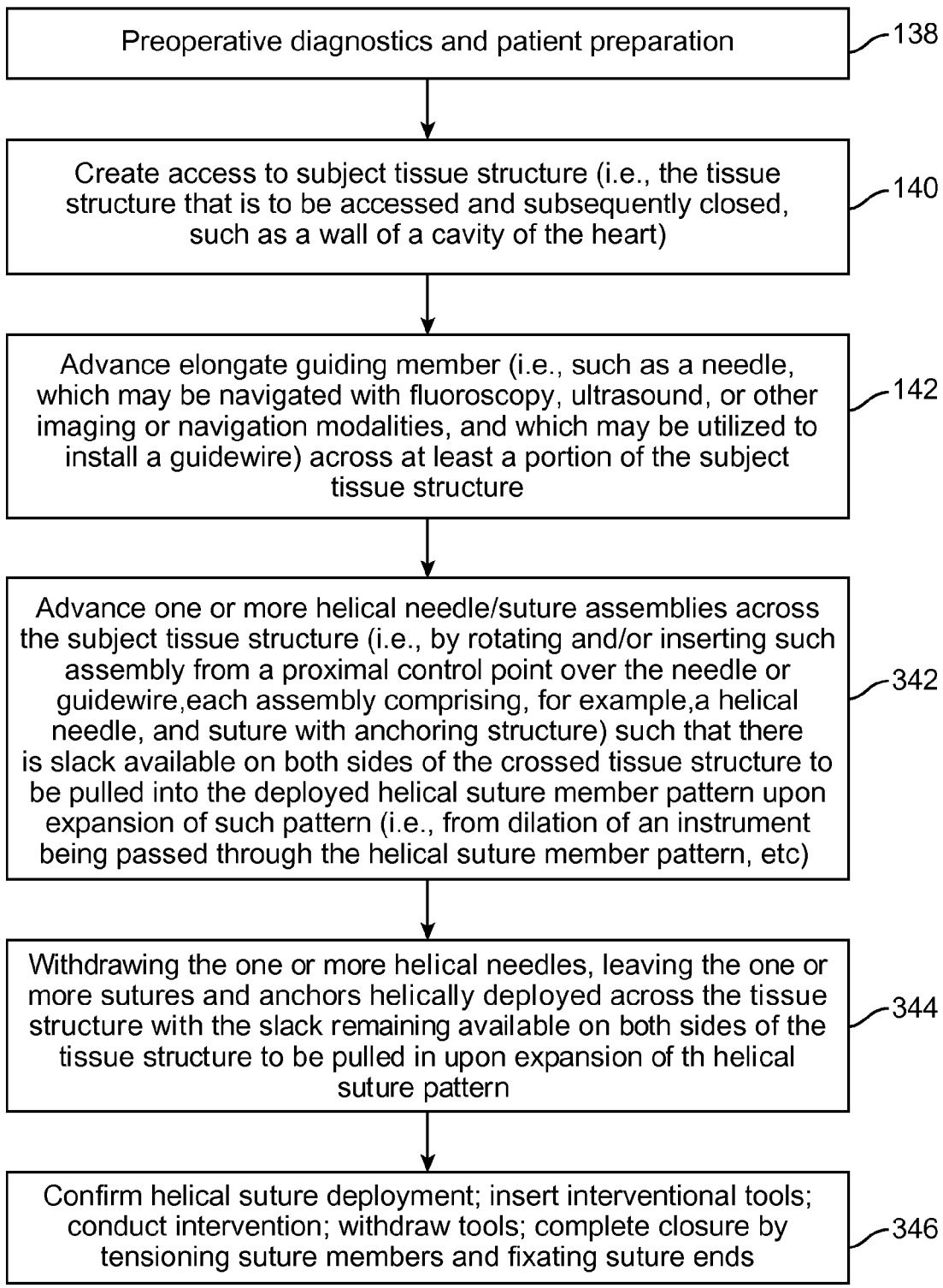
FIG. 26 illustrates a technique for implementing various embodiments of the subject helical closure configurations.

Referring to FIG. 26, a technique for effecting an access and closure using a configuration such as that depicted in FIG. 25 is illustrated. Referring to FIG. 26, after preoperative diagnostics and patient preparation (138), access may be created (140), and an elongate guiding member advanced (142). One or more helical needle/suture assemblies may then be advanced across the targeted tissue structure—and in this embodiment, across the distal threshold and beyond by a given length, such that there is suture member slack available on both the proximal and distal sides of the tissue structure that may be subsequently pulled in upon expansion of the helical suture pattern (342). The distal slack is created upon withdrawal of the pertinent helical needle, which leaves behind the associated anchor member with the additional suture member slack in tow (344). Subsequently an intervention, such as a valve deployment with or without an introducer type sheath member (i.e., certain valve deployment systems are configured to be passed through a sheath; others are configured to be introduced without a sheath and may be passed directly through the helical suture pattern; working instruments may comprise prosthetic valves, prothetic clips, graspers, dilators, endoscopes, catheters, balloons, occlusion devices, and ablation devices, for example), may be conducted and closure effected (346). Preferably the helical needle and suture configuration is selected to accommodate passage of one or more instruments that may expand the suture helical configuration diameter by between about 10% and about 35% during the intervention (with collapse back to closure thereafter, using tension on the suture member, which may be incremental or cyclical, as described in various embodiments above).

Figure 27:
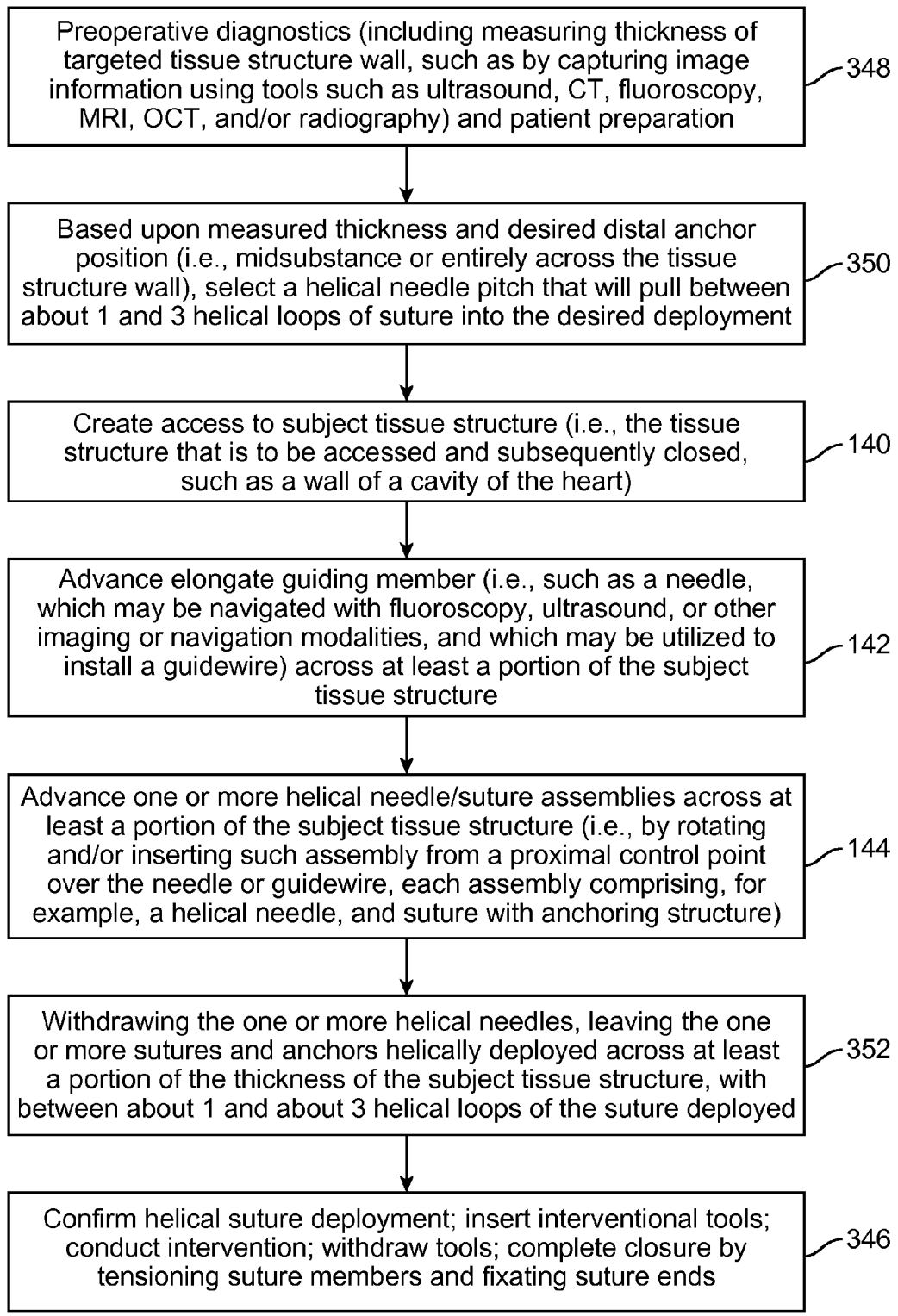
FIG. 27 illustrates a technique for implementing various embodiments of the subject helical closure configurations.

Referring to FIG. 27 another access and closure embodiment is illustrated to emphasize that a helical needle configuration may be specifically selected based on anatomical characteristics, such as the thickness of the desired portion of the tissue structure to be crossed. In other words, given the aforementioned discussions of preferences for between about 1 full helical loop and about 3 full helical loops of suture to be deployed to effect desired expandability and contraction/closure properties, the geometry of the helical needle member may be tailored to provide such functionality in view of the amount of tissue to be crossed and subsequently expanded and then collapsed to closure. Referring to FIG. 27, preoperative diagnostics and patient preparation may include measurements and planning regarding the thickness of the targeted tissue structure wall to be crossed in the intervention (348). Images may be captured using, for example, ultrasound, computed tomography (CT), fluoroscopy, magnetic resonance imaging (MRI), radiography, and/or optical coherence tomography (OCT). In another embodiment, measurements may be taken in-situ (i.e., after access has been created 140) with a measuring probe or needle, such as one configured to provide a proximal signal to an operator that the tip has reached a blood-filled cavity, wherein a distal aperature is fluidly coupled to a lumen that leads to a proximal viewing port or window for the operator to see a flash of blood as an indicator that the aperture has reached the blood-filled cavity. Further, needles or probes may be outfitted with one or more ultrasound transducers to provide for in-situ local imaging and associated measurement. Referring again to FIG. 27, based upon the measured depth of tissue traversal (i.e., how far across tissue the anchor is to be deployed), a helical pitch for a helical needle may be selected that will place between about 1 and about 3 full helical loops of suture into the desired deployment (350). With access created (140) and an elongate guiding member placed (142), one or more helical needle assemblies may be advanced to place one or more anchors and associated suture members (144). Upon withdrawal of the needles, the desired 1 to 3 helical loops of suture are left to comprise the deployed pattern (352). The suture member deployment may be confirmed, after which various interventional tools may be inserted through the deployed pattern, thereby expanding the pattern and pulling in slack to accommodate the expansion. After the intervention is completed, the tools may be withdrawn, and the closure effected by tensioning the one or more suture members (346).

Figure 28A:
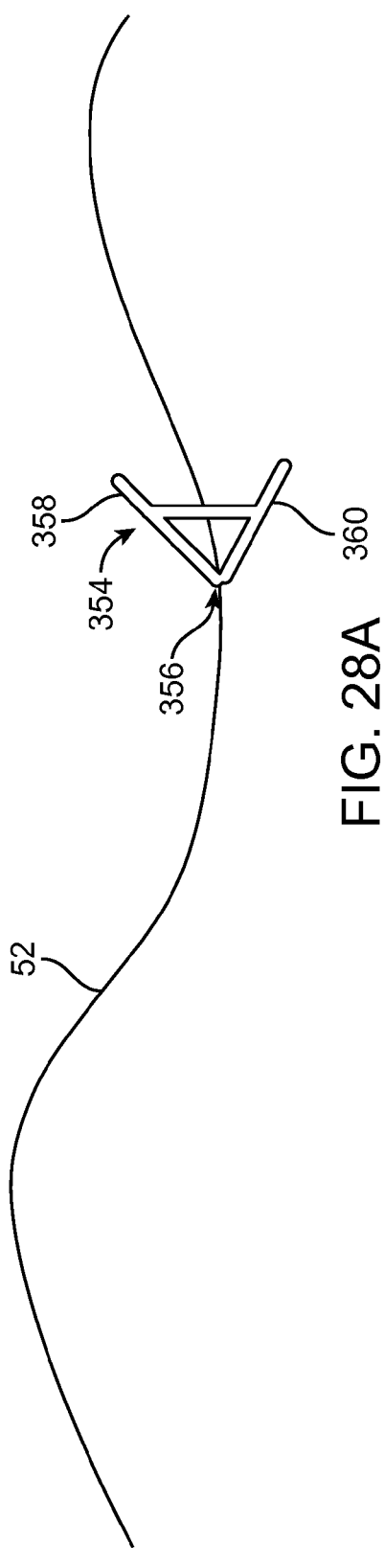
FIGS. 28A-28D illustrate configurations wherein temporary suture member fixation may be employed.
Figure 28B:
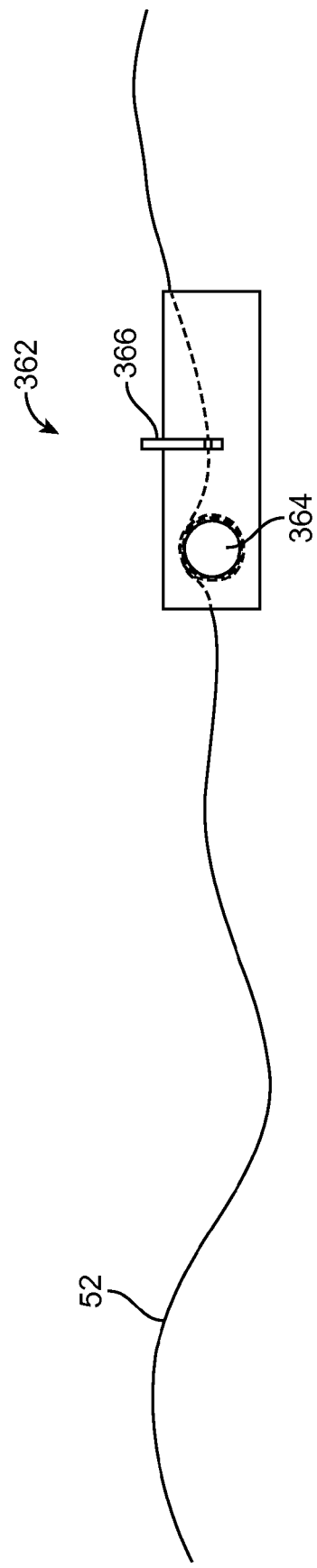
Figure 28C:
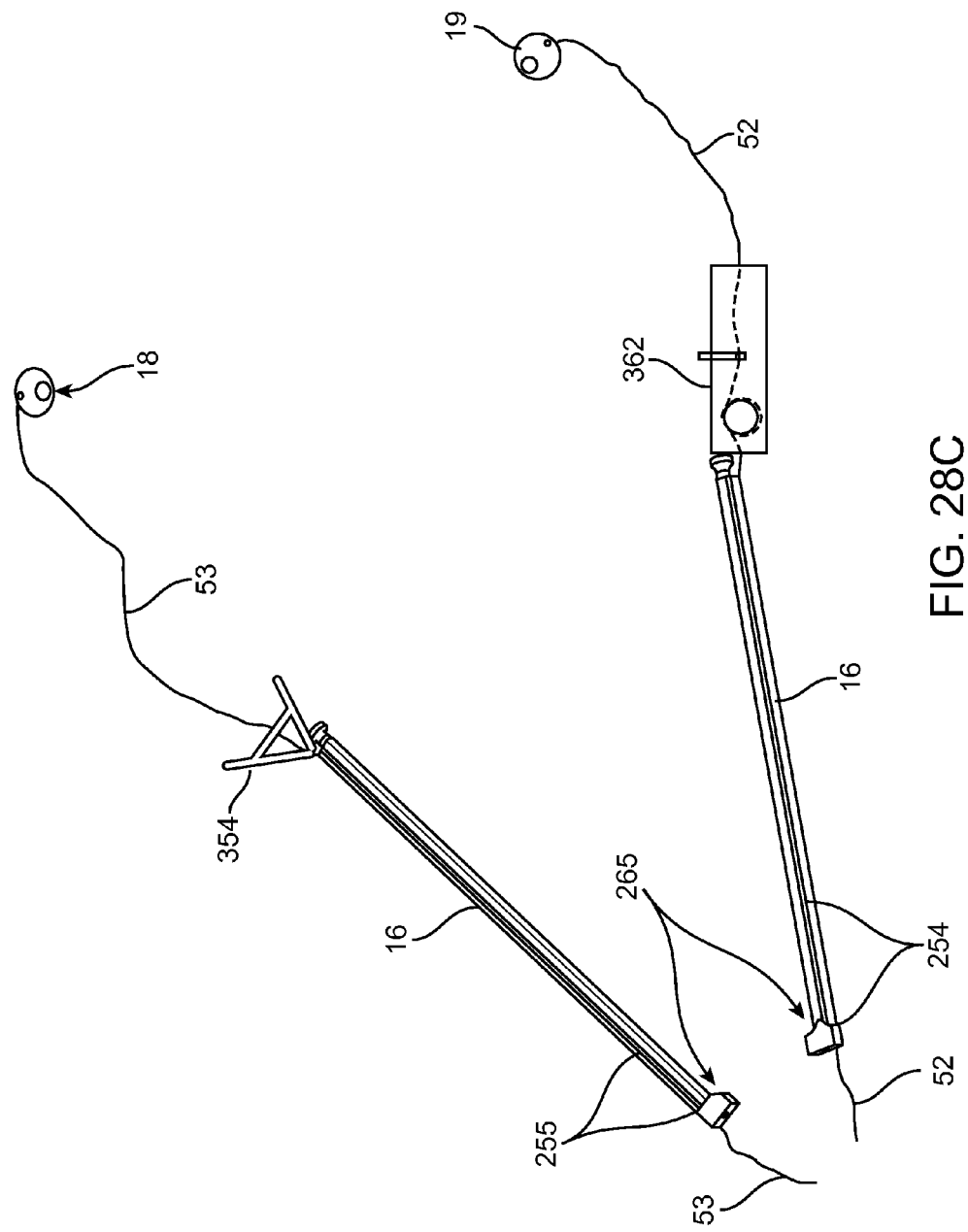
Figure 28D:
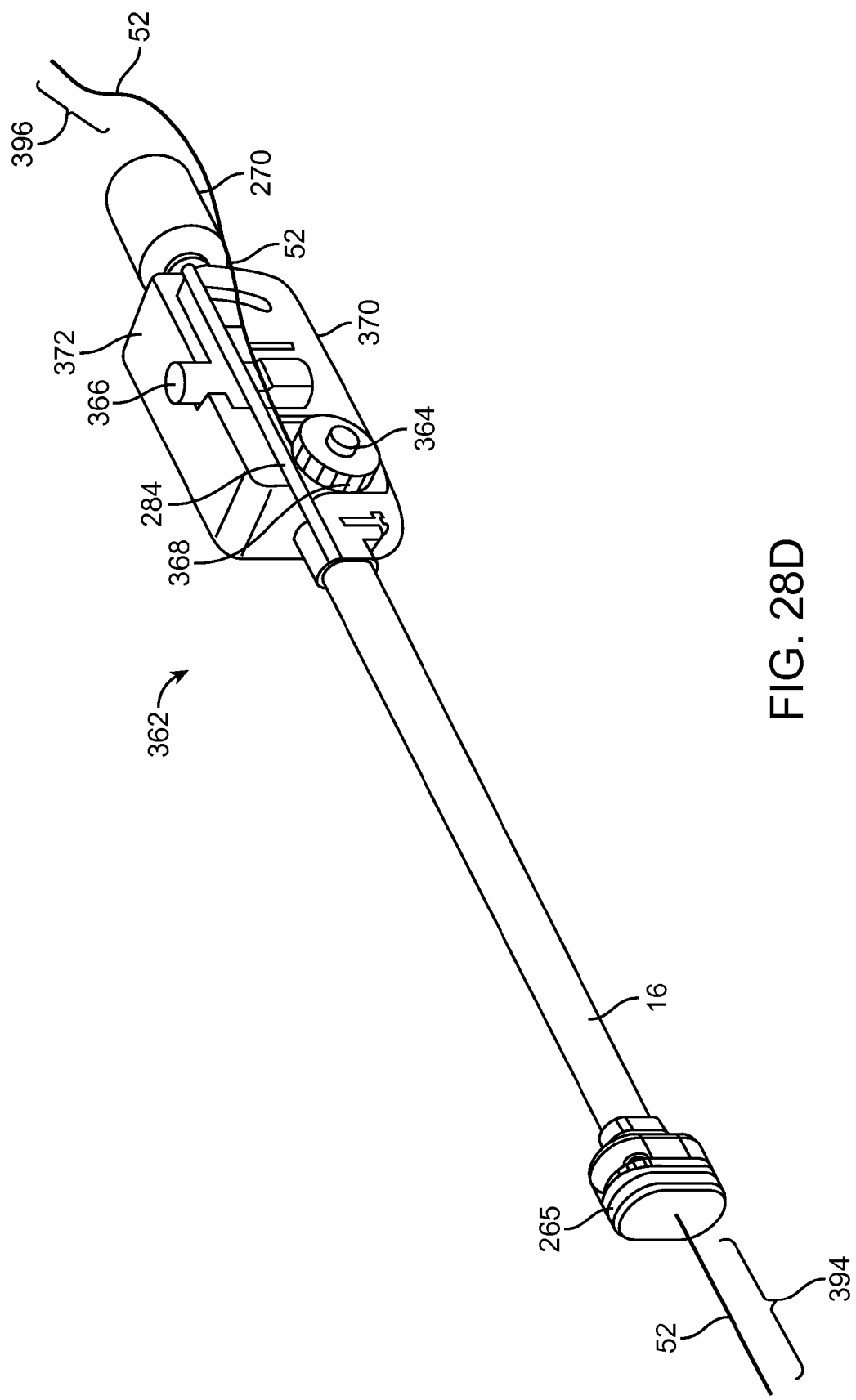

Referring to FIGS. 28A-28D, it may be desirable to transiently provide tension on one or more suture members, and to subsequently release the temporary tension in favor or more permanent tensioning, such as through a two-way/one-way controllably advanceable locking member (265), as discussed above. To provide temporary tension fixation before switching such a locking member (265) from a two-way configuration to a one-way configuration, it may be desirable to provide a pinch clamp (354), such as that depicted in FIG. 28A, or a suture member reel mechanism (362), such as that depicted in FIG. 28B. In other words, it may be desirable during the closure portion of a procedure to temporarily (i.e., with the ability to remove tension or adjust the tensioning position) tension the suture member without committing to the more permanent tensioning provided by switching a two-way/one-way controllably advanceable locking member (265) from two-way suture movement to one-way only suture movement (i.e., by operating an actuation member 284, as described above). The pinch clamp (354) may be manually installed by manual manipulation of the two spring-biased arms (358, 360) which produce a pinching load at a loading interface (356). The suture reel mechanism (362) depicted in FIG. 28B may be released with a push of a button (366) after tightening around a reel (364) in a one-way tightening configuration. Referring to FIG. 28C, the temporary tightening mechanisms (354, 362) are shown temporarily retaining tensions on suture members (52, 53) that may be configured as those depicted in FIG. 19Z-8 above. Referring to FIG. 28D, a close-up orthogonal view with a partial cross section of a suture reel mechanism (362) is depicted. The suture member (52) is passed from a location in the tissue structure through a locking member (265) that is mechanically constrained in its open (i.e., 2-way) configuration by an actuation member (284) connected to a proximal control knob (270). To temporarily tighten the distal suture portion (394), a tension may be applied to the proximal suture portion (396) which causes a ratchet reel (364) to rotate, and the ratcheted outer surface of the ratchet reel to continue to incrementally click past a pawl (370) which prevents rotation of the reel in the opposite direction, along with a suture pinch point (368) where the distal aspects of the reel meets the housing (372). Thus a one-way tightening is effected with the reel/pawl and pinch point configuration. When an operator wishes to release the tension or back off the assembly a bit, he can depress the release button (366), which depresses the pawl (370) and allows the reel (364) to rotate in a reverse direction. When an operator wishes to switch from temporary tensioning to more permanent tensioning, he can use the actuation member knob (270) to operate the actuation member (284) to change the locking member (265) from a two-way suture movement mode to a one-way-only suture movement mode, as described above.

Figure 29:
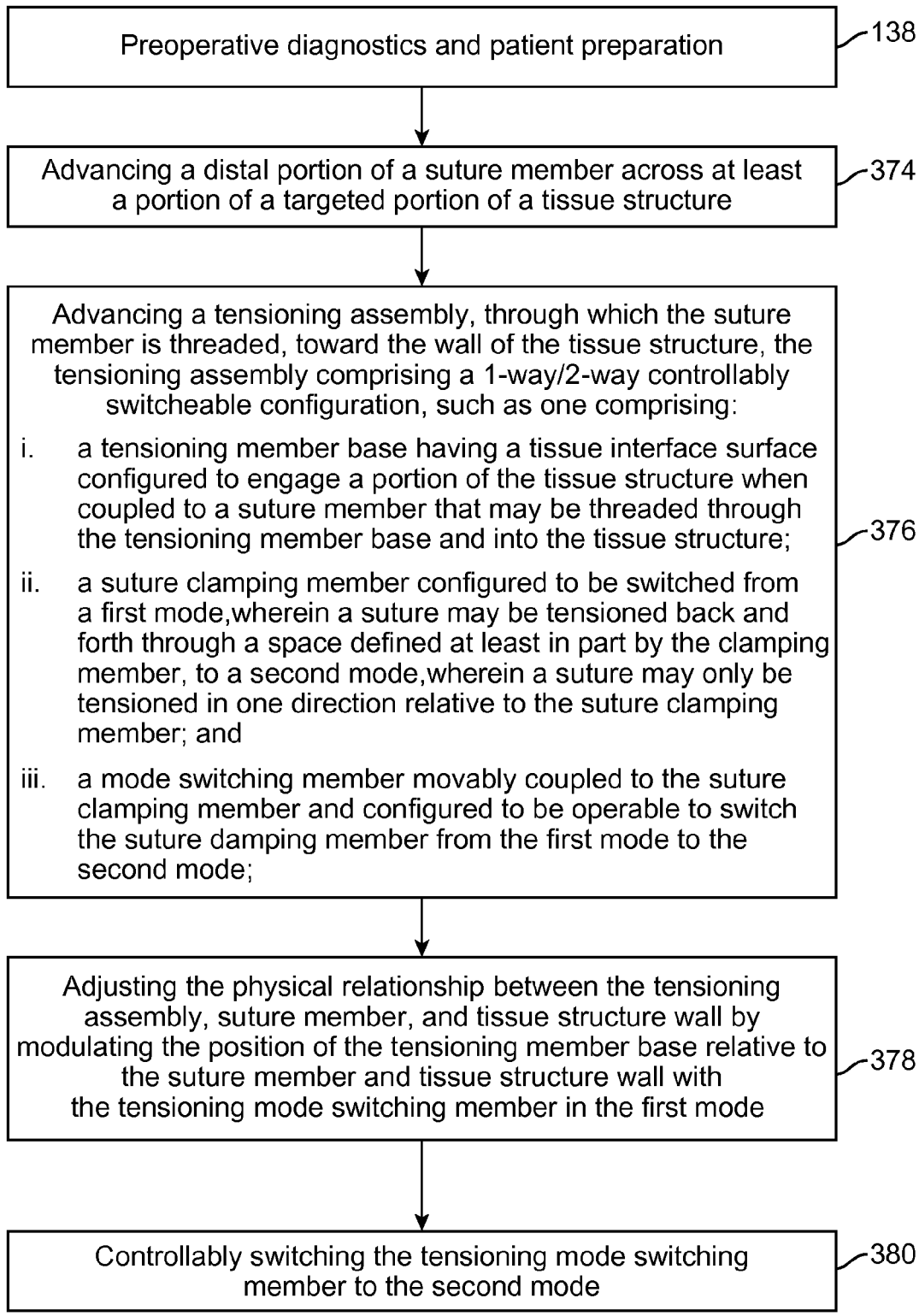
FIG. 29 illustrates a technique for implementing various embodiments of the subject helical closure configurations.

Referring to FIG. 29, a method featuring several of the above characteristics is illustrated. After preoperative diagnostics and patient preparation (138), a distal portion of a suture member may be advanced across at least a portion of a targeted tissue structure (374), as described in reference to other embodiments above. With a suture member placed in a desired configuration for an intervention and subsequent closure, a tensioning assembly may be advanced toward the wall of the tissue structure, the assembly comprising a two-way/one-way controllably switcheable locking assembly configuration, such as those described above, which may comprise a tensioning member base (i.e., such as that depicted in FIG. 19K as element 280) having a tissue interface surface configured to engage a portion of the tissue structure when coupled to a suture member that may be threaded through the tensioning member base and into the tissue structure; a suture clamping member (i.e., such as that depicted in FIG. 19K as element 278) configured to be switched from a first mode, wherein a suture may be tensioned back and forth through a space defined at least in part by the clamping member, to a second mode, wherein a suture may only be tensioned in one direction relative to the suture clamping member; and a mode switching member (i.e., such as the actuation member 284 or lock actuation member 230 described above) movably coupled to the suture clamping member and configured to be operable to switch the suture clamping member from the first mode to the second mode (376). The physical relationship between the tensioning assembly, suture member, and tissue structure may be modulated (i.e., tightened, loosened, etc) by modulating the position of the tension member base relative to the suture member and tissue structure wall (378). The tensioning mode may be switched to the second mode to permanently proceed toward a final tightening of the suture member (380). The tissue interfacing surface of the tensioning member base may comprise a thrombogenic member as shown, for example, in FIGS. 19J and 19k (element 274), or in another embodiment, a fabric pledget sock (not shown) may be configured to substantially surround or encapsulate the locking assembly (265) and encourage biointegration of the tensioning member base and adjacent portions of the tissue structure. The sock may comprise a durable polymer selected from the group consisting of: polyethylene terepthalate, polyethylene, high density polyethylene, polypropylene, polytetrafluoroethylene, expanded polytetrafluoroethylene, poly (ethylene-co-vinyl acetate), poly(butyl methacrylate), and co-polymers thereof. Alternatively, the sock may comprise a bioresorbable polymer selected from the group consisting of: polylactic acid, polyglycolic acid, polylactic-co-glycolic acid, polylactic acid-co-caprolactone, poly (block-ethylene oxide-block-lactide-co-glycolide), polyethylene glycol, polyethylene oxide, poly (block-ethylene oxide-block-propylene oxide-block-ethylene oxide), polyvinyl pyrrolidone, polyorthoester, polyanhydride, polyhydroxy valerate, polyhydroxy butyrate, and co-polymers thereof. Alternatively, the sock may comprise a bioresorbable material selected from the group consisting of: porcine collagen matrix, human collagen matrix, equine collagen fleece, gelatin, polyhyaluronic acid, heparin, poly (glucose), poly(alginic acid), chitin, chitosan, cellulose, methyl cellulose, hydroxyethylcellulose, hydroxypropylcellulose, carboxymethylcellulose; polylysine, polyglutamic acid, albumin, hydroxy apatite, cortical bone, cancellous bone, trabecular bone, bioceramic, ligament tissue, tendon tissue, dura tissue, fascia tissue, pericardium tissue, thrombin, and fibrin. The tissue-side interface of the locking assembly may be configured to be interfaced with various tissue types, as described above, including myocardium or pericardium (in which case one of the preferred method steps comprises identifying the pericardium, either directly, such as which a probe, optically—as in using visual inspection, or with tools such as ultrasound or OCT; another step may include removing at least a portion of the pericardium if direct myocardial interfacing is desired for the locking assembly).

Figure 30:
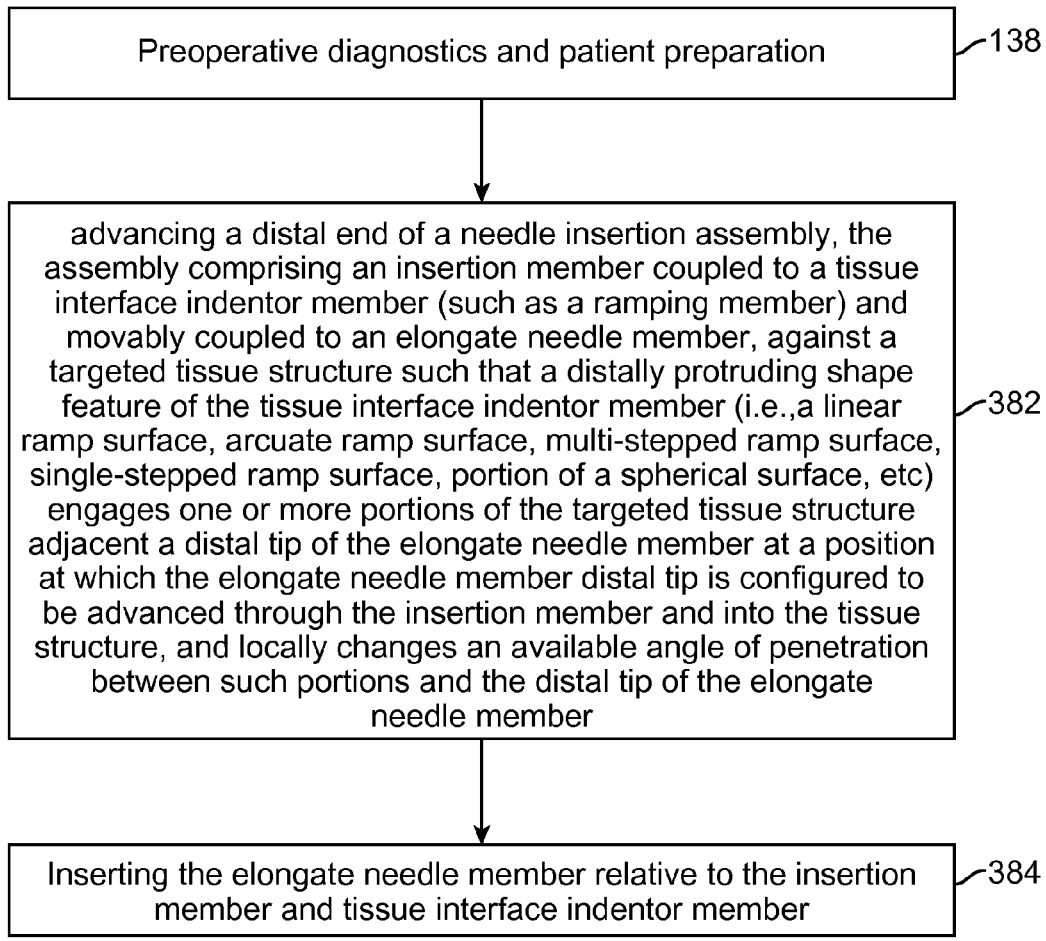
FIG. 30 illustrates a technique for implementing various embodiments of the subject helical closure configurations.

Referring to FIG. 30, one embodiment of an access and closure technique is illustrated to emphasize the use of tissue interface indentors, such as the aforementioned ramping members, to change the effective local angle of entry between an inserted needle and the subject tissue structure. Referring to FIG. 30, after preoperative diagnostics and patient preparation (138), a distal end of a needle insertion assembly may be advanced against a targeted tissue structure, with one or more tissue indentor members, in the form of protruding shape features (i.e. such as ramps, and various other shapes as described above) providing the leading mechanical edges for the assembly, these features locally deforming the interfaced tissue to provide greater effective angles of penetration between the needle members and the tissue (382). Given such configuration, the needle members may then be inserted relative to the rest of the assembly and into the targeted tissue structure, taking advantage of the preferred angle of entry (384).

Figure 31:
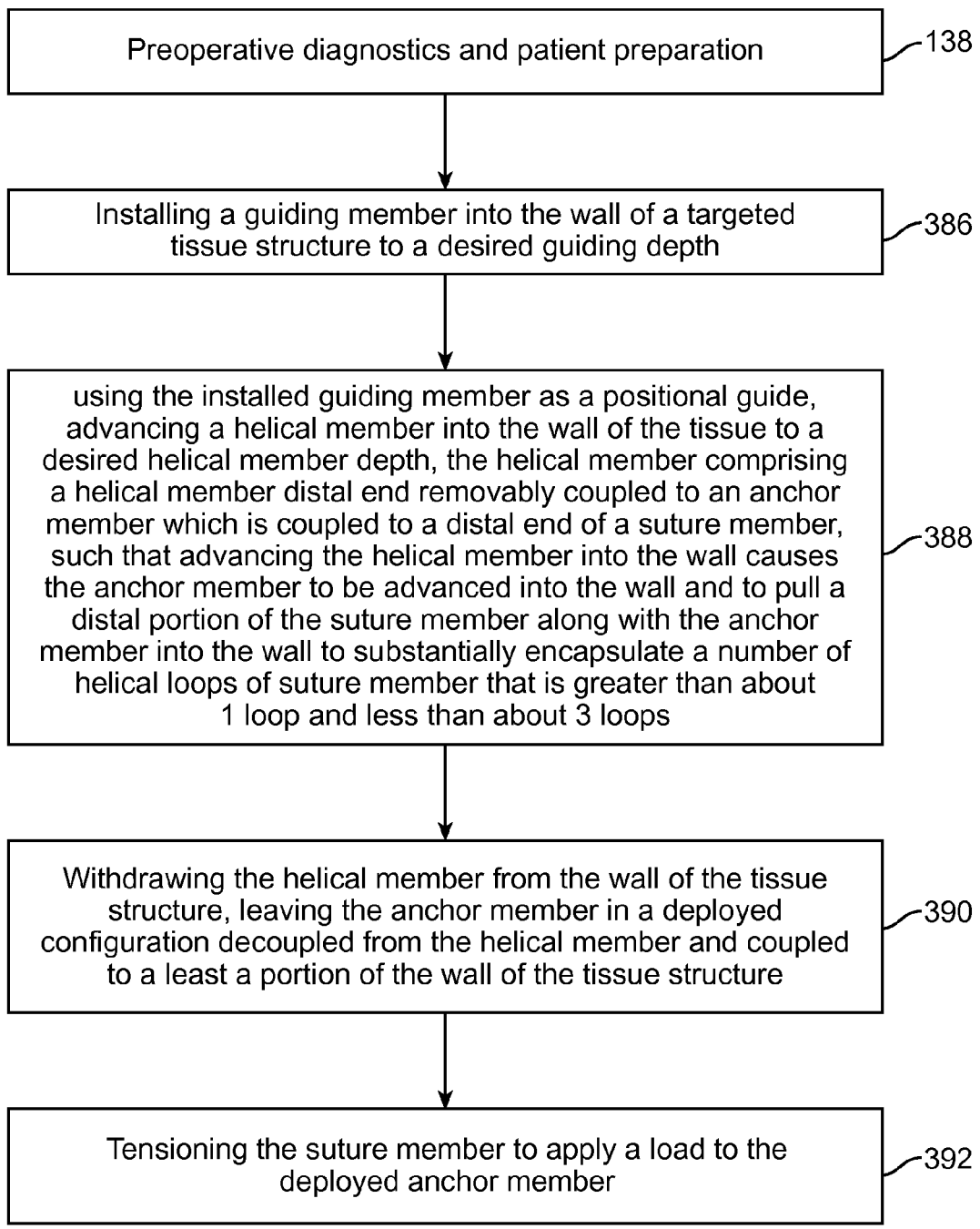
FIG. 31 illustrates a technique for implementing various embodiments of the subject helical closure configurations.

Referring to FIG. 31, one embodiment of an access and closure technique is illustrated to emphasize the importance of planning and selecting a helical needle configuration matched to the tissue geometry to be crossed, as in the embodiment of FIG. 27. Referring to FIG. 31, preoperative diagnostics and patient preparation may be conducted, which may include measurements of the tissue geometry using direct techniques or image capture techniques, as described above in reference to FIG. 27. A guiding member may be installed to a desired guiding depth (386), and using this guiding member as a positional depth guide, a helical member may be advanced into the tissue structure, preferably such that between about 1 and about 3 helical loops are deployed (388). The helical member may then be withdrawn, leaving the suture member pattern in place (390), after which the suture pattern may be expanded and later contracted, such as by tensioning the suture member (392).

It is important to note that while the subject closure technologies and configurations have been described and illustrated in the context of a trans-apical wall defect or port closure, and specifically regarding tissue structures such as the walls and apex of the ventricles of the heart, such technologies may be broadly applied to various other tissue structures wherein a closure following creation or existence of a defect is desired—such as in the gastric mucosa for trans-gastric interventions of various types (for example, following a trans-gastric access of the gall bladder or a trans-colonic retroperitoneal access), or in the uterus for various gynecological interventions (for example, following removal of a fibroid tumor residing in the wall of the uterus). For example, the subject invention may be utilized to assist in the deployment of a prosthesis such as that described in U.S. Pat. No. 7,104,949, which is incorporated by reference in its entirety. The following U.S. patent applications are also incorporated by reference herein in their entirety: Nos. 61/315,795, 61/377,670, and 61/361,365.

Any of the aforementioned deployed structures, including sutures, anchor members, and ratcheting closure device assembly components, may comprise resorbable materials in addition to the aforementioned nonresorbable materials—to facilitate combinations and permutations which may be completely resorbed, leaving behind a biologically healed transapical access wound.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject interventions may be provided in packaged combination for use in executing such interventions. These supply "kits" further may include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A method for advancing a needle into a tissue structure, comprising:
   a. advancing a distal end of a needle insertion assembly, the assembly comprising an insertion member coupled to a tissue interface indentor member and movably coupled to an elongate needle member, against a targeted tissue structure such that a distally protruding shape feature of the tissue interface indentor member engages one or more portions of the targeted tissue structure adjacent a distal tip of the elongate needle member at a position at which the elongate needle member distal tip is configured to be advanced through the insertion member and into the tissue structure, and locally changes an available angle of penetration between such portions and the distal tip of the elongate needle member; wherein the distally protruding shape feature and distal tip of the elongate needle member are operatively coupled such that the distal tip is movably coupled through a portion of the distally protruding shape feature; and
   b. inserting the elongate needle member relative to the insertion member and tissue interface indentor member.

2. The method of claim 1, wherein the elongate needle member comprises a shape selected from the group consisting of: a substantially straight shape, an arcuate shape, and a helical shape, and wherein inserting the elongate member relative to the insertion member and tissue member comprises manually manipulating a proximal end of the elongate needle member.

3. The method of claim 2, wherein the elongate needle member comprises a first helical member that defines an inner helix diameter that is substantially constant across the length of the helical member, and wherein manually manipulating comprises imparting a twisting load to the elongate needle member.

4. The method of claim 2, wherein the elongate needle member comprises a first helical member that defines an inner helix diameter that varies across the length of the helical member, and wherein manually manipulating comprises imparting a twisting load to the elongate needle member.

5. The method of claim 3, wherein the inner helix diameter is between about 5 mm and about 60 mm.

6. The method of claim 5, wherein the inner helix diameter is between about 10 mm and about 20 mm.

7. The method of claim 2, wherein the elongate needle member comprises a first helical member that is comprised of an elongate member formed into the helical shape, the elongate member having an outer diameter.

8. The method of claim 7, wherein the elongate member has a cross sectional shape selected from the group consisting of: a circular cross section, an elliptical cross section, a square cross section, and a rectangular cross section.

9. The method of claim 7, wherein the outer diameter is between about 0.5 mm and about 3 mm.

10. The method of claim 7, wherein the helical shape comprises a number of helical turns advanceable into tissue relative to the insertion member that is between about 1 and about 3.

11. The method of claim 3, wherein the helical shape has a substantially constant helix pitch along the length of the helical shape.

12. The method of claim 3, wherein the helical shape has a substantially variable helix pitch along the length of the helical shape.

13. The method of claim 4, wherein the helical shape has a substantially constant helix pitch along the length of the helical shape.

14. The method of claim 4, wherein the helical shape has a substantially variable helix pitch along the length of the helical shape.

15. The method of claim 11, wherein the helix pitch is between about 5 mm and about 20 mm.

16. The method of claim 15, wherein the helix pitch is between about 7 mm and about 13 mm.

17. The method of claim 1, wherein a distal end of the first helical member comprises a sharpened tip configured to easily dive into and cross portions of the tissue structure.

18. The method of claim 7, wherein the elongate member comprises a solid cross-sectional construct.

19. The method of claim 7, wherein the elongate member comprises a tubular construct having an inner diameter and as well as the outer diameter.

20. The method of claim 18, wherein the elongate member comprises a material selected from the group consisting of: stainless steel, nitinol alloy, titanium, cobalt chrome, and polymer composite.

21. The method of claim 19, wherein the elongate member comprises a material selected from the group consisting of: stainless steel, nitinol alloy, titanium, cobalt chrome, and polymer composite.

22. The method of claim 1, wherein the insertion member comprises a substantially rigid construct, and wherein manually manipulating comprises imparting a twisting load to the insertion member.

23. The method of claim 1, wherein the insertion member comprises a flexible construct, and wherein manually manipulating comprises imparting a twisting load to the insertion member.

24. The method of claim 1, wherein advancing the distal end of the needle insertion assembly causes the distally protruding shape feature to concentrate interfacial stresses upon the tissue structure such that the portions of the tissue structure adjacent the distal tip of the elongate needle member become locally strained about the distally protruding shape feature as the distally protruding shape feature is advanced into contact with the adjacent tissue structure portions.

25. The method of claim 24, wherein at least one surface of the distally protruding shape feature comprises a surface configuration selected from the group consisting of: a portion of a spherical surface, a linear ramp surface, an arcuate ramp surface, a multi-stepped ramp surface, and a single-stepped ramp surface.

26. The method of claim 25, wherein the surface configuration is helically wrapped about a longitudinal axis of the helical member.

27. The method of claim 24, wherein at least one surface of the distally protruding shape feature comprises a substantially perpendicular leading surface.

28. The method of claim 24, wherein the distally protruding shape feature has a cross sectional profile comprising a cross sectional shape selected from the list consisting of: a rectangle, a square, a half circle, a triangle, a polygon, a rounded rectangular shape, a rounded square shape, and a multi-arcuate shape.

29. The method of claim 1, wherein the distal tip substantially bisects the portion of the distally protruding shape feature.

30. The method of claim 1, wherein the distally protruding shape feature and distal tip of the elongate needle member are operatively coupled such that the distal tip is movably coupled adjacent a portion of the distally protruding shape feature.

31. The method of claim 25, wherein the distal tip of the elongate needle member is configured to follow a path substantially parallel to the surface configuration of the distally protruding shape feature.

32. The method of claim 24, wherein the distally protruding shape feature comprises one or more tissue traction features configured to prevent relative motion between the distally protruding shape feature and portions of the tissue structure with which it may be directly interfaced.

33. The method of claim 32, wherein at least one of the one or more tissue traction features comprises a barb.

34. The method of claim 1, further comprising preventing movement of the tissue interface indentor member relative to the targeted tissue structure portion against which it is interfaced once a desired interfacing has been achieved by advancing the needle insertion assembly against the targeted tissue structure.

35. The method of claim 34, wherein preventing movement comprises preventing rotation of the tissue interface indentor member relative to the targeted tissue structure portion.

36. The method of claim 34, wherein preventing movement comprises preventing translation of the tissue interface indentor member relative to the targeted tissue structure portion.

37. The method of claim 1, wherein advancing the distal end of the needle insertion assembly comprises manipulating the needle insertion assembly with one hand of an operator, and wherein inserting the elongate needle member comprises manipulating the elongate needle member with the other hand of the operator, such that the needle may be controllably inserted by a single operator.

* * * * *